United States Patent
Miller et al.

(10) Patent No.: US 7,902,498 B2
(45) Date of Patent: Mar. 8, 2011

(54) METHODS AND APPARATUS FOR ENHANCED ION BASED SAMPLE DETECTION USING SELECTIVE PRE-SEPARATION AND AMPLIFICATION

(75) Inventors: Raanan A. Miller, Chestnut Hill, MA (US); Erkinjon G. Nazarov, Lexington, MA (US); Lawrence A. Kaufman, Boston, MA (US); Gary A. Eiceman, Las Cruces, NM (US)

(73) Assignee: DH Technologies Development PTE. Ltd., Singapore (SG)

( * ) Notice: Subject to any disclaimer, the term of this patent is extended or adjusted under 35 U.S.C. 154(b) by 0 days.

(21) Appl. No.: 11/015,413

(22) Filed: Dec. 17, 2004

(65) Prior Publication Data
US 2005/0167583 A1   Aug. 4, 2005

Related U.S. Application Data

(60) Provisional application No. 60/531,480, filed on Dec. 18, 2003, provisional application No. 60/533,676, filed on Dec. 31, 2003, provisional application No. 60/556,414, filed on Mar. 25, 2004.

(51) Int. Cl.
*H01J 49/00* (2006.01)
(52) U.S. Cl. ............ 250/282; 250/288; 250/290
(58) Field of Classification Search .......... 250/282
See application file for complete search history.

(56) References Cited

U.S. PATENT DOCUMENTS

| | | | |
|---|---|---|---|
| 2,615,135 A | | 10/1952 | Glenn |
| 3,511,986 A | | 5/1970 | Llewellyn |
| 3,621,240 A | | 11/1971 | Cohen et al. |
| 3,931,589 A | | 1/1976 | Aisenberg et al. |
| 4,025,818 A | | 5/1977 | Giguere et al. |
| 4,201,921 A | | 5/1980 | McCorkle |
| 4,352,780 A | * | 10/1982 | Schick ............... 422/67 |
| 4,551,624 A | * | 11/1985 | Spangler et al. ......... 250/287 |
| 4,931,640 A | | 6/1990 | Marshall et al. |
| 5,019,706 A | | 5/1991 | Allemann et al. |
| 5,083,019 A | * | 1/1992 | Spangler ............ 250/286 |
| 5,175,431 A | * | 12/1992 | Eisele et al. ......... 250/288 |
| 5,218,203 A | * | 6/1993 | Eisele et al. ......... 250/288 |
| 5,235,186 A | * | 8/1993 | Robins ............. 250/288 |
| 5,420,424 A | | 5/1995 | Carnahan et al. |

(Continued)

FOREIGN PATENT DOCUMENTS

RU   1412447 A3   6/1998

(Continued)

OTHER PUBLICATIONS

"A Micromachined Field Driven Radio Frequency-Ion Mobility Spectrometer for Trace Level Chemical Detection, A Draper Laboratory Proposal Against the Advanced Cross-Enterprise Technology Development for NASA Missions," Solicitation, NASA NRA 99-OSS-05.

(Continued)

*Primary Examiner* — David A. Vanore
*Assistant Examiner* — Philiip A. Johnston
(74) *Attorney, Agent, or Firm* — Ropes & Gray LLP

(57) ABSTRACT

The invention relates generally to ion mobility based systems, methods and devices for analyzing samples and, more particularly, to sample pre-separation and amplification.

37 Claims, 82 Drawing Sheets
(7 of 82 Drawing Sheet(s) Filed in Color)

U.S. PATENT DOCUMENTS

| | | | |
|---|---|---|---|
| 5,455,417 A | 10/1995 | Sacristan | |
| 5,536,939 A | 7/1996 | Freidhoff et al. | |
| 5,654,544 A | 8/1997 | Dresch | |
| 5,723,861 A | 3/1998 | Carnahan et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,834,771 A | 11/1998 | Yoon et al. | |
| 5,838,003 A | 11/1998 | Bertsch et al. | |
| 5,869,344 A | 2/1999 | Linforth et al. | |
| 5,965,882 A | 10/1999 | Megerle et al. | |
| 6,066,848 A | 5/2000 | Kassel et al. | |
| 6,124,592 A | 9/2000 | Spangler | |
| 6,323,482 B1 | 11/2001 | Clemmer et al. | |
| 6,495,823 B1 | 12/2002 | Miller et al. | |
| 6,498,342 B1 | 12/2002 | Clemmer et al. | |
| 6,504,149 B2 | 1/2003 | Guevremont et al. | |
| 6,509,562 B1 | 1/2003 | Yang et al. | |
| 6,512,224 B1 | 1/2003 | Miller et al. | |
| 6,639,212 B1 | 10/2003 | Guevremont | |
| 6,653,627 B2 | 11/2003 | Guevremont | |
| 6,690,004 B2 | 2/2004 | Miller et al. | |
| 6,703,609 B2* | 3/2004 | Guevremont et al. | 250/287 |
| 6,713,758 B2 | 3/2004 | Guevremont | |
| 6,727,496 B2 | 4/2004 | Miller et al. | |
| 6,744,043 B2 | 6/2004 | Laboda | |
| 6,753,522 B2 | 6/2004 | Guevremont | |
| 6,770,875 B1 | 8/2004 | Guevremont | |
| 6,774,360 B2 | 8/2004 | Guevremont | |
| 6,787,765 B2 | 9/2004 | Guevremont | |
| 6,799,355 B2 | 10/2004 | Guevremont | |
| 6,806,463 B2 | 10/2004 | Miller et al. | |
| 6,806,466 B2 | 10/2004 | Guevremont | |
| 6,815,668 B2 | 11/2004 | Miller et al. | |
| 6,815,669 B1 | 11/2004 | Miller et al. | |
| 6,822,224 B2 | 11/2004 | Guevremont et al. | |
| 6,825,461 B2 | 11/2004 | Guevremont et al. | |
| 6,974,951 B1* | 12/2005 | Kingston | 250/282 |
| 7,028,537 B2* | 4/2006 | Karst et al. | 73/61.55 |
| 2001/0030285 A1 | 10/2001 | Miller et al. | |
| 2002/0070338 A1 | 6/2002 | Loboda | |
| 2002/0088936 A1* | 7/2002 | Breach et al. | 250/281 |
| 2002/0134932 A1 | 9/2002 | Guevremont et al. | |
| 2003/0020012 A1 | 1/2003 | Guevremont et al. | |
| 2003/0038235 A1 | 2/2003 | Guevremont et al. | |
| 2003/0052263 A1 | 3/2003 | Kaufman et al. | |
| 2003/0070913 A1 | 4/2003 | Miller et al. | |
| 2003/0089847 A1 | 5/2003 | Guevremont et al. | |
| 2003/0132380 A1 | 7/2003 | Miller et al. | |
| 2004/0094704 A1 | 5/2004 | Miller et al. | |
| 2004/0136872 A1 | 7/2004 | Miller et al. | |
| 2004/0232326 A1 | 11/2004 | Guevremont et al. | |
| 2005/0029449 A1 | 2/2005 | Miller et al. | |
| 2005/0040330 A1 | 2/2005 | Miller et al. | |
| 2005/0051719 A1 | 3/2005 | Miller et al. | |
| 2005/0056780 A1 | 3/2005 | Miller et al. | |
| 2005/0116160 A1* | 6/2005 | Guevremont | 250/282 |
| 2005/0121607 A1 | 6/2005 | Miller et al. | |
| 2005/0133716 A1 | 6/2005 | Miller et al. | |
| 2005/0139762 A1 | 6/2005 | Miller et al. | |
| 2005/0167583 A1 | 8/2005 | Miller et al. | |
| 2005/0173629 A1 | 8/2005 | Miller et al. | |
| 2005/0194527 A1 | 9/2005 | Guevremont et al. | |
| 2005/0194532 A1 | 9/2005 | Guevremont et al. | |
| 2006/0186334 A1* | 8/2006 | Jolliffe et al. | 250/288 |

FOREIGN PATENT DOCUMENTS

| | | |
|---|---|---|
| RU | 1485808 | 10/1998 |
| SU | 966583 | 10/1982 |
| SU | 1337934 A2 | 9/1987 |
| SU | 1627984 A2 | 7/1988 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 A1 | 2/2001 |
| WO | WO 01/22049 A2 | 3/2001 |
| WO | WO 01/35441 A1 | 5/2001 |
| WO | WO 01/69217 A2 | 9/2001 |
| WO | WO 01/69220 A2 | 9/2001 |
| WO | WO 01/69647 A2 | 9/2001 |
| WO | WO 02/071053 A2 | 9/2002 |
| WO | WO-03/067237 A2 | 8/2003 |
| WO | WO-03/067242 A1 | 8/2003 |
| WO | WO-03/067243 A1 | 8/2003 |
| WO | WO-03/067625 A1 | 8/2003 |
| WO | WO-2004/029603 A2 | 4/2004 |
| WO | WO-2004/029614 A1 | 4/2004 |
| WO | WO-2004/030022 A2 | 4/2004 |
| WO | WO-2004/030023 A2 | 4/2004 |
| WO | WO-2004/030129 A2 | 4/2004 |

OTHER PUBLICATIONS

Barnett, D.A. et al., "Isotope Separation Using High-Field Asymmetric Waveform Ion Mobility Spectrometry," Nuclear Instruments & Methods in Physics Research (200), pp. 179-185, 450(1).

Buryakov, I.A. et al., A New Method of Separation of Multi-Atomic Ions by Mobility at Atmospheric Pressure Using a High-Frequency Amplitude-Asymmetric Strong Electric Field, International Journal of Mass Spectrometry and Ion Processes (1993), pp. 143-148, 128.

Buryakov, I.A. et al., "Separation of Ions According to Mobility in a Strong AC Electric Field," Sov. Tech. Phs. Lett. (1991), pp. 446-447, 17(6).

Burykov, I.A. et al., Device and Method for Gas Electrophoresis, Chemical Analysis of Environment, edit. Prof. V.V. Malakhov, Novosibirsk; Nauka (1991), pp. 113-127.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Eiceman, G.A. et al., "Miniature radio-frequency mobility analyzer as a gas chromatographic detector for oxygen-containing volatile organic compounds, pheromones, and other insect attractants," J. Chromatography, (2001), pp. 205-217, 917.

Guevremont, R. and Purves, R., High Field Asymmetric Waveform Ion Mobility Spectrometry-Mass Spectrometry: An Investigation of Leucine Enkephalin Ions Produced by Electrospray Ionization, J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Guevremont, R. et al., "Atmospheric Pressure Ion Focusing in a High-Field Asymmetric Waveform ion Mobility Spectrometer," Review of Scientific Instruments, (1999), pp. 1370-1383, 70(2).

Handy, Russell et al., "Determination of nanomlar levels of perchlorate in water by ESI-FAIMS-MS," JAAS (2000), pp. 907-911, 15.

Krylov, E.V., "A Method of Reducing Diffusion Losses in a Drift Spectrometer," Technical Physics, (1999), pp. 113-16, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., A MEMS Radio-Frequency Ion Mobility Spectrometer for Chemical Vapor Detection, Sensors and Actuators, (2001), pp. 301-12, A91.

Miller, R.A. et al., A Novel Micromachined High-Field Asymmetric Waveform-Ion Mobility Spectrometer, Sensors and Actuators B, (2000) pp. 300-306, B67(3).

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., High Sensitivity GC-FIS for Simultaneous Detection of Chemical Warfare Agents, Mine Safety Appliances Co., Pittsburgh, PA USA, (2000), AT-Process, pp. 124-136, 5(3, 4), CODEN: APJCFR ISSN: 1077-419X.

Vaidyanathan, S., et al., "Flow-Injection Electrospray Ionization Mass Spectrometry of Crude Cell Extracts for High-Throughput Bacterial Identification," J. Am. Soc. Mass. Spectrom., (2002) pp. 118-128, 13.

Crylov, E.V., "Comparison of the Planar and Coaxial Field Asymmetrical Waveform Ion Mobility Spectrometer (FAIMS)," International Journal of Mass Spectrometry, 225, (2003) pp. 39-51.

Barnett, D.A. et al., "Evaluation of Carrier Gases for use in High-Field Asymmetric Waveform Ion Mobility Spectrometry," Journal of the American Society for Mass Spectrometry, vol. 11, No. 12, pp. 1125-1133, Dec. 2000.

\* cited by examiner

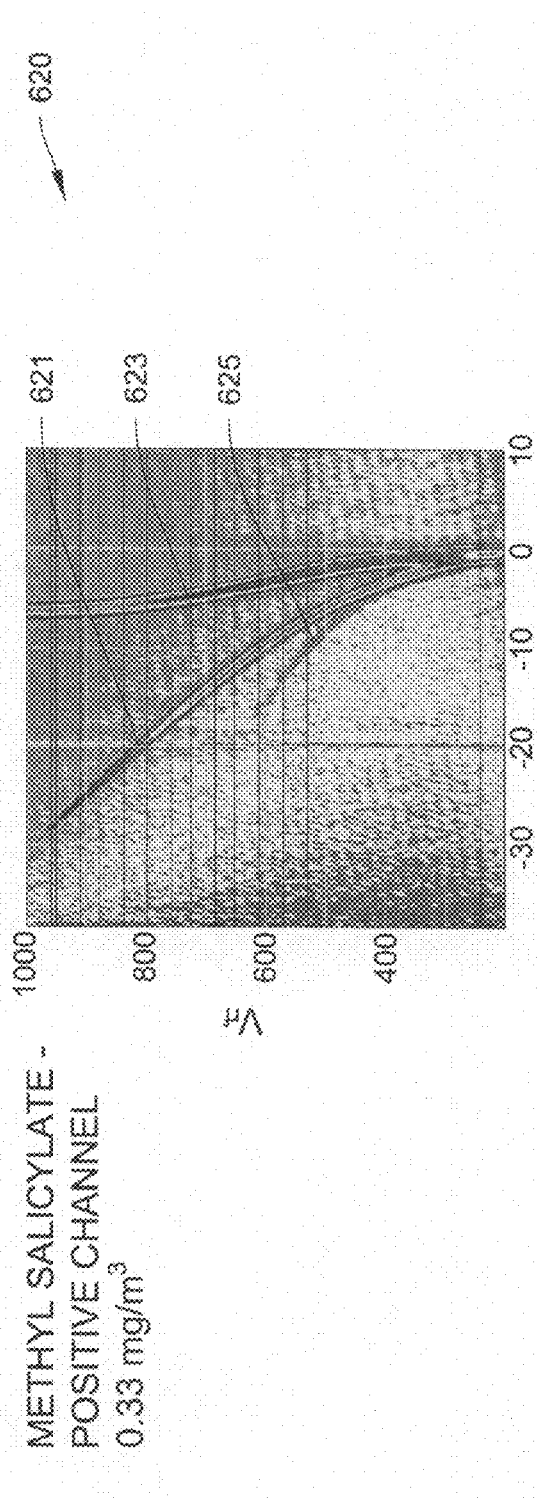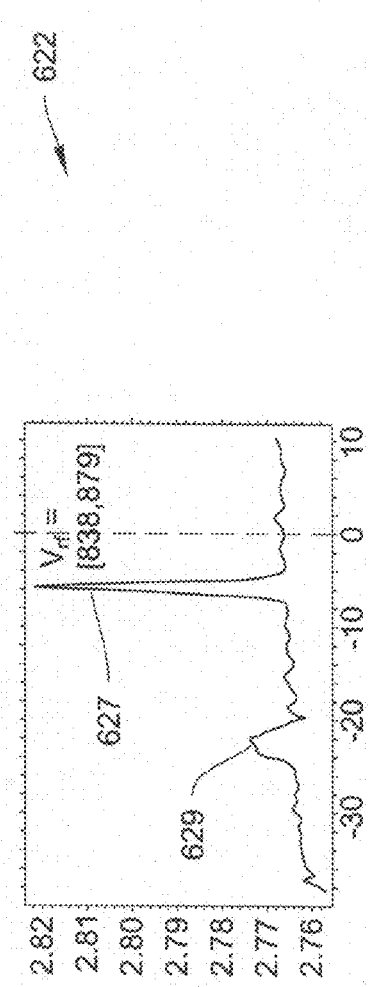
Figure 15A
Figure 15B

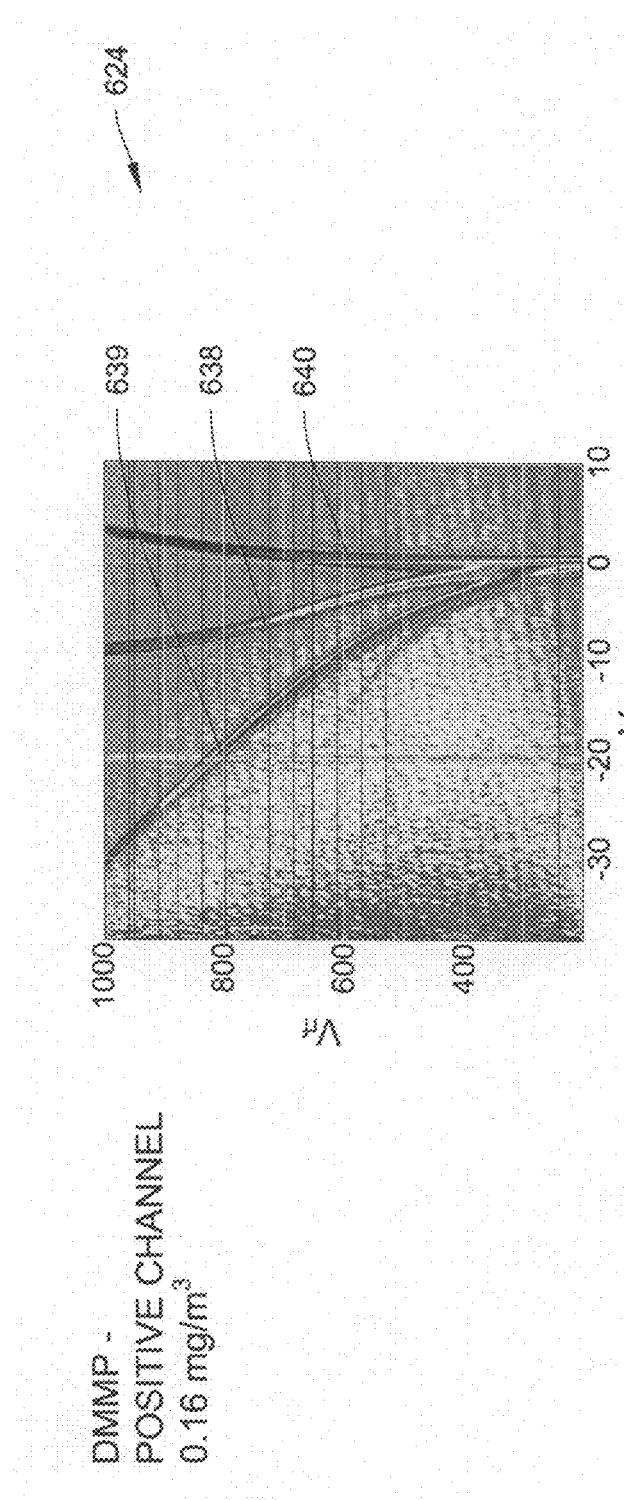
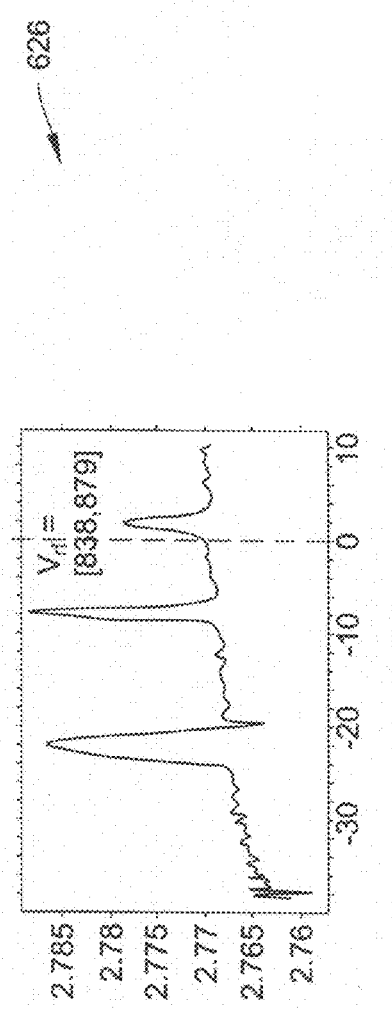
Figure 16A
Figure 16B

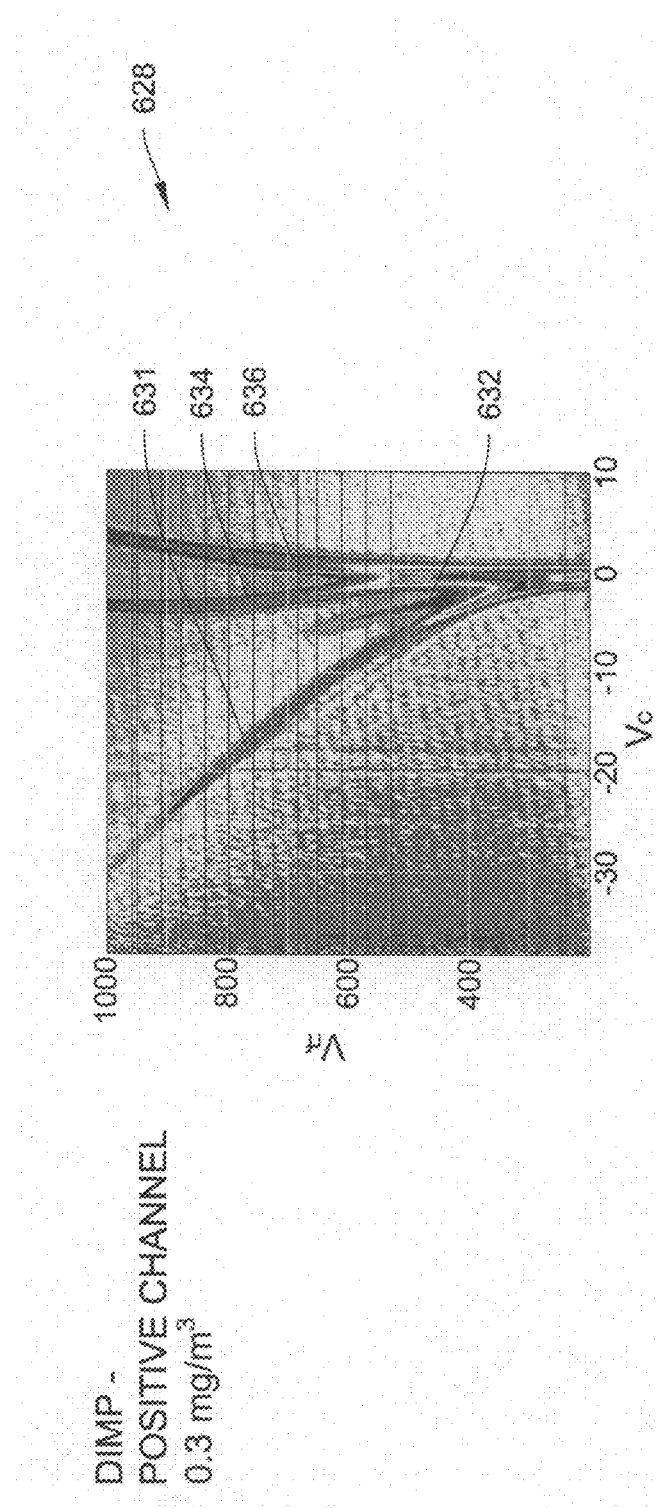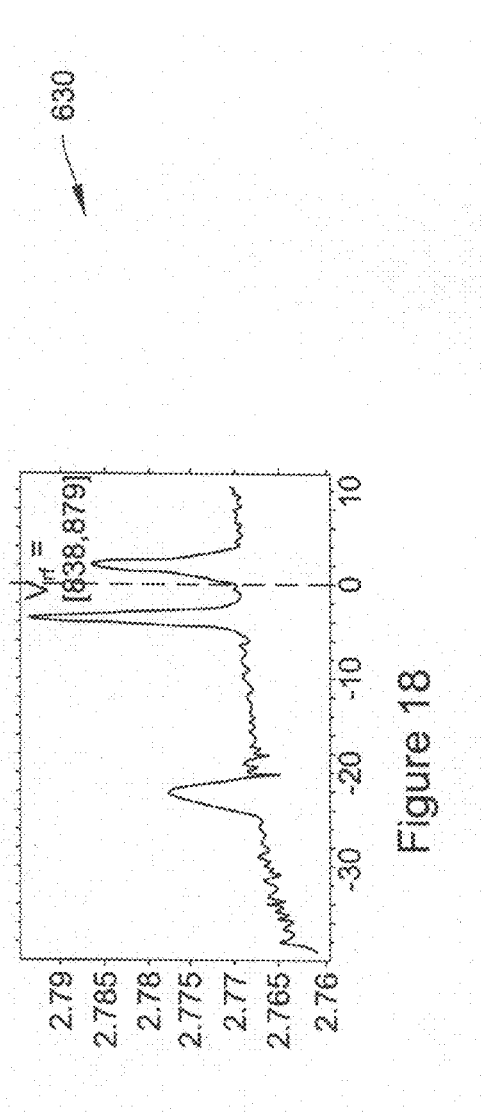
Figure 17
Figure 18

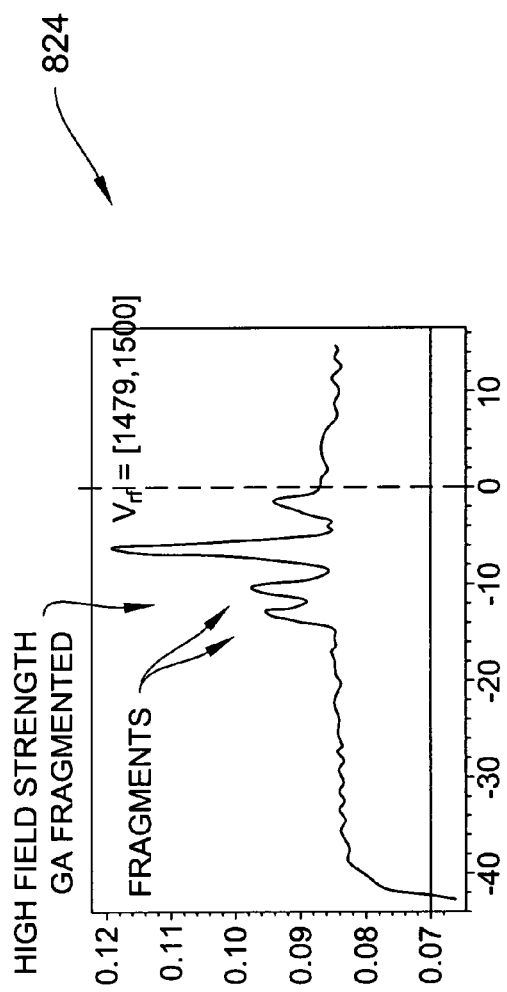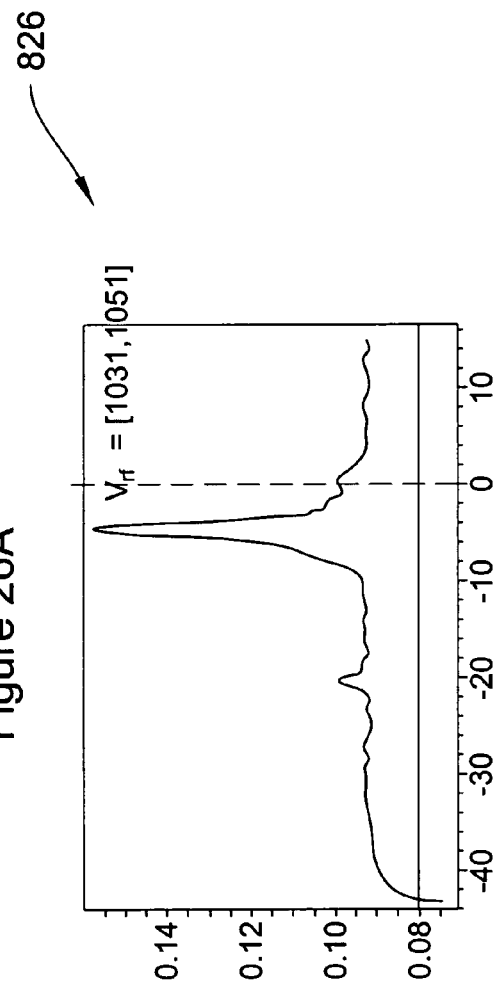

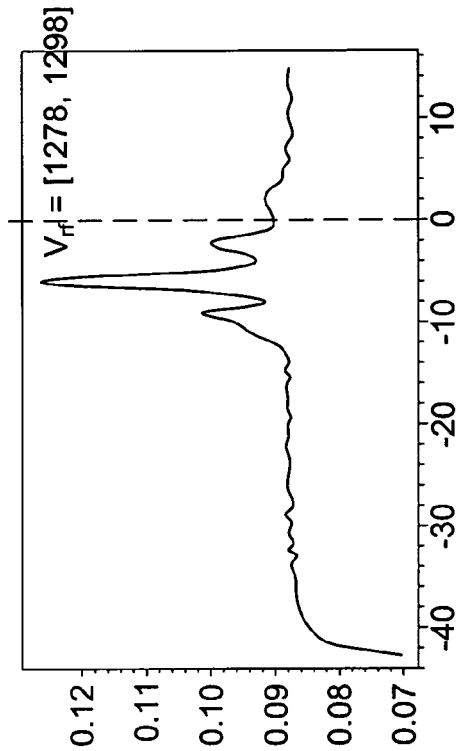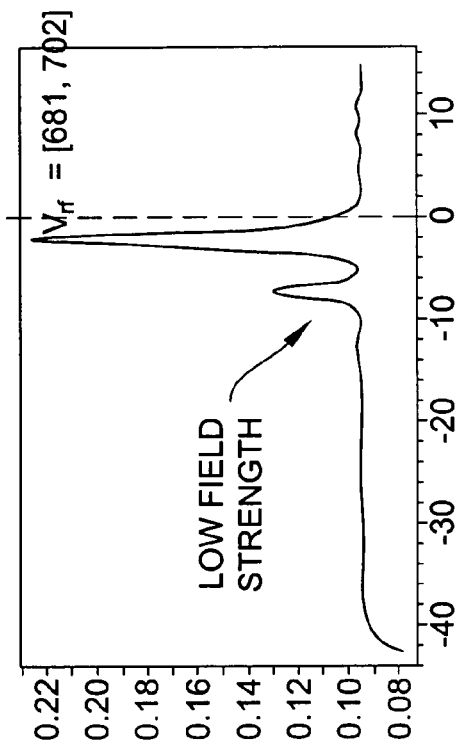

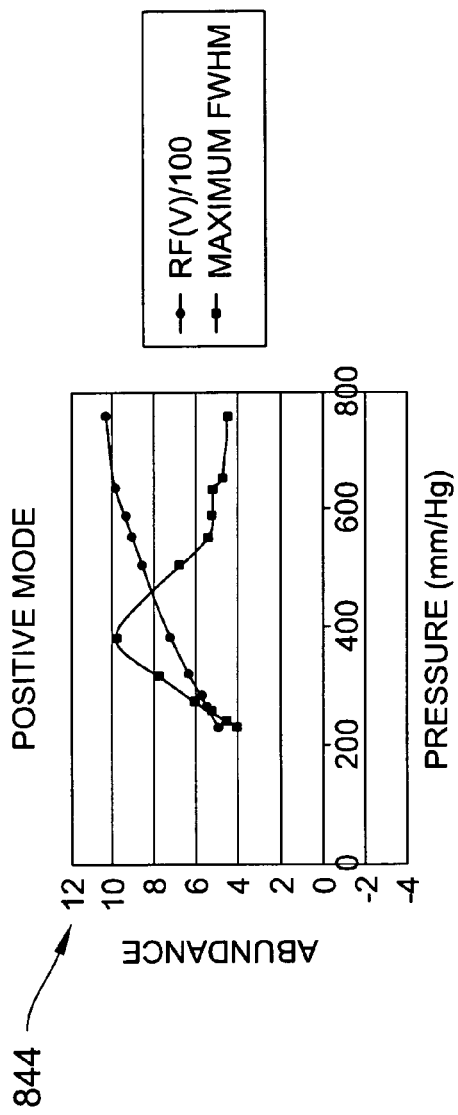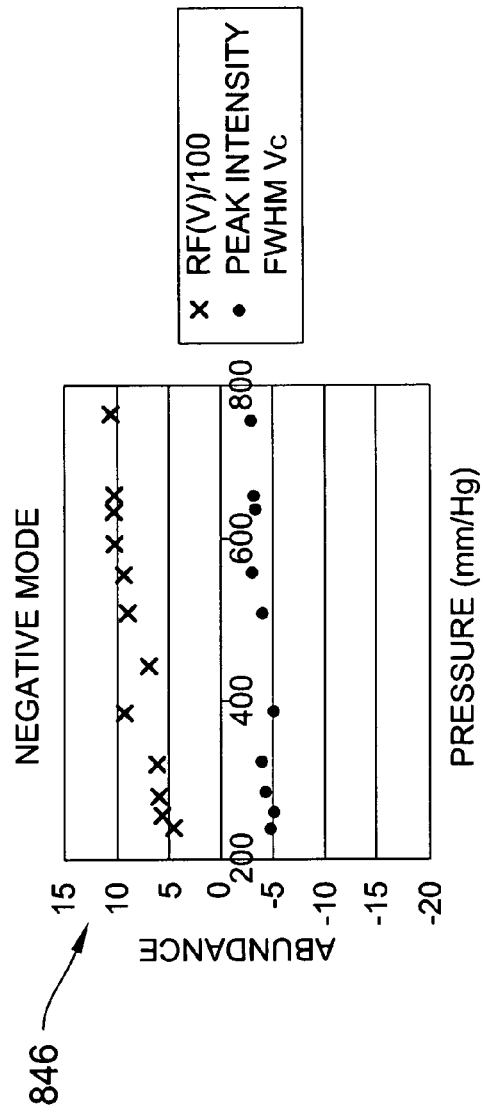
Figure 28A
Figure 28B

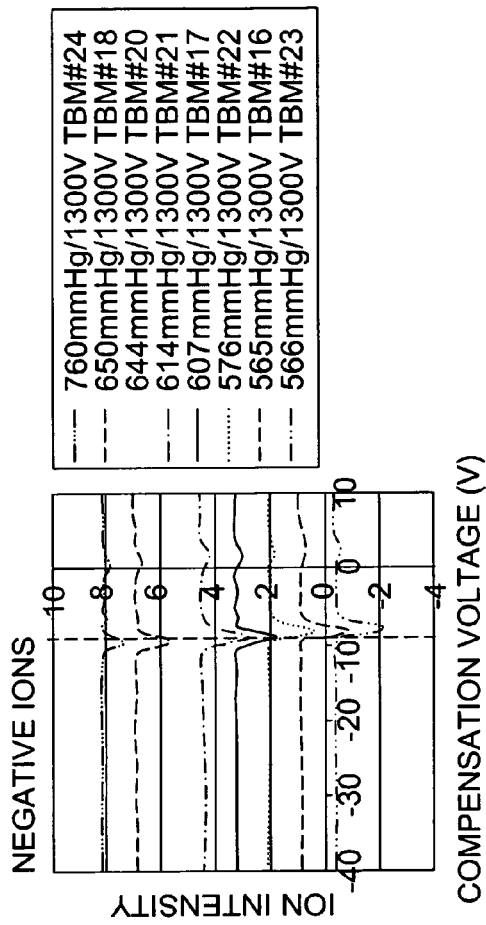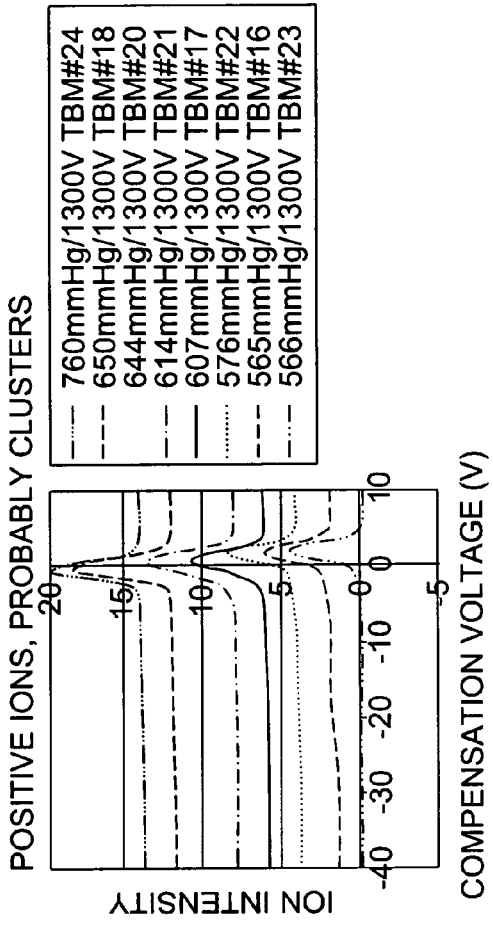
Figure 29A
Figure 29B

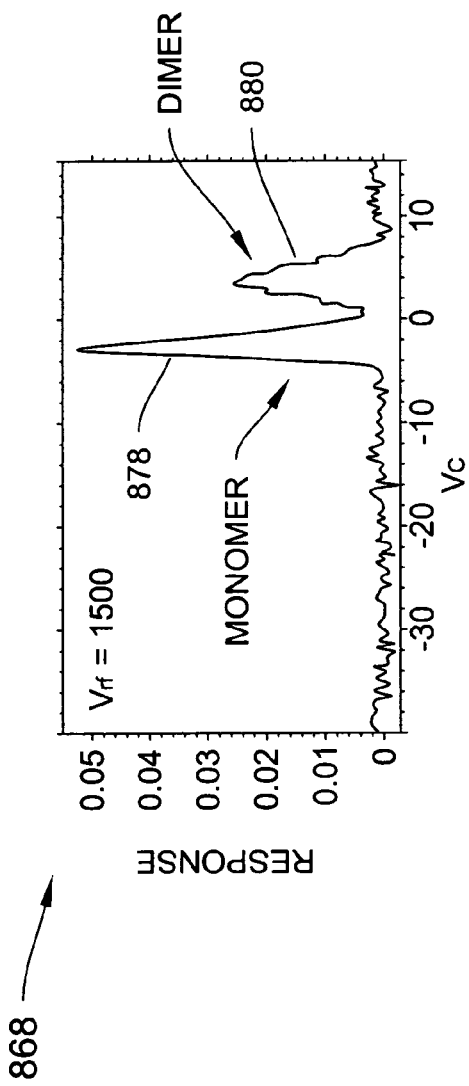
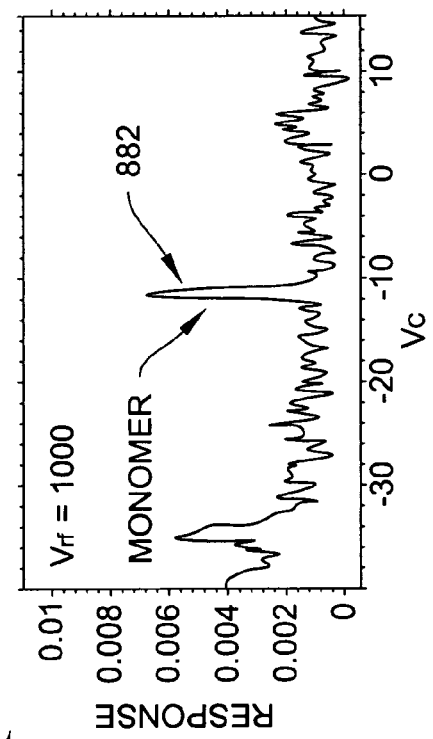
Figure 32A
Figure 32B

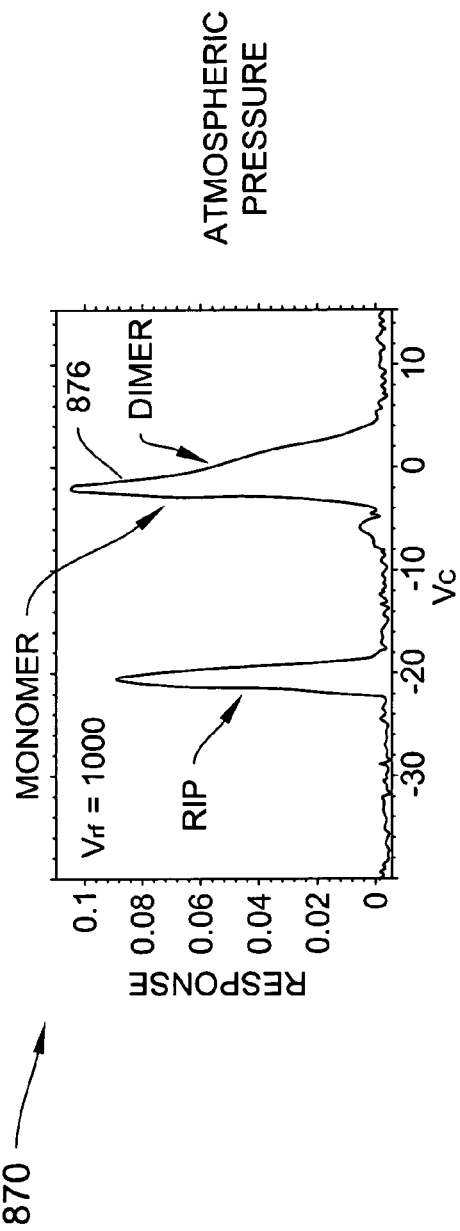
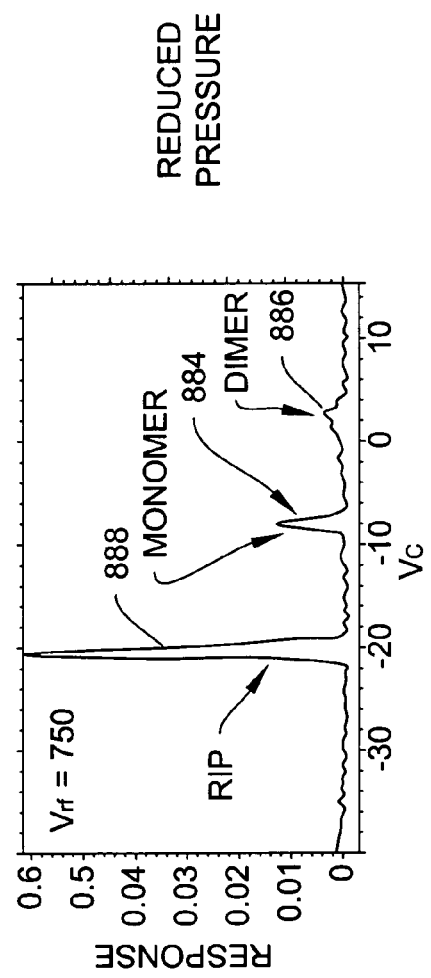
Figure 32C
Figure 32D

Protonated Monomer

| | Acetone | Butanone | Pentanone | Hexanone | Heptanone | Octanone | Nonanone | Decanone |
|---|---|---|---|---|---|---|---|---|
| Formula | $C_3H_6OH^+$ | $C_4H_8OH^+$ | $C_5H_{10}OH^+$ | $C_6H_{12}OH^+$ | $C_7H_{14}OH^+$ | $C_8H_{16}OH^+$ | $C_9H_{18}OH^+$ | $C_{10}H_{20}OH^+$ |
| m/z (amu) | 59 | 73 | 87 | 101 | 115 | 129 | 143 | 157 |
| $\alpha_2$ [% - Td] | $3.14 \times 10^{-3}$ | $2.7 \times 10^{-3}$ | $2.1 \times 10^{-3}$ | $1.7 \times 10^{-3}$ | $1.2 \times 10^{-3}$ | $8.4 \times 10^{-4}$ | $6.5 \times 10^{-4}$ | $4.6 \times 10^{-4}$ |
| $\alpha_4$ [% - Td] | $-9.54 \times 10^{-8}$ | $-1.4 \times 10^{-7}$ | $-1.2 \times 10^{-7}$ | $-1.1 \times 10^{-7}$ | $-8.8 \times 10^{-8}$ | $-6.9 \times 10^{-8}$ | $-6.6 \times 10^{-8}$ | $-5.2 \times 10^{-8}$ |

Figure 37

Proton Bound Dimer

| | Acetone | Butanone | Pentanone | Hexanone | Heptanone | Octanone | Nonanone | Decanone |
|---|---|---|---|---|---|---|---|---|
| Formula | $(C_3H_6O)_2H^+$ | $(C_4H_8O)_2H^+$ | $(C_5H_{10}O)_2H^+$ | $(C_6H_{12}O)_2H^+$ | $(C_7H_{14}O)_2H^+$ | $(C_8H_{16}O)_2H^+$ | $(C_9H_{18}O)_2H^+$ | $(C_{10}H_{20}O)_2H^+$ |
| m/z (amu) | 117 | 145 | 173 | 201 | 229 | 257 | 285 | 303 |
| $\alpha_2$ [% - Td] | $1.34 \times 10^{-3}$ | $8.0 \times 10^{-4}$ | $1.9 \times 10^{-4}$ | $1.9 \times 10^{-4}$ | $2.5 \times 10^{-5}$ | $-3.5 \times 10^{-5}$ | $-2.2 \times 10^{-4}$ | $-3.5 \times 10^{-4}$ |
| $\alpha_4$ [% - Td] | $-1.77 \times 10^{-7}$ | $-1.2 \times 10^{-7}$ | $-6.0 \times 10^{-8}$ | $-8.0 \times 10^{-8}$ | $-6.8 \times 10^{-8}$ | $-6.9 \times 10^{-8}$ | $-4.8 \times 10^{-8}$ | $-3.2 \times 10^{-8}$ |

Figure 38

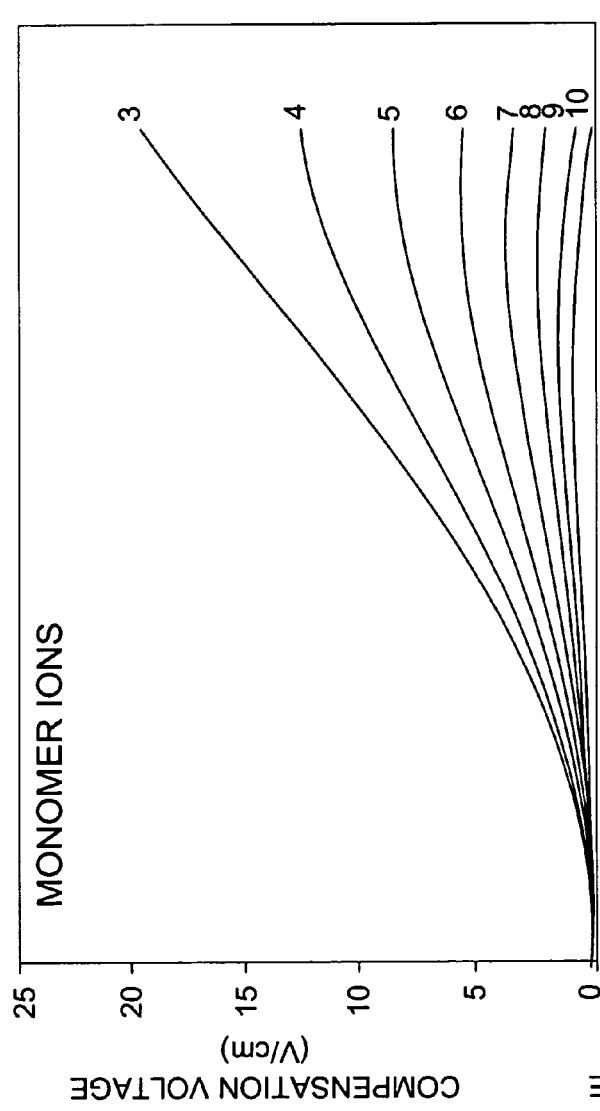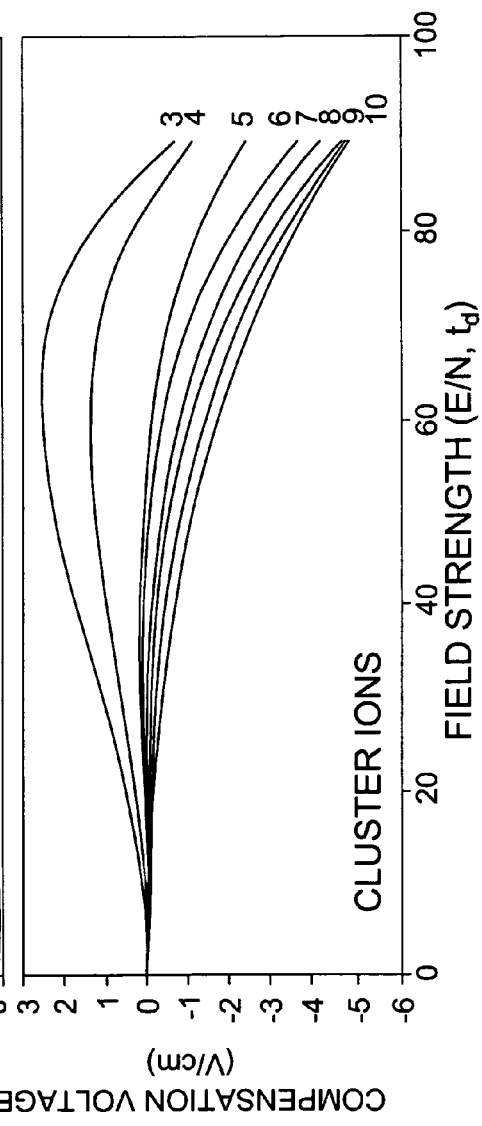
Figure 39A
Figure 39B

| COMPOUND ID | | | | | | | |
|---|---|---|---|---|---|---|---|
| $V_{DISP1}$ | $V_{C11}, a_{11}$ | ... | $V_{C1n}, a_{1n}$ | ... | | | |
| ... | | | | | | | |
| $V_{DISP\,m}$ | | | | | $V_{Cm1}, a_{m1}$ | | |
| $V_{DISP\,m2}$ | | | | | | $V_{Cm2}, a_{m2}$ | |
| $V_{DISP\,mn}$ | | | | | | | $V_{Cmn}, a_{mn}$ |

P

| COMPOUND ID | | | | |
|---|---|---|---|---|
| $V_{RF1}$ | $V_{C11}, A_{11}, L_{11}$ | $V_{C12}, A_{12}, L_{12}$ | ⋯⋯ | $V_{C1n}, A_{1n}, L_{1n}$ |
| $V_{RF2}$ | $V_{C21}, A_{21}, L_{21}$ | $V_{C22}, A_{22}, L_{22}$ | ⋯⋯ | $V_{C2n}, A_{2n}, L_{2n}$ |
| ⋮ | ⋮ | ⋮ | | ⋮ |
| $V_{RFm}$ | $V_{Cm1}, A_{m1}, L_{m1}$ | $V_{Cm2}, A_{m2}, L_{m2}$ | ⋯⋯ | $V_{Cmn}, A_{mn}, L_{mn}$ |
| $V_{FRAG}$ | | | | |

$L = \{\text{monomer, cluster, RIP}\}$

Figure 40E

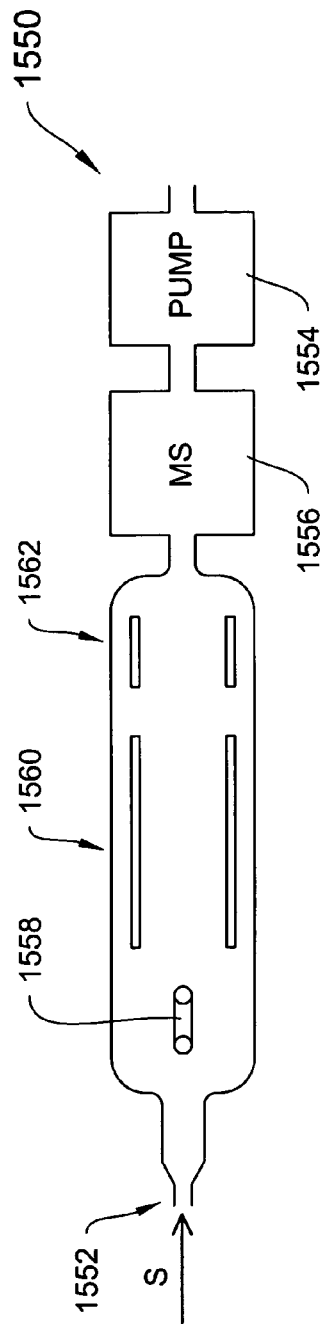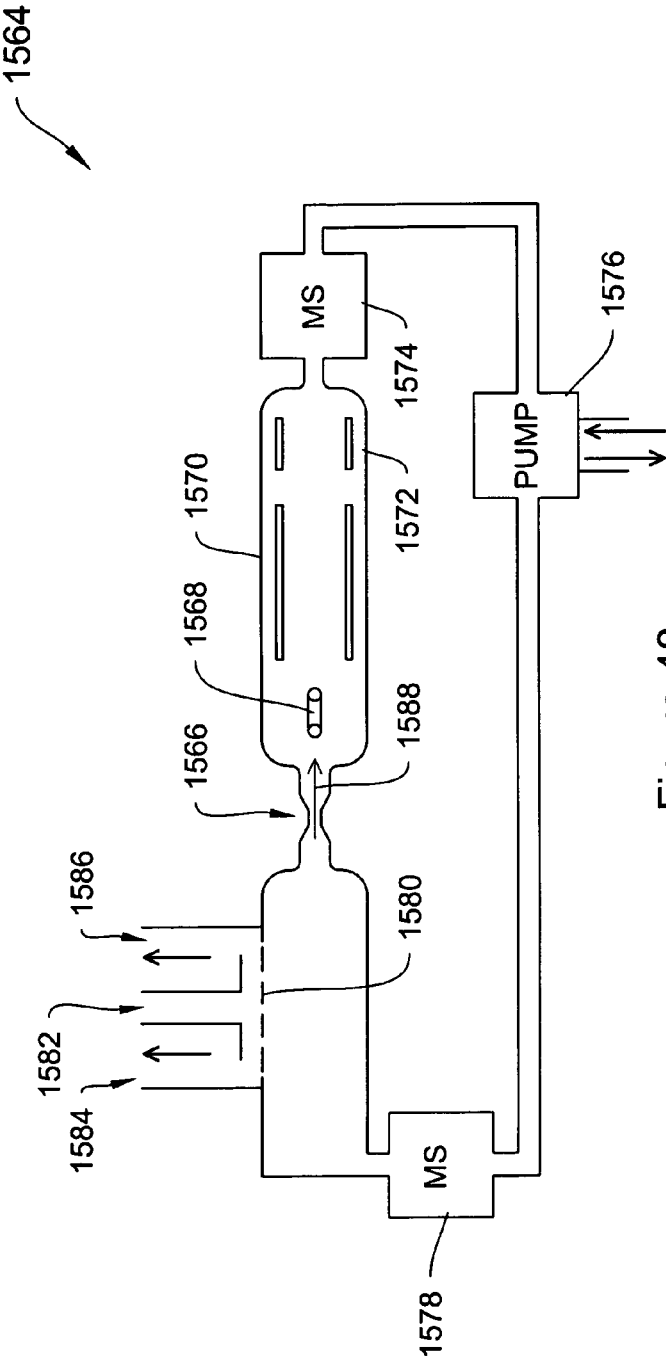
Figure 47
Figure 48

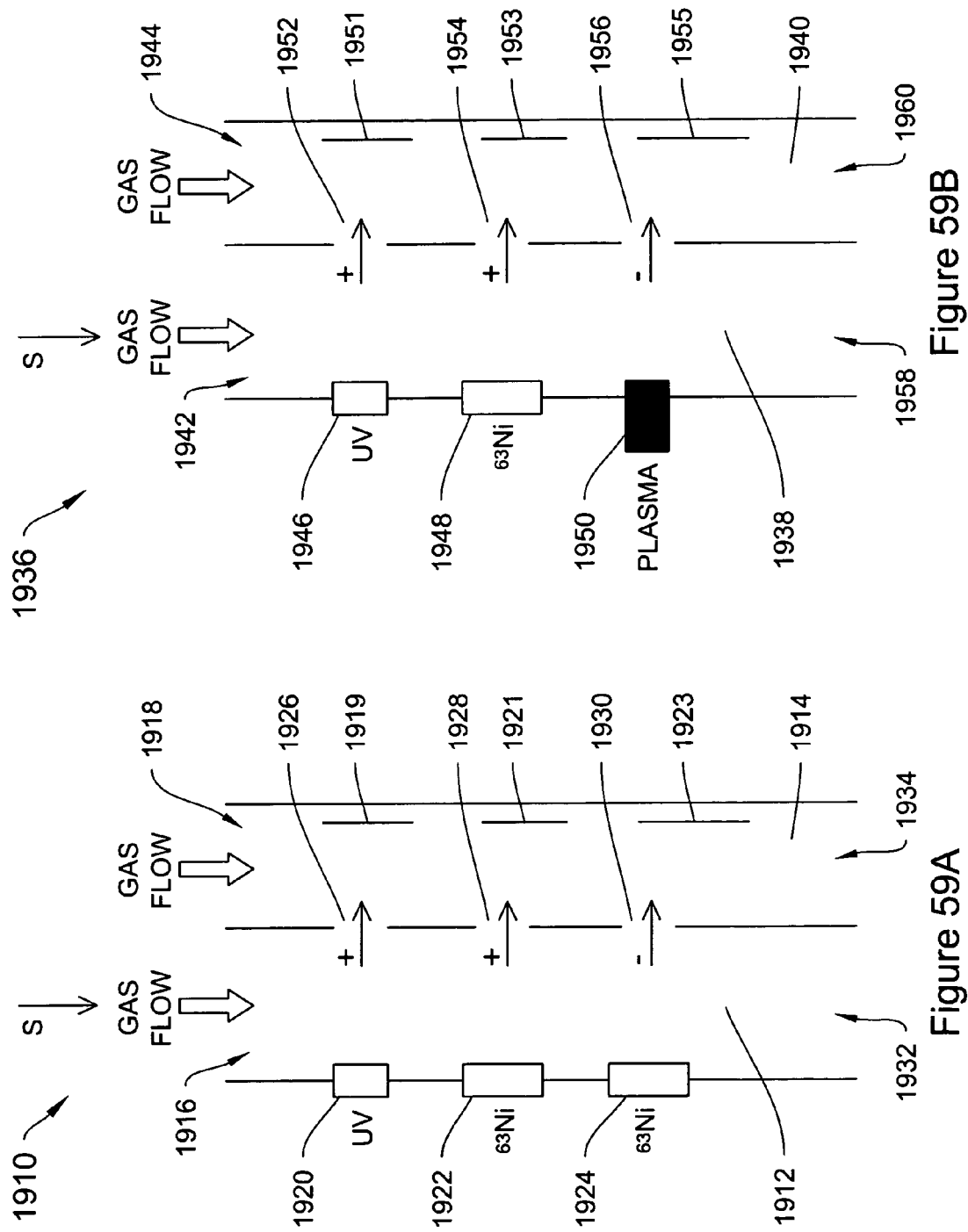

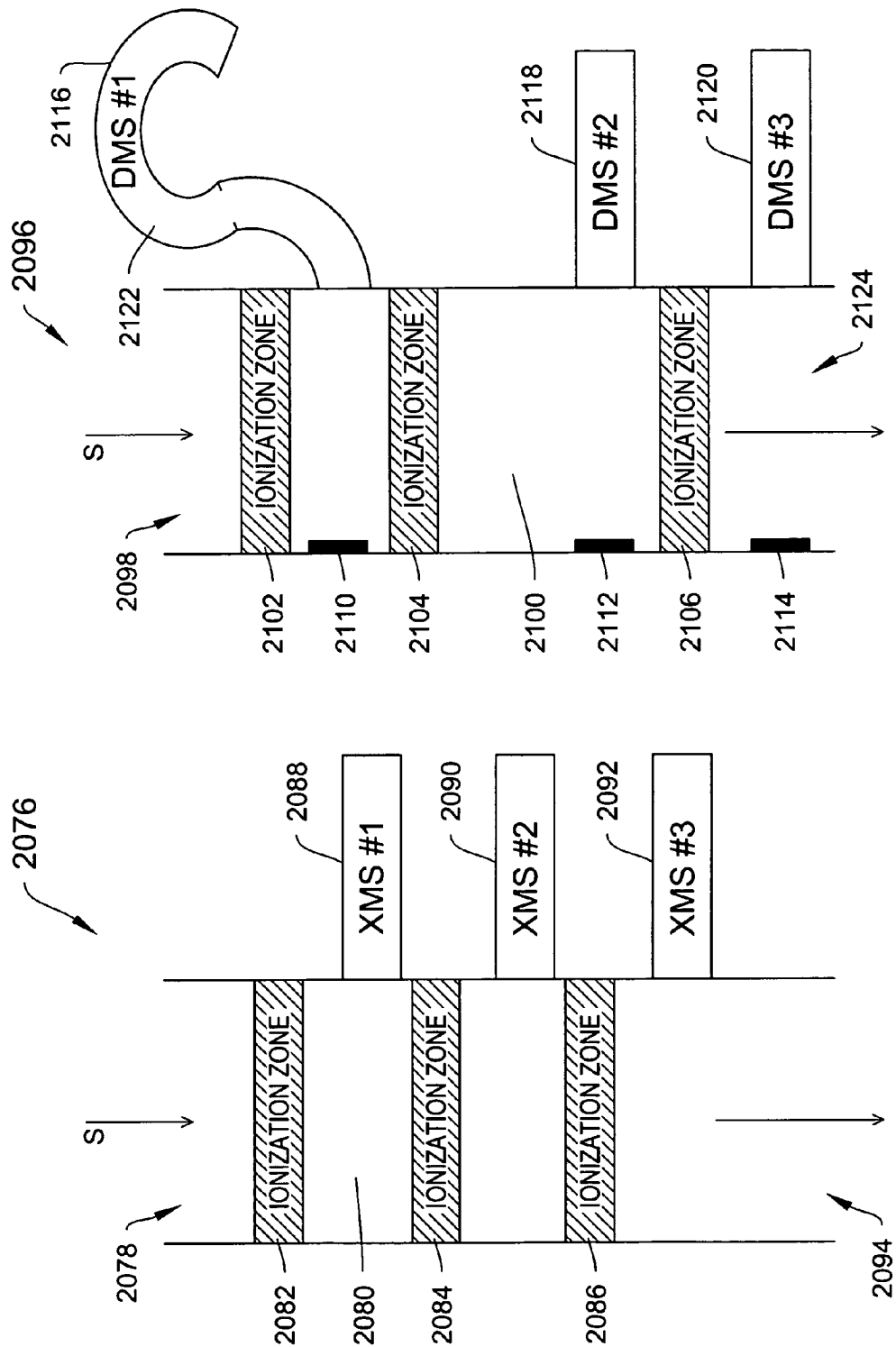

METHODS AND APPARATUS FOR ENHANCED ION BASED SAMPLE DETECTION USING SELECTIVE PRE-SEPARATION AND AMPLIFICATION

REFERENCE TO RELATED APPLICATIONS

This application claims the benefit of and priority to: U.S. Provisional Application No. 60/531,480, filed on Dec. 18, 2003, entitled "Pre-Separation for Matrix Compounds for Analysis, Filtering, or Detection"; U.S. Provisional Application No. 60/533,676, filed on Dec. 31, 2003, entitled "Pre-Separation for Matrix Compounds for Analysis, Filtering, or Detection"; and U.S. Provisional Application No. 60/556,414, filed on Mar. 25, 2004, entitled "Chemical Amplification System for DMS." The entire teachings of the above referenced applications are incorporated herein by reference.

This application also incorporates by reference the entire contents of the following co-pending U.S. patent applications: U.S. Ser. No. 10/187,464, filed on 28 Jun. 2002; U.S. Ser. No. 10/215,251, filed on 7 Aug. 2002; U.S. Ser. No. 10/462,206, filed on 13 Jun. 2003; U.S. Ser. No. 10/684,332, filed on 10 Oct. 2003; U.S. Ser. No. 10/734,499, filed on 12 Dec. 2003; U.S. Ser. No. 10/738,967, filed on 17 Dec. 2003; U.S. Ser. No. 10/797,466, filed on 10 Mar. 2004; U.S. Ser. No. 10/821,812, filed on 8 Apr. 2004; U.S. Ser. No. 10/824,674, filed on 14 Apr. 2004; U.S. Ser. No. 10/836,432, filed on 30 Apr. 2004; U.S. Ser. No. 10/840,829, filed on 7 May 2004; U.S. Ser. No. 10/866,645, filed on 10 Jun. 2004; U.S. Ser. No. 10/887,016, filed on 8 Jul. 2004; U.S. Ser. No. 10/894,861, filed on 19 Jul. 2004; U.S. Ser. No. 10/903,497, filed on 30 Jul. 2004; U.S. Ser. No. 10/916,249, filed on 10 Aug. 2004; U.S. Ser. No. 10/932,986, filed on 2 Sep. 2004; U.S. Ser. No. 10/943,523, filed on 17 Sep. 2004; U.S. Ser. No. 10/981,001, filed on 4 Nov. 2004; and U.S. Ser. No. 10/998,344, filed 24 Nov. 2004.

FIELD OF THE INVENTION

The invention relates generally to mobility-based systems, methods and devices for analyzing samples. More particularly, in various embodiments, the invention relates to improving the detection capability of ion mobility based systems using pre-separation and amplification of selected ion species of a sample.

BACKGROUND

There are a number of different circumstances in which it is desirable to perform analysis to identify compounds in a sample. Such samples may be taken directly from the environment or they may be provided by front end specialized devices to separate or prepare compounds before analysis. There exists, a demand for low cost, compact, low-power, accurate, easy to use, and reliable devices capable of detecting compounds in a sample.

One class of known analyzers are mass spectrometers (MS). Mass spectrometers are generally recognized as being the most accurate type of analyzers for compound identification. However, mass spectrometers are quite expensive, easily exceeding a cost of $100,000 or more and are physically large enough to become difficult to deploy everywhere the public might be exposed to dangerous chemicals. Mass spectrometers also suffer from other shortcomings such as the need to operate at relatively low pressures, resulting in complex support systems. They also need a highly trained operator to tend to and interpret the results. Accordingly, mass spectrometers are generally difficult to use outside of laboratories.

A class of chemical analysis instruments more suitable for field operation is known as Field Asymmetric Ion Mobility Spectrometers (FAIMS) or Differential Mobility Spectrometers (DMS), and also known as Radio Frequency Ion Mobility Spectrometers (RFIMS) among other names. Hereinafter, FAIMS, DMS, and RFIMS, are referred to collectively as DMS. This type of spectrometer subjects an ionized fluid (e.g., gas, liquid or vaper) sample to a varying high-low asymmetric electric field and filters ions based on their field mobility.

The sample flows through a filter field which allows selected ion species to pass through, according to a compensation voltage (Vcomp) applied to filter electrodes, and specifically those ions that exhibit particular mobility responses to the filter field. An ion detector then collects ion intensity/abundancy data for the detected ions. The intensity data exhibits attributes, such as "peaks" at particular compensation voltages.

A typical DMS device includes a pair of electrodes in a drift tube. An asymmetric RF field is applied to the electrodes across the ion flow path. The asymmetric RF field, as shown in FIG. 1, alternates between a high or "peak" field strength and a low field strength. The field varies over a particular time period (T), frequency (f) and duty cycle (d). The field strength E varies with an applied field voltage (Vrf) and the size of the gap between the electrodes. Ions pass through the gap between the electrodes when their net transverse displacement per period of the asymmetric field is zero. In contrast, ions that undergo a net displacement eventually undergo collisional neutralization on one of the electrodes. In a given RF field, a displaced ion can be restored to the center of the gap (i.e. compensated, with no net displacement for that ion) by superimposing a low strength direct current (dc) electric field (e.g., by applying Vcomp across the filter electrodes) on the RF. Ions with differing displacement (owing to characteristic dependence of mobility in the particular field) pass through the gap at differing characteristic compensation voltages. By applying a substantially constant Vcomp, the system can be made to function as a continuous ion filter. Alternatively, scanning Vcomp obtains a spectral measurement for a sample. A recorded image of the spectral scan of the sample is sometimes referred to as a "mobility scan" or as an "ionogram."

Examples of mobility scans based on the output from a DMS device are shown in FIGS. 2A and 2B. The compounds for which scans are depicted are acetone and an isomer of xylene (o-xylene). The scan of FIG. 2A resulted from a single compound, acetone, being independently applied to the DMS analyzer. The illustrated plot is typical of the observed response of the DMS device, with an intensity of detected ions dependent on Vcomp. For example, the acetone sample exhibits a peak intensity response at a Vcomp of approximately −2 Vdc.

FIG. 2B illustrates the results when analyzing a mixture of acetone and o-xylene. The combined response shows two peaks in approximately the same region as for the independent case. The compounds in the mixture can be detected by comparing the response against a library, for example, of stored known responses for independently analyzed compounds, or libraries of mixtures. Thus, the scans for independently analyzed compounds, such as the scan of FIG. 2A for acetone, can be stored in a computer system, and when compound responses such as that in FIG. 2B are observed, the relative locations of the peaks can be compared against the stored responses in the library to determine the constitution of the compound.

A specific RF field voltage and field compensation voltage Vcomp permits only ion species having a particular ion mobility characteristic to pass through the filter to the detector. By noting the RF level and compensation voltage and the corresponding detected signal, various ion species can be identified, as well as their relative concentrations (as seen in the peak characteristics).

Consider a plot of ion mobility dependence on Vrf, as shown in FIG. 3. This figure shows ion intensity/abundancy versus RF field strength for three examples of ions, with field dependent mobility (expressed as the coefficient of high field mobility, $\alpha$) shown for species at greater, equal to and less than zero. The velocity of an ion can be measured in an electric field (E) low enough so that velocity (v) is proportional to the electrical field as v=KE, through a coefficient (K) called the coefficient of mobility. K can be shown to be related to the ion species and gas molecular interaction properties. This coefficient of mobility is considered to be a unique parameter that enables the identification of different ion species and is determined by, ion properties such as charge, size, and mass as well as the collision frequency and energy obtained by ions between collisions.

When the ratio of E/N, where N is gas density, is small, K is constant in value, but at increasing E/N values, the coefficient of mobility begins to vary. The effect of the electric field can be expressed approximately as $K(E)=K(0)[1+\alpha(E)]$, where K(0) is a low voltage coefficient of mobility, and $\alpha$ is a specific parameter showing the electric field dependence of mobility for a specific ion.

Thus, as shown in FIG. 3, at relatively low electric field strengths, for example, of less than approximately 8,000 V/cm, multiple ions may have the same mobility. However, as the electric field strengths increase, the different species diverge in their response such that their mobility varies as a function of the applied electric field. This shows that ion mobility is independent of applied RF field voltage at relatively low RF field strengths, but is field-dependent at higher RF field strengths.

FIGS. 2A and 2B demonstrate that species can have a unique behavior in high fields according to mobility characteristics. The ions passing through the filter are detected downstream. The detection signal intensity can be plotted as a characteristic detection peak for a given RF field voltage and field compensation voltage Vcomp. Peak intensity, location, and shape are typically used for species identification.

However, a problem occurs in that the peaks, as seen in the typical DMS spectra, are generally broad in width. Therefore, compounds exhibiting intensity peaks at similar compensation voltages may be difficult to separate from each other. Consequently, there may be particular conditions under which two different chemicals generate indistinguishable scans for a particular Vcomp and a particular RF field voltage, or for other combinations of filter field/flow channel parameters. In such a case, it is may not be possible to differentiate between the two different compounds. Another problem may occur when two or more chemical species have the same or almost the same ion mobility characteristic for a particular set of field/flow channel parameters. This is most likely to happen in the low electric field regime (referred to herein as Ion Mobility Spectrometry or IMS), where many existing ion mobility spectrometer systems operate. Therefore, if two or more chemical species have the same or almost the same mobility characteristic, then their spectroscopic peaks will overlap, and identification and quantification of individual species will be difficult or impossible.

FIG. 4 is a graph of Vcomp versus Vrf according to an illustrative embodiment of the invention, but also highlighting the above described prior art drawback. More particularly, FIG. 4 depicts a graph of Vcomp versus Vrf for four compounds: lutidine; cyclohexane; benzene; and dimethyl-methlphosphonate (DMMP). Each curve shows the location of detected ion intensity peaks, such as those circled at 100, at the various (Vrf, Vcomp) locations, which in total provide the peak characteristics for each particular compound. As shown, there is a region 100 in which the intensity peaks and mobility curves for DMMP and cyclohexane overlap with each other. As can be seen, operating in a Vrf region of from approximately 2,500 Vpeak to approximately 2,650 Vpeak, at a Vcomp of about −6 Vdc to about −8 Vdc, one would find it virtually impossible to discriminate between the two compounds based on a single Vcomp scan at a single Vrf. Specifically, in a conventional spectral scan approach that plots intensity/abundance versus Vcomp over a range of Vcomp for a single Vrf plots the overlapping peaks as a single peak.

Another drawback of conventional mobility based ion detection systems is that they are susceptible to competitive ionization, such as atmospheric pressure competitive ionization (APCI). APCI occurs when one compound is preferentially ionized over another compound. If a desired compound is not ionized into an ion species, a mobility-based detector will not identify or detect the presence of that compound. Systems have been developed that remove compounds from a sample that preferentially ionize to enable a desired compound to then be ionized and detected. For example, a gas chromatograph (GC) has been employed as a front end for a DMS to pre-separate a sample into its constituent compounds before detection. However, GCs are generally slow, and add complexity and expense to mobility-based detection systems.

Also, conventional mobility based ion detection systems are not sensitive enough to detect very small amounts of chemical or biological agents which may pose a health risk to humans.

Accordingly, there is a need for improved ion mobility based compound identification using sample ion species pre-separation and amplification.

SUMMARY OF THE INVENTION

The invention addresses the deficiencies of the prior art by providing, in various embodiments, improved mobility based systems, devices and methods for analyzing constituents in a sample. More particularly, in various embodiments, the invention provides for improved sample detection using techniques, such as ion species pre-separation and/or ion species amplification.

As discussed above, atmospheric pressure competitive ionization (APCI) may cause compounds with the highest proton affinity (PA) and/or highest electron affinity (EA) to capture preferentially or take up the charge from an ionization source. If there is a limited amount of charge available, for example, in a compact DMS system with limited power resources, the amount of available charge may not be sufficient to charge or ionize all of the molecules in a sample matrix. Thus, if only some of the molecules in a sample matrix are ionized, only that limited amount of molecules may be detected, resulting in erroneous analysis of a chemical matrix. Furthermore, certain compounds may not be ionized due to APCI, resulting in no detection of these compounds.

According to one aspect, the invention pre-separates certain ion species of a sample to reduce, and in some cases, eliminate the problem of competitive ionization within ion based mobility detection analyzers. The invention includes embodiments that eliminate or mitigate the effects of competitive ionization by separating ion species before sample detection to prevent one ion species from consuming the charge intended to be used to ionize another ion species.

According to one embodiment, neutrals, i.e., molecules of a sample that are not ionized, are mixed with a new supply of charge, e.g., reactant ions or a plasma field, to enable further APCI reactions to occur. The newly created ions may then be removed for analysis or simply discarded. This process may be repeated until a desired compound type is ionized and detected using an analyzer.

In one implementation, a sample matrix is exposed to an ionization source to cause particular compounds in the sample to be ionized, the ionized compounds to be removed, and the residual neutrals to be re-circulated. The ionization source may be, for example, an UV source, laser, plasma source, soft X-ray source, or reactant ions. Repeated interrogation of chemical compounds in a sample based on competitive ionization and the reaction of residual and/or un-reacted neutrals provides a comprehensive measure of the chemical composition of the sample, without the need for traditional GC techniques.

The process of competitive ionization and the removal of product ions may be repeated, enabling incremental isolation of product ions and neutrals. Additionally, chemical ionization may be employed to inject fresh charge using reactant ions.

According to one aspect, the invention ionizes sample molecules to cause a subset of the sample molecules to combine to form first product ions. It then separates the first product ions from a first un-ionized group of sample molecules. Next, it ionizes a subset of the first un-ionized group of sample molecules to form second product ions, and separates the second product ions from a second un-ionized group of sample molecules.

In one embodiment, the invention flows the first un-ionized group of sample molecules and the first product ions through a first field to separate the first product ions from the first un-ionized group of sample molecules. According to one implementation of this embodiment, the inventions flows the second un-ionized group of sample molecules and the second product ions through a second field to separate the second product ions from the second un-ionized group of sample molecules. In some implementations, the first and second fields are the same field. However, in other implementations, the first and second fields are different fields.

In an alternative embodiment, the invention employs a mechanical separation for separating the first product ions from the first un-ionized group of sample molecules. According to another alternative embodiment, the invention employs a chemical process for separating the first product ions from the first un-ionized group of sample molecules.

According to another embodiment, the invention, subsequent to extracting the second product ions, ionizes a subset of the second un-ionized group of sample molecules to form third product ions, and separates the third product ions from a third un-ionized group of sample molecules.

The invention employs various approaches for ionizing the sample molecules. In some instances, the invention mixes the first reactant ions with the sample molecules to form the first product ions. The invention may also mix the second reactant ions with the first un-ionized group of sample molecules to form the second product ions. According to one feature, the invention controls an effluent flow to control contact time between the first reactant ions and the sample molecules.

According to another feature, the invention injects the first reactant ions into a flow of the sample molecules to mix the sample molecules to with first reactant ions.

According to one approach, the invention exposes the sample molecules to a first ionization source to form the first product ions, and re-circulates the first un-ionized group of sample molecules to expose them to the first ion source to form the second product ions. According to an alternative approach, the invention exposes the sample molecules to a first ion source to form the first product ions, and flows the first un-ionized group of sample molecules to expose them to a second ion source to form the second product ions.

According to one embodiment, the invention flows the sample molecules along a first flow path past a first ionization source to form the first product ions and then directs the first product ions along a second flow path to separate the first product ions from the first un-ionized group of sample molecules. The invention may further flow the first un-ionized group of sample molecules past a second ionization source in the first flow path to form the second product ions and then direct the second product ions into the second flow channel to separate the second product ions from a second un-ionized group of sample molecules. The invention may further flow the second un-ionized group of sample molecules past a third ionization source in the first flow channel to form the third product ions and then direct the third product ions into the second flow channel to separate the third product ions from a third un-ionized group of sample molecules.

The invention employs various approaches to directing product ions. In some instances, the directing includes attracting the first product ions into the second flow channel. In other instances, the directing includes deflecting the first product ions into the second flow channel. The directing may also include directing the first product ions into the second flow channel via an opening in a barrier between the first and second flow channels. In certain instances, the first flow path includes a substantially cylindrical portion while the second flow channel is substantially enclosed. Alternatively, the second flow path may be substantially unenclosed.

In certain embodiments, the invention mixes the sample molecules with one or more dopants to improve separation of the first product ions from the first un-ionized group of sample molecules. The dopants may include any one or combination of methylene bromide ($CH_2Br_2$), methylene chloride ($CH_2Cl_2$), chloroform ($CHCl_3$), water ($H_2O$), methanol ($CH_3OH$), and isopropanol.

According to another aspect, the invention ionizes sample molecules to cause a subset of the sample molecules to combine to form first product ions and separates the first product ions from a first un-ionized group of sample molecules. Subsequent to separating the first product ions, the invention ionizes a subset of the first un-ionized group of sample molecules to form second product ions and separates the second product ions from a second un-ionized group of sample molecules. Then, the invention analyzes the sample based at least in part on the first and second product ions.

In one embodiment, the invention flows the first and second product ions to the first analyzer and processes the information from the first analyzer about the first and second product ions to perform an analysis of the sample. In an alternative embodiment, the invention flows the first product ions to a first analyzer, flows the second product ions to a second analyzer, and processes the information from the first and second analyzers about the first and second product ions to perform an analysis of the sample. The first and second analyzers may be in series or parallel with each other. In certain instances, the invention analyzes the sample based at least in part on at least one of the first and second groups of un-ionized sample molecules.

In another embodiment, the invention directs the first product ions from a first flow channel into an analyzer flow channel and causes a flow from the analyzer flow channel toward a first flow channel containing the first product ions and the first group of un-ionized sample molecules. The flow is directed from the analyzer to inhibit the first un-ionized groups of sample molecules from entering the analyzer flow channel.

In another embodiment, a system for pre-separating a sample includes a first ionizer for ionizing sample molecules to cause a subset of the sample molecules to combine to form first product ions and a first separator for separating the first product ions from a first un-ionized group of sample molecules. The system also includes a second ionizer for ionizing a subset of the first un-ionized group of sample molecules to form second product ions and a second separator for separating the second product ions from a second un-ionized group of sample molecules. The first and second ionizers may be the same ionizer or different ionizers. Also, the first and second separators may be the same separator or different separators.

In another embodiment, a compact DMS system includes a sample pre-separation unit for pre-separating product ions from un-ionized sample molecules, a filter unit for passing particular ones of the product ions, and a detection unit for detecting the particular ones of the product ions passed by the filter unit.

In addition to being used for analysis, the invention may be used for selectively cleaning and/or conditioning samples, e.g., for removing selected molecules from a sample stream. For example, certain semiconductor industry or other process control applications require ultra pure or clean gasses. In these processes, water molecules are considered a contaminant in a gas stream of Nitrogen or Argon. In certain embodiments of the invention, water within a gas sample may be preferentially ionized and then removed from the gas stream while purified Argon or Nitrogen are then used in a low pressure chemical vapor deposition or for another semiconductor application.

While current mobility based analyzers such as DMS, IMS, and MS systems are sensitive, there is a need to detect concentrations in ranges lower than parts-per-trillion (ppt). For instance, a very small number of anthrax spores may cause significant health effects. However, existing analyzers may not be sensitive enough to detect the charge generated by such a small number of spores. One technique for overcoming this limitation involves concentrating and/or amplifying the number of molecules of a sample, in time, to enable an analyzer to produce a larger signal for detection.

In embodiment, the invention ionizes the molecules of a sample and then filters the ionized sample to pass particular ion species of a sample constituent to a detector. The invention mixes the constituent from the detector with additional molecules of the sample and then ionizes the mixture of the constituent and the additional molecules of the sample. The invention then filters the ionized mixture to pass a concentration of the particular ion species of the constituent to the detector. The preceding steps of mixing, ionizing, and filtering may be repeated until a desired concentration of the particular ion species of the constituent is achieved and detected.

In other embodiments, the invention provides improved sample collection, filtration, detection, measurement, identification and/or analysis (collectively "analysis") using, for example: dispersion characteristics; sample fragmentation; and/or sample processing variations, such as and without limitation, variations in flow channel/filter field conditions. Such conditions may include, any spectral changes, including, without limitation changes in: pressure; temperature; humidity; field strength, duty cycle, and/or frequency; field voltage amplitude, frequency and/or duty cycle; detector bias voltage magnitude and/or polarity; and/or filter field compensation voltage magnitude and/or polarity.

In one practice, the invention employs one or more of the above to provide a library of spectral signatures for a plurality of known species, and identifies unknown species by comparing at least a portion of a spectral signature for the unknown species to at least a portion of one or more of the spectral signatures stored in the library. The spectral signature is a compilation of spectral information for a particular species. The spectral information may include, without limitation, spectral peak amplitude; spectral peak width; spectral peak slope; spectral peak spacing; spectral peak quantity; relative shifts in spectral peaks due, for example, to changes in processing conditions; spectral discontinuities; Vrf versus Vcomp characteristics or any other characteristics of any of the above described conditions plotted against any one or more other above described conditions.

According to one aspect, the invention provides improved ion-based systems, methods and devices for analyzing samples by varying a first sample processing condition over a first plurality of values, and one or more second sample processing conditions over a second plurality of values to determine spectral information for a sample. In one particular embodiment, the invention scans a field compensation voltage Vcomp over a range of values for one or more Vrf values to generate a spectral representation at each of the one or more Vrf values.

According to one feature, the invention adjusts a third sample processing condition to narrow the widths of the resulting spectral peaks of the determined ion spectral information. Such width reduction reduces spectral peak overlap for samples having similar mobility characteristics, improves resolution of an ion mobility-based analyzer, and thus, provides more accurate discrimination between sample species. In one configuration, the third sample processing condition includes pressure in a sample flow channel, and the invention reduces the pressure in the sample flow channel to decrease the width of the spectral peaks.

According to another feature, the invention adjusts a third sample processing condition to change a location of the resulting spectral peaks of the determined ion spectral information, relative to a Vcomp at which they occur. Since peaks of differing species may shift differently, such shifts can provide improved discrimination between peaks of species having similar mobility characteristics. In one configuration, the third sample processing condition includes Vrf, and the invention applies more than two field voltages Vrf to provide peak shifting information for species identification.

According to another feature, the invention adjusts a third sample processing condition to provide spectral information regarding both positive and negative ions of the sample. More particularly, in one configuration, the invention provides both negative and a positive bias voltages to multiple detector electrodes concurrently or to a single detector electrode alternatively to provide both negative and positive mode scans. Since compounds that have similar ion mobility characteristics relative to one mode may have differing ion mobility characteristics relative to the other mode, adjusting the polarity of a bias voltage to detector electrodes can further improve sample analysis.

In a further embodiment, the invention employs various n-dimensional representations of ion spectral information, to enhance the quality of spectral signatures, improve differentiation between species having similar ion mobility characteristics, and thus, improve identification accuracy, specifically, and sample analysis, generally. By way of example, in one configuration, the invention scans Vcomp for >2 field voltages Vrf, to capture additionally, for example, spectral peak shift information. The invention then generates an n-dimensional representation of the spectral information that aggregates the spectral information captured by scanning Vcomp at each Vrf. In one example, the n-dimensional representation is a two-dimensional plot of Vrf versus Vcomp aggregating the spectral information captured by scanning Vcomp at each of the >Vrf field voltages. In a further example, the aggregated representation is a three-dimensional representation aggregating the spectral information captured from scanning Vcomp at the >2 Vrf field voltages.

According to one approach, the three-dimensional representation is a plot of ion intensity as a function of Vrf and Vcomp. According to one implementation, Vcomp and Vrf are represented in special coordinates, such as x- and y-coordinates, and variations in ion intensity at the (Vcomp,Vrf) coordinates is represented in variations of any color-related feature, including without limitation, variations in gray scale, color saturation, or color at those coordinates. Such color-related representations provide easily recognized distinctions between species that were difficult or impossible to distinguish between, without the n-dimensional aggregation of the invention.

In a related implementation, a curve circumscribing the color-related differences may be generated and the color-related differences themselves may be discarded. In this way, the invention can provide a two-dimensional representation of the spectral peaks, for example, on a Vcomp versus Vrf grid, while still incorporating the spectral information captured by scanning Vcomp over a plurality of Vrf values. In another alternative implementation, Vcomp, Vrf, and ion intensity are mapped into a three-dimensional (x,y,z) spatial representation.

According to a related embodiment, any or all of the spectral information may be represented in n-dimensional space as a function of any or all of the processing variations to create >3 dimensional spectral signatures for both known and unknown species. Conventional n-dimensional cluster matching techniques may then be employed for identifying the unknown species.

In any of the above described n-dimensional representations, any or all of the spectral information represented may be incorporated into the spectral signatures for known species and stored in the library of such signatures. Conventional pattern recognition techniques may be employed to correspond at least portions of the spectral signatures from unknown species with at least portions of the signatures from known samples stored in the library to identify the unknown species. In other implementations, both the library of signatures and the captured signatures from the unknown species are represented as mathematical descriptions, and any suitable approach for making comparisons between such mathematical descriptions may be employed to identify the unknown species.

According to another embodiment, the invention employs fragmentation to improve DMS analysis. Fragmentation includes breaking large molecules of samples into smaller molecules, molecule clusters, components, and/or base elements. The fragments may then be individually analyzed, in series and/or in parallel to generate more spectral information for the sample than would be otherwise available without fragmentation. Fragmentation may be achieved, for example and without limitation, by using any one or a combination of a chemical reaction, a high energy field strength, high Vrf, heating, laser light, colliding the sample molecules with other molecules, soft x-ray, electromagnetic waves, or the like. According to one feature, the invention incorporates any or all of the above described spectral information for the fragment spectral peaks into the spectral signature. According to a further feature, the invention incorporates the point (e.g. the temperature, pressure, field strength, Vrf, colliding molecule mass, colliding molecule velocity, laser intensity, laser frequency, x-ray intensity etc.) into the spectral signature.

According to other aspects, the invention provides various serial and parallel combinations of ion-based analyzers employing features, including those summarized above. In additional aspects, the invention provides various compact, handheld, lightweight and low power based analyzers, for example, for detecting chemical warfare agents (CWAs), Toxic Industrial Compounds (TICs), and/or Toxic Industrial Materials (TIMs).

The invention will now be described with reference to various illustrative embodiments.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing and other objects, features, advantages, and illustrative embodiments of the invention will now be described with references to the following drawings in which like reference designations refer to the same parts throughout the different views. These drawings are not necessarily drawn to scale, emphasis instead being placed upon illustrating principles of the invention.

FIG. 15A is a three-dimensional color dispersion plot illustrating detection of methyl salicylate over a range of field voltages and field compensation voltages with varying ion intensity represented in varying color according to an illustrative embodiment of the invention.

FIG. 15B is a two-dimensional graph of ion intensity versus field compensation voltage for methyl salicylate at a single field voltage.

FIG. 16A is a three-dimensional color dispersion plot illustrating detection of DMMP over a range of field voltages and field compensation voltages with varying ion intensity represented in varying color according to an illustrative embodiment of the invention.

FIG. 16B is a two-dimensional graph of ion intensity versus field compensation voltage for DMMP at a single field voltage.

FIG. 17 is a three-dimensional color dispersion plot illustrating detection of DIMP over a range of field voltages and field compensation voltage with varying ion intensity represented in varying color according to an illustrative embodiment of the invention.

FIG. 18 is a two-dimensional graph of ion intensity versus field compensation voltage for DIMP at a single field voltage.

FIGS. 26A-26H are two-dimensional graphs of ion intensity versus field compensation voltage at particular field voltages, the two-dimensional graphs being of the type combinable into the three-dimensional color dispersion plot of FIG. 25, according to an illustrative embodiment of the invention.

FIGS. 28A and 28B are graphs of ion intensity versus pressure showing a quantifiable effect on positive and negative background spectra, respectively, caused by a decrease in pressure according to an illustrative embodiment of the invention.

FIGS. 29A and 29B are graphs of ion intensity at a plurality of pressures versus field compensation voltage showing the effect of varying pressure on negative and positive tert-butylmercaptan or tert-butylithiol (TBM) spectra, respectively, according to an illustrative embodiment of the invention.

FIGS. 32A-32D are graphs of ion intensity versus field compensation voltage showing improved detection resolution for agent GF at reduced pressures according to an illustrative embodiment of the invention.

FIGS. 37 and 38 are tables, each including a collection of detection data for a group of monomer and dimers (clusters) of eight ketones respectively, that were used to generate the curves in the graphs of FIGS. 36A and 36B.

FIGS. 39A and 39B are graphs of a ratio of field strength to gas density (E/N) versus field compensation voltage that illustrate the results of calculating normalized alpha parameter curves.

FIG. 40E shows a diagram of a more complex data structure.

FIGS. 47-53 are conceptual block diagrams respectively of chemical and/or biological agent detection systems using various configurations of a DMS analyzer system, recirculation system, and other components according to an illustrative embodiment of the invention.

FIG. 59A is a conceptual diagram of a sample pre-separation system including two flow channels and multiple (and optionally different) ionization sources for selective ion separation from a sample matrix according to an illustrative embodiment of the invention.

FIG. 59B is a conceptual diagram of a sample pre-separation system having two flow channels and multiple (and optionally different) ionization sources for selective ion separation from a sample matrix where at least one of the ionization sources is a plasma ionization source.

FIG. 65 is a conceptual diagram of a sample pre-separation and analysis system using multiple ionization zones and multiple analyzers to analyze various ions of a sample matrix according to an illustrative embodiment of the invention.

FIG. 66 is a conceptual diagram of a sample pre-separation and analysis system using multiple ionization zones and DMS analyzers, including a DMS with a drift tube and ion filter region arbitrarily curved, according to an illustrative embodiment of the invention.

DESCRIPTION OF ILLUSTRATIVE EMBODIMENTS

As described above in summary, the invention is generally directed to systems, methods and devices for providing improved detection, measurement, discrimination and analysis (collectively "analysis") of compounds. The compounds analyzed may include any compound, both organic and inorganic, without limitation elements, chemicals, and biologicals. In particular illustrative embodiments, the invention is directed to improved ion mobility-based compound analysis. Particular features of the invention include, use of dispersion plots, sample fragmentation and/or pressure controls to improve discrimination between compounds having similar or overlapping ion mobility characteristics.

Although the illustrative embodiments of the invention are described in terms of Field Asymmetric Ion Mobility Spectrometers (FAIMS), also known as Differential Mobility Spectrometers (DMS), or Radio Frequency Ion Mobility Spectrometers (RFIMS) among other names (collectively DMS), the features of the invention may be similarly employed in combination with ion mobility spectrometry (IMS), time of flight (TOF) IMS, gas chromatography (GC), Fourier transform infrared (FTIR) spectroscopy, mass spectrometry (MS), and liquid chromatography mass spectrometry (LCMS).

Figure 5:
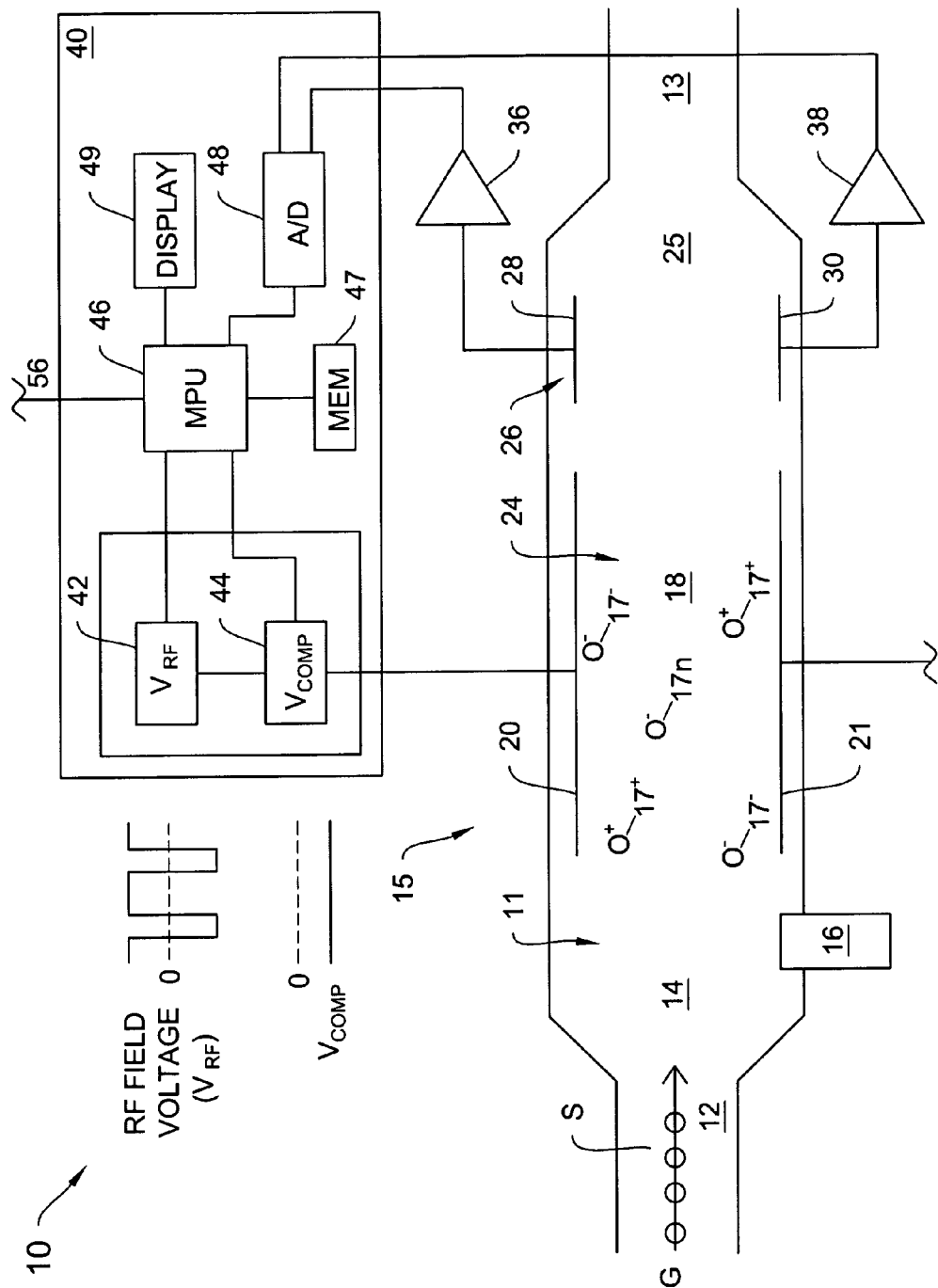
FIG. 5 is a conceptual diagram of a DMS according to an illustrative embodiment of the invention.

FIG. 5 is a block diagram of a DMS system 10 of the type that may employ the invention. The system 10 includes a flow section 15 and a processor section 40. The flow section 15 includes a flow channel 11 extending from a flow inlet 12 to a flow outlet 13. Opposing filter electrodes 20 and 21 are located within the flow channel 11. Detector electrodes 26 and 30 are also located within the flow channel 11. The processor section 40 includes an RF voltage generator 42 for providing an RF field voltage to the filter electrodes 20 and 21, and direct current (dc) voltage generator 44 for providing a dc compensation voltage Vcomp to the filter electrodes 20 and 21. The processor section 40 also includes a processor 46 for controlling the voltage generators 42 and 44, and for processing inputs from the ion detectors 28 and 30 by way of the amplifiers 36 and 38 the A/D converter 48. The processor section 40 also provides a display 49 for providing analysis information to a user. One feature of the system 10 is that it may be contained in a hand held unit weighing less than about one pound.

In operation, a sample S enters the flow channel 11 at the flow channel inlet 12. The sample S may, for example, be drawn in from the environment or received from a front end device, such as another DMS, an IMS, TOFIMS, GC, FTIR, MS, or LCMS. The sample S may be mixed with an effluent, such as a gas, liquid or vapor. In the instant example, a carrier gas CG is employed to flow the sample S through the flow channel 11. Upon entering the flow channel 11, the sample S flows into an ionization region 14. The sample is ionized by an ionization source 16 as it flows through the ionization region 14, creating a set of ionized molecules 17+, 17−, with some neutral molecules 17n, of various chemical species in the sample S. This may include, for example, monomer ions and cluster ions. Such clusters may be created when a monomer combines with water molecules or other background molecules, and the combination is ionized.

The carrier gas CG then carries the ionized sample S into the ion filter field 18 located between the opposing filter electrodes 20 and 21 of the ion filter 24. Filtering proceeds based on differences in mobility in the filter field 18 of the various ions included in the sample S. Ion mobility is influenced, for example, by ion size, shape, mass and charge. The field generator 42 applies an asymmetric field voltage Vrf across the filter electrodes 20 and 21 to cause the field strength within the filter field 18 to alternate between high and low field strengths. The ions 17+, 17− and 17n move in response to the field, based on their mobility characteristics. Typically, an ion's mobility in the high field strength condition differs from its mobility in the low field strength condition. This mobility difference produces a net transverse displacement of the ions as they travel longitudinally through the filter 24. The transverse displacement defines an ion trajectory for each of the sample S ions.

As described above, the voltage generator 44, under the control of the processor 46, applies a dc compensation voltage Vcomp across the electrodes 20 and 21. The compensation voltage Vcomp causes particular ion species to be returned toward the center of the flow path 14, and thus enables them to exit the filter field 18, without colliding with either of the filter electrodes 20 or 21 and without being neutralized. Other species, for which the applied Vcomp is not sufficient ultimately collide with the filter electrodes 20 and 21 and are neutralized. The neutralized ions are purged, for example, by the carrier gas CG, or by heating the flow path 11.

The illustrative system 10 of FIG. 5 also can discriminate between ions based on differences in polarity, as is the case with the ions 17− and 17+. According to one feature, the system 10 of FIG. 5 can be operated to concurrently, or in some instances, substantially simultaneously detect both positive and negative ions in the sample S. This feature enables identification of two compounds concurrently, or in some instances, substantially simultaneously. This feature also enables concurrent or substantially simultaneous detection of two modes of a single compound.

In operation, the two species of ions 17+ and 17−, enter the detection region 25, where further separation occurs followed by their intensity determination. In an illustrative embodiment, the electrode 28 of the detector 26 may be positively biased to attract the ions 17− and repel the ions 17+. Alternatively, the electrode 30 of the detector 26 may be biased negatively to attract the ions 17+ while repelling the ions 17−. The signals generated by the ions collecting at the detector electrodes 28 and 30 are amplified by respective amplifiers 36 and 38 and provided to the processor 46 by way of the A/D converter 48. According to one feature, the processor 46 compares the digitized signals from the A/D converter 48, with a library of ion intensity curves for known compounds stored in the memory 47, to identify compounds in the sample S. The results of the comparison operation can then be provided to an appropriate output device, such as the display 49, or may be provided to an external destination by way of an interface 56.

According to a further illustrative embodiment, the system 10 is calibrated prior to employing it for analyzing a sample. More particularly, the library of ion intensity curves for known species of ions at particular Vcomp and Vrf settings is created and stored in the memory 47. According to one feature, once the system 100 is calibrated, it may be used continuously, without need for further calibration. However, it is also within the scope of the invention to calibrate the system 10 using the reactant ion peak (RIP) or a dopant peak, for example.

According to various illustrative embodiments, field strength within the filter field 18 resulting from an applied field voltage Vrf may have values ranging from about 1,000 V/cm to about 30,000 V/cm, or higher. The frequency of Vrf may have values ranging from about 1 to about 20 megahertz (MHz), with the higher frequencies having an approximately 30 percent duty cycle.

It should be noted that the system 10 may be tuned by employing any suitable operating values of, for example, Vrf, Vcomp, field strength, Vrf duty cycle, Vrf wavelength and Vrf frequency. Additionally, as described in further detail below, to improve analysis, the system 10 may be tuned by varying values of other flow channel conditions, such as and without limitation, temperature, pressure, humidity, flow rate, doping and carrier gas CG composition. As also described below in more detail, multiple scans of the sample S taken, for example, by recirculating the sample S and/or processing the sample in parallel and/or in series with one or more additional DMS, IMS, TOFIMS, GC, FTIR, MS, or LCMS, at differing flow channel and/or filter field conditions may be employed to improve analysis of the sample S.

According to one illustrative embodiment, the processor 46 causes the voltage generator 44 to scan or sweep a range of field compensation voltages Vcomp for a particular RF field strength as controlled by the applied Vrf to obtain a first spectrum for the sample S. Then, Vrf is set to a different level and the Vcomp is once again scanned to establish a second spectrum for the sample S. This information can be compared to a library of spectral scans in a similar fashion as that described above to identify a compound in a sample.

If a particular combination of peaks in a spectral scan is known to indicate the presence of a particular compound, data representing the multiple peaks can be stored and future detection data can be compared against this stored data. For example, under controlled filter field conditions, such as at a raised field strength, a clustered compound may become declustered. The detection results in a signature of peaks that can be used to identify the source compound being detected even as detected in a single scan.

According to one illustrative application, the invention is used for detecting sulfur-containing compounds in a hydrocarbon background. In one example, negative and positive ions are separately detected. The detected data enables a quantitative measurement of concentration of these sulfur-containing compounds, independent of the hydrocarbon background.

In another illustrative application, the invention is used for detecting trace amounts (parts per million (ppm), parts per billion (ppb), or parts per trillion (ppt)) of mercaptan in varying and even high hydrocarbon backgrounds. The system 10 of FIG. 5 is also able to characterize hydrocarbon gas backgrounds. For example, the invention is capable of detecting mercaptans, such as ethyl mercaptan in a methane background, and is also capable of detecting a gas, such as methane, in a mercaptan background.

In this practice of the invention, where mercaptans were detected in hydrocarbon background, the asymmetric voltage applied to the ion filter electrodes ranged from about 900 to about 1.5 kV (high field condition), and a low voltage of about −400 to about −500 V (low field condition). The frequency ranged from about 1 to about 2 MHz, and the high frequency had an approximate 30% duty cycle, although other operating ranges may be employed. In one embodiment, the detector electrodes were biased at +5v and −5v. With this arrangement, the mercaptans can be detected by the negative mode (−5v) detector and the hydrocarbon gases can be detected by the positive mode (+5v) detector.

The system 10 employs various conventional components. By way of example, the amplifiers 36 and 38 may be Analog Devices model 459 amplifiers. Additionally, the A/D converter may be included on a National Instruments circuit component (model 6024E) for digitizing and storing the scans, and may include software for displaying the results as spectra, topographic plots, dispersion plots or graphs of ion intensity versus time. Alternatively, such software may be stored in the memory 47 and may control the processor 46. The ionization source may be, for example, a plasma, laser, radioactive, UV lamp, or any other suitable ionization source.

According to one illustrative embodiment, Vrf is applied across the filter electrodes 20 and 21. However in some configurations, Vrf is applied to one filter electrode, e.g., electrode 20, and the other electrode, e.g., electrode 22, is tied to ground. Vcomp is then applied to one of the filter electrodes 20 and 21, or alternatively, across the filter electrodes 20 and 21, according to the ions species to be passed. According to another feature, the detector electrodes 28 and 30 are biased with a floating bias, such as with the electrode 28 being biased at −5 Vdc and the electrode 30 being biased at +5 Vdc, leads to good performance for detection of mercaptans in hydrocarbon or air backgrounds.

Figure 6:
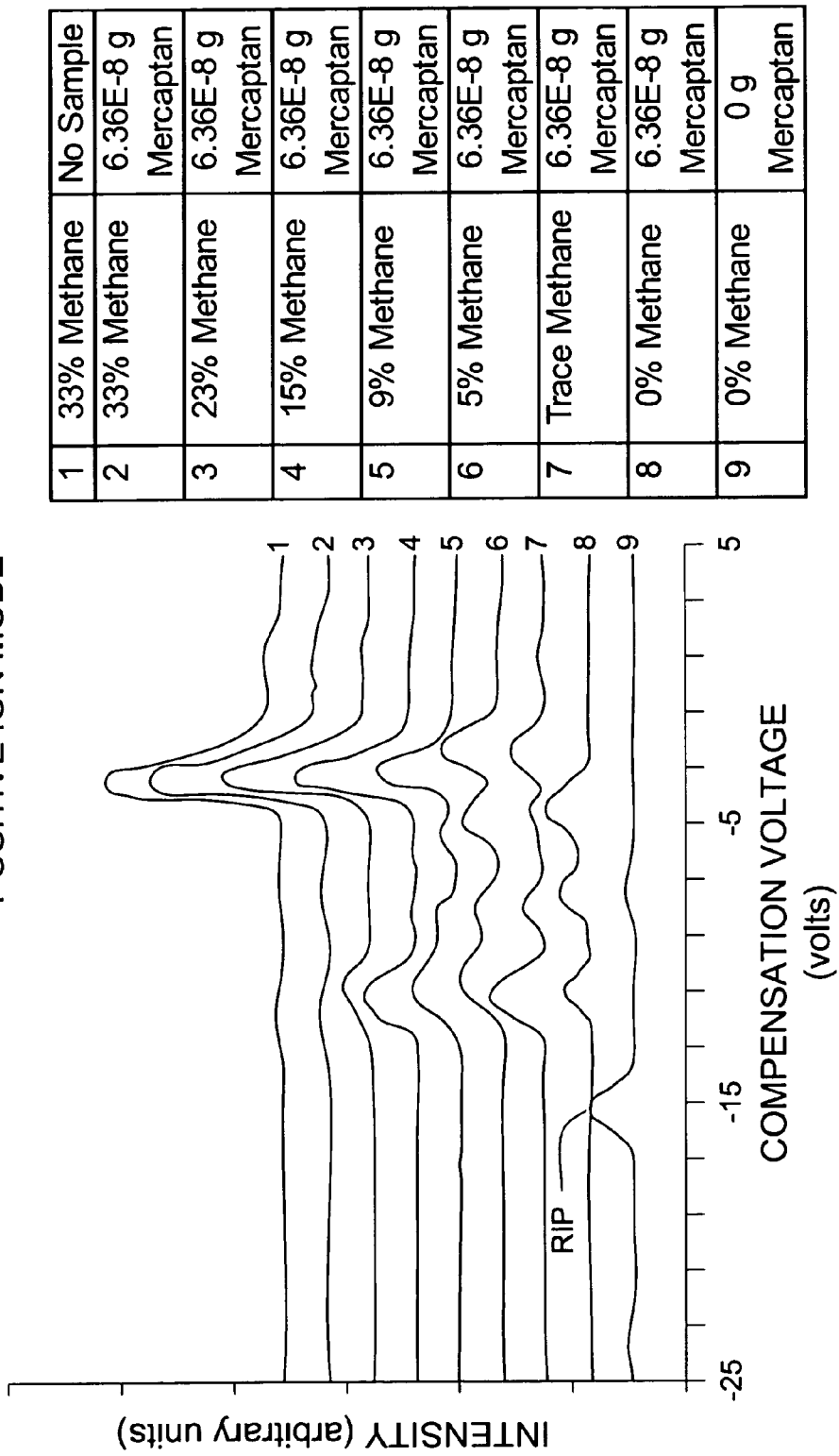
FIG. 6 is a graph of ion intensity versus field compensation voltage for positive mode spectra for a sample containing various amounts of ethyl mercaptan as measured in a DMS.
Figure 7:
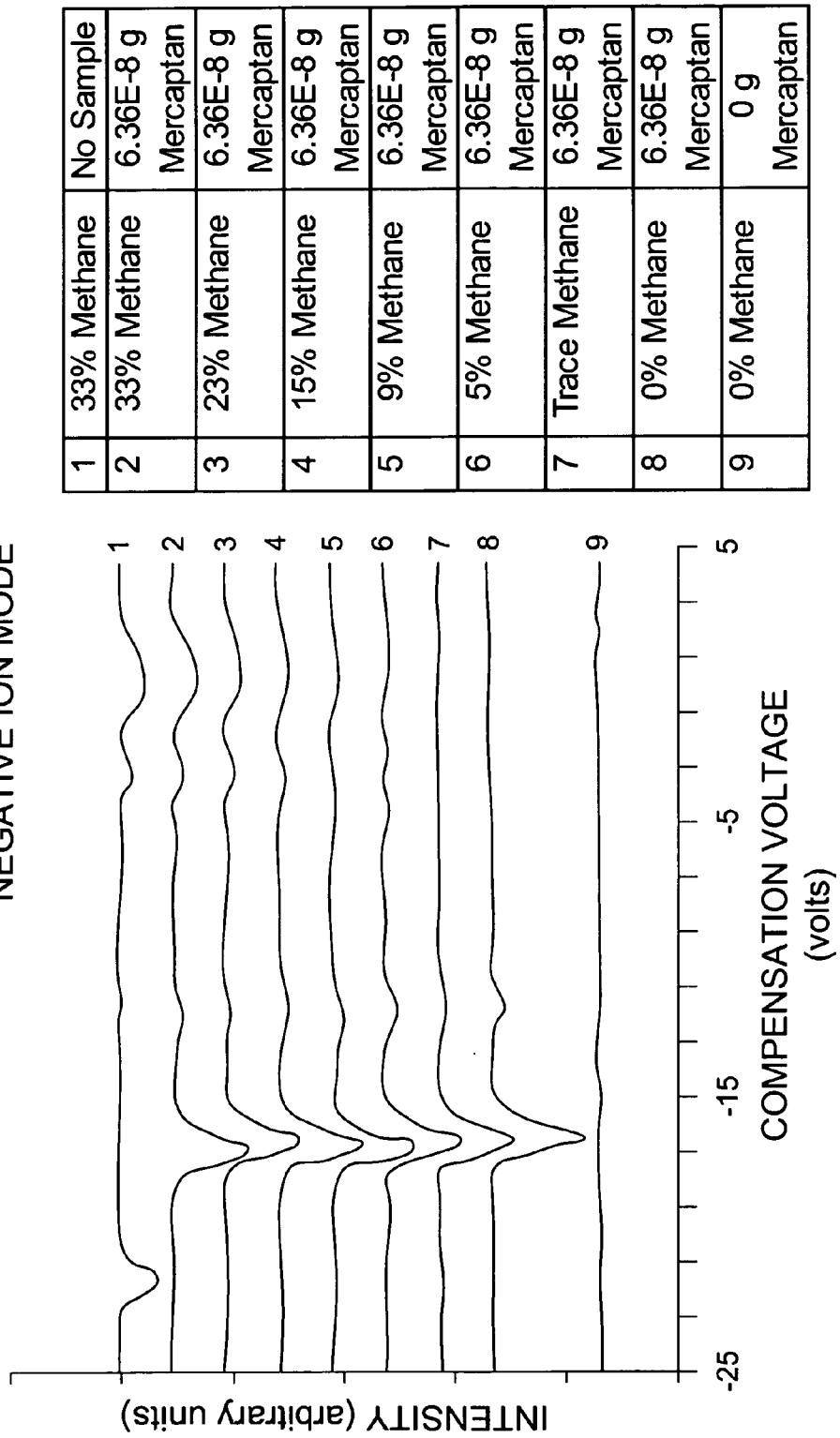
FIG. 7 is a graph of ion intensity versus compensation voltage for negative mode spectra of a sample containing various amounts of ethyl mercaptan.

FIG. 6 is a graph of ion intensity versus field compensation voltage for "positive mode" spectra for a sample containing varying amounts of ethyl mercaptan as measured in a DMS system of the type depicted at 10 in FIG. 5. For positive mode detection, the detector electrode 28 is negatively biased and attracts positive methane ions 17m+ for detection. FIG. 7 is a graph of ion intensity versus compensation voltage for "negative mode" spectra of a sample containing various amounts of ethyl mercaptan. For negative mode detection, the detector electrode 30 is positively biased and attracts the negative mercaptan ions 17m− for detection. As can by seen from FIGS. 6 and 7, the mercaptan signatures are captured independent of the air-hydrocarbon carrier gas CG background, at various dosage levels and the detected sample peaks are fully isolated from the background. As can be seen in FIG. 6, the reactant ion peak (RIP) is isolated; and as shown in FIG. 7, the background (sample #9) is flat.

As mentioned above, the detector electrodes 28 and 30 can be oppositely biased to enable concurrent, or in some configurations, substantially simultaneous detection of both positive and negative ions. Even in a sample such as mercaptan, which when ionized may have predominantly negative ions, detecting both positive and negative ions provides improved analysis accuracy over a single mode detection approach. This, in turn, improves identification accuracy and confidence, and reduces the likelihood of false positives and false negatives.

For example, Sulfur hexafluoride (SF6) can be well detected in the negative mode. However, the response in the positive mode, while alone not definitive, has a profile, and thus in combination with the negative mode, is confirmative and provides a lower likelihood of a false detection. According to one feature, the invention can detect SF6 in single mode (e.g., only negative mode detection) or dual mode (both negative and positive mode detection), seriatim, concurrently, or simultaneously.

SF6 gas is used in atmospheric tracer applications to monitor air flow, as a tracer for leak detection in pipes to point detect sources of leaks, in power plants to isolate switches to reduce, or prevent breakdown of the switches, among other uses. Isolation and detection of SF6 is often found to be a difficult proposition.

According to one illustrative application, a system of the invention is employed to detect SF6 in air. According to a further illustrative embodiment, the invention provides a portable, battery powered unit for the detection of SF6 with a sensitivity of about $1 \times 10^{-9}$ atm cc/sec SF6 (0.01 PPM). In this illustrative embodiment, the invention may be used, for example, in the power industry to ensure the leak tightness of High Voltage Switchgear and in the laboratory for testing fume hoods to the ASHREA 110 specification. Other applications include torpedo head, pipework systems, and air bag integrity testing. The high sensitivity, rugged design and ease of use and set up of the invention are advantageous for many applications that involve the detection of SF6.

Figure 8:
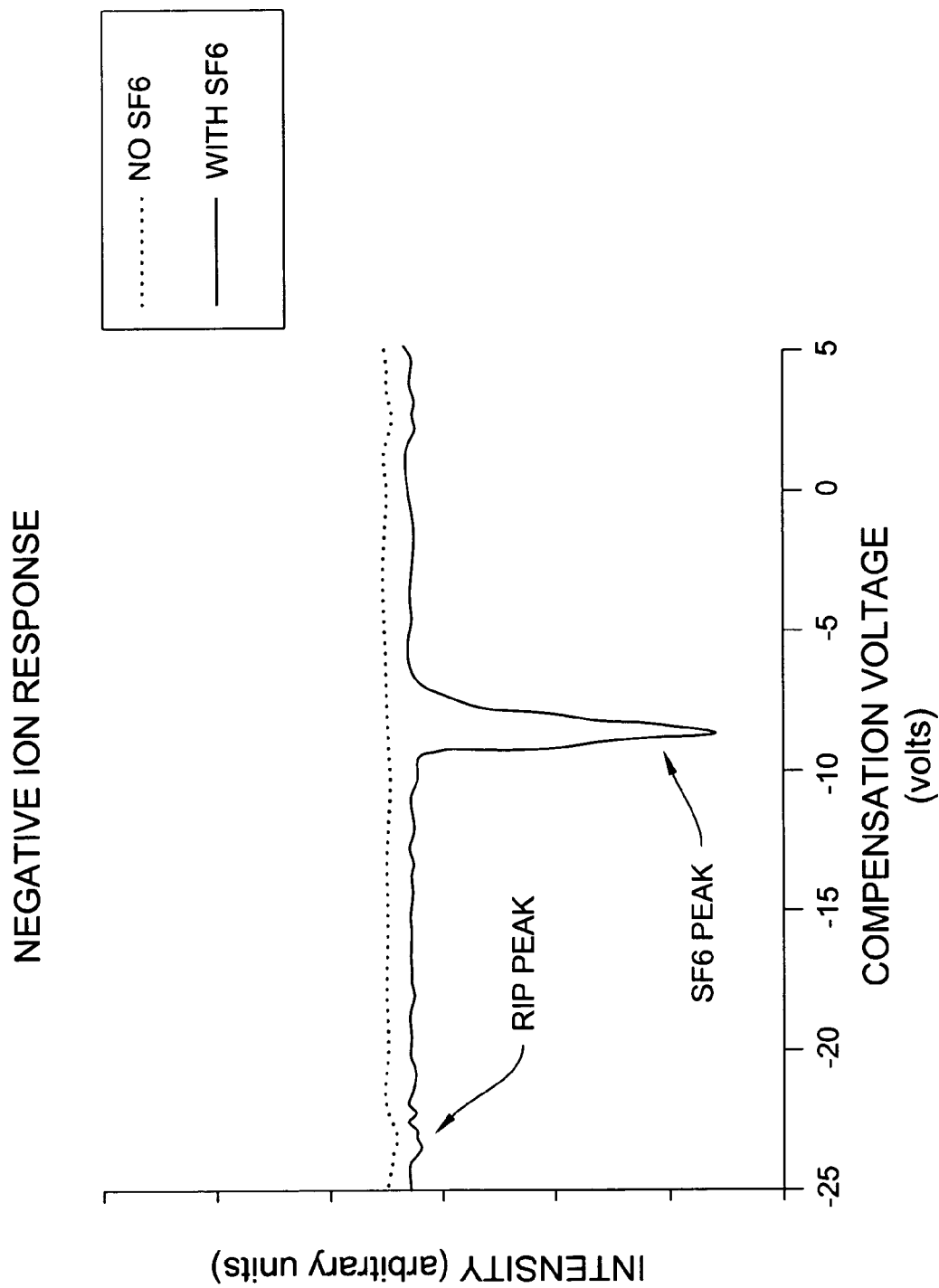
FIG. 8 is a graph of ion intensity versus field compensation voltage illustrating negative mode separation between monomer and reactant ion peak (RIP) detections for sulfur hexafluoride (SF6).
Figure 9:
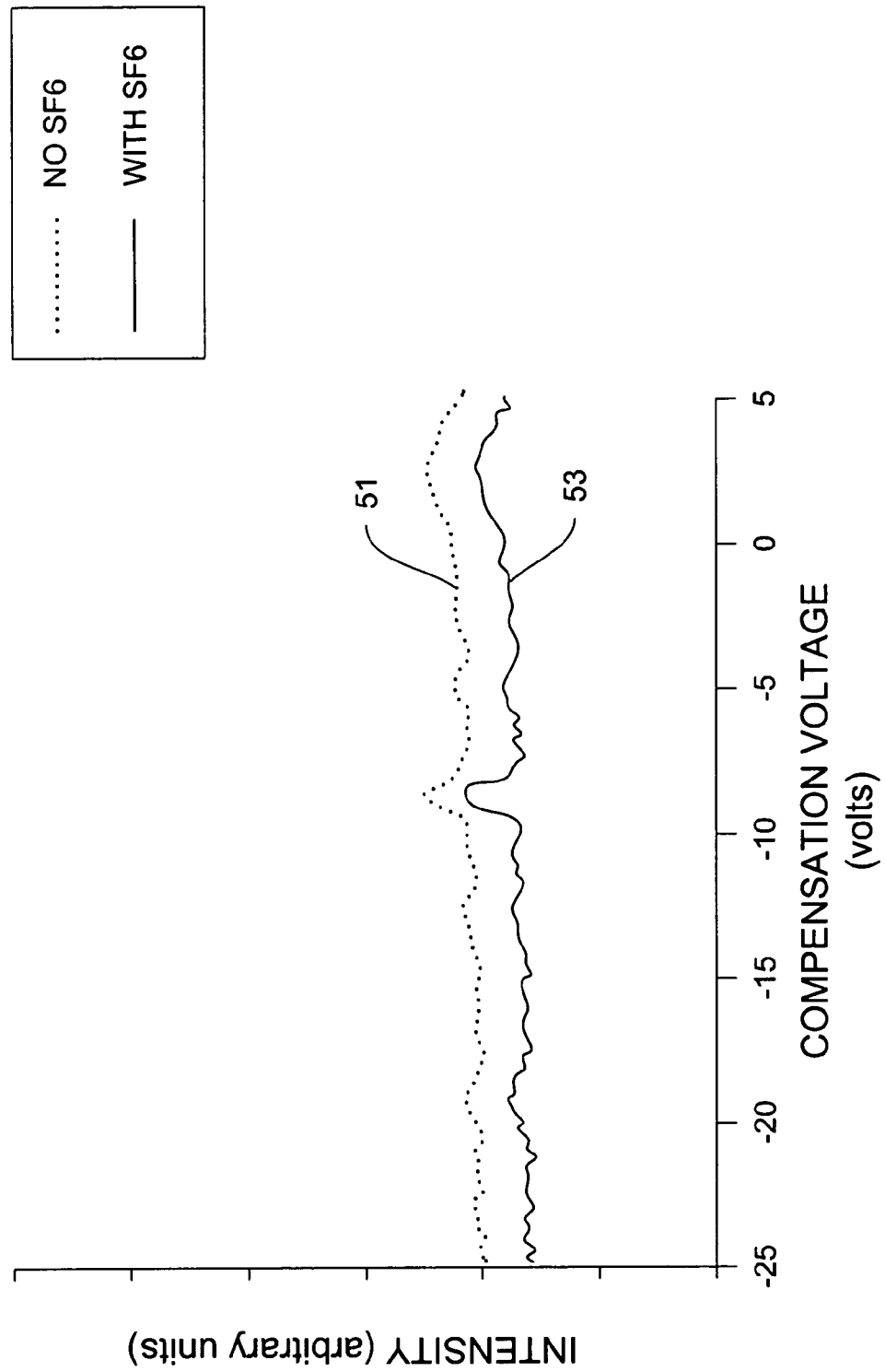
FIG. 9 is a graph of ion intensity versus field compensation voltage illustrating the positive mode separation between monomer and reactant ion peak (RIP) detections for sulfur hexafluoride (SF6).
Figure 10:
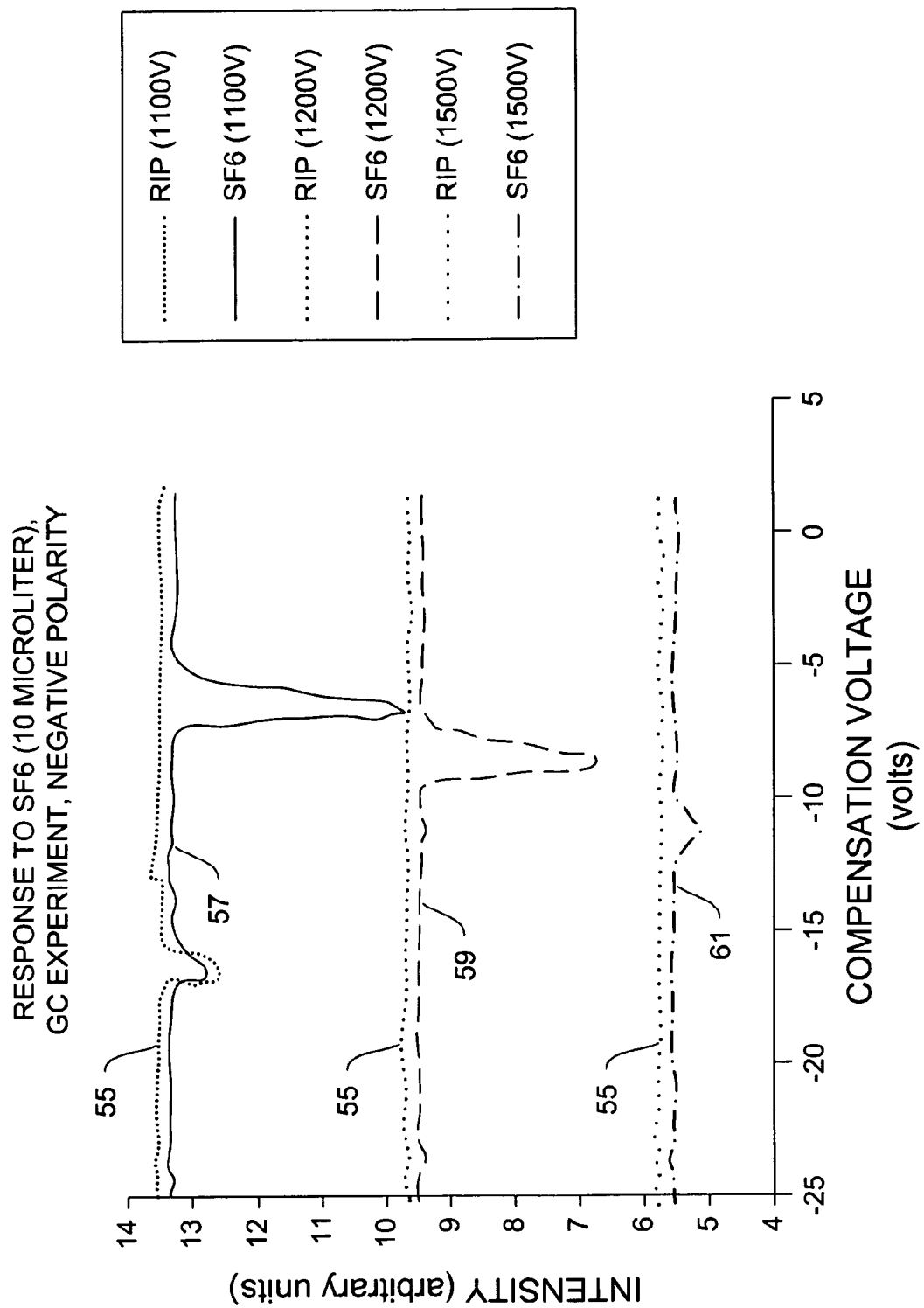
FIG. 10 is a graph of ion intensity versus field compensation voltage illustrating a DMS response at various RF voltage levels in the negative ion mode and also showing the RIP detected in absence of SF6.
Figure 11:
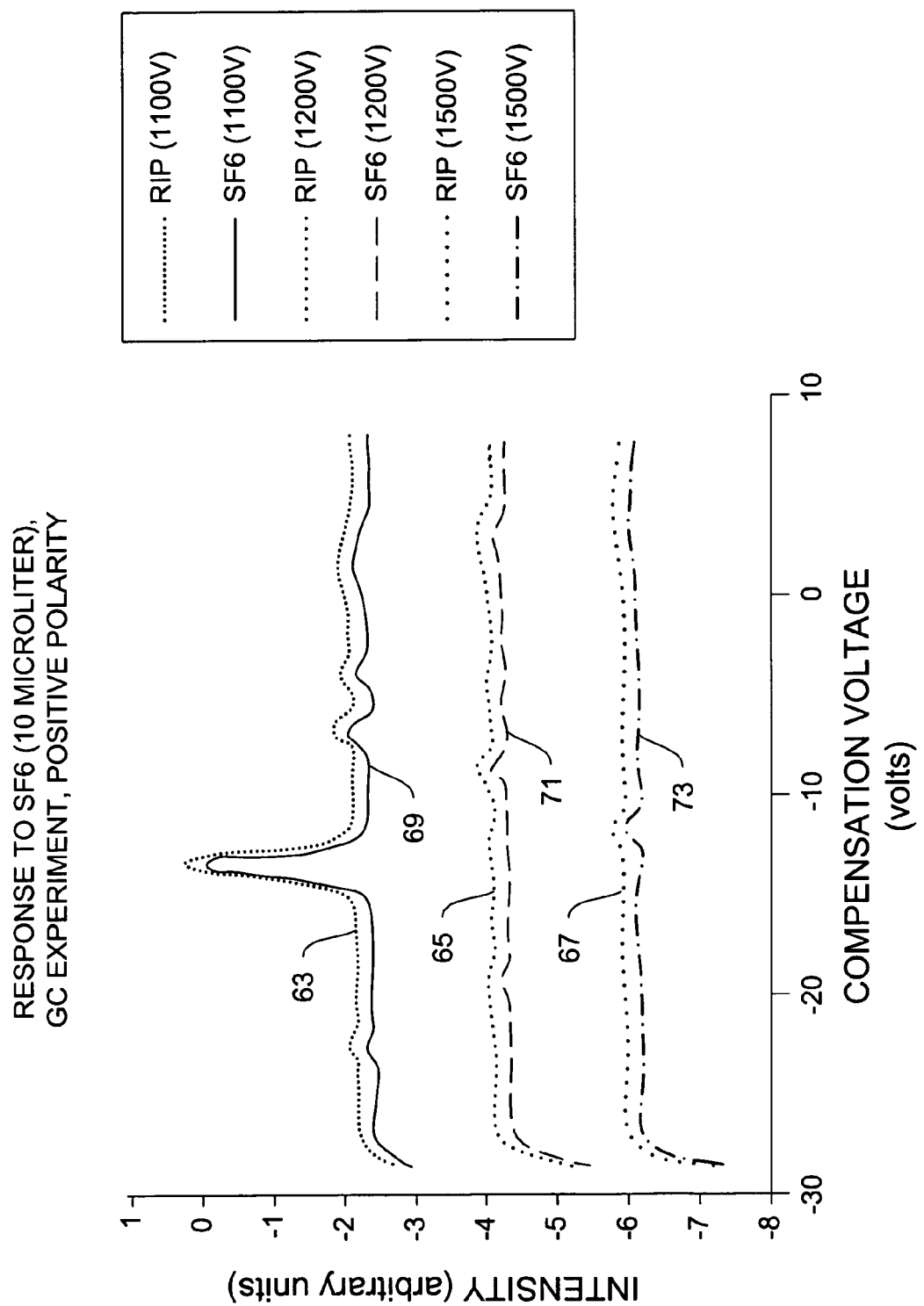
FIG. 11 is a graph of ion intensity versus field compensation voltage illustrating a DMS response in the positive ion mode where the SF6 peak is not isolated from the RIP.

FIG. 8 is a graph of ion intensity (y-axis) versus Vcomp x-axis) for negative mode detection of SF6 according to an illustrative embodiment of the invention. As can be seen, application of the invention provides a distinct peak for the SF6, separate from the reactant ion peak. FIG. 9 provides a similar plot for SF6 for positive mode detection. As can be seen, for positive mode detection, there is no significant difference between the signal 51 without the SF6 present and the signal 53 with the SF6 present. FIG. 10 shows a plot of intensity (y-axis) versus Vcomp x-axis) for SF6 at three different field voltages Vrf (shown at 57, 58 and 61 for negative mode detection along with the RIP 55 detected in absence of SF6. FIG. 11 shows a similar plot to that of FIG. 10, for positive mode detection. As would be expected, the positive mode detection curves 69, 71 and 73, substantially track their corresponding RIP curves 63, 65 and 67, respectively. As mentioned above with respect FIG. 16, while alone this is not definitive, it is an expected detection and therefore may be used as confirmative when combined with a definitive SF6 negative mode detection.

According to another feature, the above described library data for known ion species intensity signatures for known device characteristics may be accessed for either single mode or simultaneous positive and negative mode detections. By comparison with historical detection data for the device, these peaks can be more clearly identified as the tell-tale spectra of the mercaptan. Both spectra give an indication of the mercaptan, qualitatively and quantitatively. Although the advantages of the simultaneous positive and negative mode detection is described above with respect to mercaptan, they may be employed to the analysis of any sample, and are especially useful with real-time analysis of complex samples, such as ones containing mercaptans and hydrocarbon gas, which have similar ion mobility characteristics, and are therefore, difficult to discriminate between.

The foregoing demonstrates favorably obtaining multiple detection data from a single mobility scan for identification of detected ion species in a sample. This innovation is useful in many applications. Notwithstanding this valuable innovation, a still higher level of confidence and further reduced false positives may be obtained by (1) obtaining multiple detection data from multiple ion mobility scans, and (2) further processing such data to extract device independent attributes, such as a mobility coefficient, $\alpha$.

According to one illustrative "multiple scan" embodiment, ions are identified based not on a single set of field conditions, but instead on multiple ion intensity scans taken at at least two and possibly additional numbers of field conditions (e.g., at at least two field measurement points). Detections are correlated with the Vrf and Vcomp, at the at least two different field conditions, to characterize a given detected compound. Because multiple detection data are associated with a given ion species of interest, more accurate detections can be made. Comparison with stored data results in reliable identification of detected compounds.

Strategies for identifying detected ions based on data in spectral peaks or in mobility curves include: curve matching, peak fitting, deconvolution (for overlapping peaks), multi-dimensional mapping, for example, employing three-dimensional representations, including (x,y,z, etc.) spatial coordinate systems and/or (x,y, etc.) coordinate systems, with z- or other values represented by color variations. These techniques enable identification of detected ion species based peaks in a single scan, including simultaneous positive and negative mode detections, and also in multiple scans. The goal is the same: analysis of multiple detection data that can be used to definitively identify, detect, measure or otherwise analyze the species of a detected ion.

Figure 1:
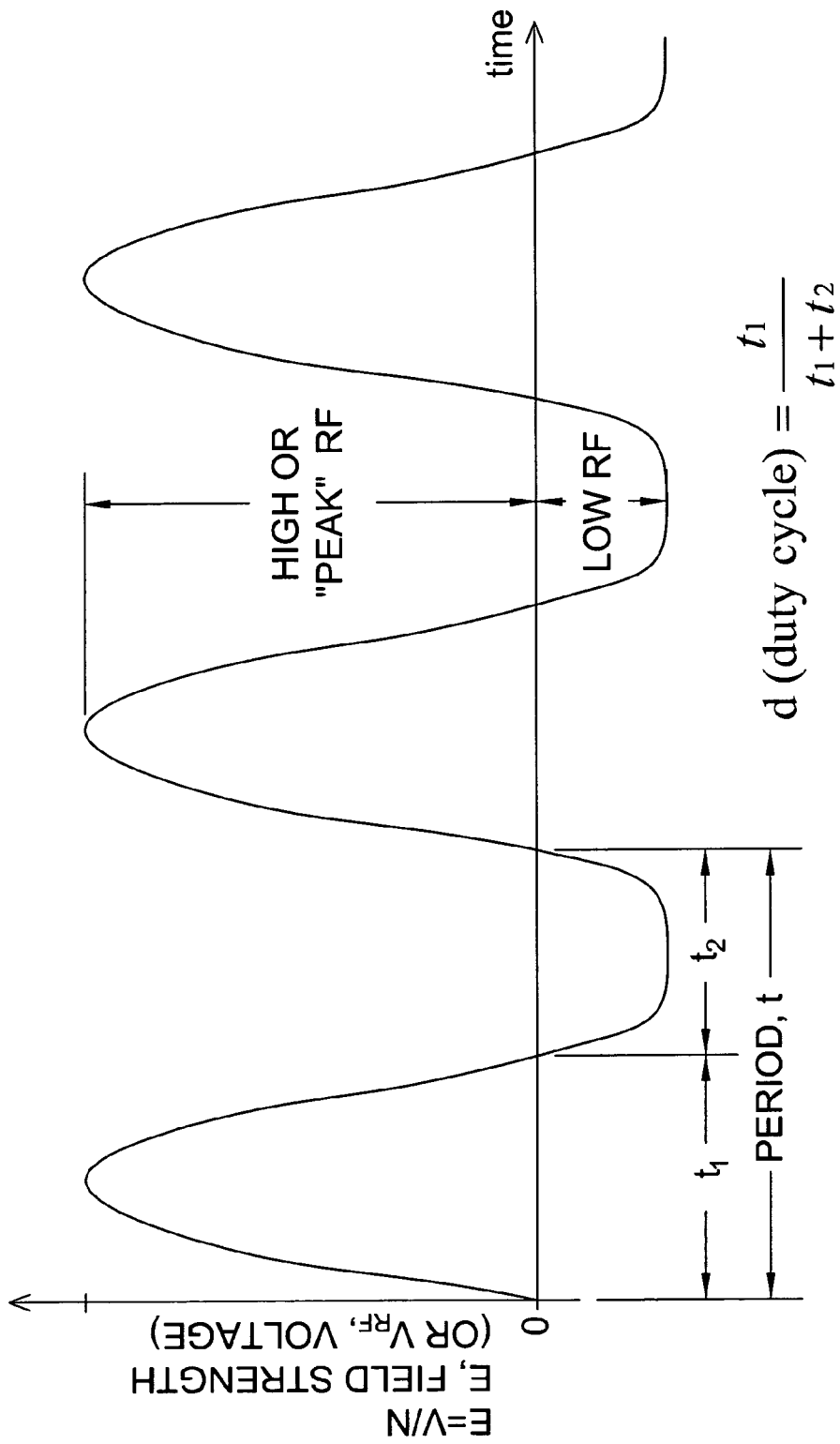
FIG. 1 is a graph depicting an asymmetric field having a peak RF, time period, and duty cycle.
Figure 2A:
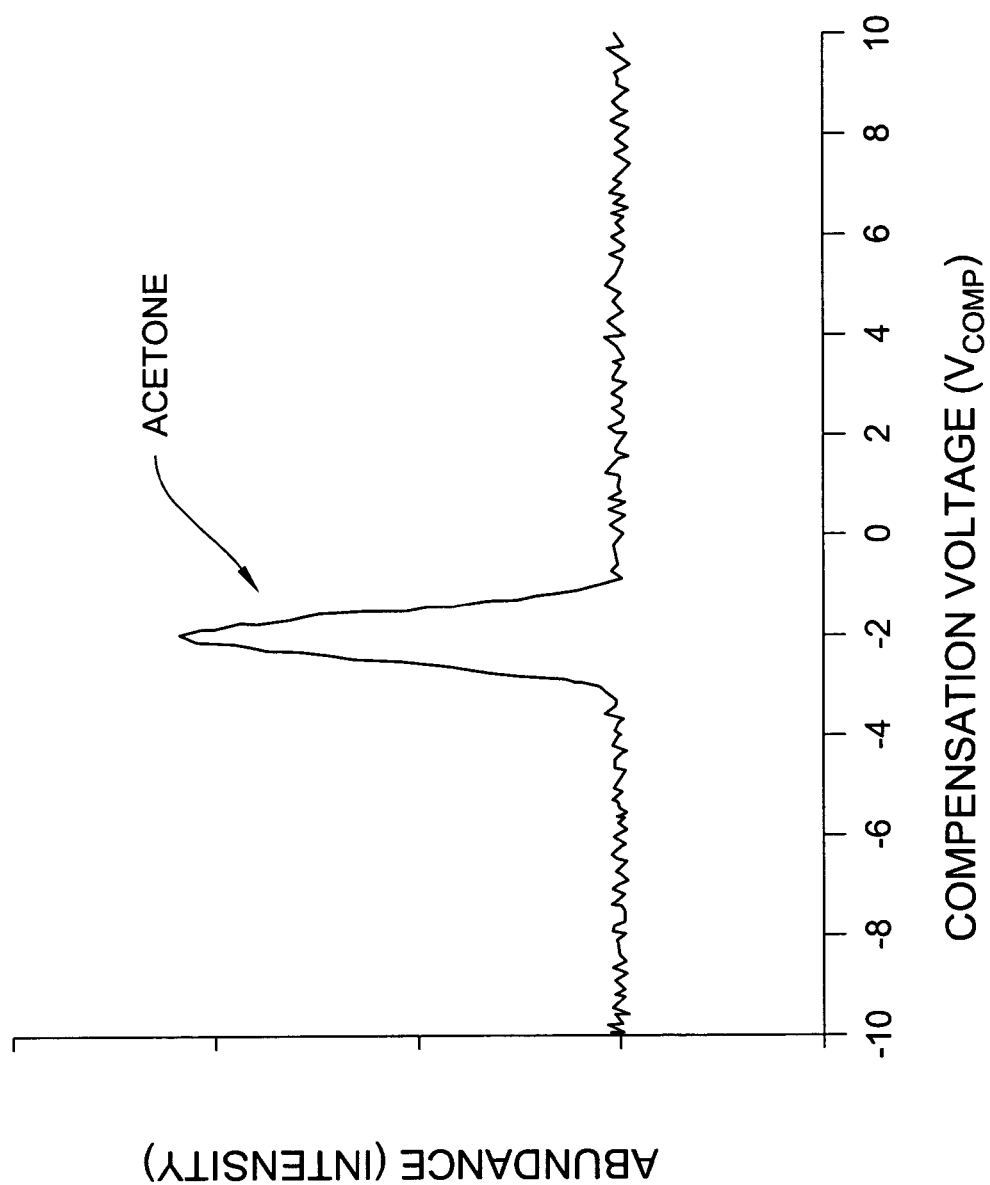
FIGS. 2A and 2B are graphs showing ion abundance (intensity) versus applied field compensation voltage for acetone alone and for a combination of ortho-xylene and acetone, respectively, as detected in a field asymmetric ion mobility spectrometer.
Figure 2B:
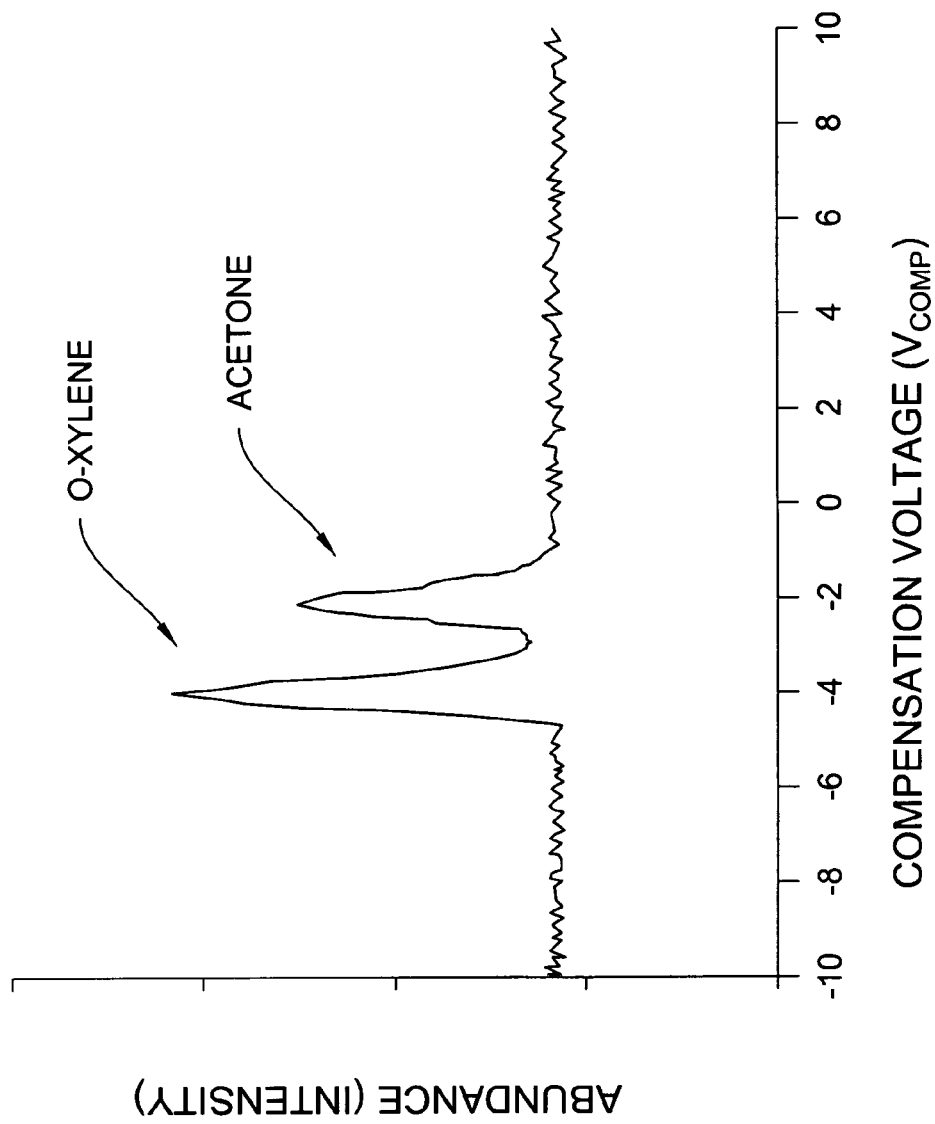
Figure 4:
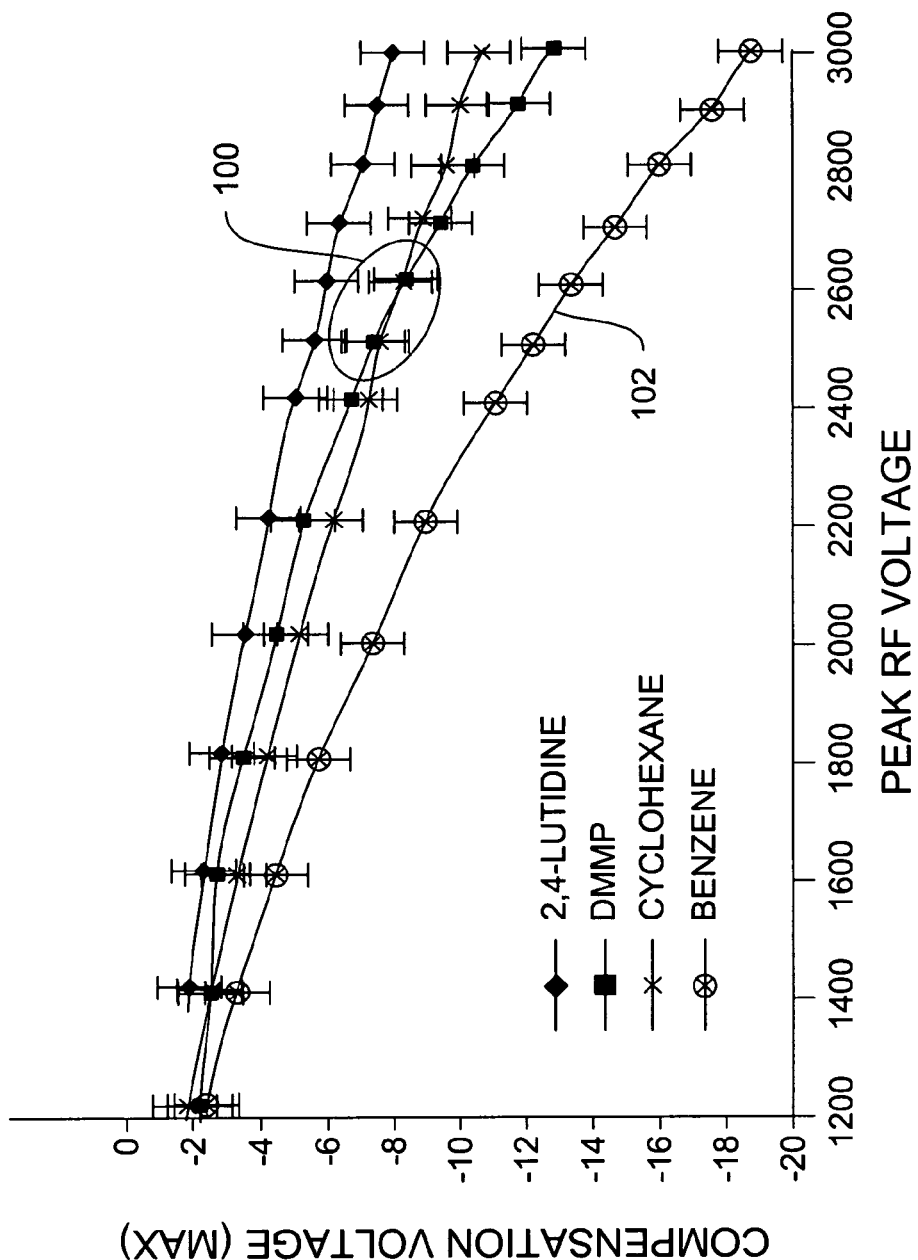
FIG. 4 is a graph of Vrf versus Vcomp indicating intensity peak locations according to an illustrative embodiment of the invention and conceptualizing drawbacks of prior art approaches.

As described above, different ion species of chemicals exhibit different mobility as a function of the compensated applied Vrf. Thus, by applying a set of different Vrf voltages and measuring the Vcomp at the ion abundance peak locations, for example, as detected by the detector 26 of FIG. 1, for the various compounds, a family of measurement points characteristic of a compound can be developed. This family of points can then be plotted to determine the ion mobility curve signature for specific species as a function of Vrf and Vcomp, for example, as shown in FIG. 4. As also described above, such data can be stored and compared with data from scans of unknown compounds to identify the unknown compounds. While some comparison approaches perform curve matching, other approaches determine an ion intensity for a particular ion species for two nearby field strength and Vcomp conditions. The slope between the two data points is calculated and employed as a signature for the particular ion species. The selection of measurement points and the number of measurement points may be adjusted for the specificity required for a particular application. The minimum number of measurement points is two, which at least identifies an aspect (such as slope) of the characteristic curve for a compound, given the known field values.

Although performing slope and/or curve matching for an individual or for multiple scans, where a single filter field/flow channel condition is varied, may provide sufficiently accurate results for some applications, one illustrative embodiment of the invention recognizes that multiple scans taken while varying multiple filter field and/or flow channel conditions can provide improved results. By way of example, according to one illustrative embodiment, the invention steps Vrf through a plurality of values and scans Vcomp at each of the plurality of Vrf values to generate unique sets of data, which better distinguish between compounds and, thus, provide more accurate identification of detected compounds. This approach can be employed to create a data store of more accurate ion mobility signatures for compounds of interest.

According to one illustrative embodiment, the invention incorporates information regarding shifts in an ion abundance peak for a particular ion species at multiple filter field/flow channel conditions into the spectral signature for a compound. More specifically, at a particular Vrf (Vrf1) an ion abundance peak may be detected at a particular Vcomp (Vcomp1). However, the ion abundance peak may shift to be detected at a second Vcomp (Vcomp2) for a second Vrf (Vrf2). One illustrative embodiment of the invention recognizes that, in many instances, the ion peak shift from Vcomp1 to Vcomp2 in response to varying Vrf from Vrf1 to Vrf2 is indicative of a particular ion species. Similar measurements of unknown compounds can be compared against this portion of the spectral signature to aid in identification of the unknown compound.

Figure 12:
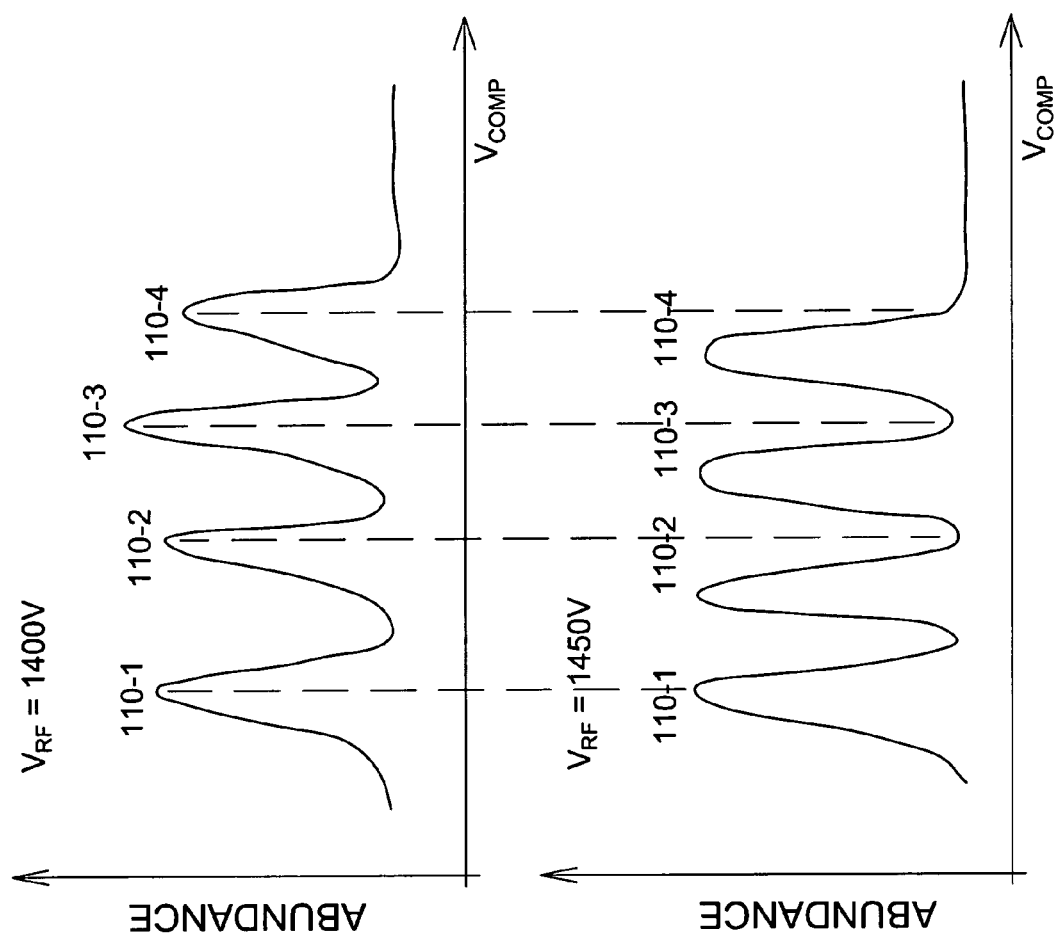
FIG. 12 is graph of ion intensity (abundance) versus field compensation voltage illustrating an ability to improve discrimination between detected ion species by observing ion spectral peak shifts corresponding to a change in field strength.

FIG. 12 depicts an example illustrating the above described ion abundance spectral shift due to a change in Vrf from 1400 Vpeak to 1450 Vpeak over a scanned Vcomp. In FIG. 12, the peaks 110-1, 110-2, 110-3, and 110-4 occur at a particular field compensation voltages Vcomp, for Vrf at 1400 Vpeak (corresponding to a field strength of 28,000 V/cm), but shift to be located at different compensation voltages in response to Vrf being changed to 1450 Vpeak (corresponding to a field strength of 29,000 V/cm). As can be seen from FIG. 12, even small changes in a field condition, such as a change in Vrf, can cause a measurable ion peak shift, and can thus provide significant additional information to the ion spectral signature. In the specific example of FIG. 12, the shift in ion peak due to the change in Vrf is employed when making a comparison to ion spectral signatures for known compounds to identify an unknown compound.

Figures 13A, 13B:
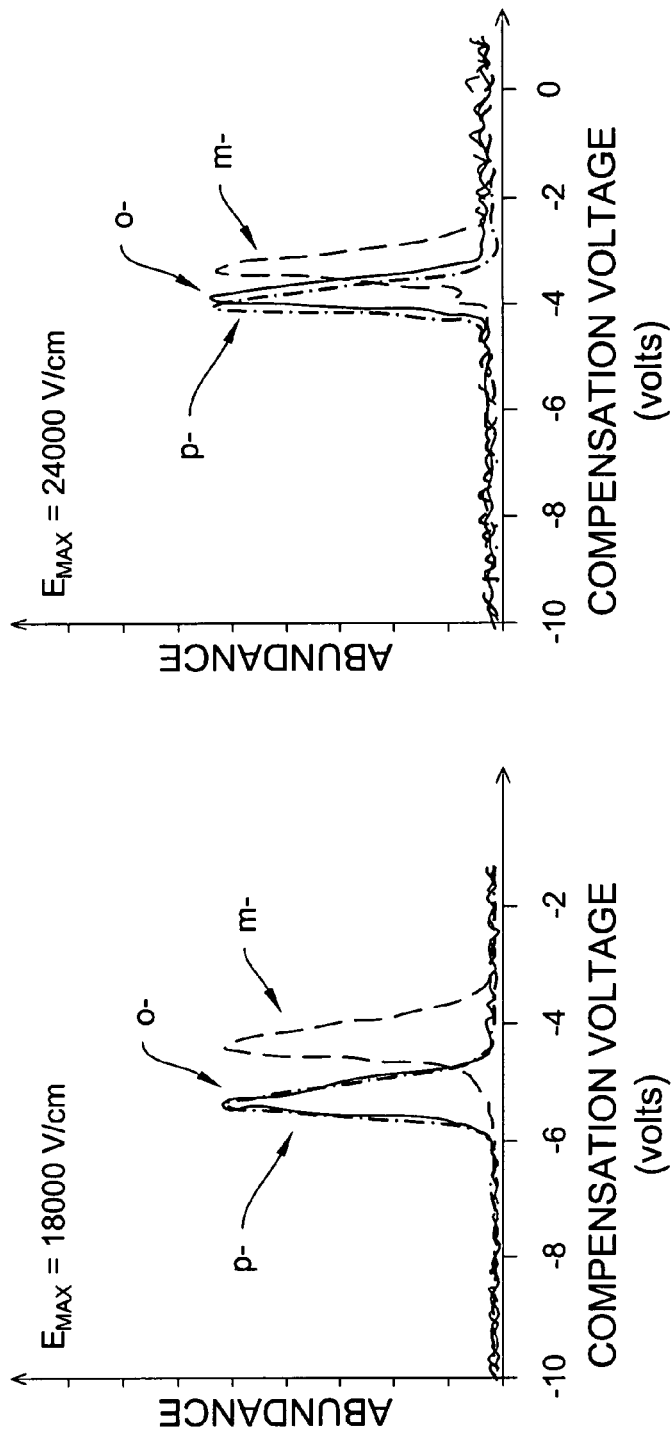
FIGS. 13A and 13B are graphs of ion intensity (abundance) versus field compensation voltage illustrating an ability to improve discrimination between detected ion species by observing ion spectral peak shifts due to reducing field strength.

FIGS. 13A and 13B show an experimental example illustrating how ion spectral peak shifting can be employed to identify an unknown species. In FIGS. 13A and 13B, in a field strength of about 24000 V/cm, peaks for three different isomers of xylene in a sample, p-, o-, and m-, were detected. In FIG. 13A, the peaks for p- and o- are indistinguishable, while the peak for m- is well defined. To further evaluate the sample, a second detection (FIG. 13B) was performed at a lower field strength of 18000 V/cm. As can be seen in FIG. 13B, the peak shift due to the change in field strength causes the three different isomers p-, o-, and m- of xylene to be more clearly distinguishable, and thus more accurately identified. As can be seen from FIGS. 13A and 13B, better discrimination between species is not always a result of applying a higher field strength. More particularly, in this example, the p- and o-xylene isomers become more distinguishable at a reduced field strength.

Figure 14A:
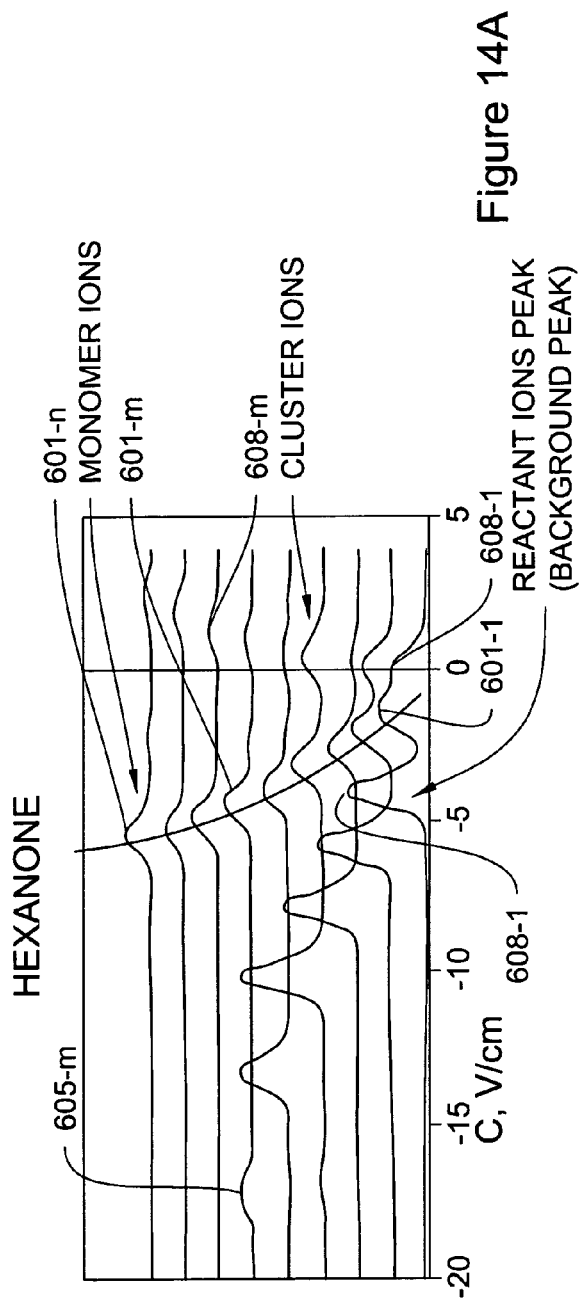
FIGS. 14A and 14B are graphs of ion intensity at multiple field strengths versus field compensation voltage, showing the affect of changes in compensation voltage on specific spectra, and show the divergent behavior of monomer, cluster, and reactant ion peak (RIP) detections with changes in field strength and field compensation voltage.
Figure 14B:
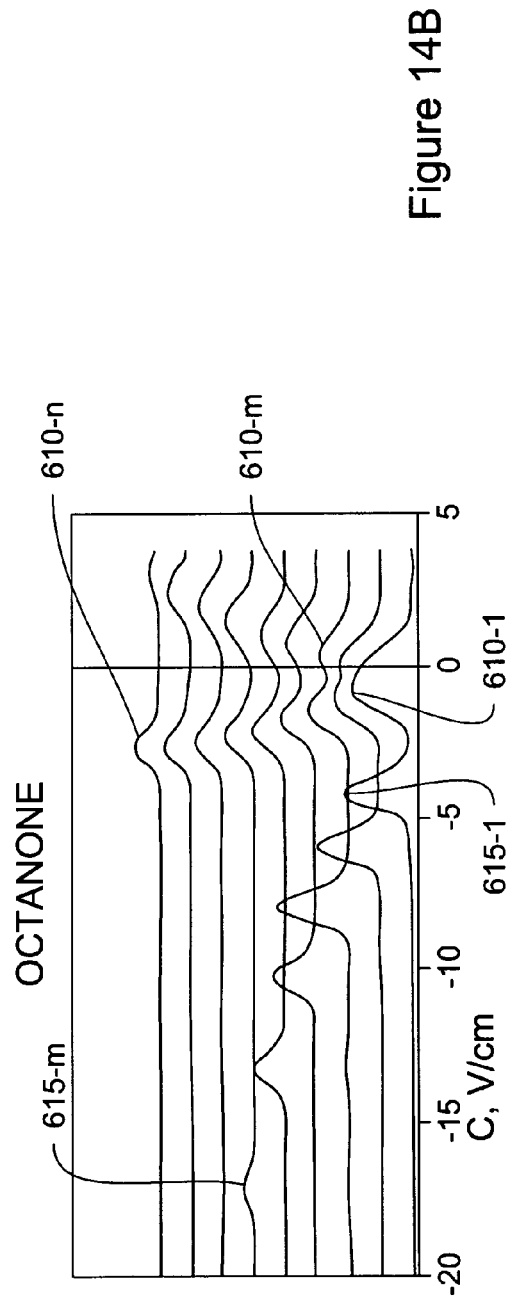

According to another illustrative embodiment and as mentioned above, the invention generates detection data over a range of applied filter field/flow channel conditions. For example, FIGS. 14A and 14B show the effect of changes in field strength on the location of detection peaks at different Vcomp levels for hexanone and octanone, as detected in a DMS system of the type depicted at 10 in FIG. 1. The curves are offset on the vertical axis, with the offset increasing as electric field strength increases. While various operating ranges are possible, as an illustration, FIGS. 14A and 14B may be understood as presenting peak Vrf between a low of about 620 Vpeak (lowermost plot in each) and a high of around 1450 Vpeak (uppermost plot in each). Several attributes are noted in this series of responses. For example, referring specifically to the hexanone plot of FIG. 14A, a monomer peak of 601-1 of particular interest is somewhat obscured in the lowest field strength condition. However, at the highest applied field strength, the peak 601-$m$ corresponding to hexanone is clearly discernable from the other peaks.

Several phenomena have occurred with the increase in increasing applied field strength. First, a reactant ion peak (RIP) 605-1 is relatively dominant in the low field strength detection. However, as electric field strength is increased, the RIP 605-$m$ shifts to the left at a more rapid rate than the monomer ion peak 601-$m$ of interest. This is because the α parameter for the mobility coefficient for the reactant ion species is different than the a parameter for the monomer ion of interest.

In addition, the relative amplitude of the RIP 605 decreases markedly with the increase in the electric field strength. Thus, RIP 605-$m$ is observed at much lower amplitude and well separated from the monomer peak 601-$m$ of interest at a specific field condition. While the monomer peaks 601 also shift, they do not shift by the same amount, or by as much. Thus, by analyzing the compound over a range of applied field conditions, a condition can be discovered at which the RIP 605 shifts away from or off the scale of other observed peak voltages. In some cases, this allows easier detection of the monomer ion peak 601 of interest.

Similar behavior is observed in the monomer peaks 610-1, 610- . . . , 610-$n$ observed for octanone and the resulting reactant ion peaks 615-1 to 615-$m$. This information can thus be used to identify a species by comparing a family of response curves to a stored family of known response curves.

Another observed effect shown in both FIGS. 14A and 14B is that a group of cluster ions 608 and 610 are seen. The cluster ions 608 represent clusters of chemical materials in the sample. Typical cluster ions, having a heavier chemical weight, have peaks that are shifted differently from monomer ion peaks of interest. In this example, the cluster peaks shift in a direction away from the direction of shift of the monomer peaks with increasing applied field strength. This characteristic feature of cluster ions, observed with this sample, can also be stored and utilized in recognizing the hexanone and/or octonone ions. The curves shown in FIGS. 14A and 14B are but one example of how applying a range of field/flow channel conditions to detect a given sample can be utilized to an advantage.

As mentioned above briefly, according to one illustrative embodiment, the invention employs multi-dimensional compound signatures for comparison with multi-dimensional representations of unknown compounds to identify and more generally analyze the unknown compounds. Such multi-dimensional representations may arise, for example, from plotting ion abundancy as a function of a plurality of varying filter field/flow channel conditions. Such conditions may include, without limitation, Vrf, Vcomp, filter field strength, Vrf duty cycle, Vrf wavelength and Vrf frequency; temperature, pressure, humidity, flow rate, doping and carrier gas CG composition. Multi-dimensional representations may also result from taking multiple scans of the sample S taken, for example, by recirculating the sample S and/or processing the sample S in parallel and/or in series with one or more additional DMS, IMS, TOFIMS, GC, FTIR, MS, or LCMS, at the same or differing flow channel/filter field conditions. The multi-dimensional representation, according to one illustrative embodiment, is a three-dimensional dispersion plot, employing x- and y-spatial coordinates, with a z-coordinate being represented by a variation in color.

FIG. 15A shows a three-dimensional color dispersion plot 620 depicting detection of methyl salicylate over a range of field voltages Vrf (y-axis) and field compensation voltages Vcomp x-axis), with varying ion intensity (abundance) represented in varying colors, according to an illustrative embodiment of the invention. Although, particular color coordination may vary, the dispersion plot of FIG. 15A represents the highest ion intensity in blue with yellow representing the lowest. The three-dimensional color dispersion plot 620 represents an aggregation of data from a plurality of two-dimensional graphs, such as that shown in FIG. 15B. More specifically, FIG. 15B shows a plot 622 of ion intensity (y-axis) versus Vcomp x-axis) at a particular Vrf for methyl salicylate. A plurality, illustratively more than two, of such graphs taken at a plurality, illustratively more than two, of field voltages Vrf are aggregated to provide the color plot 620 of FIG. 11A. Aggregating a plurality of scans taken at a plurality of filter field voltages Vrf (and thus, field strengths) provides a more discriminating scan than a single scan taken at a single Vrf. One reason for this is that the aggregated scans incorporate the above discussed peak shifting that occurs due to the changes in Vrf. As can be seen, the three-dimensional representation of FIG. 15A provides three signature peaks 621, 623, and 625, as opposed to the two peaks 627 and 629 of FIG. 15B.

The effect of the increased resolution provided by employing dispersion plots, is even more evident, when trying to distinguish between compounds having similar ion mobility characteristics. By way of example, FIGS. 16A and 16B show positive mode plots 624 and 626 for DMMP, while FIGS. 17 and 18 show positive mode plots 628 and 630 for DIMP. More specifically, FIGS. 16B and 18, plot ion intensity (y-axis) versus Vcomp x-axis) at a particular Vrf for DMMP and DIMP, respectively. As shown, both FIGS. 16B and 18 included three peaks of similar magnitude, located at a approximately the same field compensation voltages, and similarly spaced apart. Distinguishing between DMMP and DIMP, based solely on the individual plots 626 and 630 of FIGS. 16B and 18 is at best unreliable, and at worst impossible. However, referring to FIGS. 16A and 17, the three-dimensional plots 624 and 636 are easily visually distinguishable.

More particularly, the DMMP color plot 624 of FIG. 16A shows three clear peaks 638, 639 and 640, while the DIMP color plot 628 shows four clear peaks 631, 632, 634 and 636. While the peaks 638, 639 and 640 nearly overlay the peaks 631, 634 and 636, the fourth blue peak 632 for DIMP, which is lacking for DMMP, easily distinguishes the DMMP scan from the DIMP scan. Also, the branches 634 and 636 of the color plot 628 are closer together than the branches 638 and 640 of the color plot 624. Additionally, the color distribution (e.g., saturation) throughout the branches of the three-dimensional color plot 624 is not the same as the color distribution throughout the branches of the plot 628. As in the case of previously discussed signature scans, three-dimensional signature scans of the type depicted in FIGS. 15A-18 may be stored in a library for known compounds. At least portions of one or more of the stored scans may be compared with at least portions of similar scans of unknown species to identify and generally analyze the unknown species. Any suitable pattern matching approach, including conventional pattern matching approaches, may be employed for such comparison.

It should be noted that although the above discussed dispersion plots of FIGS. 15A, 16A and 17 employ color changes to indicate intensity, changes in any color-related feature, such as changes in color saturation, gray scale or black and white may be employed instead or in combination. Additionally, in a further illustrative embodiment, the invention generates a curve circumscribing the intensity peaks, and the color-related information may be discarded. By way of example, in this illustrative embodiment, the outlines, for example, for the intensity peaks 632, 634 and 636 would remain, without the color-related information. Removing the color-related information provides a two-dimensional dispersion representation of, for example, Vrf versus Vcomp that also takes into account the spectral information gained from aggregating a plurality of Vcomp scans at a plurality of Vrf values. Any or all of this two-dimensional information may be incorporated into the above discussed signature information.

As described above, various illustrative comparison approaches may employ pattern matching using, for example, the above described two- and/or three-dimensional dispersion plots. However, in other illustrative embodiments, the information provided by the dispersion plots is stored in the library as mathematical relationships, and suitable conventional approaches for comparing such mathematical relationships are employed to identify the unknown species.

According to another illustrative embodiment, Vcomp may be plotted on the x-axis, Vrf on the y-axis, and ion intensity on the z-axis. Thus, instead of showing ion intensity as color, saturation, gray scale or black and white variations, as in the three-dimensional color plots 620, 624, and 628, ion intensity may be depicted/conceptualized in a topographical manner. Multi-dimensional signature representations of this sort may also be stored in the library of known species and used in the same fashion as the above described ion mobility signatures. In other embodiments of the invention, more than three dimensions may be employed, for example, plotting spectral data as clusters in n-dimensional space and employing known cluster matching algorithms.

A processor, such as the processor 46 of FIG. 5, may be programmed in a conventional fashion to automatically step an analyzer, such as the system 10, through a range of field voltages Vrf and a scanned Vcomp, and provide the data to a display or other system for processing and generation of a three-dimensional dispersion plot.

Another analysis improving effect can be observed with the application of relatively high field strengths. Specifically, complex ion groupings can be fragmented, for example, by applying a high field strength to the sample. Sample fragmentation is a useful technique for enhancing species separation, detection, and identification. Fragmentation includes a process in which large molecules of samples are broken up into smaller molecules, components, or fragments prior to sample detection. This enables the components of the group to be individually detected and more generally analyzed.

Figure 19:
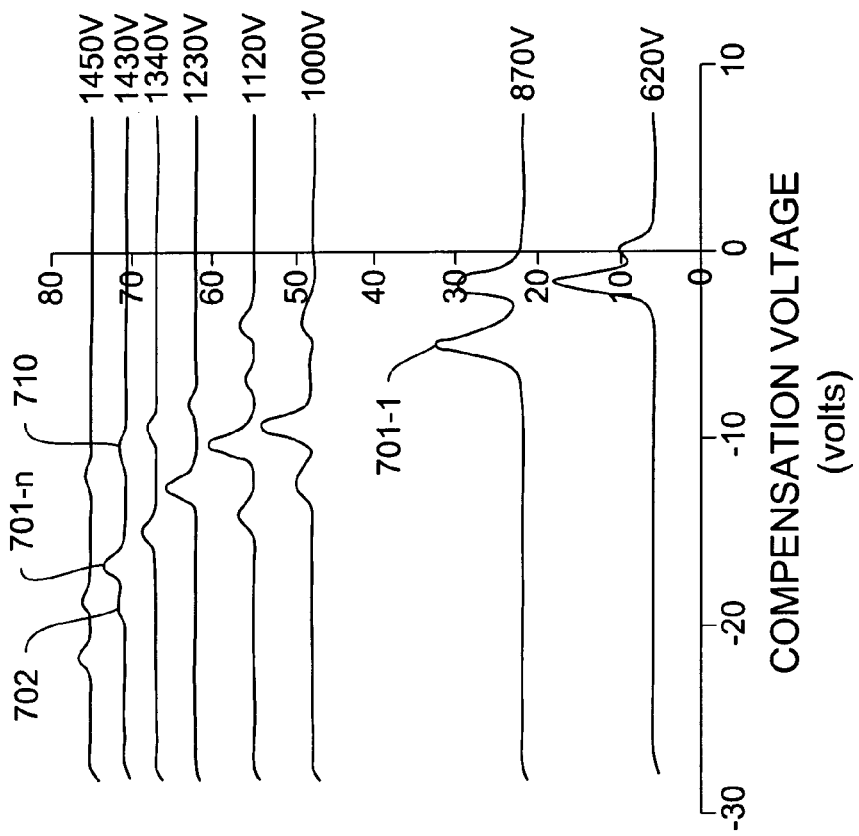
FIG. 19 is a graph of ion intensity at a plurality of field voltages versus field compensation voltage illustrating the effects of changes in field conditions on location of individual detection peaks and the ability to separate the detection.

FIG. 19 is an example of such an effect on a mercaptan sample. In particular, a range of background voltages (from 620-1450 Vpeak) were applied to an ethyl mercaptan spectra in which a general shift of ion peak behavior can be seen as electric field conditions are strengthened. However, a fragmentation condition can also be observed. Specifically, at lower applied field conditions, strong single peak is observed, such as at 701-1. However, as electric field strength is increased, multiple peaks 701-n, 702, . . . 710 are observed in a spectra. By observing and recording the peak locations, not only at the low voltage field conditions, but also at a range of field conditions, this fragmentation behavior can be further exploited to better identify compounds. According to one feature, data indicating the peak RF voltage at which fragmentation occurs is incorporated into the stored spectral signatures for the known samples. According to another feature, the locations of the fragment peaks are also or instead incorporated into the stored spectral signatures for further use for matching detection data with known data.

Figure 20A:
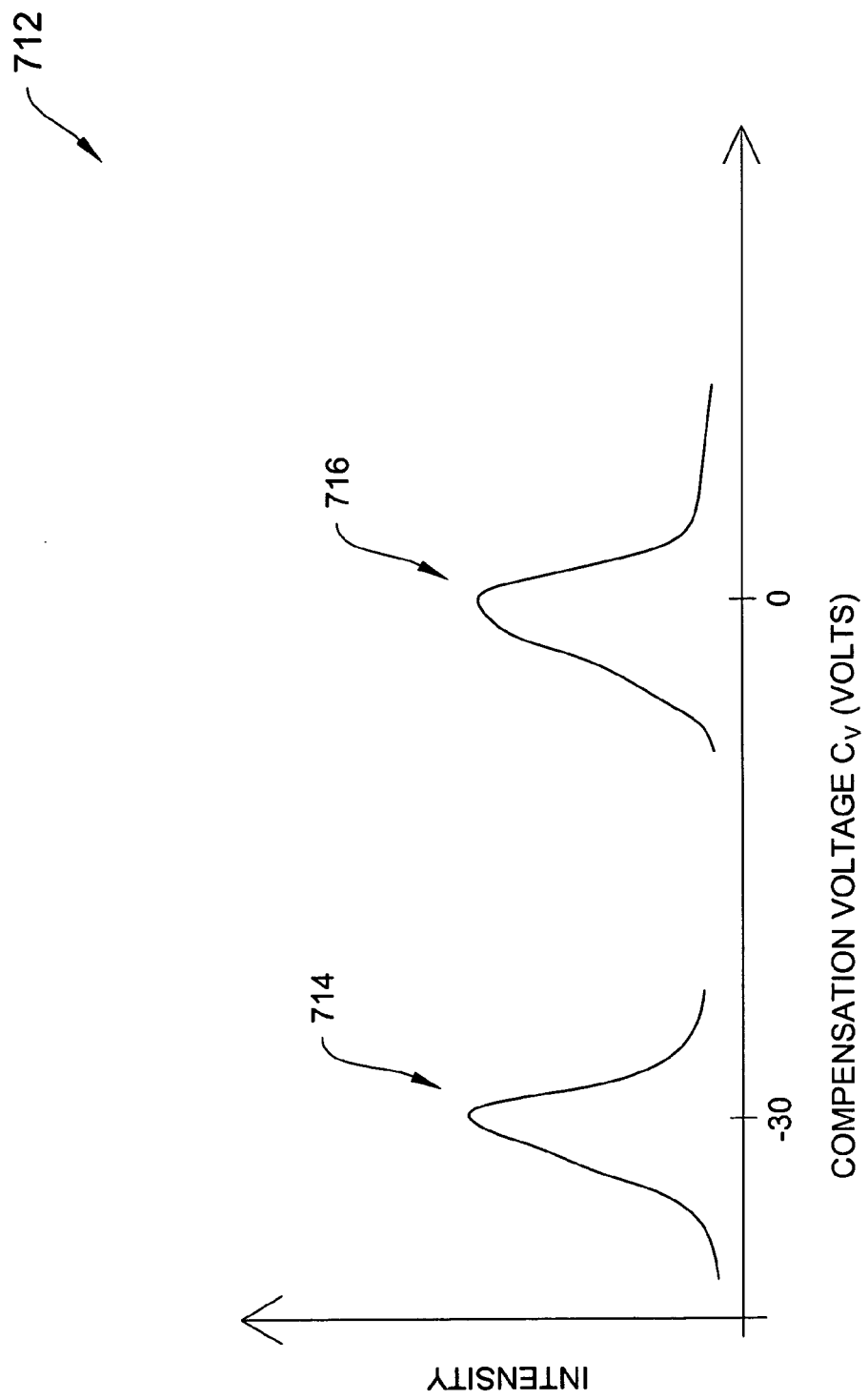
FIG. 20A is a graph of ion intensity versus field compensation voltage illustrating the separation of detection peaks at different compensation voltages between light and heavy molecules according to an illustrative embodiment of the invention.

FIG. 20A is a graph 712 of ion intensity (y-axis) versus field compensation voltage Vcomp x-axis) illustrating the separation of detection peaks at different compensation voltages between light and heavy molecules according to an illustrative embodiment of the invention. The graph 712 shows that light molecules associated with the RIP background peak 714 may be identified at an arbitrary −30 Vdc compensation voltage, while heavier molecules tend to be clustered and form a peak 716 at about 0 Vdc compensation. By fragmenting a sample of heavy molecules and detecting the fragments using, for example, a DMS or IMS system, a plurality of ion intensity peaks, each associated with a fragment, may be used to create a unique signature of the sample to enable subsequent identification of that sample. Fragmentation of a sample may be achieved, for example and without limitation, by using any one or a combination of a chemical reaction, a high energy field at high strength, high field voltage, heating, laser light, colliding the sample molecules with other molecules, soft x-ray, or the like.

Figure 20B:
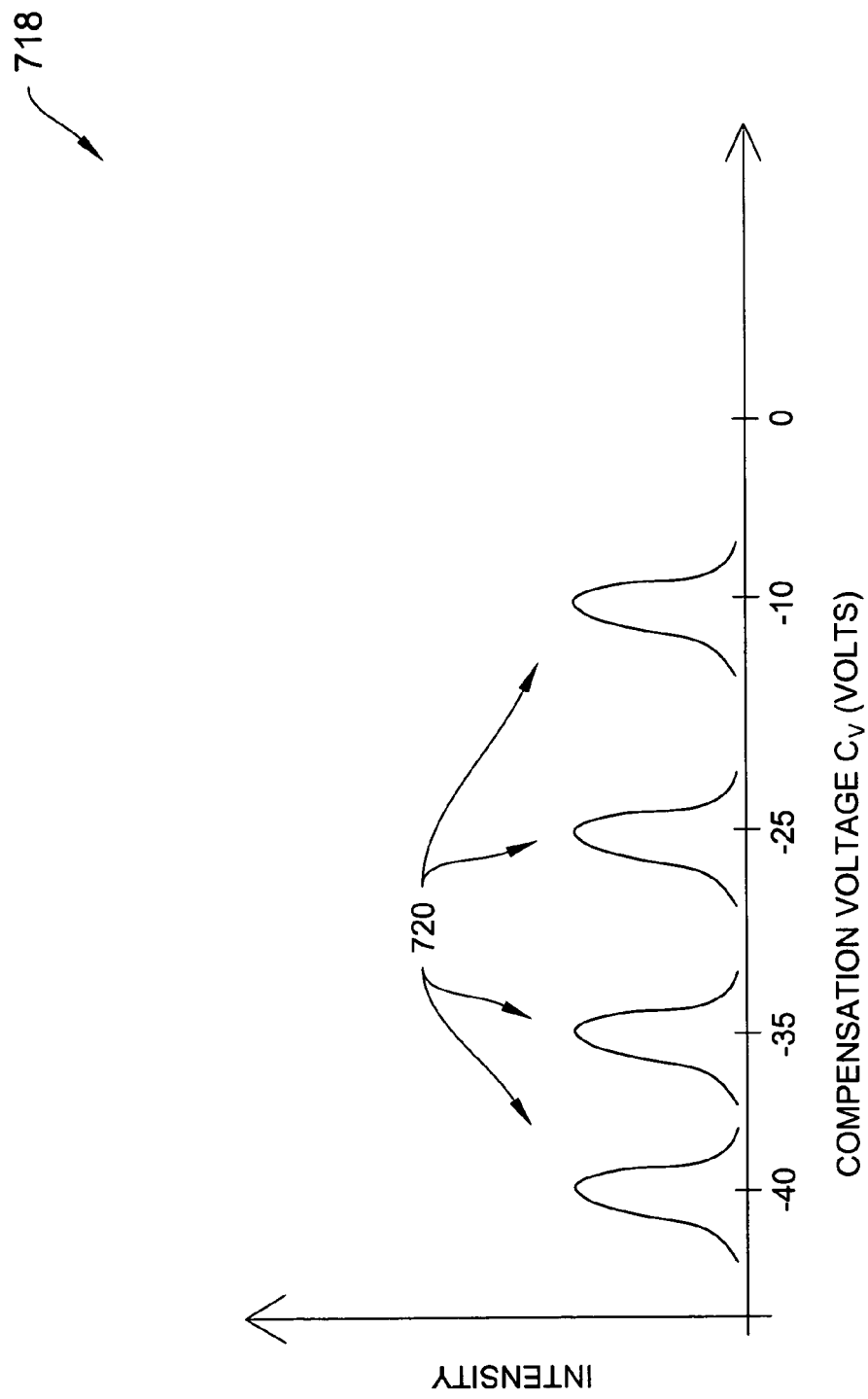
FIG. 20B is a graph of ion intensity versus field compensation voltage showing the increase in number of peaks detected after sample fragmentation according to an illustrative embodiment of the invention.

FIG. 20B is a graph 718 of ion intensity (y-axis) versus field compensation voltage x-axis) showing the increase in number of peaks detected after sample fragmentation according to an illustrative embodiment of the invention. The graph 718 shows that fragments are lighter, and therefore, have lower mass and higher associated compensation voltages, resulting in improved resolution of and differentiation between the fragments. Also, the graph 718 shows an increased number of peaks 720 associated with the fragmented sample, which increases the collective data that may be used to fingerprint the compound. The additional detection data enable a more accurate identification of the detected species, such as by comparing the signature detected with a set of signatures in a look up table and by other techniques disclosed herein.

Figure 21:
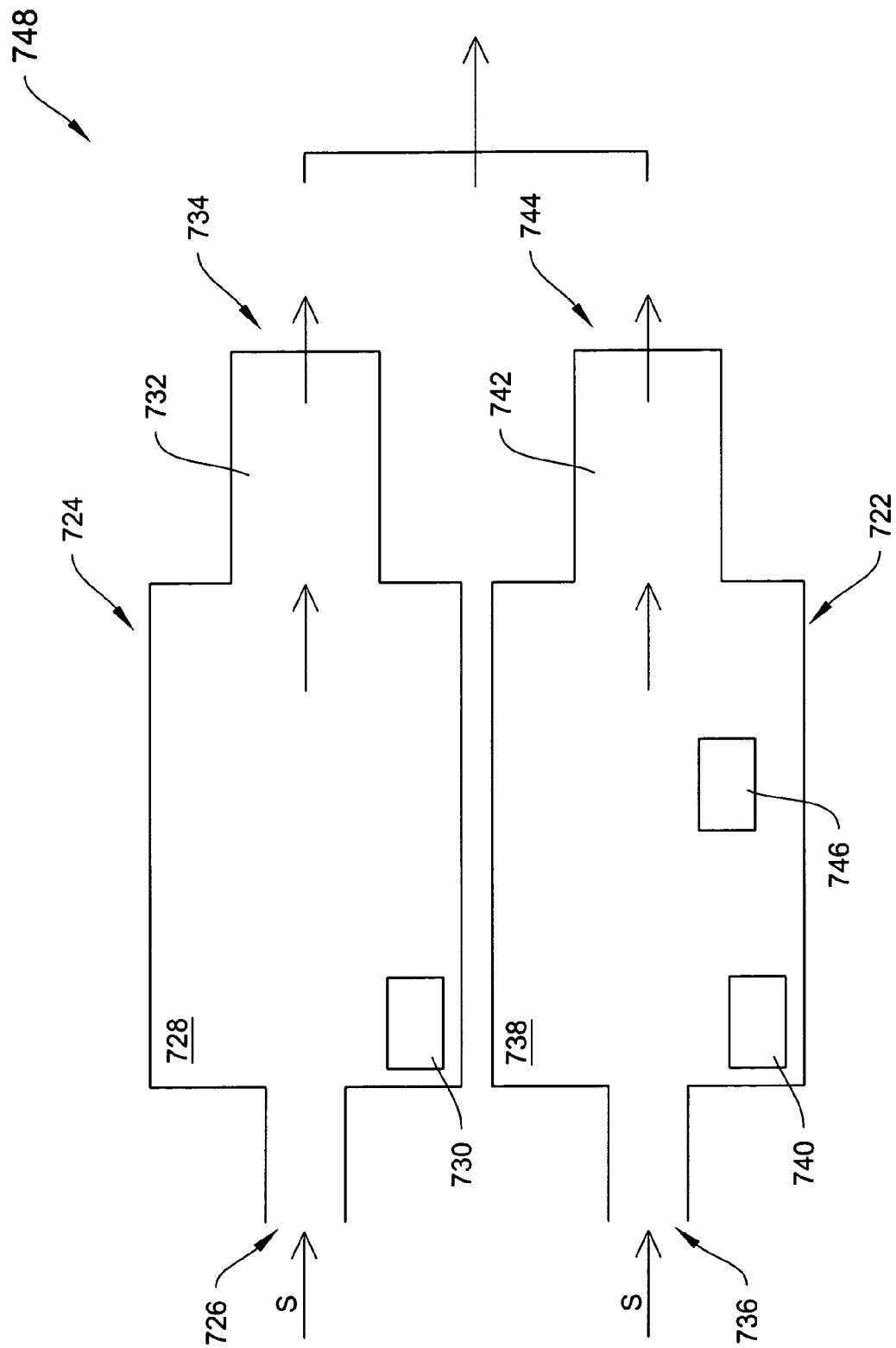
FIG. 21 is a conceptual diagram of a DMS system using fragmentation operating in parallel with a DMS system not using fragmentation to improve sample analysis according to an illustrative embodiment of the invention.

FIG. 21 is a conceptual block diagram of a dual channel detection system 748 including a first DMS system 722 using fragmentation and forming a first channel operating in parallel with a second DMS system 724 not using fragmentation and forming a second channel to improve sample analysis according to an illustrative embodiment of the invention. As shown, the DMS system 724 includes a sample inlet 726, ionization region 728, ion source 730, analyzer region 732, and outlet 734. Similarly, the DMS system 722 includes a sample inlet 736, ionization region 738, ion source 740, analyzer region 742, and outlet 744. The DMS system 722, however, also includes a fragmentation energy source 746 within the ionization region 738. The analyzer regions 732 and 742, respectively, include a DMS filter and detector to enable detection and identification of samples. In operation, the dual channel detection system 748 operates DMS systems 722 and 724 concurrently, simultaneously or alternatively. With respect to the DMS system 724, a sample S is introduced into ionization region 728 via the sample inlet 726. The ionization source 730 may then ionize the sample S into positive and/or negative ions that are then delivered to the analyzer region 732. The analyzer region 732 performs filtering and detection of the sample which then exits the DMS system 724 via the outlet 734. The DMS system 722 operates in a similar manner as the DMS system 724, but with an additional fragmentation source 746. Thus, when the sample S enters ionization region 738 of DMS system 724, the fragmentation source 746 breaks up/fragments the sample S molecules into lighter, less massive molecules. These lighter molecules are then delivered to analyzer region 742 for filtering and detection.

Thus, the dual channel detection system 748 using DMS systems 722 and 724 may improve sample analysis by substantially simultaneously analyzing a sample S and its fragments to create a more complete signature of the sample. Alternatively, the dual channel detection system 748 may selectively compare the fragmentation spectra, depending on the sample species to be detected and the need for better discrimination from other interferants or compounds.

Figure 22:
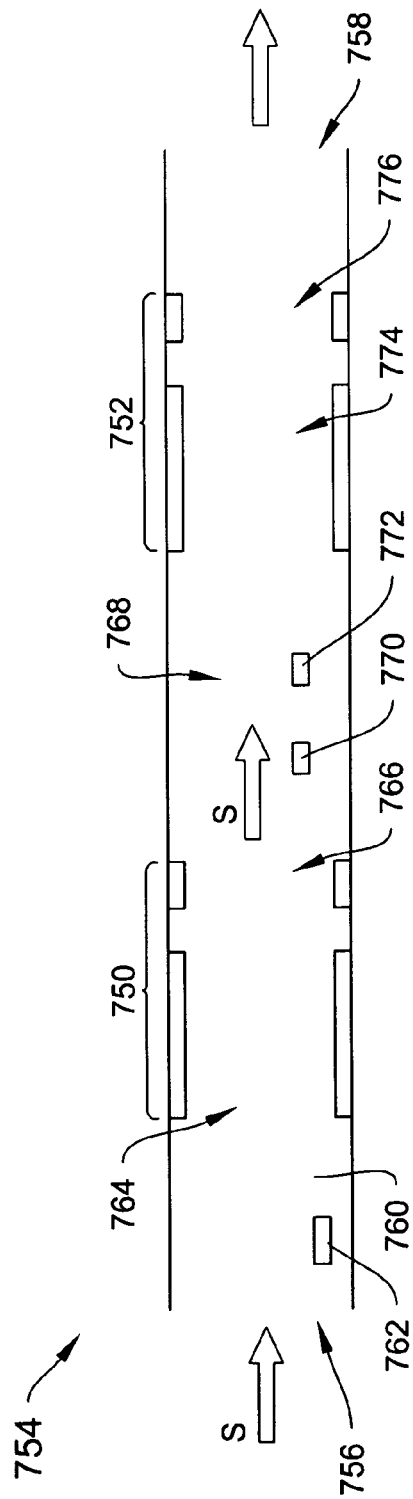
FIG. 22 is a conceptual diagram of a DMS system not using fragmentation operating in series with a DMS system using fragmentation to improve sample analysis according to an illustrative embodiment of the invention.

FIG. 22 is a conceptual diagram of a DMS system 750, not using fragmentation, and operating in series with a DMS system 752 using fragmentation to improve sample analysis according to an illustrative embodiment of the invention. The combination of the DMS systems 750 and 752 form a serial detection system 754. As shown, the serial detection system 754 includes a sample inlet 756, the DMS system 750, the DMS system 752, and an outlet 758. The DMS system 750 includes an ionization region 760, ion source 762, ion filter 764, and detector 766. The DMS system 752 includes an ionization region 768, ion source 770, fragmentation source 772, ion filter 774, and detector 776.

In operation, a sample S is introduced into the serial detection system 754 via the sample inlet 756. The DMS system 750 ionizes the sample S using the ionization source 762 within the ionization region 760. Then, the ionized sample S is delivered to the ion filter 764. The ion filter 764 applies a combination of field and field compensation voltage to the sample S to allow selected ion species to reach and be detected by the detector 766.

Figure 23B:
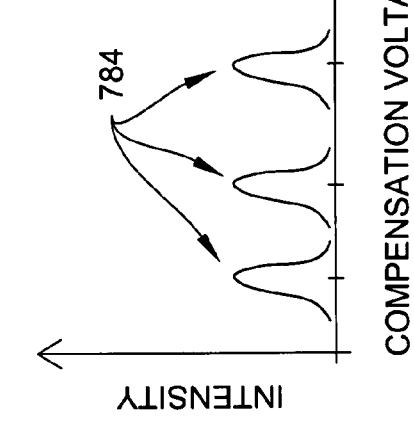
FIG. 23B is a graph of ion intensity versus field compensation voltage showing peak detection for the DMS system of FIG. 22 using fragmentation.
Figure 23A:
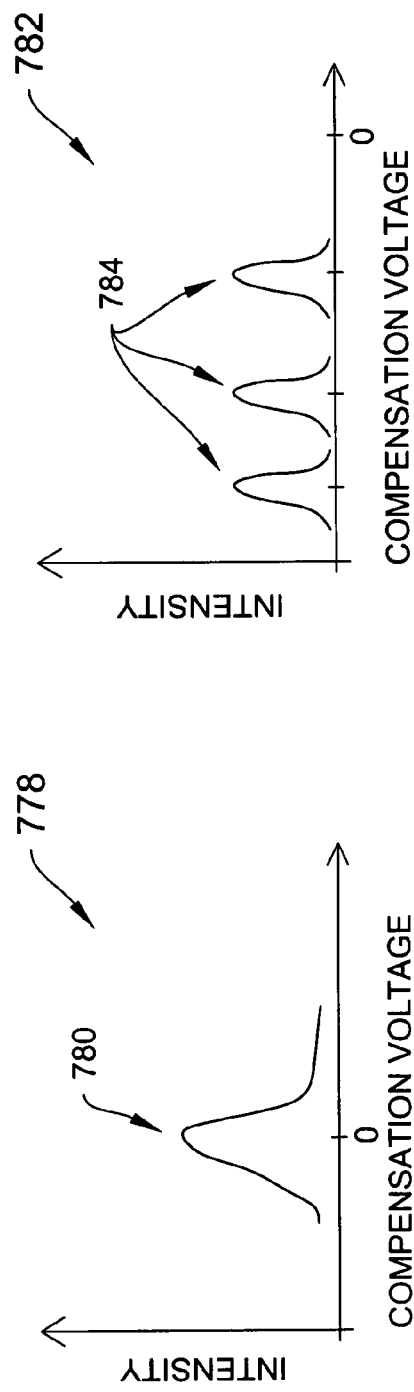
FIG. 23A is a graph of ion intensity versus field compensation voltage showing peak detection for the DMS system of FIG. 22 not using fragmentation.

FIG. 23A is a graph 778 of ion intensity (y-axis) versus Vcomp x-axis) showing peak detection for the DMS system 750. As shown previously, when no fragmentation occurs, the relatively heavy sample molecules cluster to form a peak 780 at Vcomp=approximately 0 Vdc.

After analysis by the DMS system 750, the sample S is delivered to the DMS system 752, where the sample S is ionized by an ionization source 770, and also fragmented by the fragmentation source 772. The fragmentation source 772 may be a radioactive source, a high energy voltage source or the like with enough energy to break up the relatively large sample molecule into a plurality of fragment molecules, fragments, components, or atoms. Then, the fragments are delivered to the ion filter 774 whereupon a combination of filter field voltages Vrf and field compensation voltages Vcomp applied a plurality of filter field conditions to the fragments to filter them before detection by the detector 776.

FIG. 23B is a graph 782 of ion intensity versus compensation voltage showing peak detection for the DMS system 752 of FIG. 22 using fragmentation. As shown previously, when fragmentation occurs, the relatively lighter fragments form a plurality of ion intensity peaks 784 at various distinct field compensation voltages Vcomp.

Thus, the serial detection system 754 using the DMS systems 750 and 752 may improve sample analysis by serially detecting a sample S and its fragments to create a more complete signature or fingerprint of the sample. Alternatively, the serial detection system 754 may selectively compare the fragmentation spectra depending on the sample species to be detected and the need for better discrimination from other interferants or compounds.

Figure 24:
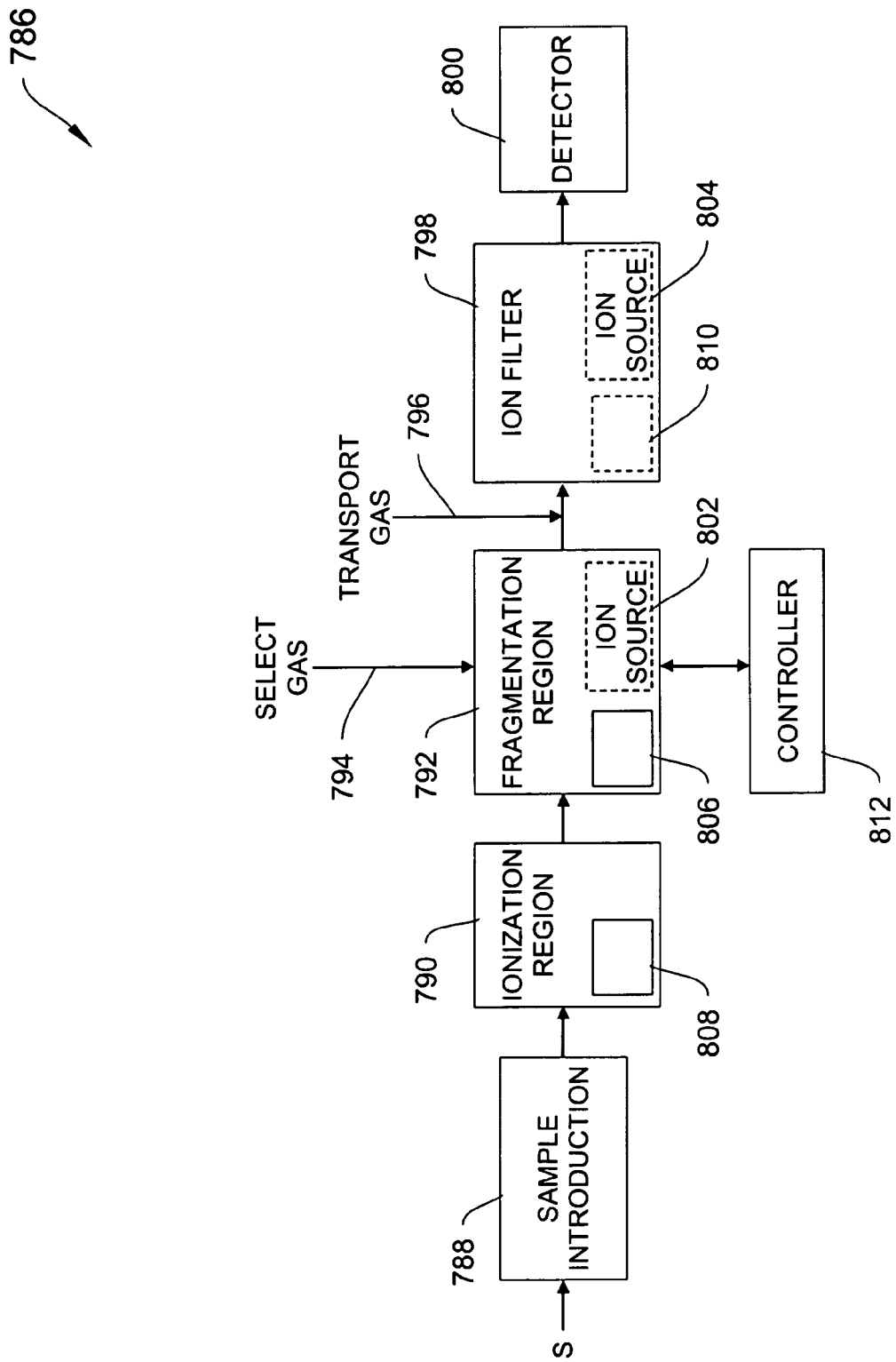
FIG. 24 is a conceptual block diagram of a DMS system including a fragmentation region according to an illustrative embodiment of the invention.

FIG. 24 is a conceptual block diagram of a DMS system 786 including a fragmentation region 792 according to an illustrative embodiment of the invention. As shown, the DMS system 786 includes a sample introduction region 788, ionization region 790, fragmentation region 792, fragmentation source 806, fragmentation effluent inlet 794, transport effluent inlet 796, ion filter 798, detector 800, and controller 812. An ionization source 802 may optionally be located within the fragmentation region 792. An ionization source 804 may optionally be located within ion filter 798.

In operation, a sample S is introduced into sample introduction region 788. The sample introduction region 788 may perform pre-separation of the sample S to reduce the amount of interferants or unwanted compounds. The ionization source 808 then ionizes the sample S in the ionization region 790. Once the sample S is delivered to the fragmentation region 792, the fragmentation source 806 fragments the relatively heavy molecules of the sample S into a plurality of lighter fragments. Alternatively, a fragmentation gas including fragmentation molecules may be introduced into fragmentation region 792 via fragmentation gas inlet 794. The fragmentation gas molecules, upon colliding with the sample S molecules, cause a portion of the sample S molecules to break up into sample S fragments.

After fragmentation, a transport effluent, such as a carrier gas CG may be introduced via the transport effluent inlet 796 to deliver the sample S fragments to the ion filter 798. After filtering, the fragments are then detected by the detector 800. The ionization source 802 may optionally be located in the fragmentation region 792. Furthermore, as in the case of all of the previously described illustrative embodiments, the fragmentation source 806 may function additionally as a ionization source. The ionization source 804 may optionally be located in the ion filter 798. Furthermore, the ion filter 798 may also act as either a fragmentation source 810 or an ionization source 804.

It should be noted that although the previously described embodiments refer to separate ionization and fragmentation sources, in other illustrative embodiments, a single source may attend to both fragmentation and ionization. Additionally, any of the previously described fragmentation approaches may be employed in addition to or in replacement of the fragmentation sources of FIGS. 21, 22 and 24. The controller 821 may switch fragmentation on and off as needed by activating or deactivating the fragmentation source 806 or by introducing or not introducing a fragmentation effluent via fragmentation effluent inlet 794.

The foregoing fragmentation techniques and system implementing these fragmentation techniques may be used to enhance the detection of a sample S, such as without limitation, Sarin gas, also known as:

GB
Zarin
Phosphonofluoridic acid, methyl-, isopropyl ester
Phosphonofluoridic acid, methyl-, 1-methylethyl ester
Isopropyl methylphosphonofluoridate
Isopropyl ester of methylphosphonofluoridic acid
Methylisoproposfluorophosphine oxide
Isopropyl Methylfluorophosphonate
0-Isopropyl Methylisopropoxfluorophosphine oxide
0-Isopropyl Methylphosphonofluoridate
Methylfluorophosphonic acid, isopropyl ester
Isoproposymethylphosphonyl fluoride Sarin, a colorless and odorless gas, has a lethal dose of 0.5 milligram for an adult. It is 26 times more deadly than cyanide gas and is 20 times more lethal than potassium cyanide. Just 0.01 milligram per kilogram of body weight in a pinprick sized droplet will kill a human.

Figure 25:
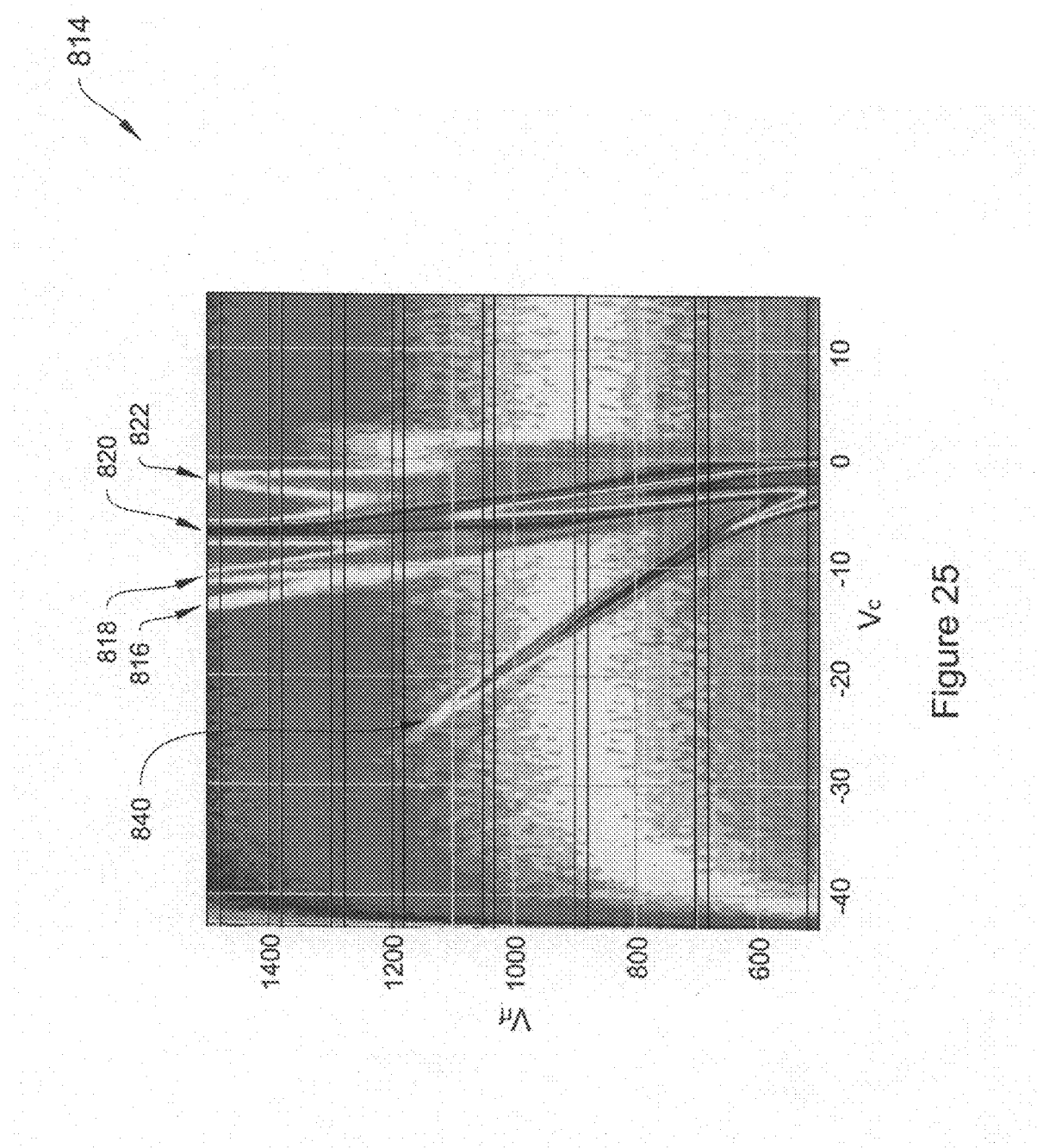
FIG. 25 is a three-dimensional color dispersion plot illustrating detection of agent GA according to an illustrative embodiment of the invention.
Figures 26C, 26D:
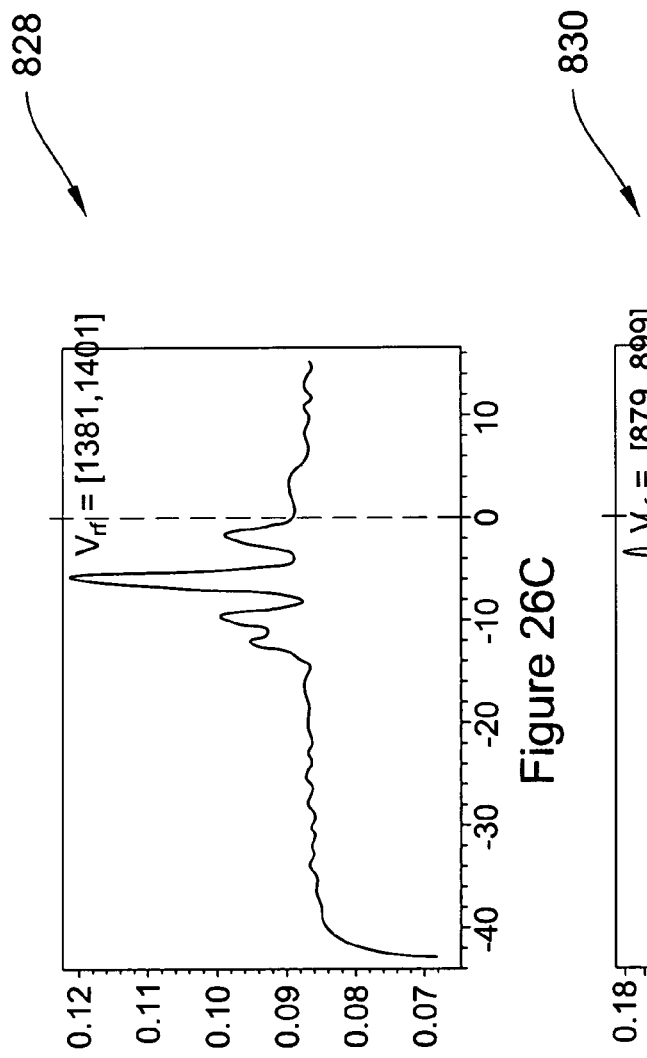
Figure 26G:
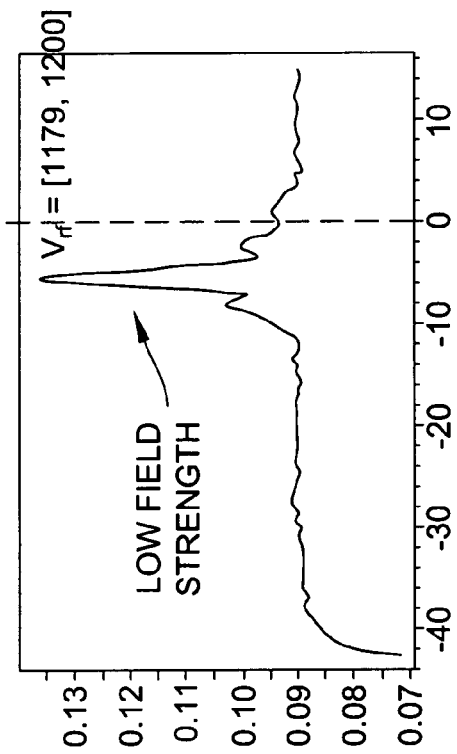
Figure 26H:
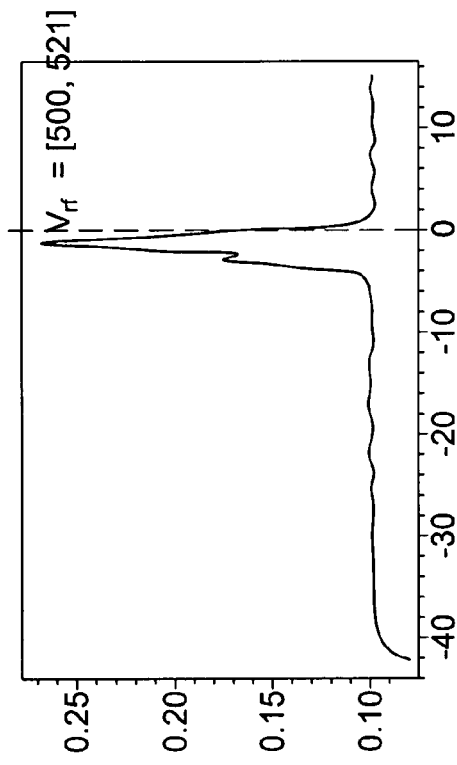

FIG. 25 is a three-dimensional color dispersion plot 814 of the type described above with respect to FIGS. 15A-18 and illustrating detection of agent GA over a range of field voltages Vrf and field compensation voltages Vcomp with varying ion intensity presented in varying color according to an illustrative embodiment of the invention. The color dispersion plot 814 includes branches 816, 818, 820, and 822 that represent the detection of fragments of agent GA using, for example, DMS system 786 having a $Ni^{63}$ ionization source for fragmentation of the GA sample at 0.14 ng/l. The branch 840 represents an original peak before fragmentation.

FIGS. 26A-26H depict two-dimensional graphs 824, 826, 828, 830, 832, 834, 836, and 838 of ion intensity (y-axis) versus Vcomp x-axis), each at a particular Vrf. As described above with respect to FIGS. 15A-18, the two-dimensional graphs 824, 826, 828, 830, 832, 834, 836, and 838 are aggregated into the three-dimensional color dispersion plot 814 of FIG. 25. As discussed previously, the color dispersion plot 814 improves the analysis process of a particular species such as agent GA or GB, for example, because it takes into account peak shifts due to changes in Vrf, and because the color nature of the three-dimensional dispersion plot 814 makes more evident the signature behavior of particular ion species in relation to other ion species, especially after fragmentation.

As described above with respect to FIGS. 15A, 16A, and 17, the dispersion plot of FIG. 25, may employ color saturation, gray scale variations, black and white variations and/or peak outlines in place of the color variations depicted.

The fragmentation techniques described herein are not limited to DMS systems and may be employed with other mobility-based detection systems such as ion mobility spectrometry (IMS), time of flight (TOF) IMS, gas chromatography (GC), Fourier transform infrared (FTIR) spectroscopy, mass spectrometry (MS), liquid chromatography mass spectrometry (LCMS), surface acoustic wave (SAW) sensors, and the like.

Another technique for improving ion species detection, identification and analysis generally is operating the mobility-based detection system, such as any of the systems described herein, below atmospheric pressure. By operation below atmospheric pressure, the separation between ion intensity detection peaks is increased and the width of the peaks is narrowed. This provides improved resolution, resulting in improved system discrimination and sensitivity. By operating, for example a DMS system at various pressure conditions, the change in ion species behavior with respect to pressure may be measured and used as another characteristic for identifying ion species. According to various illustrative embodiments, the invention performs ion scans at pressures between about 0.2 and about 0.9 atmospheres, less than about 0.3 atmospheres, less than about 0.4 atmospheres, less than about 0.5 atmospheres, less than about 0.6 atmospheres, less than about 0.7 atmospheres, or less than about 0.8 atmospheres.

Figure 27A:
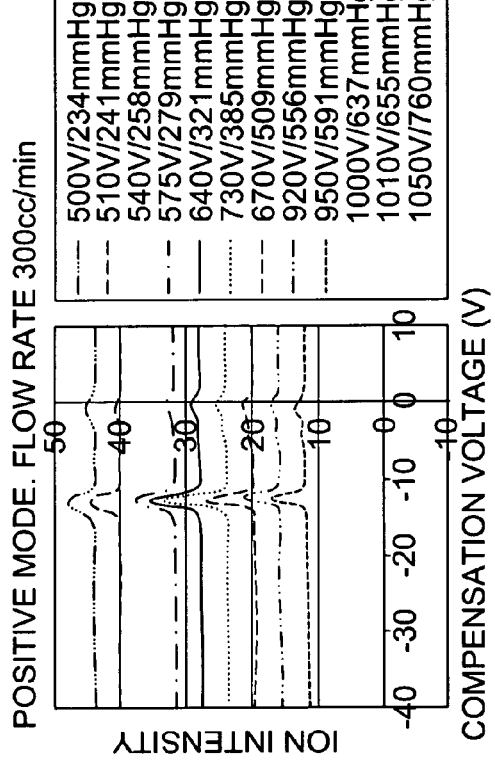
FIGS. 27A and 27B are graphs of ion intensity at a plurality of pressures versus field compensation voltage according to an illustrative embodiment of the invention.

FIG. 27A is a graph 840 of background (RIP) ion intensity versus field compensation voltage at a plurality of pressures for a DMS system in positive ion detection mode according to an illustrative embodiment of the invention. The graph 840 shows that the field voltage may be adjusted to maintain the ion intensity peak within the same compensation voltage position as the pressure within a DMS system is adjusted. More specifically, according to the graph 840, as the pressure decreases, the field voltage decreases to maintain the ion intensity peak for a species at the same compensation voltage. Furthermore, changes in pressure at lower pressures result in the need for greater changes in field voltage to maintain a constant compensation voltage. For example, when reducing the pressure by approximately 100 mmHg from 760 mmHg to 655 mmHg, the reduction in field voltage is approximately 40 Vpeak from about 1050 Vpeak to about 1010 Vpeak. For approximately the same pressure reduction from 655 mmHg to 556 mmHg, the reduction in Vrf is approximately 90 volts from about 1100 Vpeak to about 920 Vpeak. Thus, the field voltage decrease is approximately twice as great for changes in pressure in the 600 mmHg range, which indicates that the resolution is improved at reduced pressure.

Figure 27B:
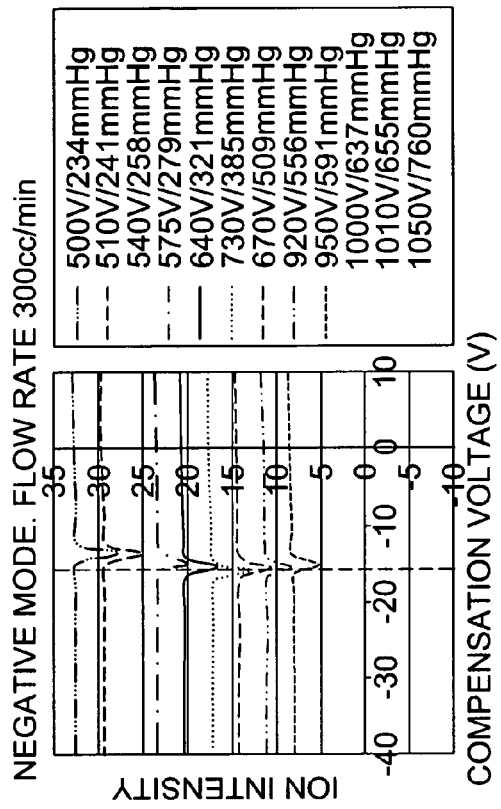

FIG. 27B is a graph 842 of background (RIP) ion intensity versus field compensation voltage at a plurality of pressures for a DMS system in negative ion detection mode according to an illustrative embodiment of the invention. Like positive mode graph 840, the graph 842 shows that, in negative detection mode, the field voltage may be adjusted to maintain the ion intensity peak within the same compensation voltage position as the pressure within a DMS system is adjusted.

As shown by comparing the graph 840 with the graph 842, there is an offset in the ion intensity peak between the positive mode ion intensity peaks of graph 840 and negative mode ion intensity peaks of graph 842 at the same pressure and field voltage. This offset may indicate a difference in the alpha parameter between positive and negative mode detection for an ion species. The alpha parameter is discussed in further detail below. The DMS flow rate is approximately 300 cc/min in graphs 840 and 842.

FIGS. 28A and 28B depict graphs 844 and 846, respectively, of ion intensity (y-axis) versus pressure x-axis) showing a quantifiable effect on positive and negative background spectra, respectively, caused by a decrease in pressure according to an illustrative embodiment of the invention. More specifically, the graph 844 shows that field voltage is decreased by about 50% when pressure is decreased to about 0.3 atmosphere (atm). The graph 846 also shows a similar field voltage decrease of about 50% when pressure is decreased to about 0.3 atm.

FIGS. 29A and 29B depict graphs 848 and 850, respectively, showing ion intensity (y-axis) versus field compensation voltage x-axis) for a plurality of pressures and showing the effect of varying pressure on negative and positive tert-butylmercaptan and tert-butylithiol (TBM) spectra, respectively. While the graphs 848 and 850 show that field voltage decreases as pressures decrease for a particular field compensation voltage, the graphs 848 and 850 also show that the ion intensity peak positions for TBM spectra shift in the opposite direction as the ion intensity peak shifts for the background (RIP) spectra of graphs 840 and 842. Furthermore, the level of change of the ion intensity peaks in graphs 848 and 850 for TBM spectra is less than the level of change of the ion intensity peaks in graphs 840 and 842 for background spectra.

Figure 30A:
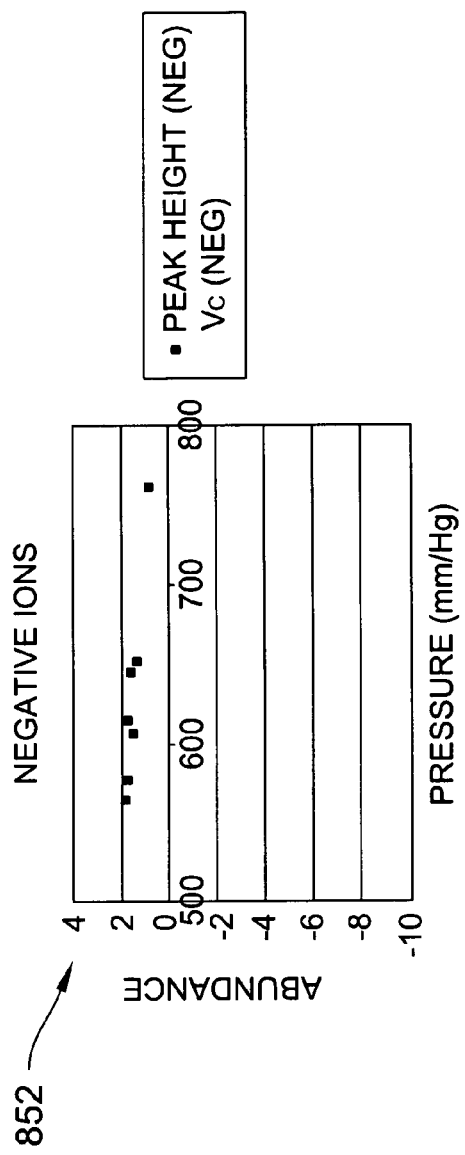
FIGS. 30A and 30B are graphs of ion intensity versus pressure showing the effect of varying pressure on negative and positive TBM ion peak parameters, respectively, according to an illustrative embodiment of the invention.
Figure 30B:
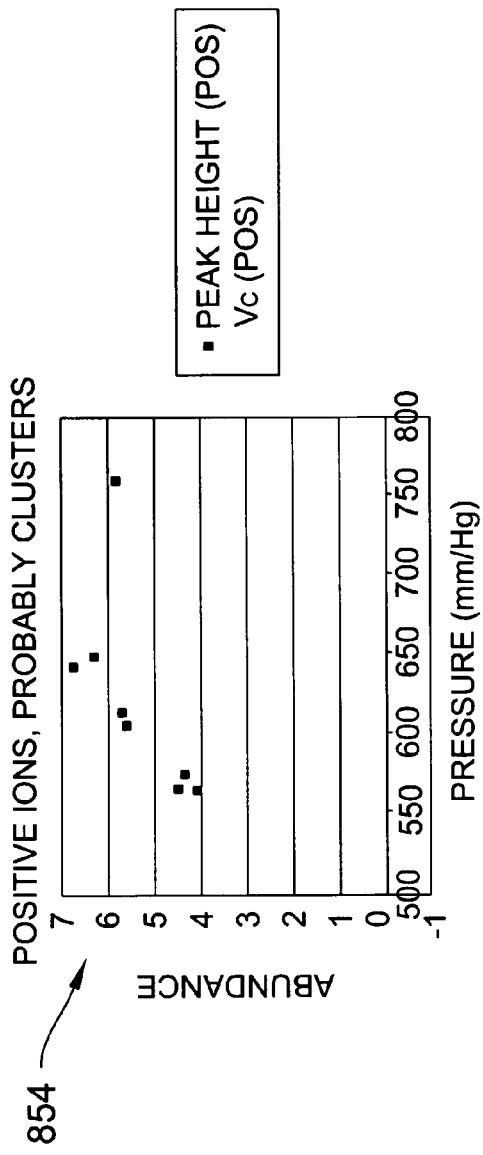

FIGS. 30A and 30B depict graphs 852 and 854 showing ion intensity (y-axis) versus pressure x-axis) and showing the effect of varying pressure on negative and positive TBM ion peak parameters, respectively. More specifically, the graph 852 shows that the ion intensity peak remains relatively constant as the pressure is varied for negative ion spectra. The graph 854 shows that the ion intensity peak remains relatively constant with the level decreasing slightly at a lower pressure for positive spectra. Because changes in pressure impact the background (RIP) and analyte spectra differently, pressure may be manipulated, regulated, or otherwise controlled in such a manner as to improve the ability of a DMS system to detect and identify ion species with better resolution while minimizing the negative effects of background spectra interference.

In certain embodiments, it may be desirable to maintain uniform detection results by maintaining a constant ratio of electric field strength to gas density N or pressure P where the ratio is expressed as E/N or E/P. Thus, when the gas operating pressure within a DMS system is decreased, the field voltage is correspondingly lowered to maintain a constant E/N or E/P. This reduction in field voltage results in a reduction in power consumption which, in turn, results in smaller, lighter weight, and lower cost detection systems.

Figure 31:
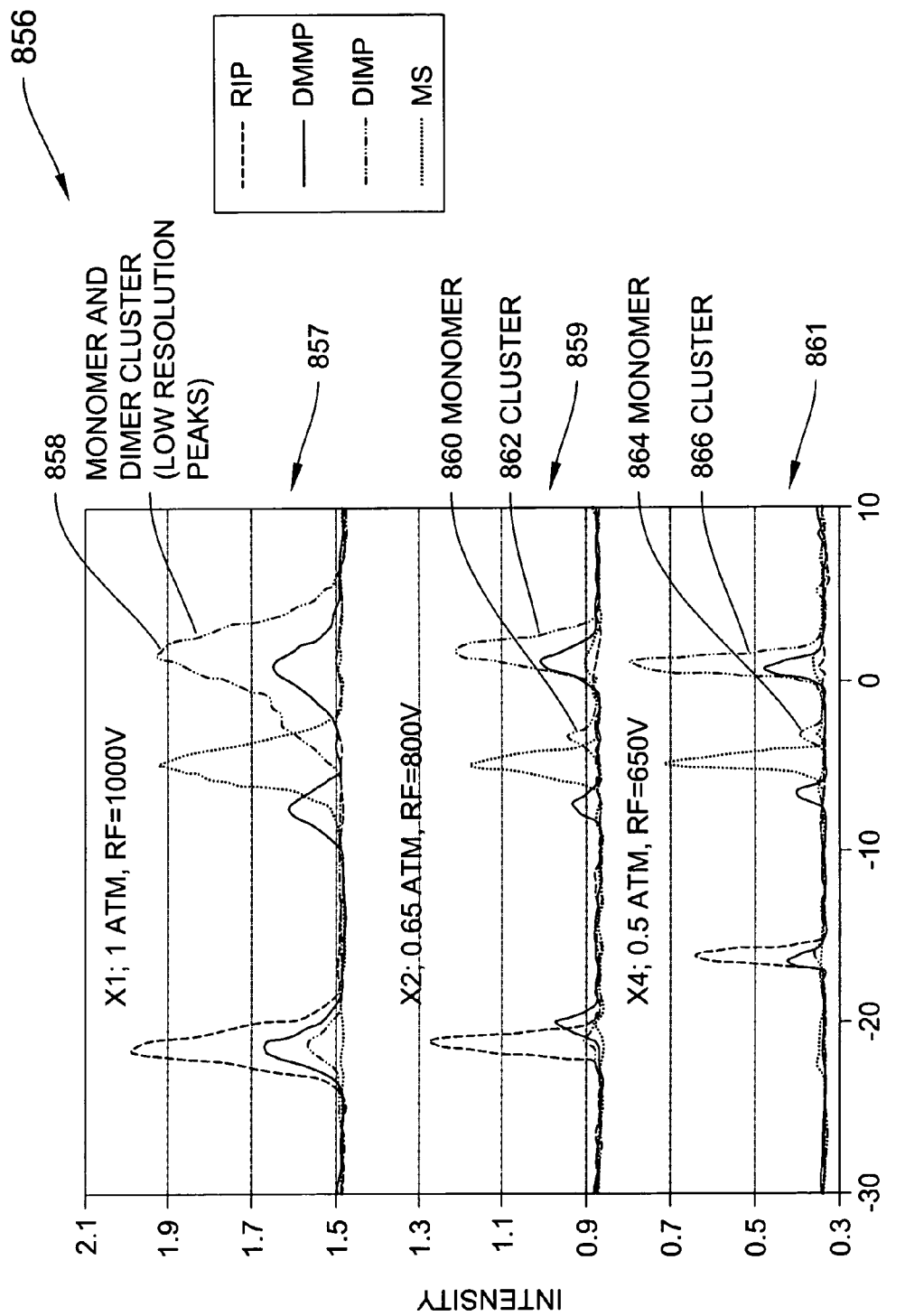
FIG. 31 is a graph that shows the effect of reduced pressure on analyte peaks for chemical warfare agents such as DMMP, DIMP, and MS.

FIG. 31 is a graph 856 showing the effect of reduced pressure on analyte peaks for chemical warfare agents, such as DMMP, DIMP, and MS. The top graph 857 shows the ion intensity results at atmospheric pressure, while the bottom two graphs 859 and 861 show the results at 0.65 and 0.5 atm, respectively. At 1 atm with field voltage at Vrf=about 1000 Vpeak, the top spectra shows the overlap 858 of monomer and dimmer cluster peaks for DIMP over a range of about 10 Vdc field compensation voltage. But at 0.65 atm and Vrf=about 800 Vpeak, the monomer peak 860 and cluster peak 862 are separated with the monomer peak 860 at Vcomp=about −3 Vdc and cluster peak 862 at Vcomp=about +1 volt. At 0.5 atm and Vrf=about 650 Vpeak, the DIMP monomer peak 864 and DIMP cluster peak 866 are each narrower with the peaks 864 and 866 at Vcomp=about −2.5 Vdc and about +1 Vdc, respectively. The narrower peaks 864 and 866 at 0.5 atm result in higher resolution for a DMS system.

FIGS. 32A-32D depict graphs 868, 870, 872, and 874, respectively, showing ion intensity (y-axis) versus Vcomp x-axis). The graphs 868, 870, 872 and 874 show improved detection resolution for agent GF at reduced pressures, according to an illustrative embodiment of the invention. The graphs 868 and 870 show the ion intensity spectra of agent GF at Vrf of 1500 and 1000 Vpeak, respectively, at 1 atm. The graphs 872 and 874 show the ion intensity spectra of agent GF at Vrf of 1000 and 750 Vpeak, respectively, at 0.5 atm. According to the graph 870, the monomer and dimer peaks overlap at peak 876 at Vrf=about 1000 Vpeak. According to the graph 868, however, the monomer peak 878 and dimer peak 880 are separated at Vrf=about 1500 Vpeak. Thus, DMS system resolution may be increased by increasing the field voltage (Vrf).

In the graph 872, the DMS system pressure is reduced to about 0.5 atm with Vrf at about 1000 Vpeak. The graph 872 shows the monomer peak 882 clearly isolated from any dimer peak, because the cluster or dimer RIP peaks are off-scale of the graph 872. In the graph 874, the field voltage Vrf is reduced to about 750 Vpeak, with a system pressure at about 0.5 atm. The graph 874 shows clear separation of the GF monomer peak 884 from the dimer peaks 886 and RIP peak 888. Thus, GF may be detected and identified by the signature peaks illustrated in graph 874 in a DMS system utilizing reduced pressure, reduced field voltage, and, therefore, reduced power.

As described above, three-dimensional color dispersion plots may be used to significantly enhance the ability of a DMS system to detect and identify ion species of interest by allowing a user or pattern recognition program to match the color patterns against a library of similar color pattern for known compounds.

Figures 33, 34:
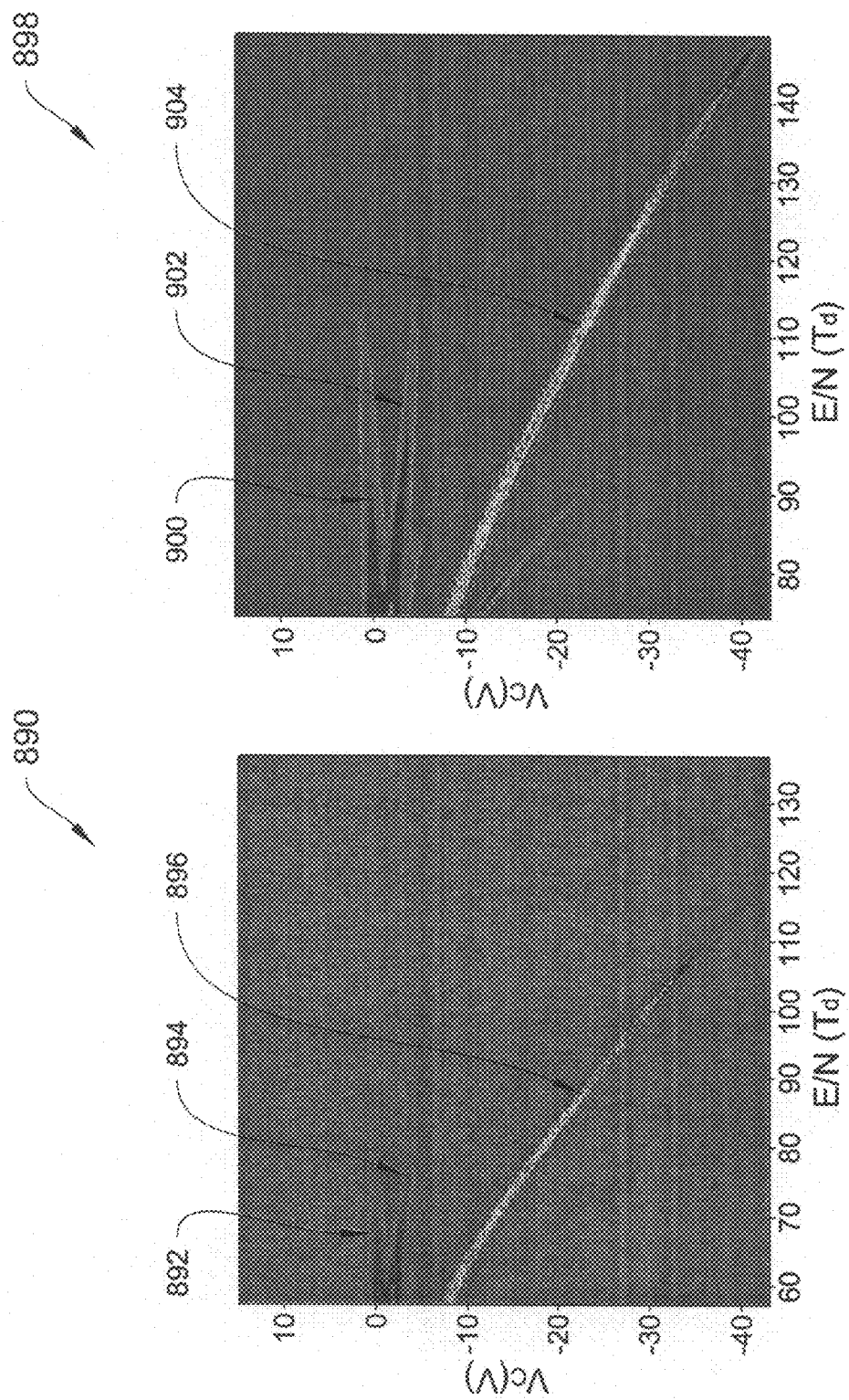
FIG. 33 is a three-dimensional color dispersion plot illustrating detection of positive ions of 0.005 $mg/m^3$ DIMP at about 0.65 atm and over a range of field voltages and field compensation voltages with varying intensity depicted by varying colors.
FIG. 34 is a three-dimensional color dispersion plot illustrating detection of positive ions of 0.005 $mg/m^3$ DIMP at about 0.5 atm and over a range of field voltages and field compensation voltages with varying intensity depicted by varying colors.

FIG. 33 is a three-dimensional color dispersion plot 890 depicting intensity of positive ions of 0.005 mg/m$^3$ DIMP at about 0.65 atm and over a range of field strengths, gas densities (E/N) and field compensation voltages Vcomp. As shown, gas density is plotted on the x-axis, Vcomp is plotted on the y-axis, and variations in intensity depicted by variations in color. The plot 890 includes several prominent branches 892, 894, and 896.

FIG. 34 plots the same information as FIG. 33, except as obtained at a decreased pressure of about 0.50 atm. As shown in plot 898, the reduction in pressure in relation to plot 890 results in significantly more prominent branches 900, 902, and 904, thus providing enhanced resolution.

Figure 35:
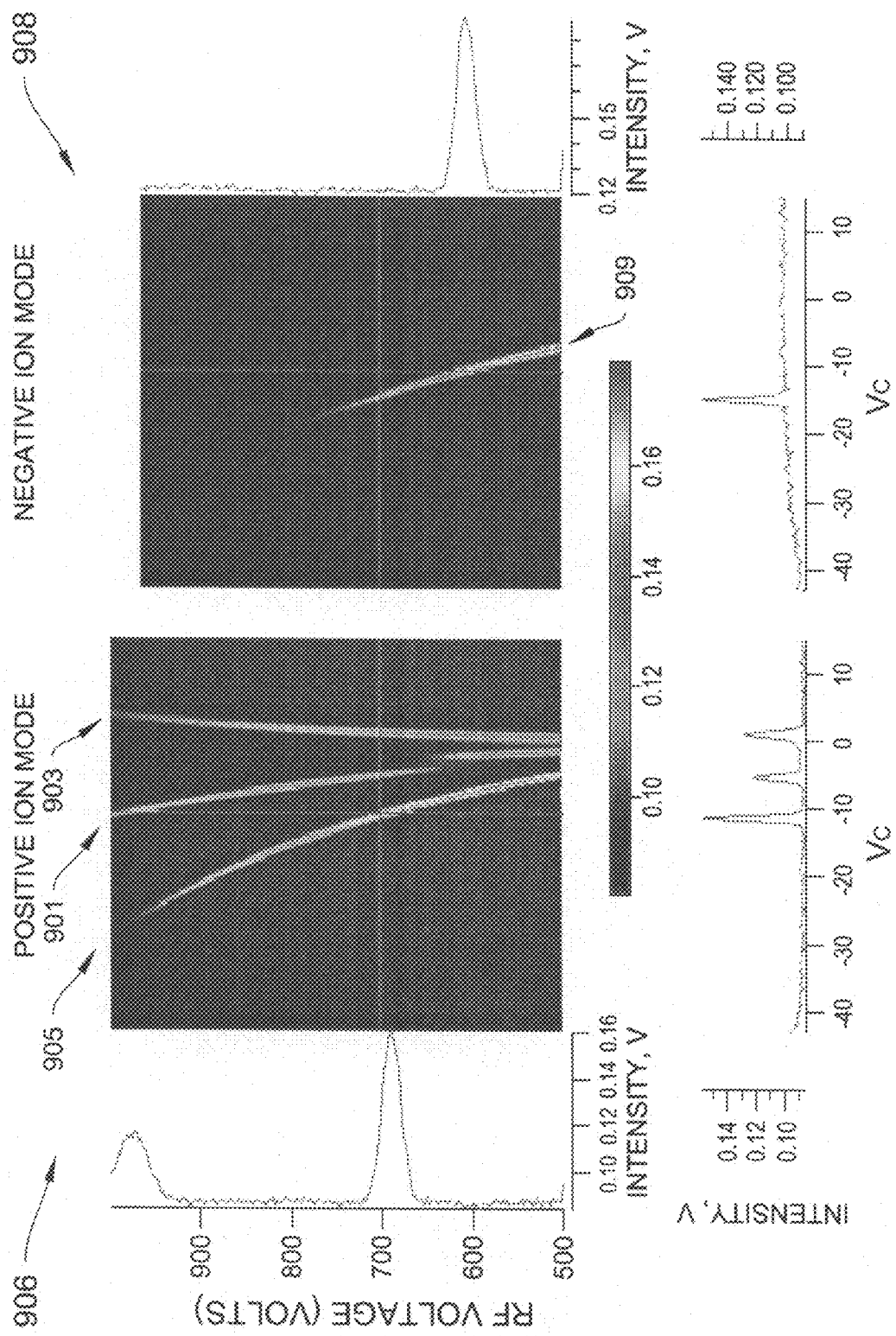
FIG. 35 is a graph that shows positive (left) and negative (right) three-dimensional color dispersion plots for 0.85 $mg/M^3$ agent GB with a relative humidity (RH)=87 in a DMS system operating at 0.5 atm and for a fragmented sample.

FIG. 35 is a graph depicting positive (906) and negative (908) mode three-dimensional color dispersion plots for about 0.85 mg/m³ of agent GB RIP, at a relative humidity (RH)=about 87%, in a DMS system operating at about 0.5 atm for a fragmented sample. The negative mode plot 908 shows only a single strong RIP branch 909, while the positive mode plot 906 shows two strong trace analyte peaks 901 and 903 to the right of the heavy background RIP branch 905. Thus, plotting three-dimensional graphs for both the positive and negative ion species of a sample provides further enhanced ion species identification over three-dimensional plots of positive or negative mode measurements alone.

The three-dimensional color dispersion plots 906 and 908, as illustrated above, may also show discontinuities in the branches, i.e., peak plots or traces, that are also useful for species identification. For example, the plot 906 includes a break in the trace or branch 901 that may be included as part of the stored signature for future comparisons.

As described above with respect to FIGS. 15A, 16A, 17 and 25, the dispersion plots of FIGS. 33 and 35, may employ color saturation, gray scale variations, black and white variations and/or peak outlines in place of the color variations depicted.

Figures 36A, 36B:
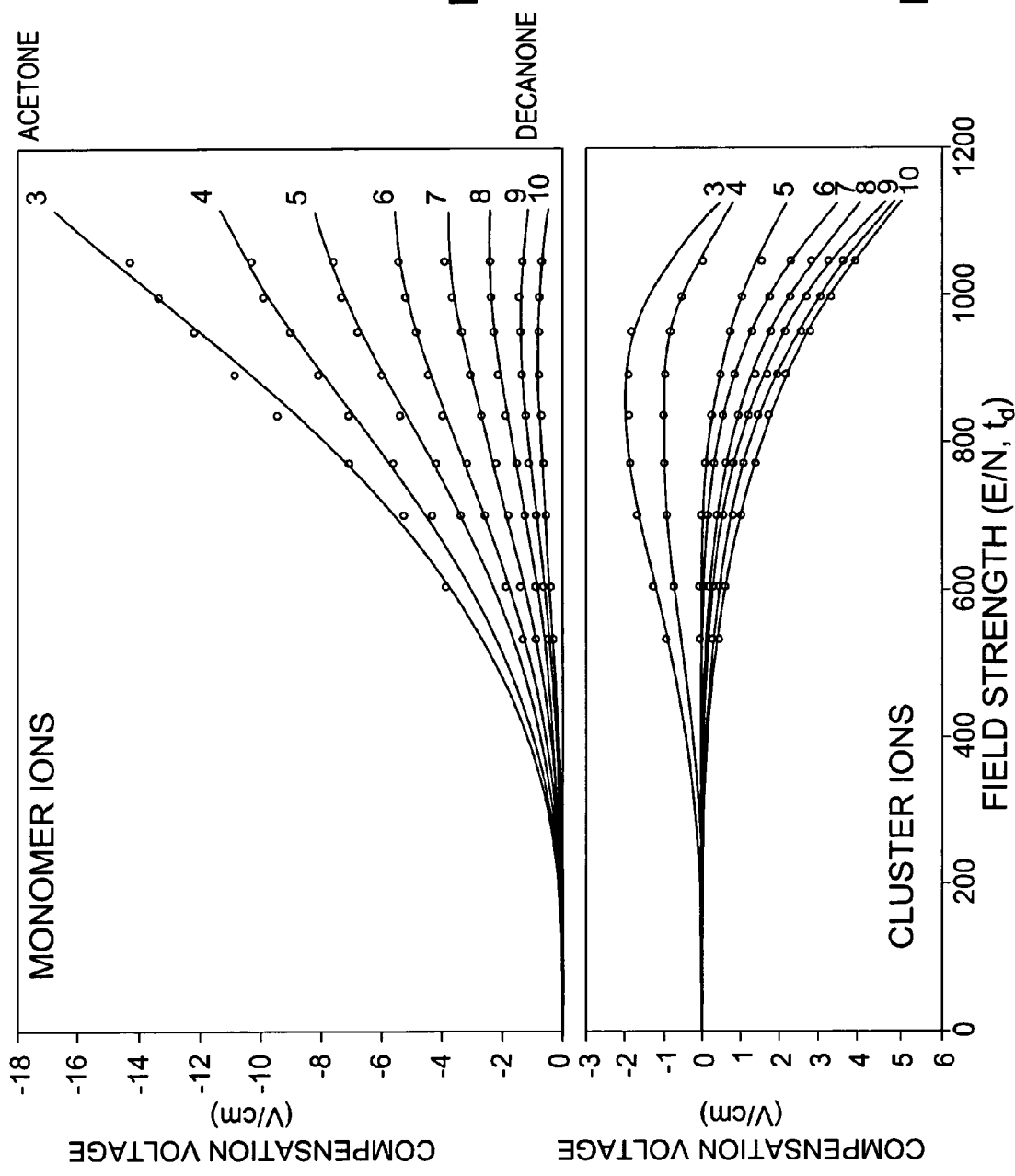
FIGS. 36A and 36B are graphs that show a plot of compensation versus field strength of detected monomer and cluster ion peaks for a family of ketones according to an illustrative embodiment.

According to another feature, the identification above described analysis approaches may be made device-independent. FIGS. 36A and 36B show experimental detection data for a homologous group of ketones, including: acetone, butanone, pentanone, hexanone, heptanone, octanone, nonanone, decanone. FIGS. 37 and 38 are tables showing monomers and clusters, respectively, for the above listed keytone species. As shown in FIGS. 36A and 36B, each species has a unique mobility curve, and thus a unique mobility signature, for the given set of field conditions. As described above, the mobility signatures may be obtained and enhanced in any of a plurality of ways. However, the identification process can be further enhanced by making it device-independent. With device independence, signature data can be created that can be used on any device. According to one illustrative embodiment, the invention accomplishes this by determining the parameters of a function derived from the fundamental mobility coefficient associated with each species.

Therefore, for example, the multiple data represented in FIGS. 36A, 36B, 37 and 48 each can be used to provide positive identification of a detected species by the unique and inherent mobility characteristic that identifies that species. According to one feature, the comparison can be made to a lookup library specific to the device in question, but also can be made to a universal set of data that is device-independent. Thus, in general, one does not wish to only compare the plot of abundance curves versus compensation voltage individually, but rather generate a plot of observed peak locations for specific compensation voltages, so that curves, slopes, signs, and various details can be discerned for each of the detected ions for comparison to a library of lookup data.

More specifically, in computing mobility signatures, we have found that an expression of the field-dependence of ion mobility, the so-called α coefficient, expressed as a function of field, can be used to generate a unique α function that is inherent for that species and is device independent. Thus the α function can be used as the unique signature of a species; this function expresses both a characteristic signature for the ion species and is device independent. In short, according to one feature, the invention recognizes that peaks change position in signature ways because they have different alpha signatures.

In one illustrative embodiment, the invention employs the a function as a mobility signature for detected species. The signature can be determined for a detected unknown compound, based on the field conditions that are used, and then this can be used to make an identification according to a lookup table of stored known signature data associated with known compounds. More particularly, in practice of a preferred embodiment of the invention, ion species are identified based on the mobility dependence of the species under various field conditions. Data is collected for the sample under test for at least two field conditions, the data is processed, and a comparison of detection data computed as an a function for the sample under test versus the stored data enables identification of the compounds in the sample.

Figure 3:
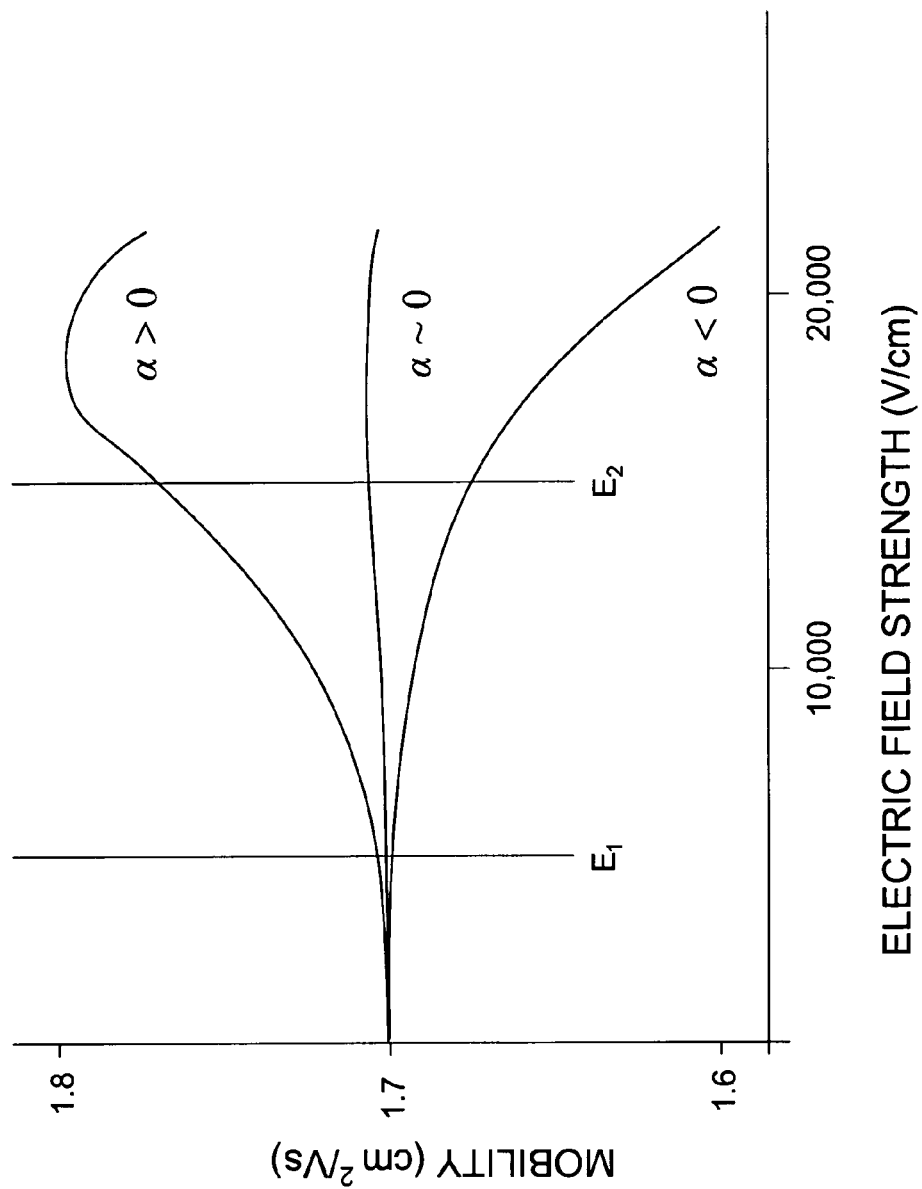
FIG. 3 is a graph of ion mobility versus electric field strength for three different compounds in a differential mobility spectrometer (DMS).

Referring again to the discussion of the α parameter, FIG. 3 is a plot of mobility versus electric field strength for three examples of ions, with field dependent mobility (expressed as the coefficient of high field mobility, α) shown for species at α greater, equal to and less than zero. For any given set of field conditions, the field strength and compensation can be correlated with an a value. This is shown in the work of Buryakov et. al., *A New Method Of Separation Of Multi-Atomic Ions By Mobility At Atmospheric Pressure Using A High-Frequency Amplitude Asymmetric Strong Electric Field, Intl J. MassSpec and Ion Proc.* (1993), at p. 145.

We have observed that knowing the α parameter alone at a particular field strength does not prevent false positives. This would occur at the intersection of the two plots in FIG. 4, at the point indicated by reference numeral 100. Without more information, knowledge of the a parameter for the respective ion species at that location does not provide unique mobility signatures for both compounds. Thus, without doing more, any number of readings at this intersection is likely to result in a detection error.

However, we have also found that we can express an ion's α mobility characteristic as a function of field, i.e., as α(E), and can define a unique mobility signature for the ion species which is device-independent. This α(E) or "alpha function" relates the size, effective cross-section, shape, and mass of the ion to field conditions. It is understood that as the applied electric field increases, the increasing electric field tends to displace, stretch, and/or break the bonds of the ion such that the stronger the field, the greater the induced dipole, quadripole, or higher order moments of the ion. These, in turn, affect the relative mobility of the specific ion. The result of relating these aspects is to define a unique mobility signature for the ion species of interest. This also turns out to be device-independent.

The relationship of the α(E) function to field conditions is shown in the following:

$$V_c(E) = \frac{<\alpha E_s f(t)>}{1 + <\alpha> + <\frac{d\alpha}{dE}E_s f(t)>} \quad (1)$$

where: Vcomp (peak position); Es-electric field strength; f(t)-waveform parameters (wave shape and so forth).

Thus, for each spectral detection, we can compute α as a function of field conditions, i.e., α(E). Specifically, the asymmetric waveform in a planar field asymmetric waveform mobility spectrometer, $E_{max}(t)=E_{max}f(t)$, is designed to satisfy the following conditions:

$$1/T \int_0^T E_s(t)dt = <E_s f(t)> = 0 \quad (3a)$$

$$<f^{2n+1}(t)> \neq 0 \quad (3b)$$

where $f(t)$—is a normalized function which describes the waveform, and $E_{max}$ is the maximum amplitude of the waveform. The waveform is designed such that its average value is zero (equation 3a) while the polarity of the electric field during one period is both positive and negative. The addition of the compensation field, C, to the waveform $E_s(t)$ yields Equation 4:

$$E(t)=E_s(t)+C=E_s f(t)+C \quad (4)$$

so the average ion velocity over a period of the asymmetric waveform can be written as:

$$V=<V(t)>=<K(E)E(t)> \quad (5)$$

Only ions with average velocity of zero, v=0, will pass through the gap without neutralization. An expression for the compensation field required to enable an ion to pass through the gap can be obtained by substituting Equations 2, 3, and 4 into Equation 5 as shown in Equation 6:

$$C = \frac{<\alpha E_s f(t)>}{1+<\alpha.>+<\frac{d\alpha}{dE}E_s f(t)>}. \quad (6)$$

The value of this compensation electric field can be predicted precisely when the alpha parameter for the ion species, the waveform $f(t)$, and the amplitude of the asymmetric waveform $E_{max}$ are known.

A procedure for extraction of $\alpha(E)$ from experimental measurements of the electric field dependence of the mobility scans is thus known. In this section, some additional considerations regarding the alpha parameter and methods to determine this parameter are described. First, emphasis must be given that the alpha parameter is a function (not a number) and the physical and chemical information about an ion is contained in the shape of the $\alpha(E)$ curve. The method of representing this curve is incidental to the topic. The only criterion critical in these methods is that the calculated values for mobility (i.e. $K(E)=K_o\{1+\alpha(E)\}$) should be as close as possible to the experimental values. The function for $\alpha(E)$ can be represented as an even power series or in complex form. In either instance, the curves of experimental results and calculations should agree closely. Thus, the quality of the approximation is limited by the accuracy of the experimental results and has been illustrated. Discerning the quality of a model based upon two parameters, three parameters, or a nonlinear function with five parameters was difficult. All approximations were located within the error of $\Delta C_1$ (at ±9%).

In this work, a simple uniform method is described to represent the function of $\alpha(E)$, which will be suitable for comparison of results obtained under different experimental conditions. These methods could be used for differing asymmetric waveforms or different designs of IMS drift tubes: linear, cylindrical, or planar DMS. In general then, the criteria for choosing the level of approximation of alpha is first to ensure that the method of extracting the alpha parameter uses the least number of individual parameters of the experimental device. Second, the result should contain the fewest number of adjustable parameters, and the approximation curves should be within the experimental error bars. In the next section, the general method to extract the alpha parameter is described and then applied in the subsequent section.

The function of $\alpha(E)$ can be given as a polynomial expansion into a series of electric field strength E degrees as shown in Equation 7:

$$\alpha(E) = \sum_{n=1}^{\infty} \alpha_{2n} \cdot E^{2n} \quad (7)$$

Substituting Equation 7 into Equation 6 provides a value of the compensation voltage as shown in Equation 8 where an uneven polynomial function is divided by an even polynomial function. Therefore an odd degree polynomial is placed after the identity sign to approximate experimental results:

$$C = \frac{\sum_{n=1}^{\infty} \alpha_{2n} S^{2n+1} \langle f^{2n+1}(t) \rangle}{1+\sum_{n=1}^{\infty}(2n+1)\alpha_{2n} S^{2n} \langle f^{2n}(t) \rangle} \quad (8)$$

$$\equiv \sum_{n=1}^{\infty} c_{2n+1} S^{2n+1} \langle f^{2n+1} \rangle$$

This allows the a comparison of the expected coefficient (approximated) to be compared to the values of alpha parameter as shown in Equation 9:

$$c_{2n+1} = \alpha_{2n} \langle f^{2n+1} \rangle - \sum_{k=1}^{n-1}(2(n-k)+1)c_{2k+1}\alpha_{2(n-k)}\langle f^{2(n-k)}\rangle \quad (9)$$

Alternatively, alpha parameters can be calculated by inverting the formula by using an approximation of the experimental results per Equation 10:

$$\alpha_{2n} = \frac{1}{\langle f^{2n+1}\rangle}\left\{c_{2n+1}+\sum_{k=1}^{n-1}(2(n-k)+1)c_{2k+1}\alpha_{2(n-k)}\langle f^{2(n-k)}\rangle\right\} \quad (10)$$

Any number of polynomial terms (say 2n), in principle, can be determined from Equation 10 though a practical limit exists as the number of polynomial terms in the experimental result of the approximation $c_{2n+1}$ should be higher than the expected number of alpha coefficients $\alpha_{2n}$. Since the size of n depends on the experimental error, the power of the approximation of the experimental curves $C(E_s)$ cannot be increased without limit. Usually N experimental points of $C_i(E_{si})$ exist for the same ion species and experimental data can be approximated by the polynomial using a conventional least-square method. Finally, the number series terms cannot exceed the number of experimental points so increasing the number of series terms above the point where the fitted curves are located within the experimental error bars is unreasonable. In practice, two or three terms are sufficient to provide a good approximation shown in prior findings. The error in measurements must be determined in order to gauge the order of a polynomial for alpha. The sources of error in these experiments (with known or estimated error) were:
1. Error associated with measurement and modeling of the RF-field amplitude (~5%);
2. Error in $C(E_s)$ from a first-order approximation of Equation 4 (~3%), and
3. Error in measuring the compensation voltage (~5-8%).

An approximate error may be ~10% and there is no gain with approximations beyond two polynomial terms; thus, alpha can be expressed as $\alpha(E/N)=1+\alpha_1(E/N)^2+\alpha_2(E/N)^4$ with a level of accuracy as good as permitted by the measurements.

A standard least-square method (regression analysis) was used to approximate or model the experimental findings. For N experimental points with $C_i(E_{si})$ and for $C=c_3S^3+c_5S^5$ a function $y=c_3+c_5x$ can be defined where $y=C/S^3$; $x=S^2$ so $c_5$ and $c_3$ are given by Equations 11 and 12, respectively:

$$c_5 = \frac{\sum_{i=1}^{N} x_i \sum_{i=1}^{N} y_i - N \sum_{i=1}^{N} x_i y_i}{\left(\sum_{i=1}^{N} x_i\right)^2 - N \sum_{i=1}^{N} x_i} \quad (11)$$

$$c_3 = \frac{1}{N}\left(\sum_{i=1}^{N} y_i - c_5 \sum_{i=1}^{N} x_i\right) \quad (12)$$

Through substituting experimental value $c_3$, $c_5$, values for $\alpha_2$ and $\alpha_4$ can be found per Equations 13 and 14:

$$\alpha_2 = \frac{c_3}{\langle f^3 \rangle} \quad (13)$$

$$\alpha_4 = \frac{c_5 + 3c_3\alpha_2\langle f^2 \rangle}{\langle f^5 \rangle} \quad (14)$$

In order to calculate $\alpha_{2n}$, knowledge is needed for the approximations of experimental curves for $C(E_s)$ and for the function $f(t)$—which is a normalized function describing the asymmetric waveform.

For example, nine data points were identified for each of the eight ketones of FIGS. 36A, 36B, 37, and 38, based on the data collected in the tables of FIGS. 37 and 38. These can be used to compute the α curve for that species, such as with a piecewise linear approximation to the α curve. For example, two data points for butanone are a(Vcomp-a, Vrf-a) and b(Vcomp-b, Vrf-b). Between these two points, the slope and sign of the butanone curve can be computed. More complete characterization of the curve, such as with polynomial curve fitting, is also possible.

Now this data set becomes part of a data store for use in identification of the species of an unknown detected ion species for which two data points are collected and the corresponding curve data is computed. In short, in an illustrative practice of the invention, we collect data on at least two closely associated points (peaks) for a given ion sample and generate the curve data accordingly. Once we have the detected and computed data, we assume this approximates the alpha curve and therefore do a lookup to our stored data. Upon finding a match, we can then positively identify the sample.

In FIGS. 39A and 39B (monomers and clusters, respectively) we computed unique α curves for keytone ions (acetone, butanone, pentanone, hexanone, heptanone, octanone, nonanone, decanone) based on data collected in the tables of FIGS. 37 and 38, plotting the percent change in α against the change of field strength for the various data collected. These plots of percent change in α against field strength express a unique signature for each of these ion species. This is loaded in our data store for later comparison: the signature data includes the RF field strength and the compensation voltage at which the peak is detected. We also associate with it the identifying data for the known α function associated with that detected peak location and field conditions for each species.

FIGS. 39A and 39B thus express the a function for individual ketones spanning electric fields of 0 to 80 Td (~23 kV/cm), expressed as a percentage change in alpha as a function of field conditions. These plots are fundamental signature features of these ion species that are independent of the drift tube parameters and can be used in other mobility spectrometers. Thus, the a function can be favorably used in practice of the invention to provide a mobility identification data set that is device-independent.

These results are surprising and demonstrate that for chemicals with the same functional group, protonated monomers of a single type exhibit a broad range of behavior vis-à-vis the dependence of coefficients of mobility on electric fields. This difference in behavior for a common moiety suggests that the effect from the electric field must be associated with other aspects of molecular structure. One possible interpretation is that ions are heated during the high field and the effect on the protonated monomer should be striking. These ions with structures of $(H_3O)^+$ M $(H_2O)_n$, or perhaps $(H_3O)^+$ M $(H_2O)_n(N_2)_2$, should be prone to dissociations with slight increases in ion temperature caused by the high field conditions. Thus, ion cross-sections and mobilities would accompany declustered small ions at high fields.

Referring again to FIG. 39A, it should be noted that there is approximately a 20% increase in α(E) for the protonated monomer of acetone with high fields. As the molecular weight of the keytone is increased, ion heating is less pronounced and reflected in the α(E) function. The α(E) function for proton bound dimers (clusters) is consistent with decreases in mobility under high field conditions. Consequently, the basis for the α(E) function differs from that of protonated monomers. Indeed, the proton bound dimer for decanone undergoes about a 5% decrease at high fields. The cause for a decrease in mobility at high fields has no existing model but should be due to increased collisional size or increased strength of interaction between the ion and the supporting gas.

Furthermore, if we were to do the same for the cyclohexane and DMMP in FIG. 4, the computed alpha curves would differ accordingly. In this manner, the invention can distinguish ion species even when their mobility curves overlap, as long as we have at least a second detection data set to associate with each detected species in question. Therefore, the invention achieves a high level of assurance for the accuracy of identifications.

Thus we have shown that the fundamental dependence of mobility for ions in high electric field can be obtained from field asymmetric ion mobility spectrometry. Functions of dependence can be extracted from experiments using known methods to treat imperfect waveforms. These findings show an internal consistency with a homologous series of ketones, and also indicates a mass dependence not previously reported.

Focusing attention now on FIGS. 40A-40F a specific sequence of steps is described that may be carried out to perform species identification in several of the embodiments of the invention. These steps are provided by way of illustration and not limitation. In this illustration, the sequence of steps may be performed by the microprocessor 46 of the ion mobility spectrometer device 10 of FIG. 5. The microprocessor 46 provides digital control signals to the RF dispersion voltage (Vrf) generator 42 and compensation voltage (Vcomp) generator 44 to control the drive voltages for the filter 24. The voltage generators 42 and 44 may also include, for example, digital-to-analog converters, not shown in detail in FIG. 5.

The microprocessor 46 coordinates the application of specific RF dispersion voltages Vrf and compensation voltages Vcomp, also taking into account the function of observing responses from the detector 26 as read through the analog to digital converter 48. By detecting attributes (such as the peaks) of observed abundances of a particular ion species across a range of Vrf voltages, the microprocessor 46 can thus take steps to identify particular compounds. These may include, for example, comparing or correlating particular "response curve" data against a library of response curve data as stored in the memory 47. They can also include computation of $\alpha$ curve parameters. The results of the comparison operation can be provided in the form of an appropriate output device such as a display or personal computer or the like, or maybe provided by electrical signals through an interface to other data processing equipment.

Figure 40A:
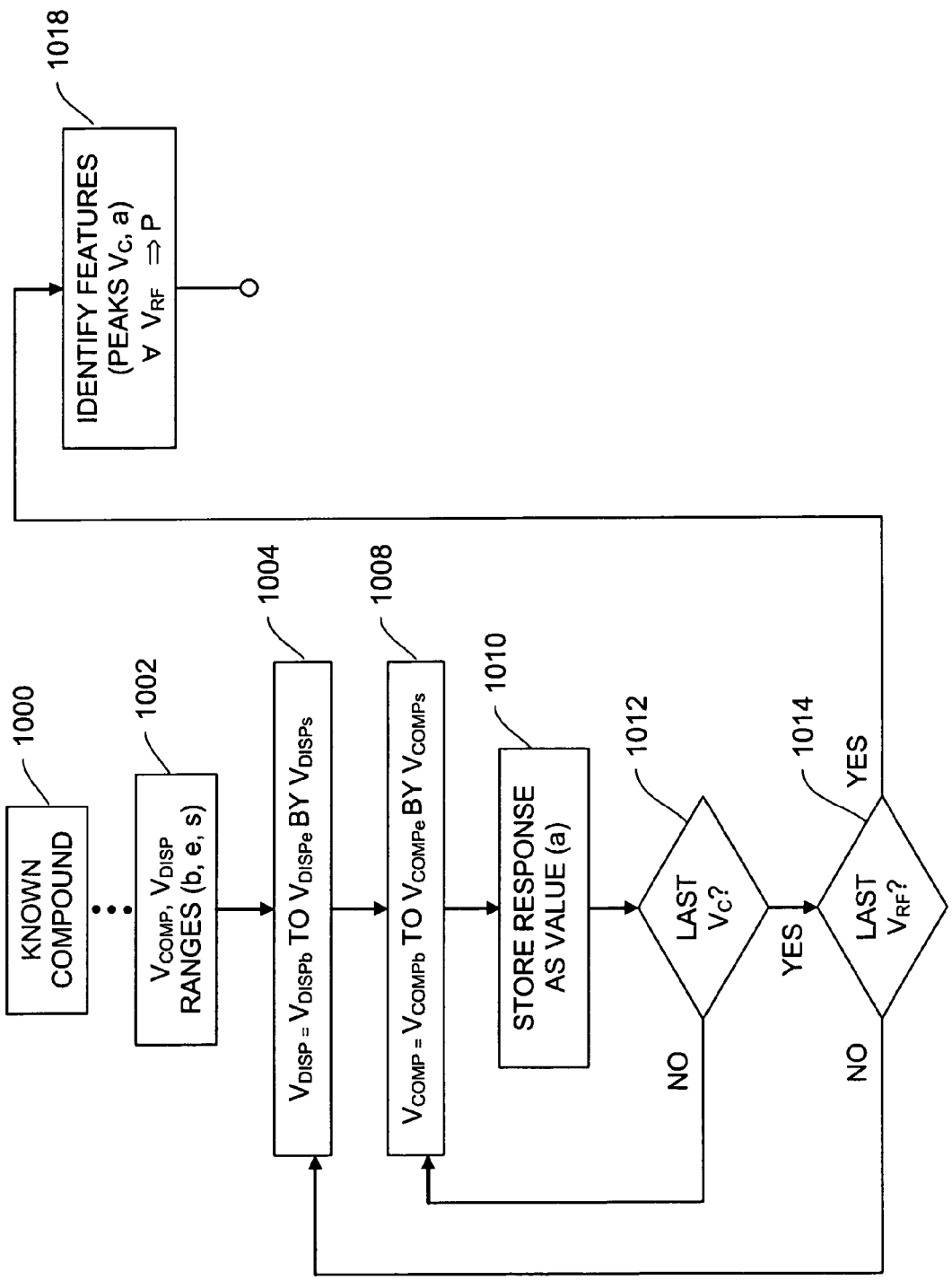
FIG. 40A is a flow diagram of an exemplary sequence of steps of a computer process used to acquire data concerning a particular chemical ion species.

As shown more particularly in FIG. 40A, a state 1000 is entered into the microprocessor 46 in which a compound is to be analyzed. Here, the compound is known and identified, such as by a user supplying an identifying text string to the computer. A sequence of steps is then performed by which data is to be acquired concerning the known chemical compound. From this state 1000, a next state 1002 is entered in which a range of dispersion voltages Vrf and compensation voltages Vcomp are determined by the processor 46. These ranges include a beginning voltage (b) and an end voltage (s) and step voltage(s) to be applied to each of the ranges Vrf is thus varied from an initial value Vrf(b) to a final value Vrf(e) by a step amount Vrf(s). Similarly, Vcomp is to be varied from Vcomp(b) to a final value Vcomp(e) by a step amount Vcomp(s).

The voltage ranges are then applied in the following steps. Specifically, step 1004 is entered in which the Vrf is allowed to step through a range of values. A state 1008 is entered next in which the compensation voltage Vcomp is also swept or stepped through a series of values or ranges. In state 1010, the response to each applied voltage is stored as a value, (a).

If the last compensation voltage has not yet been tested, then processing returns to state 1008 in which the next compensation voltage is applied. However, in state 1012, if all of the compensation voltages have been applied, then processing proceeds to a state 1014 wherein a test is made to see if all of the dispersion has been applied.

The loop continues until all of the compensation and dispersion voltages have been applied. The resulting set of data is then analyzed in a state 1018 to identify features of interest. In the specific example being described, it is the peak locations that are of interest. For each such peak in an observed response for a given applied dispersion voltage Vrf, a response value for a specific Vcomp is determined and its corresponding amplitude (a) is detected and stored.

Figure 40B:
FIG. 40B shows a diagram of a data structure for a library of stored compound data measurement information.

The response curve data, or certain attributes thereof such as the peak locations are then stored as a data object P (or table) as shown in FIG. 40B. Such an object illustratively contains an identification of the tested compound such as a text string. Also stored are a set of the applied dispersion voltages Vrf. For each such dispersion voltage Vrf, a corresponding peak compensation voltage is stored. Specifically, at least the compensation voltage Vcomp at which a peak was observed, and preferably, the corresponding amplitude of the response (abundance) observed at that peak is stored.

As previously described in detail, for a given Vrf, there may be a set of compensation voltages at which a number of "peaks" are observed. For example, as was described in connection with FIG. 14A, the sample analyzed can be made up of a compound of specific ions, including monomers, cluster ions, and reactant ion peaks. Thus, illustratively, there is an accommodation in the structure of object P to anticipate that there will be more than one peak observed in any particular mobility scan, and that the number of peaks per response curve may not always be the same number.

An example, the illustrative object P of FIG. 40B, includes a data element, where for a single RF dispersion voltage Vrf-1, peaks may be observed at compensation voltages Vc11, . . . , Vcmn having corresponding amplitudes a11, . . . , amn. This may correspond to the case of the lowest applied dispersion voltage in FIG. 14A, where numerous peaks 601-, 605-1, 608-1 are detected. However, at another dispersion voltage Vrf-m, only a single peak at Vcomp-m, am was detected. This might correspond to a case such as in the uppermost curve of FIG. 6A, where only a single peak 601-$m$ was detected.

Figure 40C:
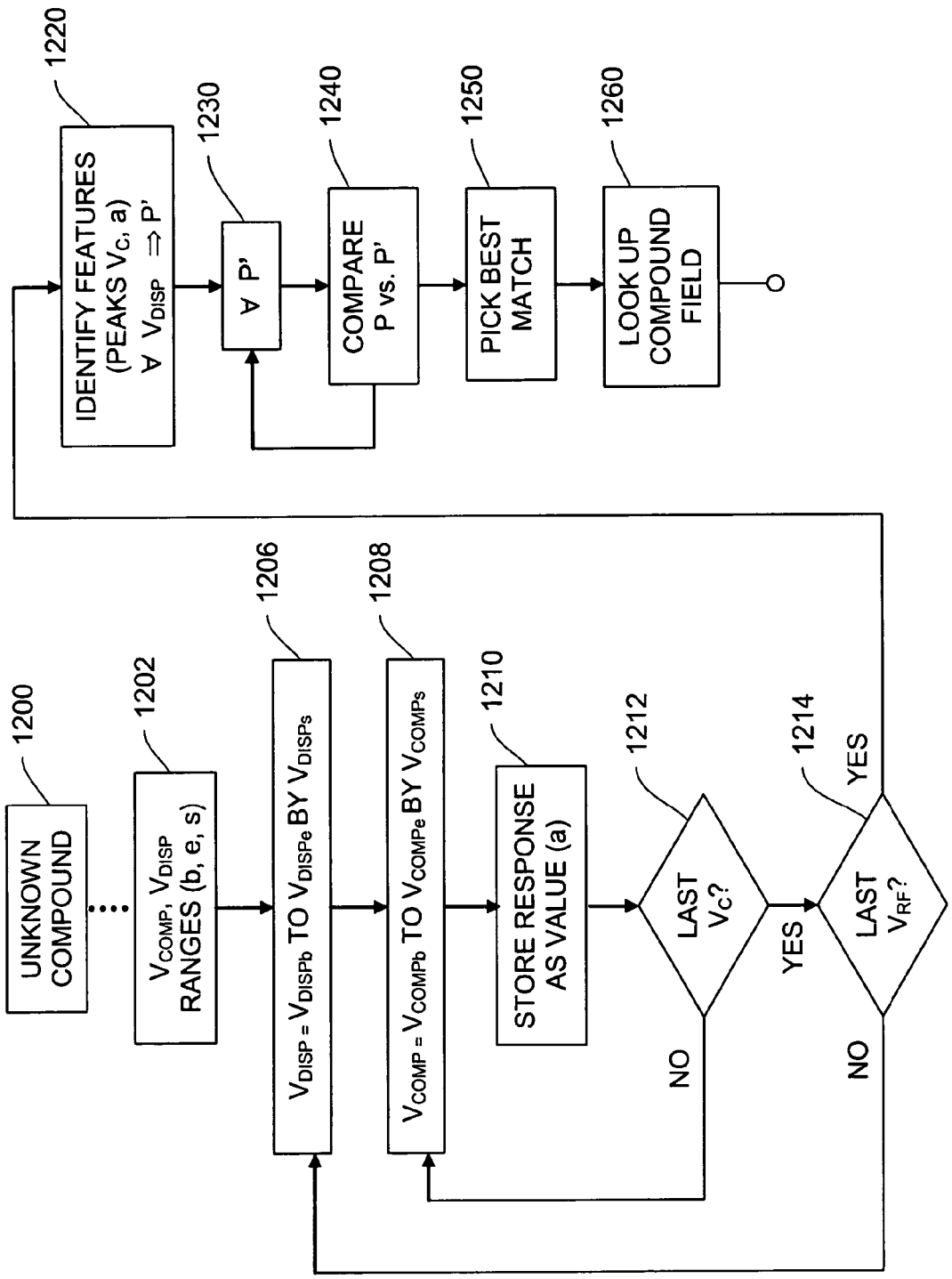
FIG. 40C is a flow diagram of a series of steps that may be applied to perform a chemical recognition.

In an illustrative application, a library of data objects P (reference vectors) is developed by performing the steps of FIG. 40A for a plurality of known compounds of interest. This then permits an instrument to eventually enter a chemical recognition state 1200 as shown in FIG. 40C. Next, a series of measurements are taken in states 1202-1214. This series is similar to the measurements taken in FIG. 40A. Specifically, a series of measurements are taken for a specified compensation and RF voltages. It should be understood that an entire set of all of the same measurements need not be taken in this mode as were taken in the chemical data acquisition mode. Specifically, not all points on a relatively dense response curve need to be taken, only enough to identify each compound.

Once the measurements are taken, a state 1220 is entered in which features, such as peaks of the response are identified for each peak, a corresponding compensation voltage and amplitude may be identified, and these stored to a candidate measurement vector P'. The candidate vector P' thus represents a series of data that needs to be tested against a number of candidate compounds. The candidate vector P' is then analyzed in states 1230 and/or 1240 by looking up corresponding counterparts in the library of reference vector objects P, and scoring a match between P and P'. These steps may be iterated until such time as a match or a best match is determined in a state 1250.

It should be understood that any number of techniques may be used to determine a degree of match between P and P'. For example, if the elements (Vcomp, a) of P and P' are considered to be data points in Euclidian geometry space, a distance can be computed. The comparison with the smallest Euclidian distance can then be selected as the best match. However, other recognition techniques may be used to determine an identity of an unknown compound, for example, more sophisticated signal processing techniques such as correlation may be used to resolve peaks; or other known pattern recognition algorithms, neural networks or artificial intelligence techniques may be used to find a best match for P'. This best match is then identified to a user, such as by looking up the compound identifier field and displaying it in state 1260.

Figure 40D:
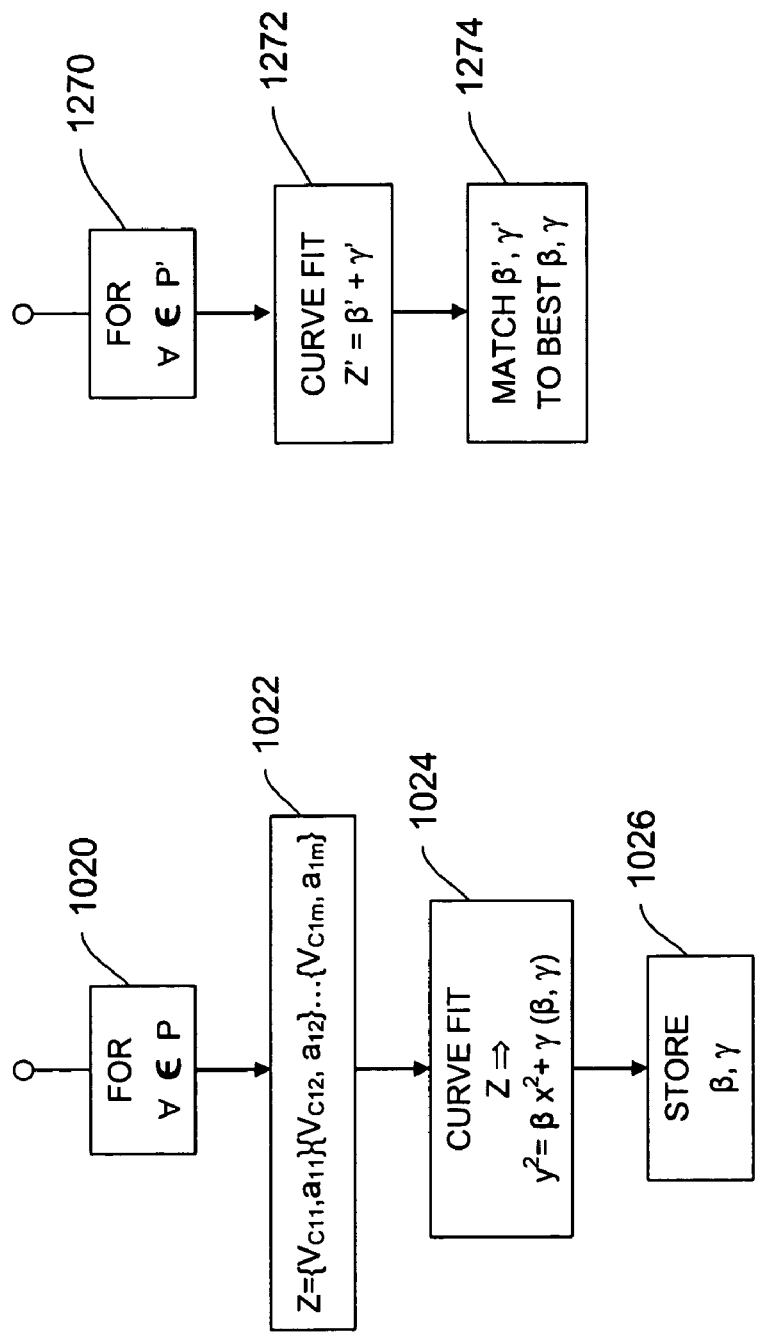
FIG. 40D is a flow diagram of a series of steps that may be added to the data acquisition and chemical recognition processes using alpha curve fitting.

FIG. 40D shows a series of steps, which may be added to the data acquisition phase and the chemical recognition phase to take advantage of second order data processing characteristics. For example, in the data acquisition state, a series of states 1020, 1022, 1024 and 1026 may be added to curve-fit specific attributes of the measured response. Specifically, a state 1020 may be entered in which for each data element of the object P a vector, z, is formed consisting of the peak compensation voltages vc11, vc12, . . . vc1*m*.

This vector is a vector of point locations for the peaks observed for a range of compensation voltages. Returning attention to FIG. 14A, briefly, this may correspond, for example, to locating the points 601-1, . . . 601-*m*, . . . 601-*n* corresponding to peak height and locations for the monomer ions of interest. A curve may then be fit through these peaks such as by applying a curve fitting algorithm, in state 1024. In the illustrated example it is assumed that a quadratic equation is fitting the peaks of the form $y^2=\beta x^2+\gamma$. The $\beta$ and $\gamma$ coefficients can then be stored in the state 1026 associated with the vector. The chemical is thus identified by a curve fit to its peak locations approximating its mobility ($\alpha$ coefficient) behavior.

If this is done, a corresponding set of steps 1270, 1272 and 1274 can be added to the recognition process to identify peaks by performing a curve fit to observe data, and then, determining $\beta$ and $\beta$ coefficients, rather than comparing raw data values in states 1270 and 1272. In state 1274, the $\beta$ and $\gamma$ coefficients are tested to determine closest matches in the P object library.

Figure 40F:
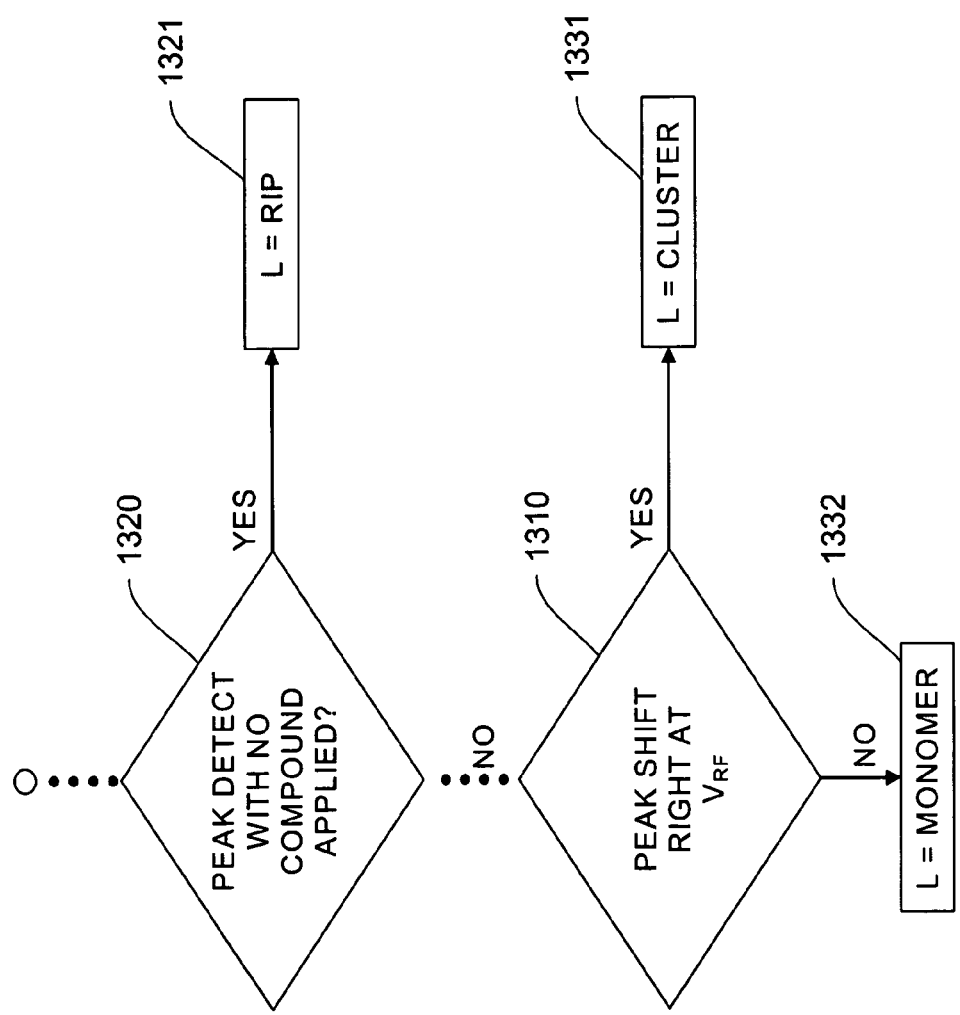
FIG. 40F is a flow diagram of a sequence of processes that may be used to distinguish monomer and cluster peak responses.

FIG. 40F shows a series of steps that may be used to identify or distinguish peaks in the acquisition phase. Here initial data may be added to the objects P by identifying peaks as a cluster peak or monomer peak. Specifically, if a peak shift over a range of field condition voltages (e.g., FIG. 14A) increases (i.e., shifts to the right), then this may be identified as a cluster peak. If the peak does not meet specific shifting criteria, it may be identified as a monomer peak. States 1310, 1331, and 1332 may thus be added to the identification process. The results of these steps adds an additional parameter L associated with each data point in the object P to further identify each peak as a monomer cluster or other peak type, as shown in FIG. 40E.

Other approaches to this may be used to label peaks. For example, reactant ion peaks (RIP) may also be identified by performing an analysis on a response of the instrument, with no sample S applied. In this mode, only the RIPs occur, and in their behavior across a range of compensation voltages can be stored. Information concerning the particular type of peak may be stored in pointer data in a state 1320, at which such a peak is detected. This information can then be added to the objects P, specifically as shown in FIG. 40E.

Figure 40G:
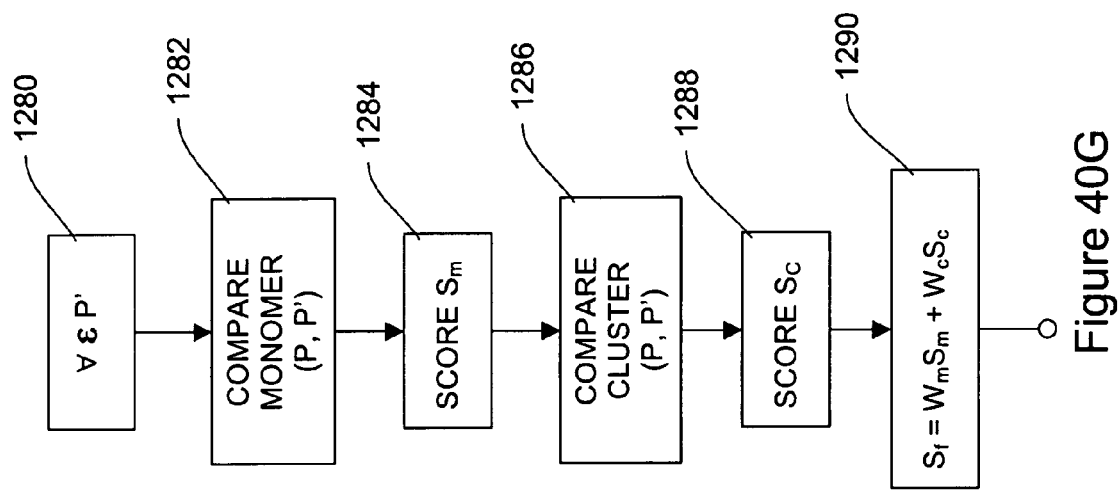
FIG. 40G is a flow diagram of a process showing the combination of monomer and cluster scoring.

FIG. 40G shows additional processing steps, which may be performed in the compound recognition state to take advantage of the situation of FIGS. 36A-38 in which monomer and cluster ion behavior is observed. Specifically, the steps of FIG. 40G may be added as further steps 1280 in the recognition phase. Here, for every candidate peak P', a corresponding monomer peak in the reference array P is compared. A score is then associated with the closest of the match in state 1284. Similarly, in state 1286, a cluster peak may be compared with its corresponding peak in the peak library P. A score sc is then determined in step 1288, depending on the closest of this match. In a state 1290, a final score sf can be associated with weighting the monomer peak score and the cluster peak score by weighting factors wm and wc. For example, in an instance where cluster peaks are expected to provide more information than monomer peaks, cluster peaks may be weighted highly and monomer peaks relatively low or zero factor. Using this weighting, both monomer and cluster peak identification can be combined to further refine compound analysis.

Figure 41:
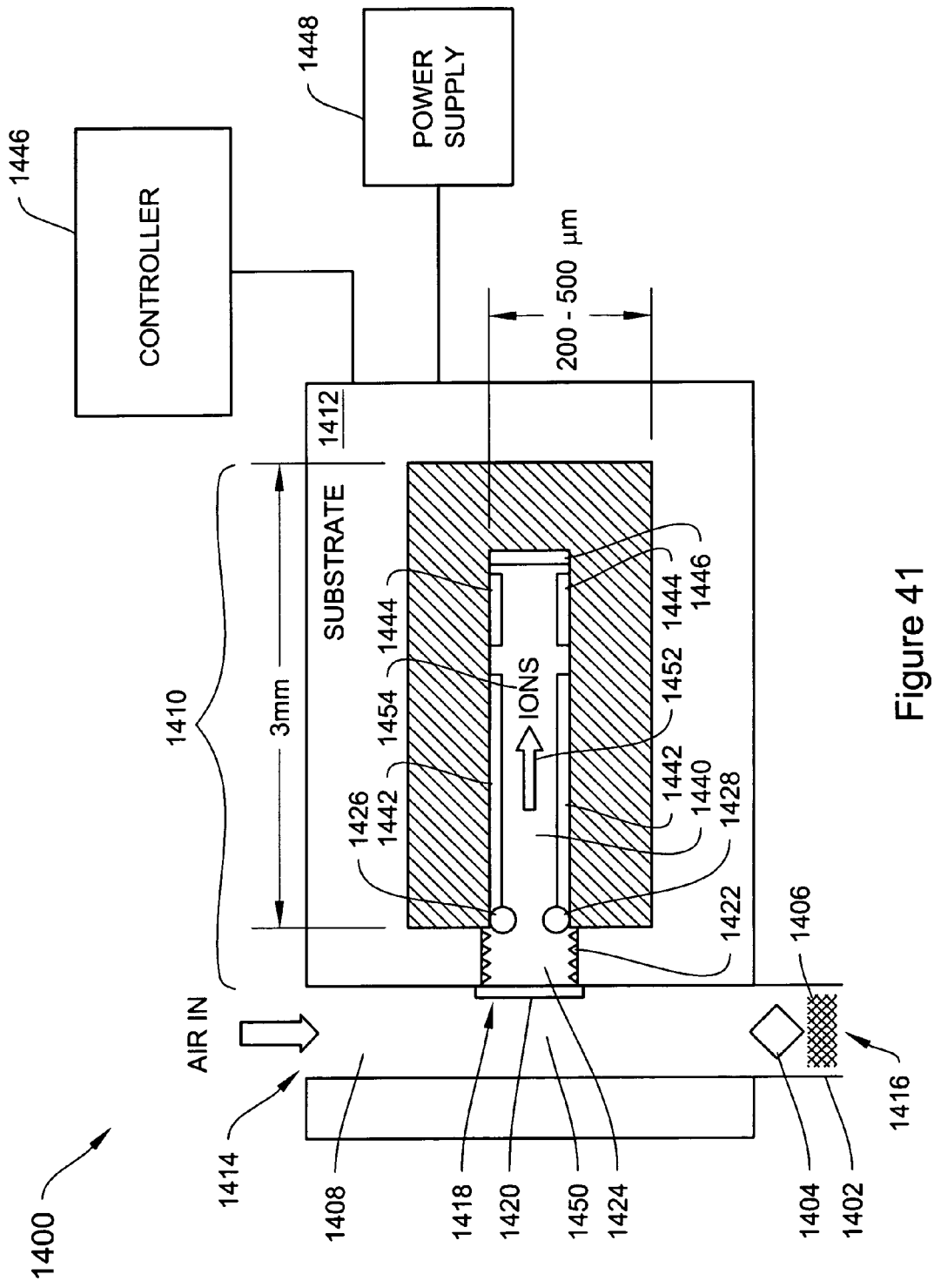
FIG. 41 is a conceptual diagram of a compact DMS analyzer system 1400 used to detect and identify chemical warfare agents (CWAs), Toxic Industrial Compounds (TICs) and Toxic Industrial Materials (TIMs) which may be released in warfare or terrorist situations according to an illustrative embodiment of the invention.

In various applications, the above described approaches to ion-based sample analysis may be employed in relatively compact, such as handheld, analyzer systems. FIG. 41 is a conceptual diagram of such a compact DMS analyzer system 1400. The DMS system may be used, for example, to analyze compounds, such as chemical warfare agents (CWAs), and Toxic Industrial Compounds (TICs), and Toxic Industrial Materials (TIMs) according to an illustrative embodiment of the invention. By operating the compact DMS analyzer system 1400 at less than atmospheric pressure, e.g., 0.5 atm, as described above, the system 1400 approximately doubles its resolution over existing state-of-the-art systems, while reducing its power consumption and size. By performing sample fragmentation, as described above, sample analysis may be further enhanced. By utilizing three-dimensional color dispersion plots, as also described above, analysis of CWAs, TICs, and TIMs is further enhanced.

The DMS analyzer system 1400 may employ an electromechanical pump, compressed gas or air, or the solid-state flow generator 1402, which includes an ion source 1404, an ion attractor 1406, and a constrained flow channel 1408 for controlling sample flow and/or pressure within the system 1400. The ion source 1404 provides a source of ions and the ion attractor 1406 attracts either positive or negative ions, depending on an applied bias voltage. The ion flow created in the constrained channel 1408 due to the ion flow generated by the interaction of the ion source 1404 with the ion attractor 1406 creates a fluid, e.g., a sample effluent, flow. In some illustrative embodiments, the DMS analyzer system 1400 may be miniaturized, such that the analyzer unit 1410 is included in application-specific integrated circuits (ASICs) embedded on a substrate 1412. A solid state flow generator of the type employed by the invention is described in further detail in co-pending and co-owned U.S. patent application Ser. No. 10/943,523, filed on 17 Sep. 2004, the entire contents of which are incorporated above by reference.

The constrained channel 1408 includes an inlet end 1414 and an outlet end 1416. The constrained channel 1408 also includes a sample introduction inlet 1418 to enable the analyzer 1410 to collect the sample gas for analysis. A preconcentrator 1420 may be employed at the sample introduction inlet 1418 to concentrate the sample and improve analysis accuracy. An ionizer 1422 provides ionization of the sample using, for example, a radioactive $Ni^{63}$ foil, or non-radioactive plasma ionizer, or other suitable ionization source within ionization region 1424. A plasma ionizer has the advantage of enabling precise control of the energy imparted to the sample gas for ionization. Ideally, the ionizer 1422 imparts only enough energy to ionize the sample gas, without producing nitric oxides (NOx's) and ozone. A fragmentation region may also be included in the system 1400. NOx's and ozone are undesirable because they can form ion species that interfere with the ionization of CWA agents. Because diffusion and mobility constants generally depend on pressure and temperature, the DMS analyzer system 1400 may include a temperature sensor 1426 and/or a pressure sensor 1428 for regulating the temperature and/or pressure of the sample gas within the analyzer unit 1410 for more accurate analysis. The analyzer 1410 may also include a humidity sensor. The analyzer 1410 also includes an analytical region 1440 with filter plates 1442 and detector plates 1444. A molecular sieve 1446 may be employed to trap spent analytes.

The controller 1446 provides control of filtering and detection while also providing an output of the detection results. The power supply 1448 provides power to the filter plates 1442, solid-state flow generator 1402, and any other component requiring electrical power. The controller electronics 1446 for Vcomp, Vrf, the ion heater pumping, the DMS ion motion, and the pre-concentrator 1420 heater may be located with the analyzer unit 1410. Also, the detector 1444 electronics, pressure 1426 and temperature 1428 sensors, and the processing algorithm for a digital processor may reside within analyzer 1410.

At atmospheric pressure, to realize the benefits of mobility nonlinearity, the DMS analyzer system 1400 illustratively employs RF electric fields of about 106 V/m, and a Vrf of about 200 Vpeak at about a $200 \times 10^{-6}$ μm gap. However, any suitable RF electric field parameters may be employed. The power supply 1448 may be remotely located relative to the analyzer unit 1410 to generate RF voltage for the filter plates 1442. At less than atmospheric pressure, the RF electric field may be reduced as described above to further reduce the power consumption and size of the DMS analyzer system 1400.

The DMS analyzer system 1400 may also interface with a personal computer (PC) or controller 1446 to utilized signal-processing algorithms that convert analyzer 1410 outputs into detection, identification, and/or measurement of analytes and concentration levels. The controller 1446 or an interfacing PC may also facilitate control and power management for the DMS analyzer system 1400. The supporting electronics for the DMS analyzer system 1400 may be implemented, for example, on an ASIC, a discrete printed circuit board (PCB), or System on a Chip (SOC).

In operation, the solid-state flow generator or electromechanical transport pump 1402 draws samples into the DMS analyzer system 1400 at the inlet 1414 and past a CWA-selective chemical membrane concentrator 1420 having an integrated heater. The CWA-selective chemical membrane pre-concentrator 1420 may also serve as a hydrophobic barrier between the analytical region 1440 of the analyzer system 1400 and the sample introduction region 1450. The membrane of the pre-concentrator 1420, illustratively, allows CWA agents to pass, but reduces the transmission of other interferants and acts as a barrier for moisture.

The pre-concentrator 1420 may use selective membrane polymers to suppress or block common interferences (e.g., burning cardboard) while allowing CWA agents or CWA simulants to pass through its membrane. Although many selective membrane materials are available, poly-dimethyl siloxane (PDMS) may be a preferred membrane/concentrator/filter to reject water vapor and collect CWA analytes. At high concentration levels, water vapor molecules may cluster to the analytes, altering the analytes' mobilities. Membrane materials such as hydrophobic PDMS tend to reduce the vapor to acceptable levels while absorbing and releasing analyte atoms. The thin membrane of the pre-concentrator 1420 may also be heated periodically to deliver concentrated analytes to the ionization region 1424 and analytical region 1440.

Except for diffusion of analytes through the membrane/filter/pre-concentrator 1420, the analytical region 1440 is generally sealed to the outside atmosphere. Thus, the analyzer system 1400 may employ elements for equalizing the pressure inside analytical region 1440 with the atmospheric pressure outside the analyzer system 1400 or maintain pressure in the analytical region 1440 at less than atmospheric pressure for improved ion intensity peak resolution. Once the sample gas molecules are ionized, the ions are driven longitudinally in the direction indicated by the arrow 1452 through the ion filter plates 1442 by static or traveling electrostatic fields, as opposed to being driven by the carrier gas. The filter plates 1442 apply transverse radio frequency (RF) field voltages and dc excitation electric compensation fields to the ions moving through analytical region 1440 to separate the species within a sample.

With water vapor removed, interferants (e.g., hydrocarbons and others) typically comprise roughly 0.10% of the incoming air volume by weight. Depending on the collection efficiency of the pre-concentrator 1420, the molecular sieve 1446 may be sized to support about 6, 9, 12 or more months of substantially continuous or continuous operation before saturating. The molecular sieve 1446 may also be configured to allow movement of air in a circulatory fashion through the ion filter electrodes 1442 and back to the ionization region 1424.

The DMS analyzer system 1400 may be used for detecting low concentrations (e.g., parts per trillion (ppt)) of CWAs, such as, without limitation, nerve and blister agents. In one illustrative embodiment, the DMS analyzer system 1400 includes a high-sensitivity, low-power, sample gas analyzer 1404 that builds on MEMS technology, but further miniaturizes the DMS analyzer system 1400 to achieve parts-per-trillion sensitivity, about 0.25 W overall power consumption (i.e., 1 Joule measurement every 4 seconds), and a size of about 2-cm$^3$ or less.

Because of the smaller analytical region 1440 and the resulting lower flow rate requirements, a low-power (e.g., mW) solid-state gas transport pump 1402, using ionic displacement, may be employed to draw an air sample into the DMS analyzer system 1400 and onto the CWA-selective chemical membrane pre-concentrator 1420. Compact DMS analyzer systems according to the invention have shown very high sensitivities to CWA simulants. By way of example, a compact DMS analyzer system according to the invention has been shown to detect methyl salycilate at parts-per-trillion (ppt) levels. The DMS analyzer system 1400 has the ability to resolve CWA simulants from interferants that cannot be resolved by current field-deployed detection technologies.

Figure 42:
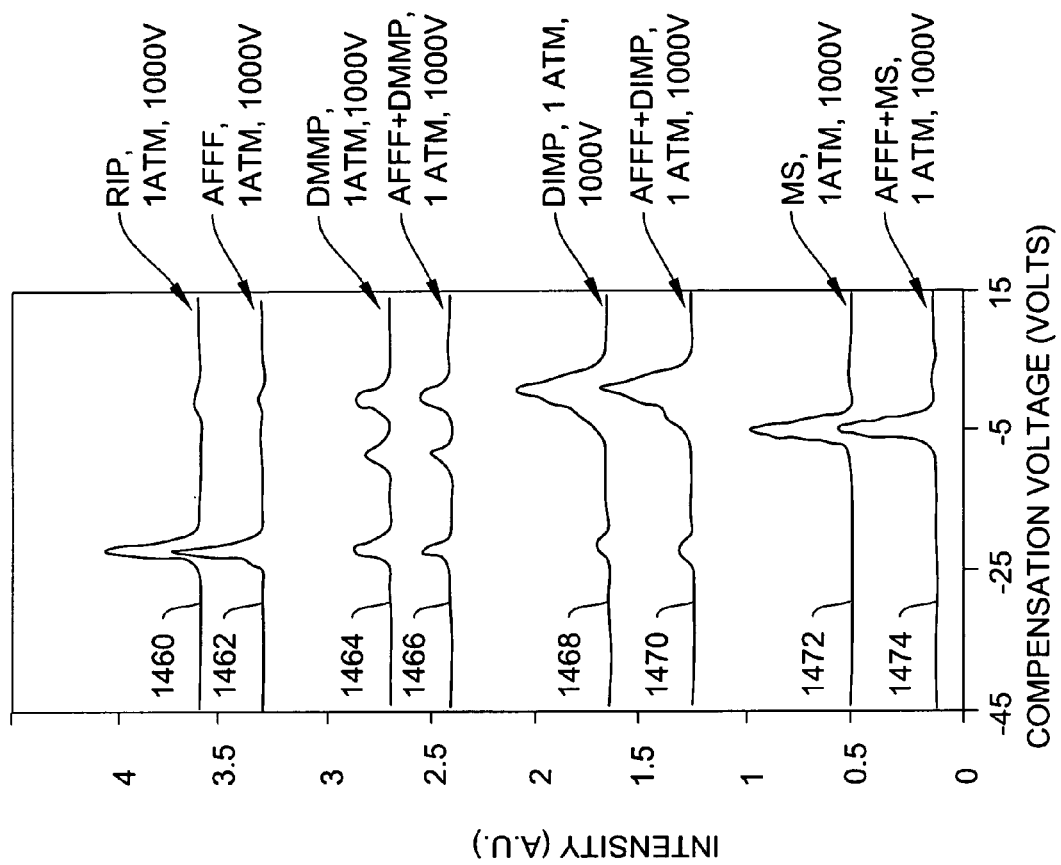
FIG. 42 is a graph of multiple plots showing experimental results for a series of warfare agent simulants selectively mixed with 1% headspace of AFFF.

FIG. 42 is a graph depicting a DMS spectra showing resolution of dimethylmethylphosphonate (DMMP) from aqueous firefighting foam (AFFF) as measured in a DMS analyzer system 1400. AFFF is one interferant that has proved extremely challenging for conventional IMS systems to resolve CWAs or other simulants. The AFFF ion intensity peak tends to overlap with the agent peak during sample detection in DMS or IMS systems.

FIG. 42 is a graph of multiple plots showing experimental results for a series of CWA simulants selectively mixed with 1% headspace of AFFF. The top plot 1460 of FIG. 42 shows RIP for a DMS analyzer system 1400 with background air but no sample present with the sensor at atmospheric pressure. In the next plot 1462, the AFFF interferant is added. This results only in a slight shift to the left (more negative compensation voltage) of the RIP ion intensity peak. Then, in plot 1464, the CWA simulant DMMP is introduced into the spectrometer and the typical monomer and dimmer peaks appear together with a corresponding reduction in the RIP peak ion intensity. When 1% AFFF is added according to plot 1468, the DMMP peaks are not effected and only a slight leftward shift of the RIP is observed. The same experiment was repeated with DIMP in plots 1468 and 1470, and the effect of AFFF was negligible. In plot 1472, MS is introduced, and according to monitored negative ion peaks, gives similar data illustrating the lack of interference with AFFF. The conclusion is that 1% AFFF has virtually no effect. Thus, FIG. 42 illustrates the ability of the DMS analysis system 1400 to resolve CWA simulants from interferants.

In one illustrative embodiment, the compact hand-held DMS analyzer system 1400 is achieved by combining the following design characteristics: (a) using the analyzer/filter/detector 1410 with improved sensitivity and size reduction; (b) using the solid-state flow generator or electromechanical pump as a gas transport pump 1402 to sample and move analytes; (c) using the CWA-selective chemical membrane pre-concentrator 1420 with integrated heater (in some configurations provided by using a solid-state generator or electromechanical pump to transfer heat from other analyzer system components to the pre-concentrator 1420) to remove water vapor and to concentrate; and/or (d) using electric field propulsion of the ions 1454 through the analytical region 1440 of analyzer 1410.

According to various illustrative embodiments, the invention improves the resolution of species identification over conventional systems, while decreasing size and power to achieve parts-per-trillion sensitivity, a less than about 0.25 mW overall power dissipation, and a size of about a 2-cm$^3$ or less in an entire system not including a power source or display, but including an RF field generator. According to some embodiments, an analyzer system of the invention has a total power dissipation of less than about 15 W, about 10 W, about 5 W, about 2.5 W, about 1 W, about 500 mW, about 100 mW, about 50 mW, about 10 mW, about 5 mW, about 2.5 mW, about 1 mW, and/or about 0.5 mW. According to further embodiments, an analyzer system according to the invention, optionally including a display (e.g., indicator lights and/or an alphanumeric display) and a power source (e.g., a rechargeable battery) compartment, along with an RF field generator, may have a total package outer dimension of less than about 0.016 m$^3$, 0.0125 m$^3$, 0.01 m$^3$, 0.0056 m$^3$, 0.005 m$^3$, 0.002 m$^3$, 0.00175 m$^3$, 0.0015 m$^3$, 0.00125 m$^3$, 0.001 m$^3$, 750 cm$^3$, 625 cm$^3$, 500 cm$^3$, 250 cm$^3$, 100 cm$^3$, 50 cm$^3$, 25 cm$^3$, 10 cm$^3$, 5 cm$^3$, 2.5 cm$^3$, with the package being made, for example, from a high impact plastic, a carbon fiber, or a metal. According to further embodiments, an analyzer system, for example, according to the invention, including an RF generator, and optionally including a display, keypad, and power source compartment, may have a total package weight of about 5 lbs, 3 lbs, 1.75 lbs, 1 lbs, or 0.5 lbs.

Table 1 provides a comparison of drift tube (e.g., the constrained channel) dimensions, fundamental carrier gas velocities, and ion velocities for a various illustrative embodiments of a DMS analyzer system 1400 depending on the flow rate (Q) available to the analysis unit. Designs 1-4 provide flow rates of varying orders of magnitude ranging from about 0.03 l/m to about 3.0 l/m. Table 1 illustrates that as the flow rate is decreased through the DMS analyzer system 1400, the filter plate dimensions and power requirements are reduced. Table 1 is applicable to a DMS analyzer system 1400 using either a sample gas or longitudinal field-induced ion motion. The time to remove an unwanted analyte is preferably less than about the time for the carrier to flow through the filter region (tratio). Also, for a particular target agent, the lateral diffusion as the ion flows through the analyzer 1410 is preferably less than about half the plate spacing (difratio). Based on this criteria, the plate dimensions may be reduced to about 3×1 mm$^2$ or smaller, while the ideal flow power may be reduced to less than about 0.1 mW. Thus, even for design 4, the number of analyte ions striking the detectors is sufficient to satisfy a parts-per-trillion detection requirement.

TABLE 1

Illustrative DMS Analyzer System Design Specifications and Characteristics

| Description | Units | Symbol | Design 1 Q = 3 l/m Baseline | Design 2 Q = 0.3 l/m Base dimen | Design 3 Q = 0.3 l/m scaled | Design 4 Q = 0.03 l/m |
|---|---|---|---|---|---|---|
| plate dimensions | | | | | | |
| length | m | L | 0.025 | 0.025 | 0.005 | 0.001 |
| width | m | b | 0.002 | 0.002 | 0.001 | 0.0004 |
| air gap | m | h | 0.0005 | 0.0005 | 0.0005 | 0.0002 |
| volume flow rate | l/min | Qf | 3 | 0.3 | 0.3 | 0.03 |
| Flow velocity | m/s | Vf | 50 | 5 | 10 | 6.25 |
| pressure drop | Pa | dPf | 1080 | 108 | 43.2 | 33.75 |
| flow power | W | Powf | 0.054 | 0.00054 | 2.16E−04 | 1.69E.05 |
| RF excitation | V | Vrf | 650 | 650 | 650 | 260 |
| design ratios | | | | | | |
| Time to remove unwanted analyte | | | | | | |
| divided b carrier time wanted ions-lateral diffusion divided | s | tratio | 0.0128 | 0.0013 | 0.0128 | 0.0160 |
| by half gap | s | difratio | 0.200 | 0.632 | 0.200 | 0.283 |
| ions to count per cycle | — | Nout | 1.22E+07 | 1.22E+06 | 1.22E+06 | 1.22E+05 |

For sample/carrier gases, there does not appear to be an electromechanical pump that operates at the preferred flow characteristics with an efficiency better than about 0.5%. With a 0.5% efficiency, an ideal flow loss of about 0.05 mW results in an actual power consumption of about 10 mW, about a factor of 100 greater than in the above discussed illustrative embodiment of the invention.

The DMS system 1400 may simultaneously detect both positive and negative ion intensity peaks which further improves detection selectivity. The combination of the positive and negative ion channel information, the shift in spectral peak as a function of applied field strength or voltage, and the display is this information in a three-dimensional manner provide a novel mechanism for chemical identification.

Figure 43:
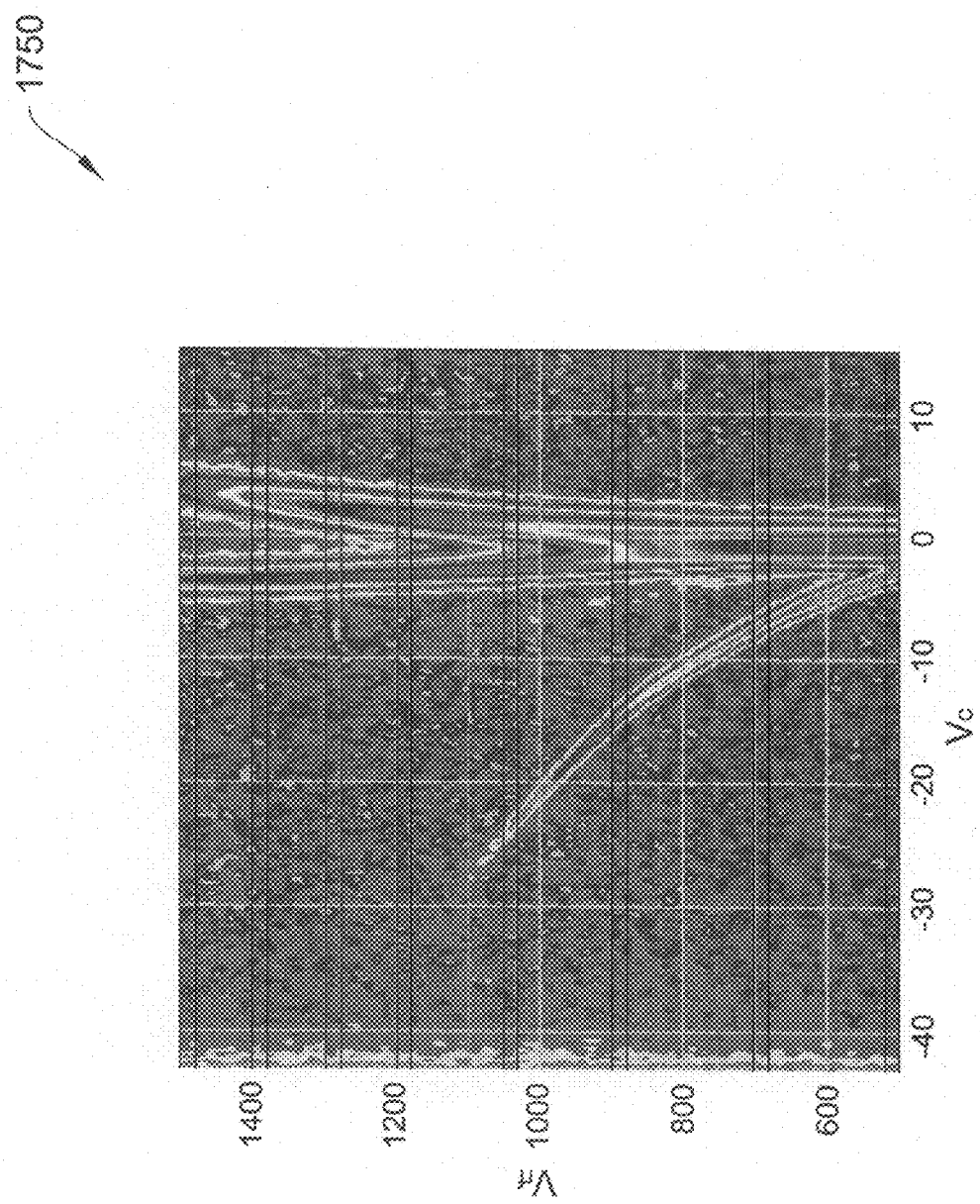
FIG. 43 is a three-dimensional color dispersion plot of the detection of positive ions of agent GA over a range of field voltages and field compensation voltages with varying intensity represented in varying color according to an illustrative embodiment of the invention.
Figure 50:
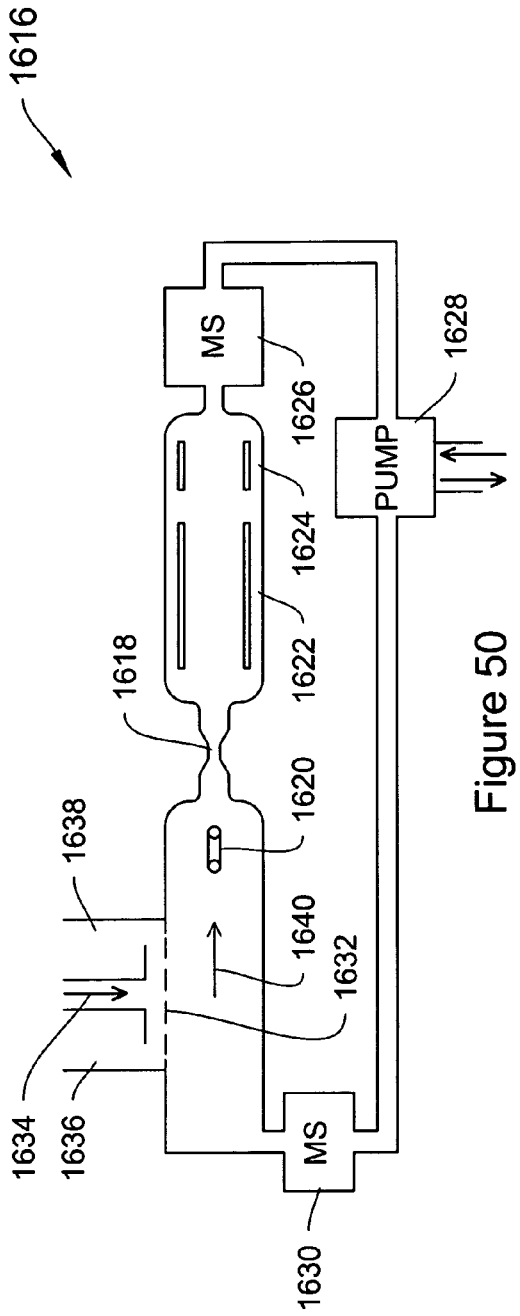

FIG. 43 is a three-dimensional dispersion plot 1750 of the detection of positive ions of agent GA over a range of field voltages and field compensation voltages with varying intensity represented in varying color according previously described illustrative embodiments of the invention. The plot 1750 illustrates the enhanced identification (selectivity) of a compound using a three-dimensional dispersion plot by, for example, a DMS system 1400. In comparison, FIG. 25 is a three-dimensional dispersion plot of negative ions of GA over a range of RF voltage versus compensation voltage with varying intensity represented in varying color that illustrates the enhanced identification (selectivity) of a compound using a three-dimensional dispersion plot by, for example, DMS system 1400. Both measurements were performed with a concentration of GA at 0.14 ng/l, a $Ni^{63}$ source, 50% RH, 3 scan averaging, and 350 cc/min carrier gas flow. The differences between the three-dimensional plots 814 of FIGS. 25 and 1750 of FIG. 50 illustrate that performing both positive and negative ion mode detection provides enhanced signature identification of ion species.

In certain illustrative embodiments, the compact DMS system 1400 of FIG. 41 and various other figures may employ features and/or be incorporated into systems described in further detail in U.S. Pat. Nos. 6,495,823 and 6,512,224, the entire contents of both of which are incorporated herein by reference.

Figure 44:
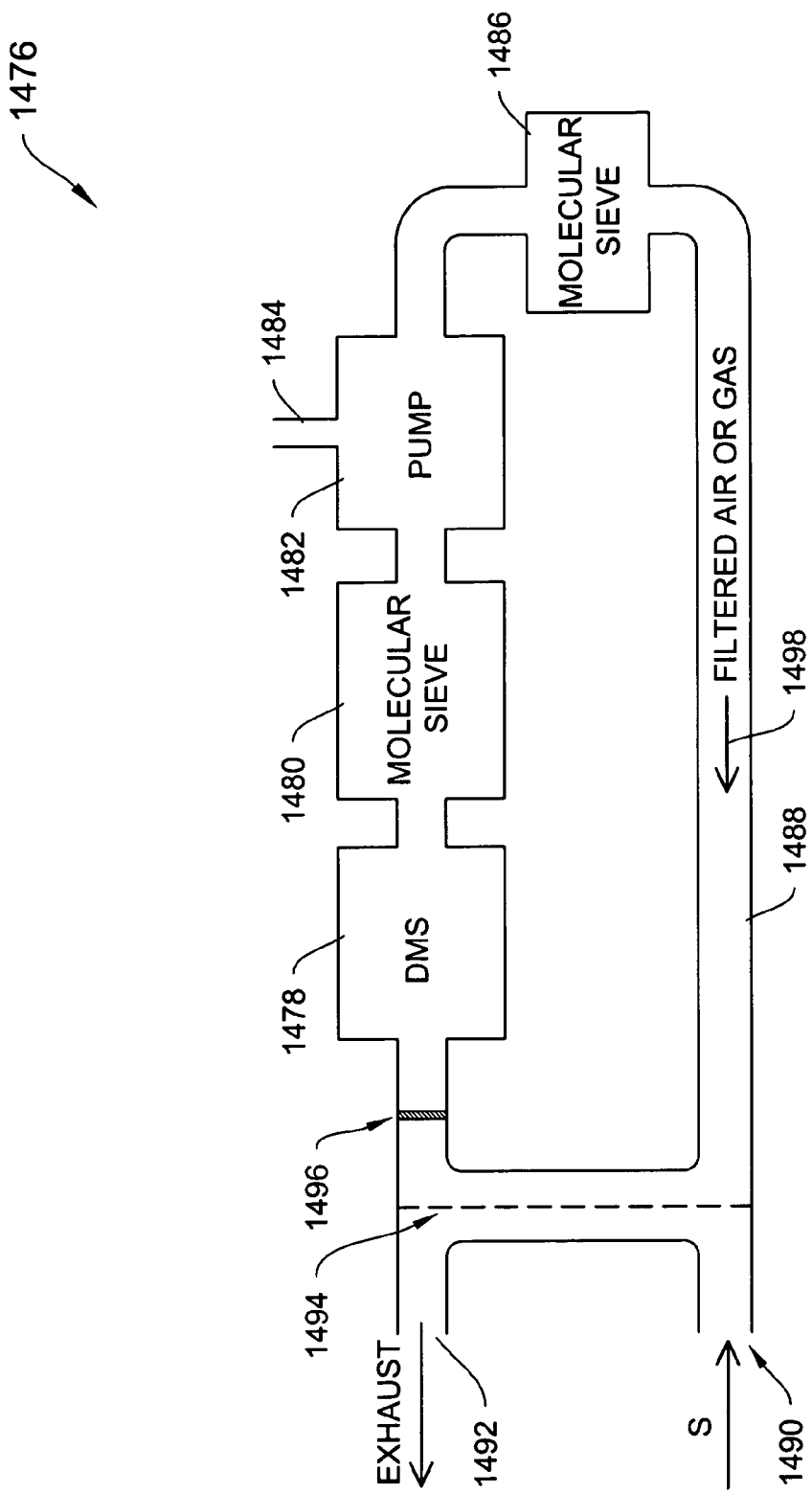
FIG. 44 is a conceptual block diagram of a chemical and/or biological agent detection system using an ion mobility analyzer system, membrane, and recirculation system according to an illustrative embodiment of the invention.

FIGS. 44-53 are conceptual block diagrams of chemical and/or biological agent detection systems using various configurations of a mobility detection analyzer system such as those depicted and described herein, a recirculation system, and other components according to illustrative embodiments of the invention. More particularly, FIG. 44 is a conceptual block diagram of a CWA and/or biological agent detection system 1476 according to an illustrative embodiment of the invention. The system 1476 employs a mobility detection system 1478, molecular sieve 1480, pump 1482 with optional vent 1484, optional second molecular sieve 1486, circulating channel 1488, sample inlet 1490, exhaust 1492, membrane 1494, and orifice 1496. The system 1476 may also employ filtered air or gas 1498 to circulate or transport a sample through the system 1476. The mobility analyzer system 1478 may be a compact DMS analyzer system 1400 of FIG. 48, DMS system 10 of FIG. 5, an IMS, a TOF-IMS, a GC-IMS, an MS or the like. The system 1476, like all of the previously described illustrative systems, may employ one or more dopants such as, methylene bromide ($CH_2Br_2$), methylene chloride ($CH_2Cl_2$), chloroform ($CHCl_3$), water ($H_2O$), methanol ($CH_3OH$), and/or isopropanol, introduced, mixed and/or flowed with the sample to enhance analysis.

In operation, the system 1476 receives a sample S at inlet 1490 and passes it through the membrane 1494 into the circulation channel 1498. The membrane 1494 may filter out unwanted interferants, if desired, in the same or similar manner as the pre-concentrator 1420 of FIG. 48. The orifice 1496 may, in a fixed, controlled, or adjustable manner, regulate the gas and/or sample flow into the analyzer system 1478 and thereby regulate or control the pressure within the analyzer system 1478. Thus, the analyzer system 1478 may operate at atmospheric pressure, below atmospheric pressure, or above atmospheric pressure. The pump 1482 maintains gas flow in the analyzer system 1478 and pressure control either independently or in coordination with the orifice 1496. Thus, in one example, the pump 1482 draws sample flow through the orifice 1496 into the analyzer system 1478 to enable detection and identification of selected ion species. The analyzer system 1478 may be a DMS system 1400 that tunably detects certain ion species by adjusting its field/flow channel conditions, such as, its Vrf and Vcomp, parameters and in some configurations, controlling the pump 1484 and/or the orifice 1496 to control pressure within the system 1400.

Once detection and identification are performed, the molecular sieve 1480 may trap spent analytes from the analyzer system 1478. Again, the pump 1484, whether electromechanical or solid-state, propels the gas, optionally through a second molecular sieve 1486, through the circulating channel 1488. The sample gas is then expelled through the membrane 1494 and the outlet 1492 or mixed and re-circulated with more sample S back into the orifice 1496.

Figure 45:
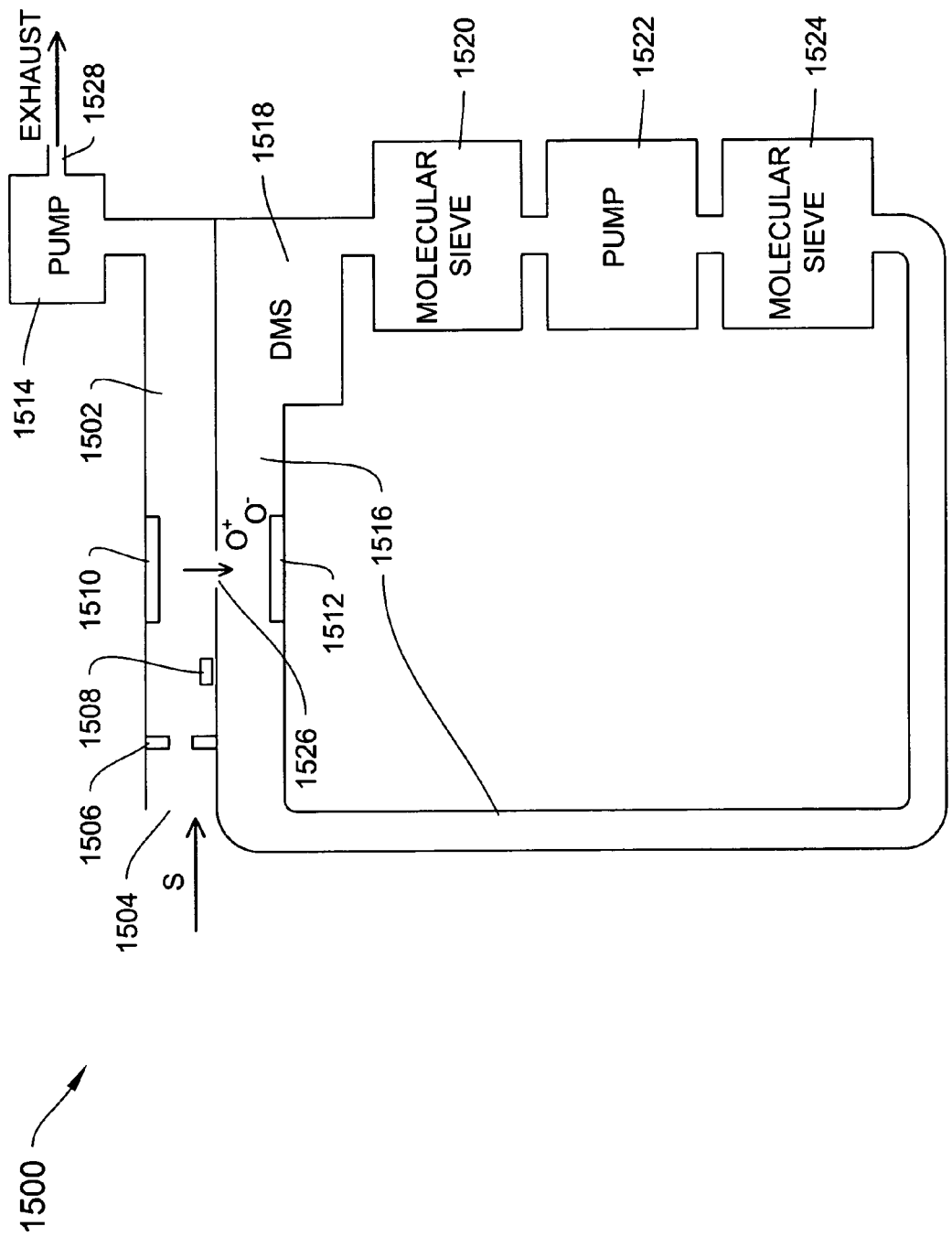
FIG. 45 is a conceptual block diagram of a chemical and/or biological agent detection system configured for reduced pressure analysis according to an illustrative embodiment of the invention.

FIG. 45 is a conceptual block diagram of a CWA and/or biological agent detection system 1500, configured for reduced pressure analysis, according to an illustrative embodiment of the invention. The system 1500 is similar to the system 1476 except that an additional sample flow channel 1502 is employed instead of a membrane. The system 1500 includes sample S inlet 1504, orifice 1506, ionization region 1508, deflector plate 1510, attractor plate 1512, channel 1502 pump 1514, second channel 1516, analyzer system 1518, molecular sieve 1520, pump 1522, and optional second molecular sieve 1524.

In operation, the system 1500 draws sample S through the sample inlet 1504 and through the orifice 1506. The orifice 1506 may be controlled, fixed, or adjustable to regulate sample gas flow and/or pressure in the channel 1502. The pump 1514 may also be used in coordination with the orifice 1506 to regulate gas flow and/or pressure within the channel 1502. The deflector plate 1510 may force, push, or selectively separate ions into the channel 1516 through the opening 1526 while the attractor 1512 may attract ions from the channel 1502 into the channel 1516. A pressure drop across the opening 1526 may be adjusted so that only sample ions enter the channel 1516 while sample neutrals are prevented from entering. The sample ions may be directly introduced into the analyzer system 1518 or the ions may be neutralized and then re-ionized in the analyzer system 1518. The analyzer system 1518 may be a DMS system, IMS system, or the like. The analyzer system 1518 may include multiple DMS, IMS, or other like systems or a combination of such systems to perform sample detection and identification. For example, system 748 of FIG. 21 or system 754 of FIG. 22 may be employed to apply conventional DMS detection in combination with fragmentation to enhance sample analysis.

The channel 1516 pump 1524 may then draw the sample S from the analyzer system 1518 through the molecular sieve 1520 and then propel the sample S, optionally through the second molecular sieve 1524. The molecular sieves 1520 and 1524 will capture most of the spent sample S analytes. Any remaining sample S is mixed with new sample S gas and returned to the analyzer system 1518 via the channel 1516. The outlet 1528 expels sample S gas from the channel 1502.

Figure 46:
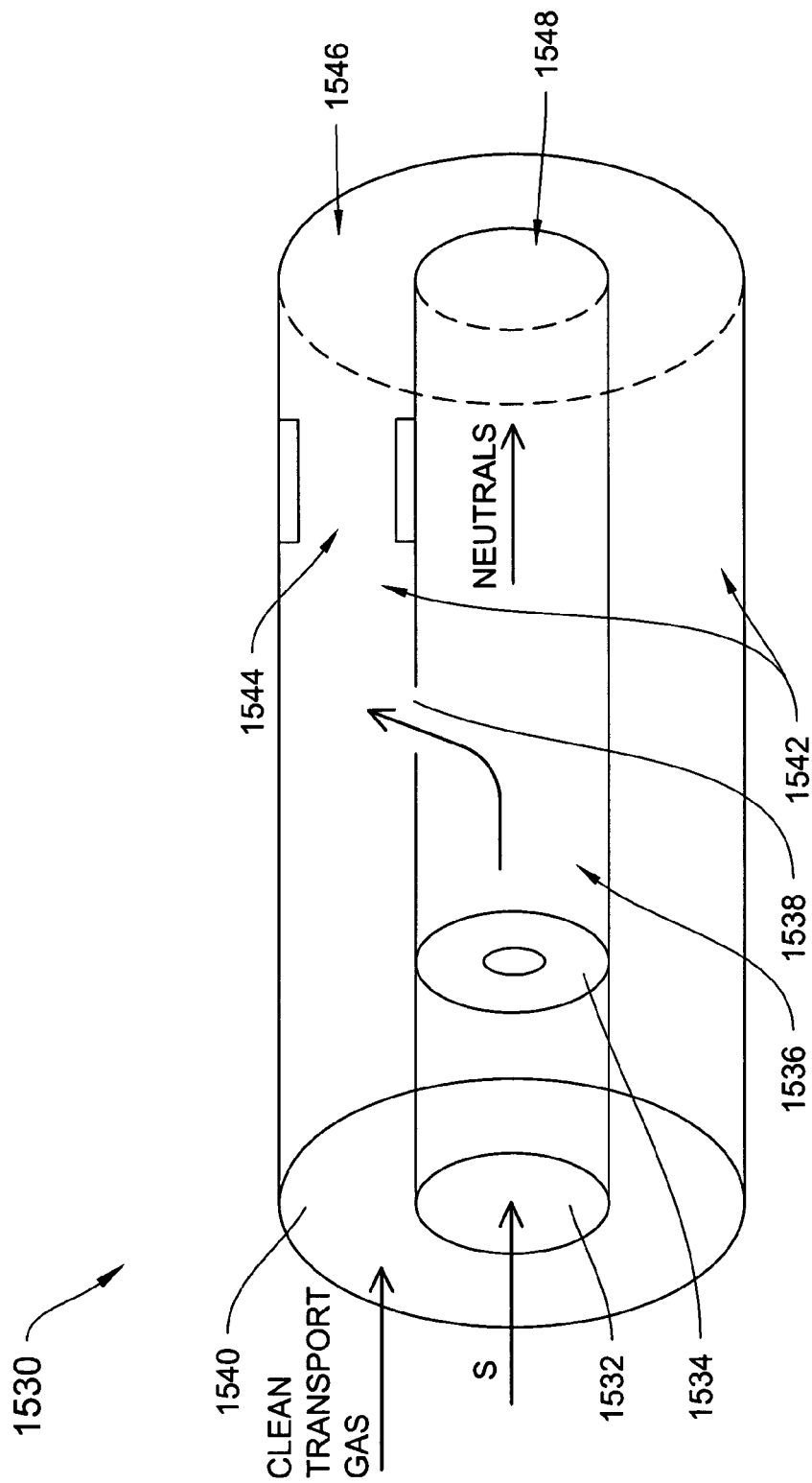
FIG. 46 is a conceptual block diagram of a chemical and/or biological agent detection system using a cylindrical DMS analyzer system, recirculation system, and multiple flow channels according to an illustrative embodiment of the invention.

FIG. 46 is a conceptual block diagram of a cylindrical or coaxial CWA and/or biological agent detection system 1530 according to an illustrative embodiment of the invention. The system 1530 includes a sample S inlet 1532, constrictor 1534, inner channel 1536, opening 1538, clean transport gas inlet 1540, outer channel 1542, analyzer system 1544, channel 1542 outlet 1546, and channel 1536 outlet 1548.

In operation, the system 1530 draws the sample S into the channel 1536 through the constrictor or orifice 1534. The constrictor 1534 may be adjustable, controllable or fixed to enable a pressure reduction below 1 atm, for example to 0.5, 0.65, or 0.85 atm, in the channel 1536. The clean transport gas inlet 1540 receives clean transport gas into the channel 1542. The channel 1542 may operate at pressures below 1 atm. The sample S may be drawn or attracted into the channel 1542 through the opening 1538 by a pressure differential with the channel 1536, an ion attractor in channel 1542, gas flow into channel 1542, or other like technique. The analyzer system 1544 then detects and identifies the ion species of the sample S and expels the sample S through the outlet 1546. The sample neutrals in the channel 1536 may be expelled through the outlet 1548.

FIG. 47 is a DMS system 1550 including an orifice 1552 at the system 1550 inlet to control pressure within the system 1550 in coordination with a pump 1554. The system also includes the molecular sieve 1556, ion source 1558, filter 1560, and detector 1562. In operation, the pump 1554 has sufficient power to draw a sample S through the orifice 1552 to then enable detection of the sample at a reduced pressure.

FIG. 48 is a DMS system 1564 including an orifice 1566, ionization source 1568, filter 1570, detector 1572, molecular sieve 1574, pump 1576, a second molecular sieve 1578, a membrane 1580, an inlet 1582, and outlets 1584 and 1586. Because the membrane 1580 is positioned upstream of the orifice 1566 and the sample flow is in direction 1588, the membrane 1580 operates at atmospheric pressure while the ionization source 1568, filter 1570, and detector 1572 operate below atmospheric pressure due to a pressure drop across the orifice 1566. It may be advantageous to operate the membrane 1580 at atmospheric pressure to prolong its useful life.

Figure 49:
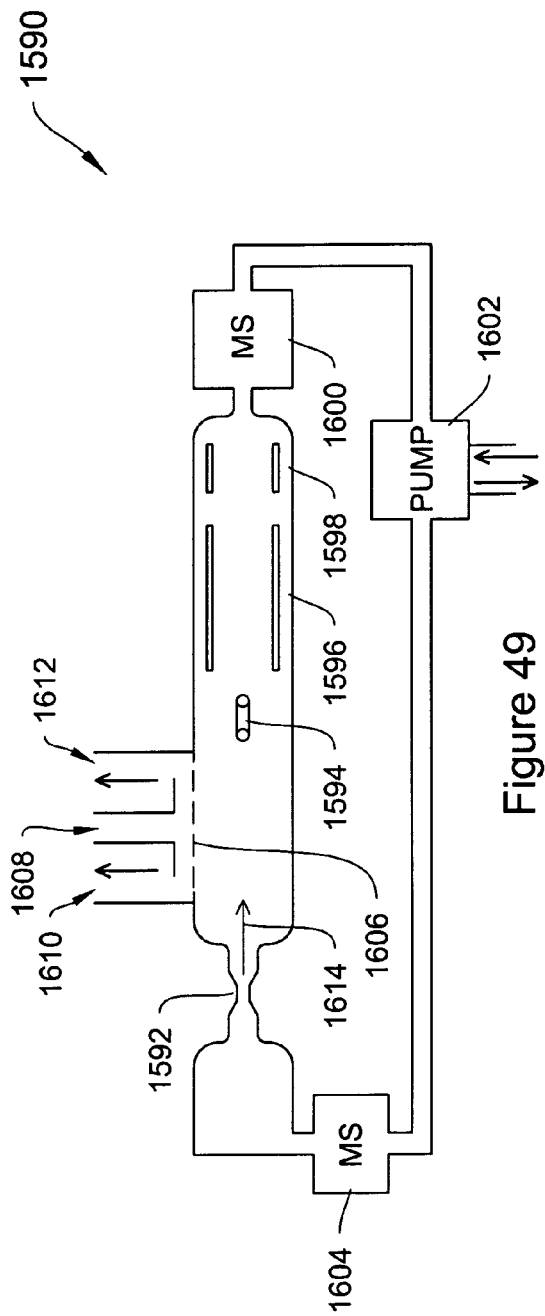

FIG. 49 is a DMS system 1590 including an orifice 1592, ionization source 1594, filter 1596, detector 1598, molecular sieve 1600, pump 1602, a second molecular sieve 1604, a membrane 1606, an inlet 1608, and outlets 1610 and 1612. Because the membrane 1606 is positioned downstream of the orifice 1592 and the sample flow is in the direction 1614, the membrane 1606 operates below atmospheric pressure along with the ionization source 1594, filter 1596, and detector 1598 due to a pressure drop across the orifice 1592. It may be advantageous to operate the membrane 1606 below atmospheric pressure.

FIG. 50 is a DMS system 1616 including an orifice 1618, ionization source 1620, filter 1622, detector 1624, molecular sieve 1626, pump 1628, a second molecular sieve 1630, a membrane 1632, an inlet 1634, and outlets 1636 and 1638. Because the membrane 1632 and the ionization source 1620 are positioned upstream of the orifice 1618 and the sample flow is in direction 1640, the membrane 1632 and the ionization source 1620 operate at atmospheric pressure while the filter 1622 and detector 1624 operate below atmospheric pressure due to a pressure drop across the orifice 1618. It may be advantageous to operate the membrane 1632 and ionization source 1620 at atmospheric pressure.

Figure 51:
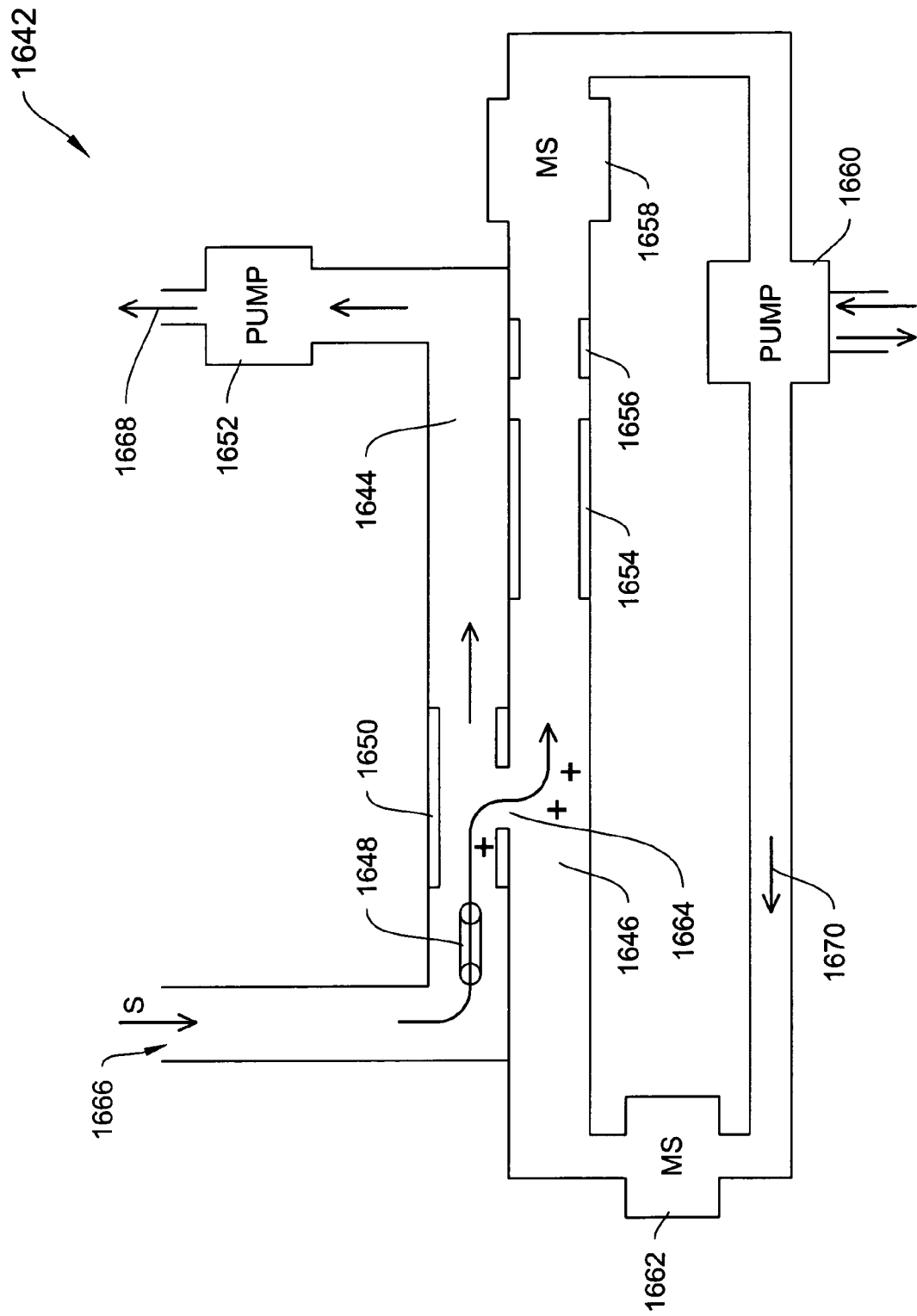

FIG. 51 is a DMS system 1642 including a first channel 1644 and a second channel 1646 operating at atmospheric pressure. The first channel 1644 includes an ionization source 1648, deflector electrode 1650, pump 1652, inlet 1666, and outlet 1668. The second channel 1646 includes a filter 1654, detector 1656, molecular sieve 1658, pump 1660, and molecular sieve 1662. An opening 1664 provides fluid communication between the channels 1644 and 1646.

In operation, the system 1642 receives a sample S at the inlet 1666 into the channel 1644. The ionization source 1648 ionizes the sample S. The ionized portions of the sample S, e.g., the positive ions, are deflected through the opening 1664 into the channel 1646 by the deflector 1650 having a positive charge. When the deflector 1650 is negatively charged, the deflector 1650 may deflect negative ions of sample S through the opening 1664 into the channel 1646. The neutrals and non-deflected ions of sample S are then drawn by the pump 1652 to the outlet 1668 and expelled from the system 1642 while the ions in the channel 1646 are filtered by the filter 1654 and detected by the detector 1656. The pump 1660 creates circulation flow in the direction 1670 within the channel 1646 to draw the sample S through the molecular sieve 1658 which collects spent analytes and then through a second molecular sieve 1662.

Figure 52:
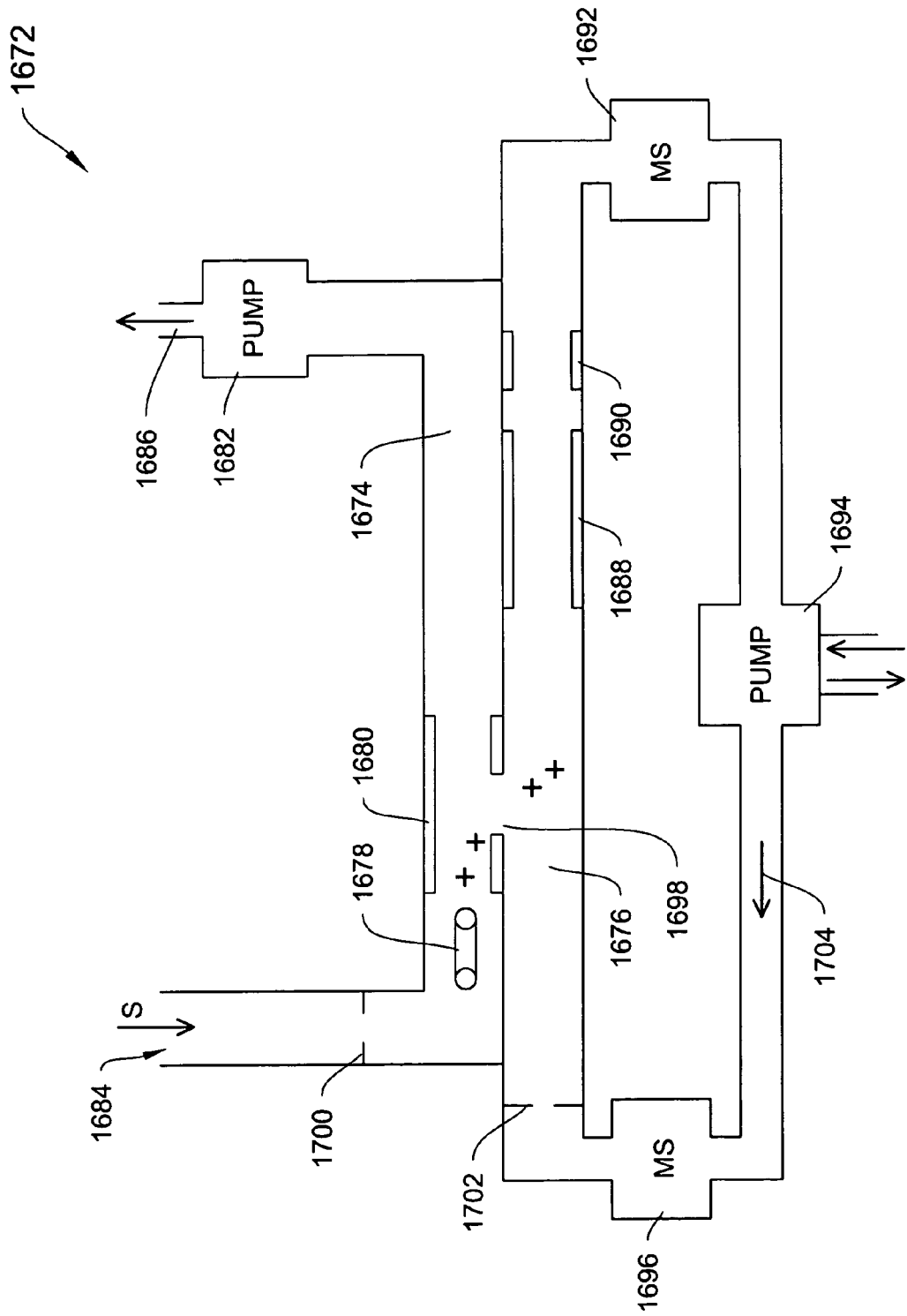

FIG. 52 is a DMS system 1672 including a first channel 1674 and a second channel 1676 operating below atmospheric pressure without a membrane. The first channel 1674 includes an ionization source 1678, deflector electrode 1680, pump 1682, inlet 1684, outlet 1686, and orifice 1700. The second channel 1676 includes a filter 1688, detector 1690, molecular sieve 1692, pump 1694, molecular sieve 1696, and orifice 1702. An opening 1698 provides fluid communication between the channels 1674 and 1676.

In operation, the system 1672 receives a sample S at the inlet 1684 into the channel 1674 and through the orifice 1700. The orifice 1700 provides a pressure drop within the channel 1674 caused by the gas and/or air flow generated by the pump 1682. The ionization source 1678 ionizes the sample S. The ionized portions of the sample S, e.g., the positive ions, are deflected through the opening 1698 into the channel 1676 by the deflector 1680 having a positive charge. When the deflector 1680 is negatively charged, the deflector 1680 may deflect negative ions of sample S through the opening 1698 into the channel 1676. The neutrals and non-deflected ions of sample S are then drawn by the pump 1682 to the outlet 1686 and expelled from the system 1672 while the ions in the channel 1676 are filtered by the filter 1688 and detected by the detector 1690. The pump 1694 creates circulation flow in the direction 1704 within the channel 1676 to draw the sample S through the molecular sieve 1692 which collects spent analytes and then through a second molecular sieve 1696.

Figure 53:
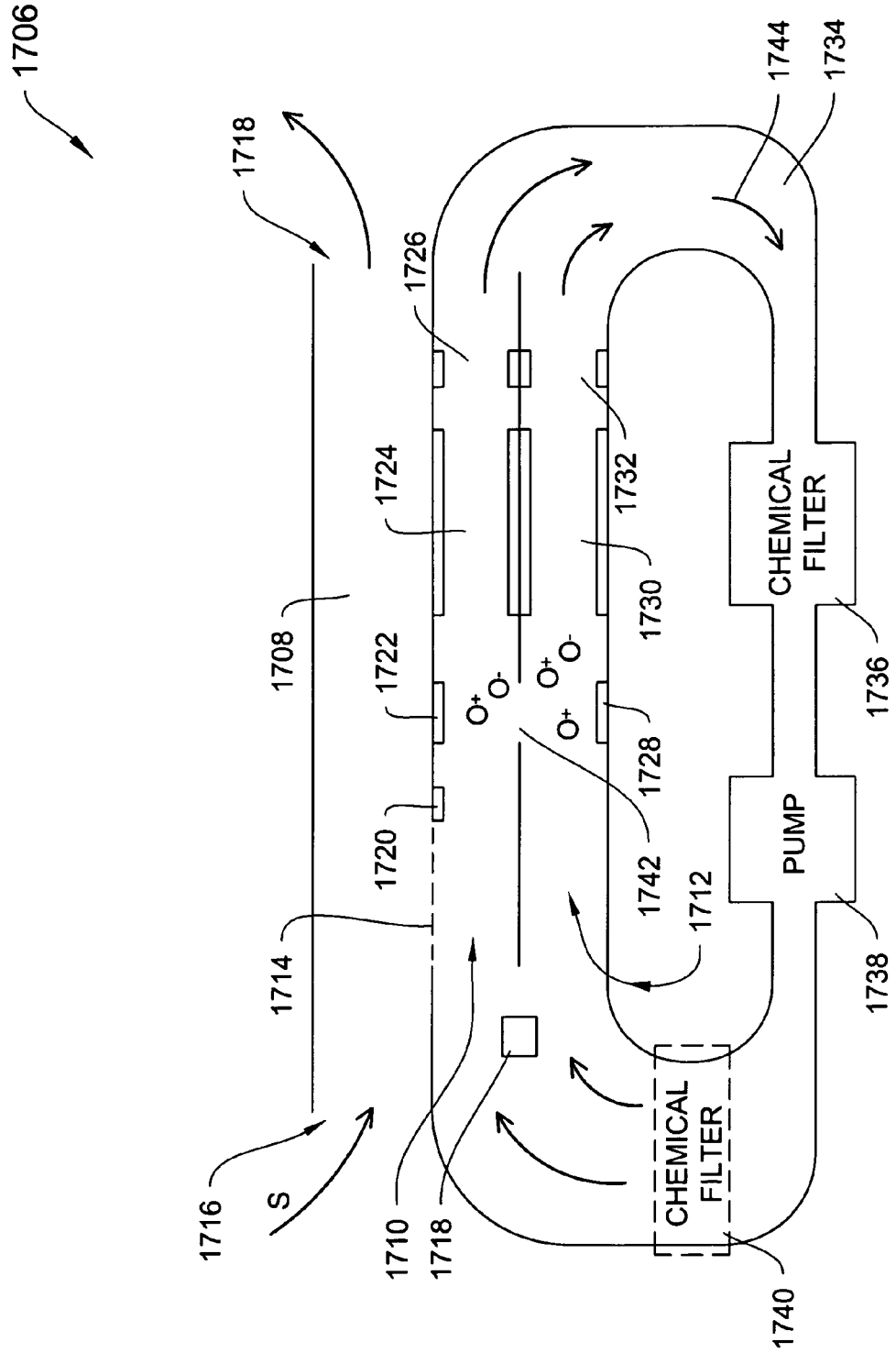

FIG. 53 is a DMS system 1706 including a first channel 1708, a second channel 1710, and a third channel 1712 with the second channel 1710 and third channel 1712 capable of operating at or below atmospheric pressure using a membrane 1714. The first channel 1708 includes an inlet 1716 and an outlet 1718. The second channel 1710 includes an ionization source 1718, optional ionization source 1720, deflector electrode 1722, filter 1724, and detector 1726. The third channel 1712 includes an attractor electrode 1728, filter 1730, and detector 1732. The combined circulation channel 1734 includes the chemical filter 1736, pump 1738, and optional chemical filter 1740. An opening 1742 provides fluid communication between the channels 1710 and 1712.

In operation, the system 1706 receives a sample S at the inlet 1716 into the channel 1708. The sample S may be introduced from a GS column. The membrane 1714 may filter a portion of the sample S and provide a pressure barrier to enable a pressure below atmospheric pressure in the channels 1710 and 1712. The channels 1710 and 1712, along with the combined circulation channel 1734, circulate filtered and clean carrier gas. The ionization source 1718 ionizes the sample S within this clean carrier gas. Optionally, a second ionization source 1720 may be employed in the channel 1710 to enhance the ability of the deflector 1722 and attractor 1728 to transfer selected ions from the channel 1710 to the channel 1712. For example, the ionized portions of the sample S, e.g., the positive ions, are deflected through the opening 1742 into the channel 1712 by the deflector 1722 when the deflector 1722 is positively charged. When the deflector 1722 is negatively charged, the deflector 1722 may deflect negative ions of sample S through the opening 1728 into the channel 1712.

The neutrals and non-deflected ions of sample S are then drawn by the pump 1738 through the channel 1710, filter 1724 and detector 1726 while the selected ions are drawn through the channel 1712, filter 1730, and detector 1732. The pump 1738 creates circulation flow in the direction 1744 within the channels 1710, 1712, and 1734 to draw the carrier gas from the channels 1710 and 1712 into the channel 1734 and through the chemical filter 1736 and, optionally, the second chemical filter 1740. The chemical filters 1736 and 1740 remove unwanted contaminants from the carrier gas. A make up gas may also optionally be introduced into the channel 1734 from an outside system.

The deflector 1722 and the attractor 1728 may be activated in a controlled manner to transport ions from the channel 1710 to the channel 1712. In the channel 1710, the non-deflected ions are filtered by filter 1724 and detected by detector 1726 while, in the channel 1712, the deflected and attracted ions are filtered by the filter 1730 and detector 1732. The resulting detected measurements from the channels 1710 and 1712 can then be compared, added, or subtracted from each other to enhance the identification of ion species. The controlled ionization of the sample S which is performed in a clean carrier gas, the detection in the channel 1712 of monomer or de-clustered ions, and the detection of clustered ions in the channel 1710 provide enhanced compound and ion species identification.

Other illustrative embodiments include systems, methods and devices for improving sample analysis, generally, and detection sensitivity, specifically, by performing sample ion species pre-separation and/or sample amplification. Such illustrative embodiments are discussed below.

Pre-separation of certain ion species of a sample reduces, and in some cases, eliminates the problem of competitive ionization within ion based mobility detection analyzers. At any atmospheric pressure or conditions where ion and/or neutral interactions have an effect on ion formation, atmospheric pressure chemical ionization (APCI) may occur. In such instances, compounds with the highest proton affinity (PA) and/or highest electron affinity (EA) preferentially capture or take up the charge from an ionization source. If there is a limited amount of charge available, for example, in a compact DMS system with limited power resources, the amount of available charge may not be sufficient to charge or ionize all of the molecules in a sample matrix. Thus, if only some of the molecules in a sample matrix are ionized, only that limited amount of molecules may be detected, resulting in erroneous analysis of a chemical matrix. Furthermore, certain compounds may not be ionized due to competitive ionization, resulting in no detection of these compounds. The invention includes embodiments that eliminate or mitigate the effects of competitive ionization by separating ion species before sample analysis or detection to prevent one ion species from consuming the charge intended to be used to ionize another ion species.

One technique for reducing the effect of competitive ionization is to use a gas chromatograph (GC) to pre-separate a sample matrix. A GC column may be used to separate multiple compounds, which may then be detected individually by a mobility-based analyzer, such as a DMS. Even a compound with a relatively low proton and/or electron affinity may be subsequently ionized and detected. A GC, however, is generally more complex, expensive, and often adds significant analysis time to provide sufficient compound separation. Typical analysis times are longer than one minute for sufficient compound separation. Thus, the invention includes systems, methods and devices for pre-separating a sample in a fast, efficient, and robust manner. According to other aspects, the invention provides such sample pre-separation in a compact package. Thus, the invention includes systems, methods and devices for pre-separating a sample in a fast, efficient, and robust manner. According to other aspects, the invention provides such sample pre-separation in a compact package.

Where further sample characterization is desired, neutrals, i.e., molecules of a sample that are not ionized, may be mixed with a new supply of charge, e.g., reactant ions or a plasma field, to enable further APCI reactions to occur. The newly created ions may then be removed for analysis or simply discarded. This process may be repeated until a desired compound type is ionized and detected using an analyzer.

In one embodiment of the invention, sample pre-fractionation is achieved by direct ionization of a sample matrix, competitive ionization by compounds of a certain type in the sample matrix, and then removal of the ionized compounds. The ionization source may be, for example, an UV source, laser, corona discharge, plasma source, soft X-ray source, or a source of reactant ions. Repeated interrogation of chemical compounds in a sample based on relative proton and electron affinities, using competitive ionization and the reaction of residual and/or un-reacted neutrals provides a comprehensive measure of the chemical composition of a sample without the need for traditional GC techniques.

The process of competitive ionization and the removal of product ions may be repeated, enabling incremental and selective isolation of product ions and neutrals. While chemical ionization involves the injection of fresh charge using reactant ions, non-chemical energy sources such as a laser or plasma or corona generator may ionize molecules of a sample.

In addition to being used for analysis, the invention may be used for selectively cleaning and/or conditioning samples, e.g., for removing selected molecules from a sample stream. For example, certain semiconductor industry or other process control applications require ultra pure or clean gasses. In these processes, water molecules are considered a contaminant in a gas stream of Nitrogen or Argon. In certain embodiments of the invention, water within a gas sample may be preferentially ionized and then removed from the gas stream while purified Argon or Nitrogen are then used in a low pressure chemical vapor deposition or for another semiconductor application.

Figure 54:
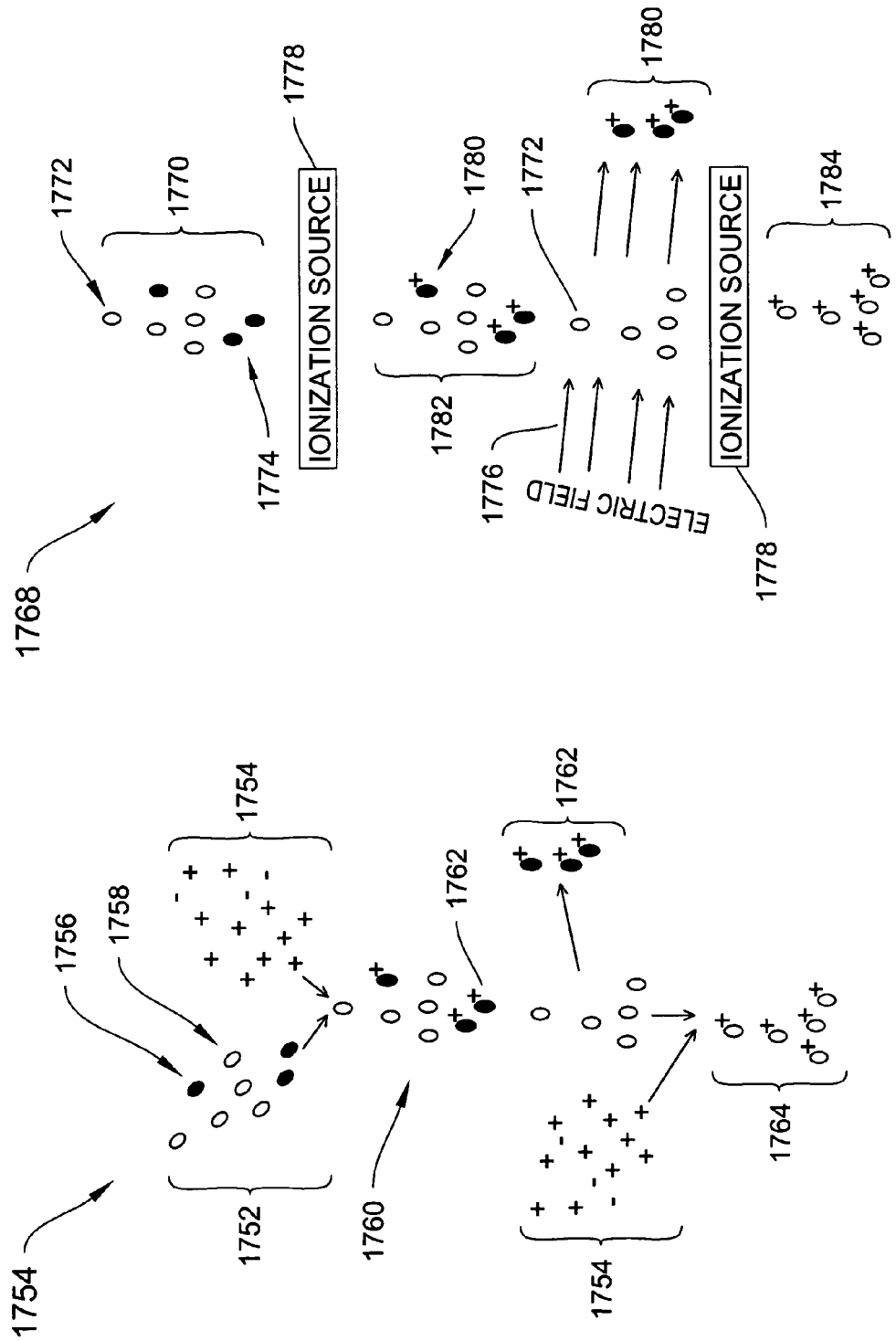
FIG. 54A is a conceptual diagram showing a pre-separation process of a sample matrix according to an illustrative embodiment of the invention.
FIG. 54B is a conceptual diagram showing a pre-separation process of a sample matrix according to another illustrative embodiment of the invention.

FIG. 54A is a conceptual diagram showing an example of a pre-separation process 1750 of a sample matrix 1752 including two types of compound molecules 1756 and 1758 according to an illustrative embodiment of the invention. The process 1750 begins by mixing reactant ions 1754 with a sample matrix of the two types of compound molecules 1756 and 1758 with a source of reactant ions 1754 to form a reactant ion and sample matrix mixture 1760.

This mixing may involve injecting (e.g., via an injection pulse) the sample matrix 1752 into a re-circulating or circular flow of gas where the mixing of reactant ions 1754 with neutral molecules 1756 and 1758 can be controlled. Also, the injection of reactant ions 1754 and subsequent extraction of product ions, e.g., product ions 1762, can be enabled using orifices in an ionization region, chamber, or gas flow path. Alternatively, a linear scheme may be employed where reactant ions 1754 are continuously introduced. In this scheme product ions, e.g., product ions 1762, are removed at discrete or variable distances from the injection point of sample matrix 1752 or the product ion formation point. In either case, the effluent flow (e.g., the flow of gas) may be used to control or adjust the residence or contact times between reactant ions 1754 and neutral molecules 1756 and 1758 to control the formation of product ions such as product ions 1762 or 1764.

Because the compound molecules 1756 are preferentially ionized by the reactant ions 1754, the mixture 1760 includes un-ionized compound molecules 1756 and product ions 1762. The product ions 1762 may be separated from the compound 1758 using chemical, electrical, magnetic, and/or a mechanical separation technique to remove the product ions 1762. The ionized molecules or product ions 1762 may then be analyzed and characterized, for example, using a DMS, IMS, MS, or any suitable analyzer system or may be discarded.

Because the first type of compound molecules 1756 are preferentially ionized to form ionized molecules or product ions 1762, the second type of compound molecules 1758 predominately are not ionized and retain a neutral charge. However, the source of reactant ions 1754 may be re-introduced to and mixed with the remaining neutral molecules 1758 to form ionized molecules or product ions 1764. These product ions 1764 may then be separated and analyzed. The process 1750 may be repeated for any sample matrix with any number of compounds by repeatedly ionizing the sample matrix and removing the resulting product ions. Due to competitive ionization, the process incrementally removes different compounds with different ionization energies, enabling a comprehensive analysis of all compounds with a chemical sample.

FIG. 54B is a conceptual diagram showing the pre-separation process 1768 of a sample matrix 1770 including two types of compound molecules 1772 and 1774 using an ionization source 1778 and electric field 1776 according to an illustrative embodiment of the invention. In this case, an ionization source 1778, such as a plasma corona, laser, UV source, or the like, is used to ionize the sample matrix 1770. Due to competitive ionization, the molecules 1774 predominantly are ionized into product ions 1780. These product ions 1780 are then exposed to the electric field 1776 which substantially removes the product ions 1780 from the ionized sample matrix 1782. The removed product ions 1780 may be analyzed or discarded.

The remaining non-ionized neutral molecules 1772 may then be ionized using the same ionization source 1778 or another ionization source to form product ions 1784. The product ions 1784 may then be analyzed using a DMS or discarded. The electric field 1776 may be generated by any one of or combination of a deflector plate deflector array, attractor plate, attractor grid, and attractor array or various other electrodes. Alternatively, a magnetic field may be employed to remove selected product ions.

Figure 55:
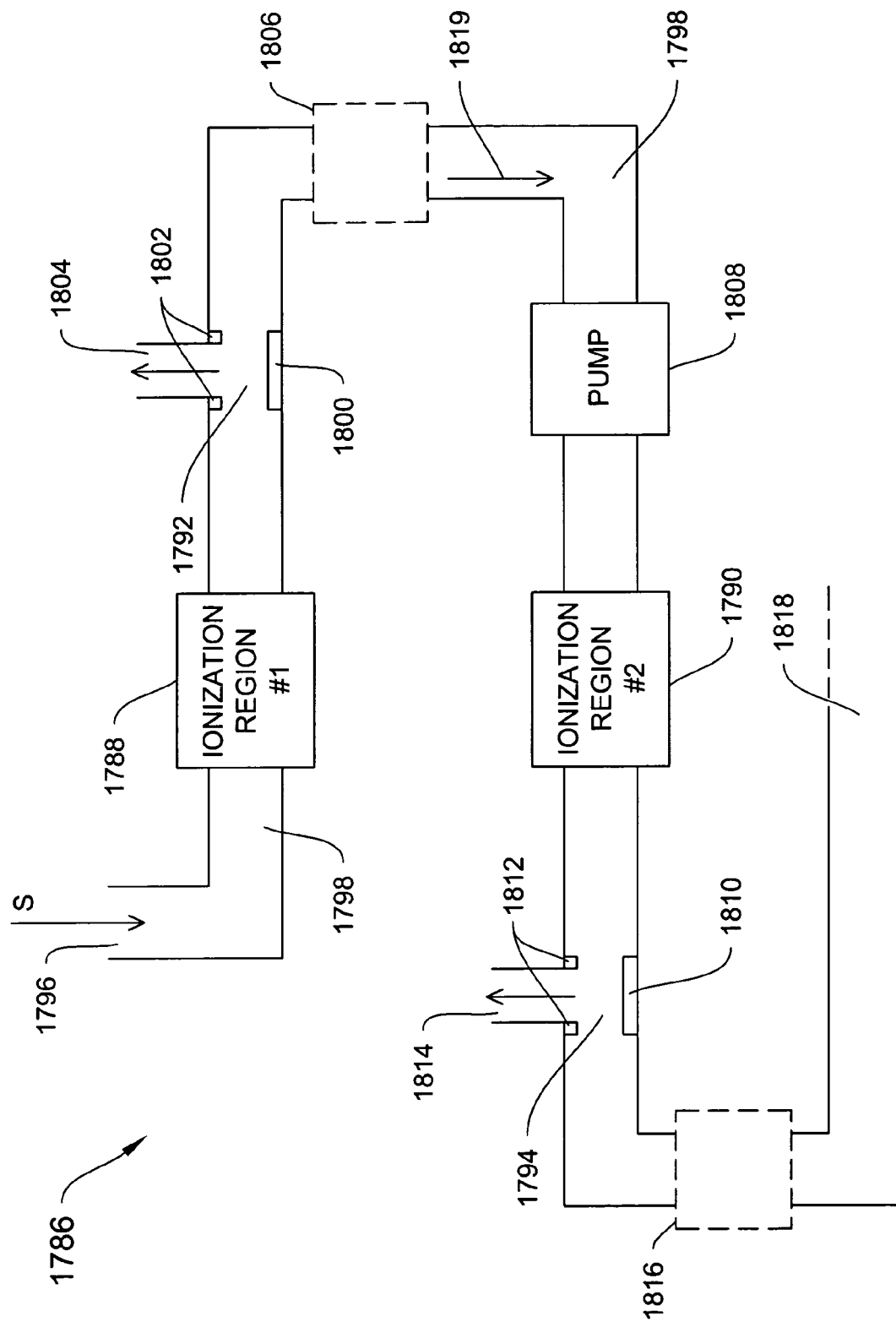
FIG. 55 is a conceptual block diagram of a sample pre-separation system using a first and second ionization region and first and second deflector regions to separate a sample matrix according to an illustrative embodiment of the invention.

FIG. 55 is a conceptual block diagram of a sample pre-separation system 1786. The pre-separation system 1786 uses first and second ionization regions 1788 and 1790 and first and second deflector regions 1792 and 1794 to separate a sample matrix S. Sample matrix S includes at least two compounds according to an illustrative embodiment of the invention. The sample pre-separation system 1786 includes an inlet 1796, gas flow channel 1798, first ionization region 1788, first deflector region 1792, first deflector plate 1800, first attractor plates 1802, first exhaust 1804, first optional analyzer 1806, pump 1808, second ionization region 1790, second deflector region 1794, second deflector plate 1810, second attractor plates 1812, second exhaust 1814, second optional analyzer 1816, and the exhaust channel 1818.

In operation, the sample matrix S is drawn into gas the flow channel 1798 through the inlet 1796 and then ionized in the first ionization region 1788. The sample S may be ionized using reactant ions or any of the non-reactant ion sources described previously. Due to the chemical properties of the molecules, the limited supply of charge leads to competitive ionization where predominantly certain types of compound molecules are ionized into product ions while other types of compound molecules predominantly remain neutral. The first deflector plate or electrode 1800 and the first attractor plates or electrodes 1802 generate an electric field that propels the product ions out of the gas flow channel 1798 and through first exhaust 1804. The first exhaust 1804 may deliver the product ions to an analyzer for detection and identification of the product ion species. Otherwise, the first exhaust 1804 may simply discard the product ions into the surrounding environment or neutralize them.

The remaining neutral molecules continue to travel in the gas flow channel 1798 and may pass through the first optional analyzer 1806. The analyzer 1806 may be a DMS system that ionizes the remaining neutral molecules, performs a non-destructive detection and identification, and then neutralizes the molecules before returning the neutrals to the gas flow channel 1798. The neutral molecules then continue to travel in the gas flow channel 1798 in the direction 1819 toward pump 1808 which propels the neutrals to the second ionization region 1790. In the second ionization region 1790, another type of compound molecule becomes predominantly ionized into product ions due to competitive ionization while one or more other compound molecules remain neutral in charge.

In the second deflector region 1794, second deflector plate 1810 and second attractor plates 1812 generate an electric field that propels the product ions out of the gas flow channel 1798 and through the second exhaust 1814. The second exhaust 1814 may deliver the product ions to an analyzer for detection and identification of the product ion species. Otherwise, the second exhaust 1814 may simply discard the product ions into the surrounding environment.

Again, the remaining neutral molecules continue to travel in the gas flow channel 1798 and may pass through an optional analyzer 1816. The analyzer 1816 may be a DMS system that ionizes the remaining neutral molecules, performs a detection and identification, and then neutralizes the molecules before returning the neutrals to the gas flow channel 1798. The neutral molecules may then continue to travel through the exhaust channel 1818 to yet further ionization regions and analyzers for further analysis or be discarded.

Figure 56B:
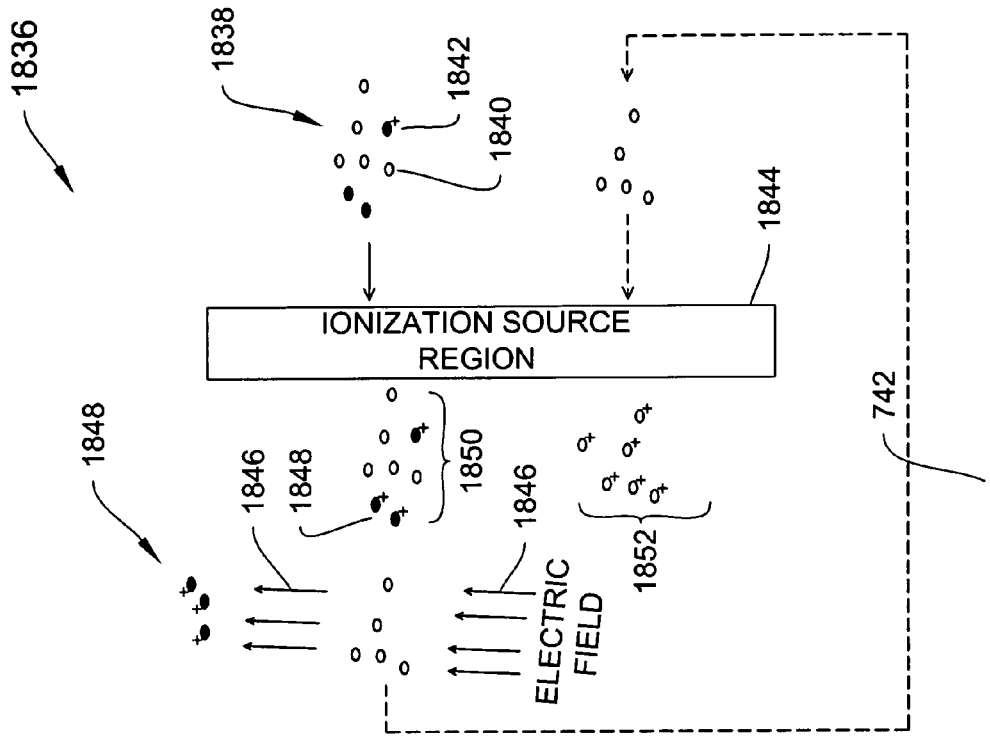
FIG. 56B is a conceptual diagram of a sample pre-separation process where a sample may be re-circulated multiple times to interact with an ionization source, such as an electric or magnetic field, to sequentially remove differing compound ions according to an illustrative embodiment of the invention.
Figure 56A:
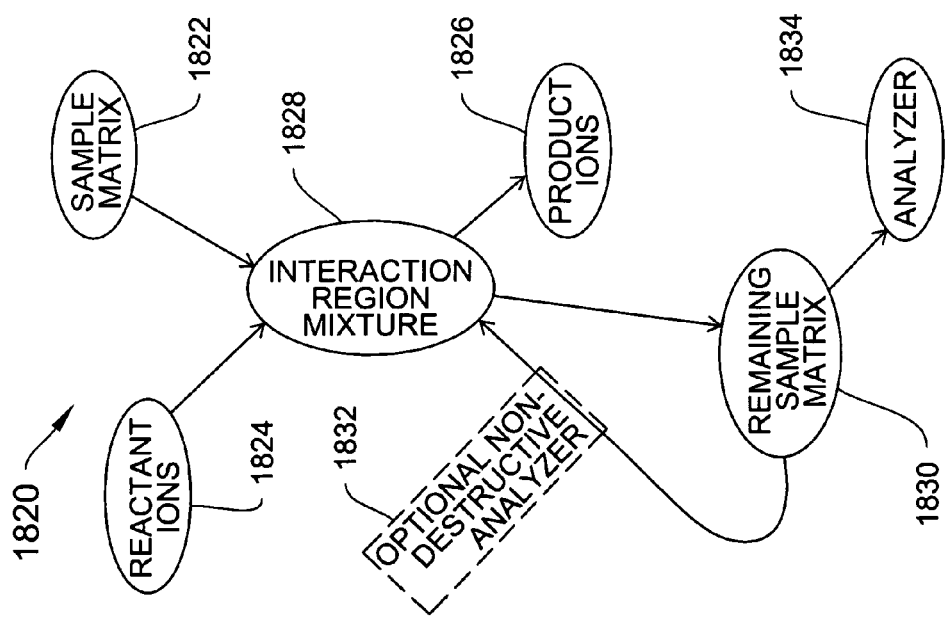
FIG. 56A is a conceptual diagram of a sample pre-separation process where a sample matrix may be re-circulated multiple times to interact with an ionization source such as reactant ions to sequentially remove differing compound product ions according to an illustrative embodiment of the invention.

FIG. 56A is a conceptual diagram of a sample pre-separation process 1820 according to a second illustrative embodiment of the invention. In the sample pre-separation process 1820, a sample matrix 1822 may be re-circulated multiple times to interact with an ionization source such as reactant ions 1824. The sample pre-separation process 1820 may remove different compound product ions 1826 from the sample matrix 1822 in each circulation. The process 1820 begins with the mixing of the sample matrix 1822 in an interaction region with a source of reactant ions 1824 to form an interaction region mixture 1828. Due to competitive ionization, the types of compounds within the sample matrix 1822 with relatively higher proton and electron affinities tend to become ionized. Other types of compounds in the sample matrix 1822 with lower proton and electron affinities tend to remain neutral.

The ionized molecules, or product ions 1826, are then removed from the mixture 1828 using previously described techniques such as an electric or magnetic field. The remaining neutral molecules 1830 are re-circulated for further ionization. Prior to further ionization, the remaining neutral molecules 1830 may optionally be subjected to mobility-based analysis using, for example, a DMS system 1832. After the analysis, the neutral molecules 1830 are then delivered to an interaction region for further mixing with reactant ions 1824.

The resulting neutral molecules 1830 may be re-circulated multiple times. Each time, the sample 1822 or remaining sample matrix 1830 interacts with reactant ions 1824 enabling the incremental removal of different compound molecules from the sample 1822. The compound removed in each re-circulation tends to have a lower proton or electron affinity than the compounds removed in a previous re-circulation. The remaining neutral molecules 1830 may also be delivered to an analyzer 1834 after a sequence of iterations for detection and identification of a desired ion species.

FIG. 56B is a conceptual diagram of a sample pre-separation process 1836 according to another illustrative embodiment of the invention. In the sample pre-separation process 1836, a sample matrix 1838 including at least two types of compound molecules 1840 and 1842, are re-circulated multiple times to interact with an ionization source 1844 and an electric field 1846. As a result, the sample pre-separation process sequentially removes different compound product ions. In this case, the ionization source 1844, such as a plasma field, laser, UV source, or like, is used to ionize the sample matrix 1838 to create an ionized sample matrix 1850. Due to competitive ionization, molecules 1842 tend to be ionized into product ions 1848 in favor of molecules 1840. These product ions 1848 are then exposed to the electric field 1846 which removes the product ions 1848 from the ionized sample matrix 1850. The product ions 1848 may be analyzed or discarded.

The remaining non-ionized neutral molecules 1840 may then be ionized by re-circulating the molecules 1840 to the same ionization source 1844 to form product ions 1852. The product ions 1852 may then be analyzed using a DMS or discarded. The electric field 1846 may be generated by any one of or combination of a deflector plate or electrode, deflector array, attractor plate or electrode, attractor grid, or attractor array. Alternatively, a magnetic field may be employed to remove selected product ions. This process may be applied to a matrix with an undetermined number of compounds by repeatedly re-circulating the sample through the same ion source to thoroughly characterize and/or identify all of the sample's constituents. The sample matrix may be introduced into the pre-separator as a plug or as a continuous stream.

Figure 57:
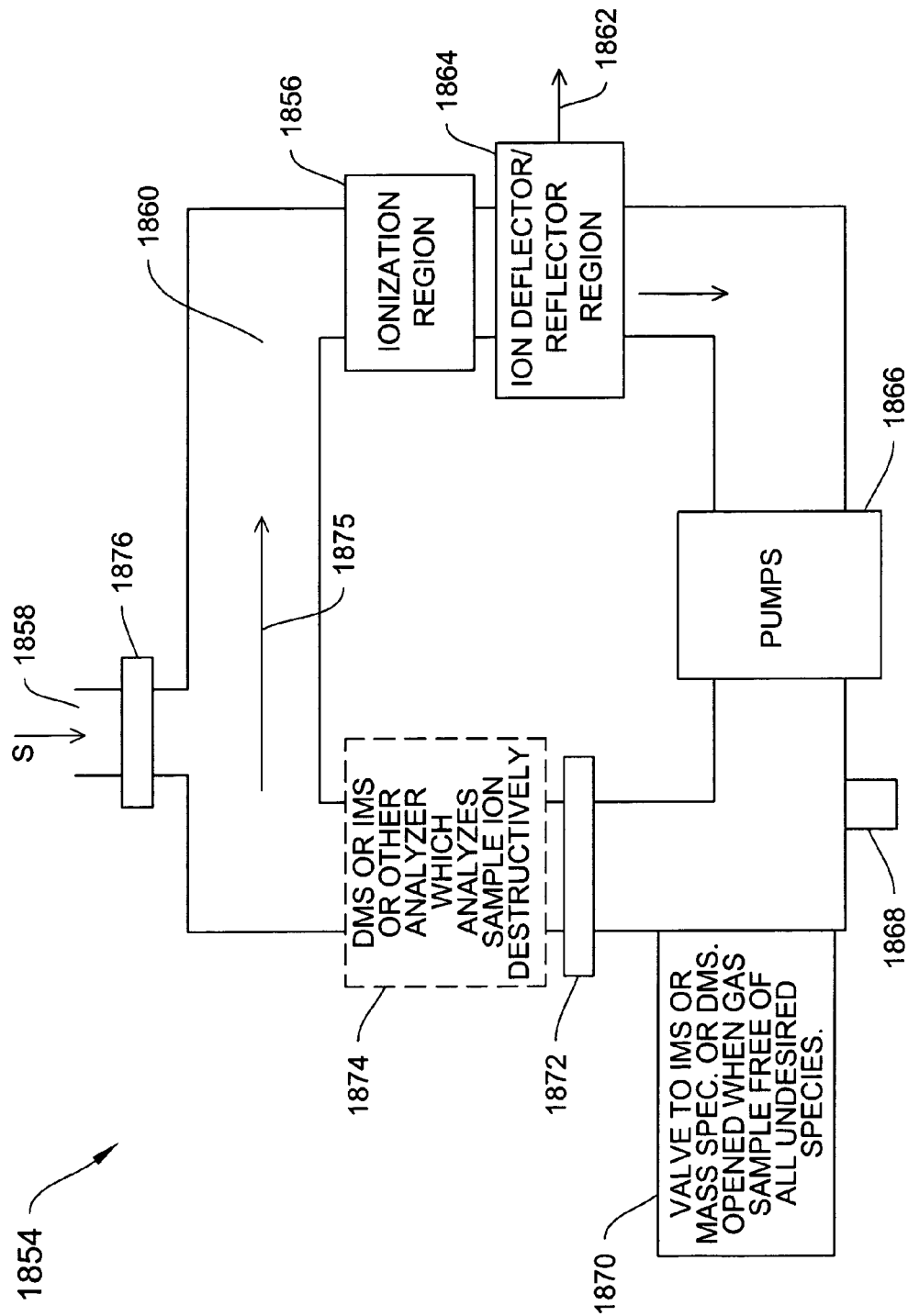
FIG. 57 is a conceptual block diagram of a sample pre-separation system capable of re-circulating a sample through an ionization region multiple times to sequentially remove differing compound ions having differing proton or electron affinities according to an illustrative embodiment of the invention.

FIG. 57 is a conceptual block diagram of a sample pre-separation system 1854 according to another illustrative embodiment of the invention. The sample pre-separation system 1854 re-circulates a sample matrix S through an ionization region 1856 multiple times. During each iteration, the sample pre-separation system 1854 removes a different compound from the sample matrix S. The compound removed on each iteration has a lower proton affinity or electron affinity than the compound removed in the prior iterations. The sample pre-separation system 1854 includes inlet 1858, inlet valve 1876, gas flow channel 1860, ionization region 1856, ion deflector/reflector region 1864, exhaust 1862, pump 1866, bleed valve 1868, analyzer valve 1870, flow channel valve 1872, and an optional analyzer 1874.

In operation, a sample matrix S is drawn into the gas flow channel 1860 through the inlet 1858 and the inlet valve 1876. The sample matrix S is then ionized in the ionization region 1856. The ionization region 1856 may utilize an ionization source such as a reactant ion source, UV source, laser, and the like to ionize the sample S. Due to competitive ionization, certain types of compound molecules predominantly are ionized into product ions while other types of compound molecules remain neutral. The deflector/reflector region 1864 includes a deflector and/or attractor electrodes that generate an electric field to propel the product ions out of the gas flow channel 1860 and through exhaust 1862. The first exhaust 1862 may deliver the product ions to an analyzer for detection and identification of the product ion species. Otherwise, the first exhaust 1862 may simply discard the product ions into the surrounding environment.

The remaining neutral molecules continue to travel in the gas flow channel 1860 through pump 1866. Pump 1866 propels the neutral molecules toward the analyzer valve 1870. The analyzer valve 1870 may be opened at certain times or in predetermined cycles to allow a portion of sample S through the valve 1870 to an analyzer. This controlled valve opening enables an analyzer such as a DMS, IMS, or MS to analyze a desired ion species without interference from undesired ion species. The gas flow channel 1860 may also include a bleed valve 1868 to enable makeup gas to be added or excessive gas to be removed from the gas flow channel 1860. Until the analyzer valve 1870 is operated, the neutral sample S molecules will continue to flow through flow channel valve 1872 and may pass through an optional analyzer 1874. The analyzer 1874 may be a DMS or like system that ionizes the remaining neutral molecules, performs a non-destructive detection and identification, and then neutralizes the molecules before returning the neutrals to the gas flow channel 1860. The neutral molecules then continue to travel in the direction 1875 through the gas flow channel 1860 and eventually return to the ionization region 1856. Another type of compound molecule becomes ionized into product ions due to competitive ionization while one or more other types of compounds molecules remain neutral in charge. This re-circulation process may be continued until an ion species is selected for analysis by operating the analyzer valve 1870.

Figure 58A:
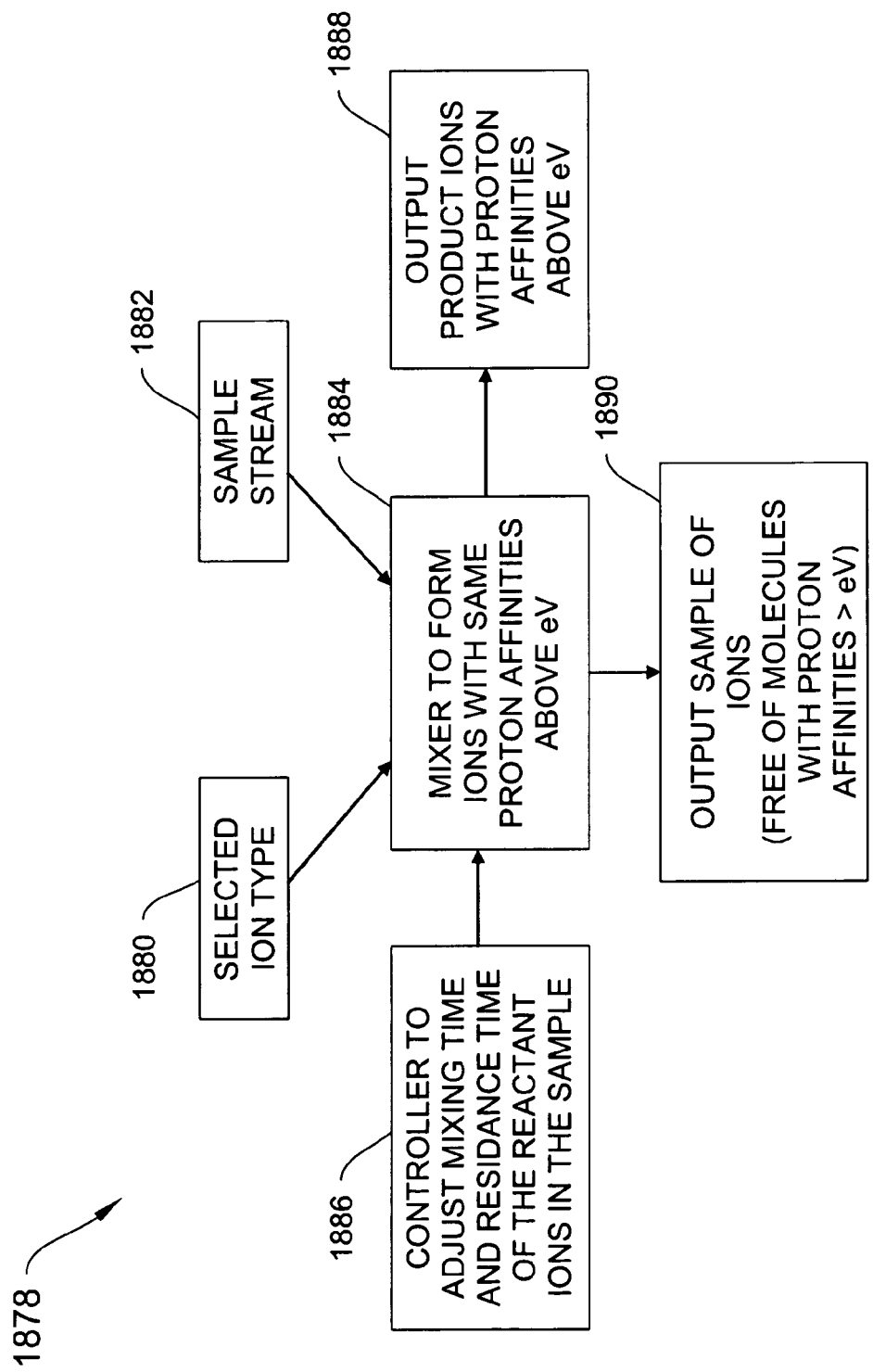
FIG. 58A is a conceptual diagram of a sample pre-separation system where selected ions are intermixed with a sample to enable the pre-separation of ions having a particular proton or electronic affinity according to an illustrative embodiment of the invention.

FIG. 58A is a conceptual diagram of a sample pre-separation system 1878 where pre-selected reactant ions are intermixed with a sample stream to enable the pre-separation of ions having a particular proton or electronic affinity according to an illustrative embodiment of the invention. The pre-separation system 1878 includes a selected reactant ion type 1880, a sample stream 1882, a mixing unit 1884, a controller unit 1886, product ions 1888, and neutral molecules 1890.

In operation, a selected reactant ion species type 1880 is introduced to the mixer 1884 along with a sample stream 1882. The reactant ion species can be, for example, oxygen ions or acetone ions. The mixer 1884 includes an interaction or mixer region that enables sample stream 1882 molecules of a relatively higher proton or electron affinity to be ionized into product ions 1888. Most molecules of a relatively lower proton or electron affinity remain neutral molecules 1890.

The controller 1886 is capable of regulating whether a single type or multiple types of reactant ions 1880 may be introduced into the mixer 1884 and mixed with the sample stream 1882. The type of reactant ion species may be selected based on a particular property such as proton affinity, mobility, electron affinity, and/or chemical activity. By introducing a certain type of reactant ion or ions 1880, the controller 1886 can determine which compound molecules or cluster of molecules of the sample stream 1882 are ionized. Thus, the controller 1886 may more precisely target particular compounds of the sample stream 1882 for further analysis or removal from the sample stream 1882. The controller 1886 may also regulate effluent and/or gas flow through the mixing and/or ionization region to control the contact time between reactant ions and sample molecules and, thereby, control the amount of ionization that occurs. This technique also applies to other types of ionization sources such a lasers, UV source, and plasma generators.

Figure 58B:
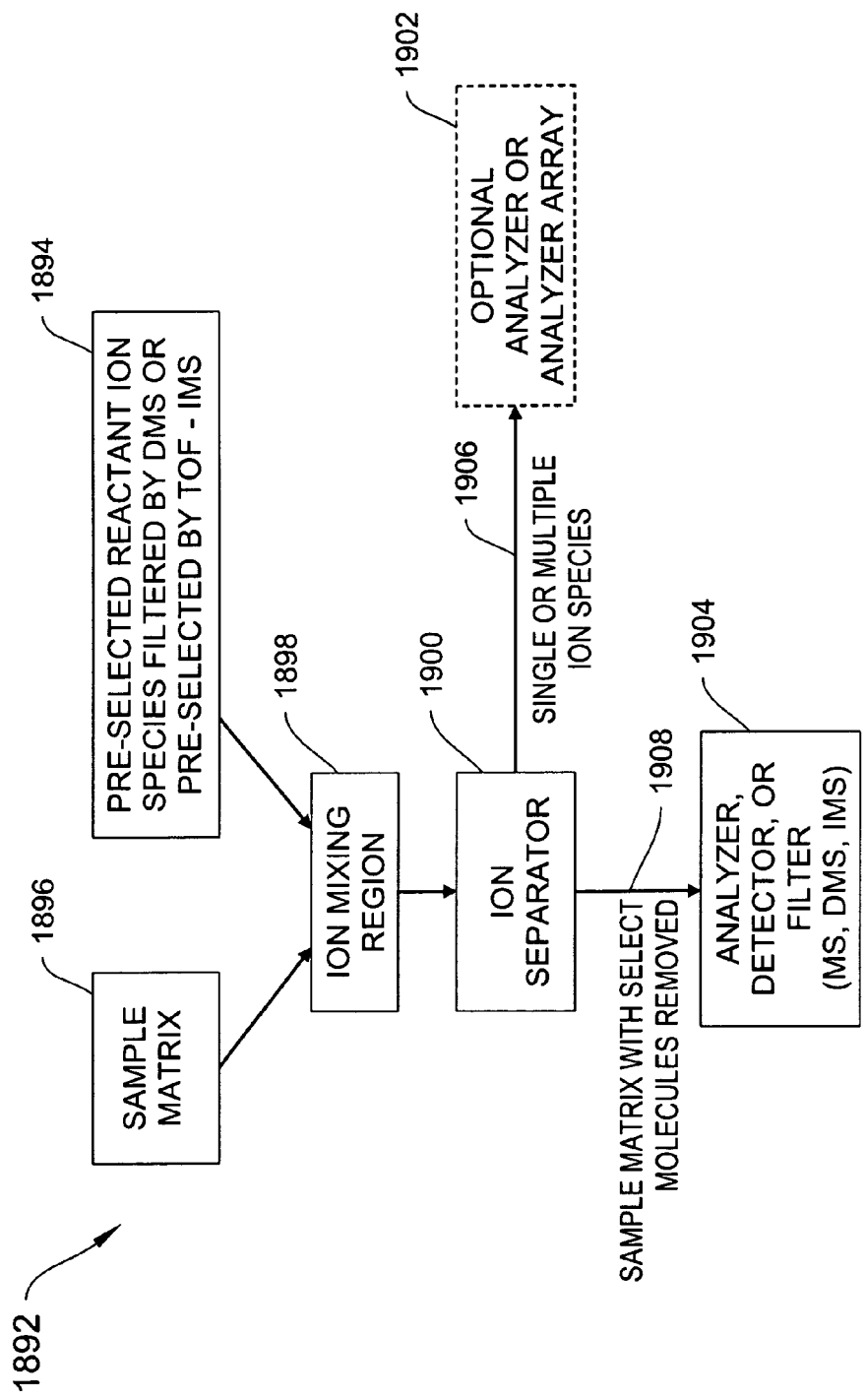
FIG. 58B is a conceptual diagram of a sample pre-separation system where selected ions, having been filtered and pre-selected, are then intermixed with a sample to enable the pre-separation of ions having a particular proton or electronic affinity according to an illustrative embodiment of the invention.

FIG. 58B is a conceptual diagram of a sample pre-separation system 1892 where pre-selected reactant ions 1894, having been filtered and pre-selected, are then intermixed with a sample matrix 1896 to enable the pre-separation of ions having a particular proton or electronic affinity according to an illustrative embodiment of the invention. The pre-separation system 1892 includes pre selected reactant ions 1894, a sample matrix 1896, an ion mixing region 1898, a product ion separator 1900, optional analyzer 1902, and an analyzer 1904.

In operation, pre-selected reactant ions 1894 of a particular species are introduced to the ion mixing region 1898 along with a sample matrix 1896. The reactant ions 1894 may be filtered and pre-selected using a DMS, IMS, MS, or like system. The ion mixer region 1898 enables the sample matrix 1896 molecules having proton or electron affinities above the proton and electron affinities of the pre-selected ions 1894 to be ionized into product ions 1906 while molecules of a relatively lower proton or electron affinity remain neutral molecules 1908. As described previously, various techniques may be utilized to remove the product ions 1906. An optional analyzer 1902 may be employed to analyze the product ions 1906. The optional analyzer 1902 may also include an array of mobility-based analyzers. The analyzer 1904, which may be a DMS, IMS, MS, or like, may be employed to analyze the remaining neutral molecules 1908.

For example, ionized molecules such as Acetone may be selectively introduced as reactant ions and mixed with a sample matrix to remove substantially all molecules with proton affinities higher than Acetone's proton affinity (812 KJ/mol). By mixing a sample matrix with sufficient Acetone ions, charge will preferentially be transferred to molecules in the sample matrix with higher proton affinities than Acetone. The ionized molecules or product ions may then be separated form the sample matrix leaving neutral molecules having proton affinities less than Acetone's proton affinity. Thus, by using a particular reactant ion species to ionize a sample matrix, selected species of a sample matrix may be removed or isolated in a more precise and controlled manner.

In certain embodiment of the invention, multiple types of ionization sources or alternating ionization sources may be employed together or in a sequential flow arrangement. Different ionization sources may be employed to selectively remove ion species having incrementally lower proton or electron affinities. Thus, molecules with higher proton or electron affinities will be removed first. For example, a sample may first be exposed to a low ionization source such as a UV source, laser, or other photo-ionization source to remove ion species with high affinities. Then, the sample may be exposed to a higher ionization source such as a radioactive $Ni^{63}$ ionization source to remove ions species with relatively lower affinities. Additional ionization sources with pre-determined ionization energies may be employed to remove additional ion species until a desired ion species remains for analysis using a DMS, IMS, MS, and like mobility-based analyzer.

FIG. 59A is a conceptual diagram of a sample pre-separation system 1910 including two flow channels wherein multiple ion separations are enabled by multiple ionization sources according to an illustrative embodiment of the invention. The sample pre-separation system 1910 includes an inlet 1916, gas flow channel 1912, inlet 1918, gas flow channel 1914, UV ionization source 1920, first $Ni^{63}$ ionization source 1922, second $Ni^{63}$ ionization source 1924, first opening 1926, second opening 1928, third opening 1930, outlet 1932, and outlet 1934.

In operation, a sample matrix S is introduced into gas flow channel 1912 through inlet 1916. The UV ionization source 1920 then ionizes the sample S matrix at a relatively low energy. Due to competitive ionization, the compound molecules of sample S having the lowest ionization energies and highest affinities, e.g., ionization energies at about or below the UV ionization energy level, are ionized to form product ions. These product ions are then deflected from gas flow channel 1912 and/or attracted into gas flow channel 1914 through the first opening 1926 by the electrode 1919. These low energy product ions may then be delivered by gas flow channel 1914 through outlet 1934 to an analyzer or discarded.

The inlet 1918 accepts gas flow into gas flow channel 1914 to enable the flow of product ions delivered from gas flow channel 1912.

For example, assume the sample matrix S includes nitric oxide species (NOx). In such a case, NO and $NO_2$ are formed by direct ionization because these are the only NOx species with ionization energies below the ionization energy of the UV source. Tables 2 and 3 provide lists of positive and negative NOx ion species equations respectively. Also, Table 4 shows the ionization energy, proton affinity, and electron affinity for selected NOx ion species.

TABLE 2

Positive NOx Ion Species Equations $NO + h\nu \rightarrow NO^+ + e^-$
$NO^+ + H_2O + M \rightarrow (H_2O)NO^+ + M$
$(H_2O)NO^+ + H_2O + M \rightarrow (H_2O)_2NO^+ + M$
$(H_2O)_{n-1}NO^+ + H_2O + M \rightarrow (H_2O)_nNO^+ + M$
$(H_2O)_3NO^+ + H_2O \rightarrow HNO_2 + (H_2O)_3H^+$

TABLE 3

Negative NOx Ion Species Equations $NO_2 + h\nu \rightarrow NO + O$
$NO_2 + O + M \rightarrow NO_3 + M$
$NO_2 + e^- \rightarrow NO_2^-$
$NO_2^- + NO_3 \rightarrow NO_2 + NO_3^-$
$NO_2^- + NO_2 \rightarrow NO + NO_3^-$

TABLE 4

NOx Ionization Energy, Proton Affinity, and Electron Affinity

|  | Ionization Energy EI (eV) | Electron Affinity EA (eV) | Proton Affinity PA (KJ/mol) |
|---|---|---|---|
| NO | 9.26 | 0.026 | 531.8 |
| $NO_2$ | 9.58 | 2.3 | 591 |
| $NO_3$ | 12.57 | 3.9 | n/a |

After ionization occurs with respect to the UV ionization source 1920, the non-ionized or neutral molecules remaining in the gas flow channel 1912 proceed to the first $Ni^{63}$ ionization source 1922. Due to the competitive ionization process, the remaining molecules of the sample matrix S with the highest affinities are ionized to form product ions. These product ions are then deflected from the gas flow channel 1912 and/or attracted into the gas flow channel 1914 through the second opening 1928 by the electrode 1921. These product ions may then be delivered by the gas flow channel 1914 through the outlet 1934 to an analyzer or discarded.

Figure 60:
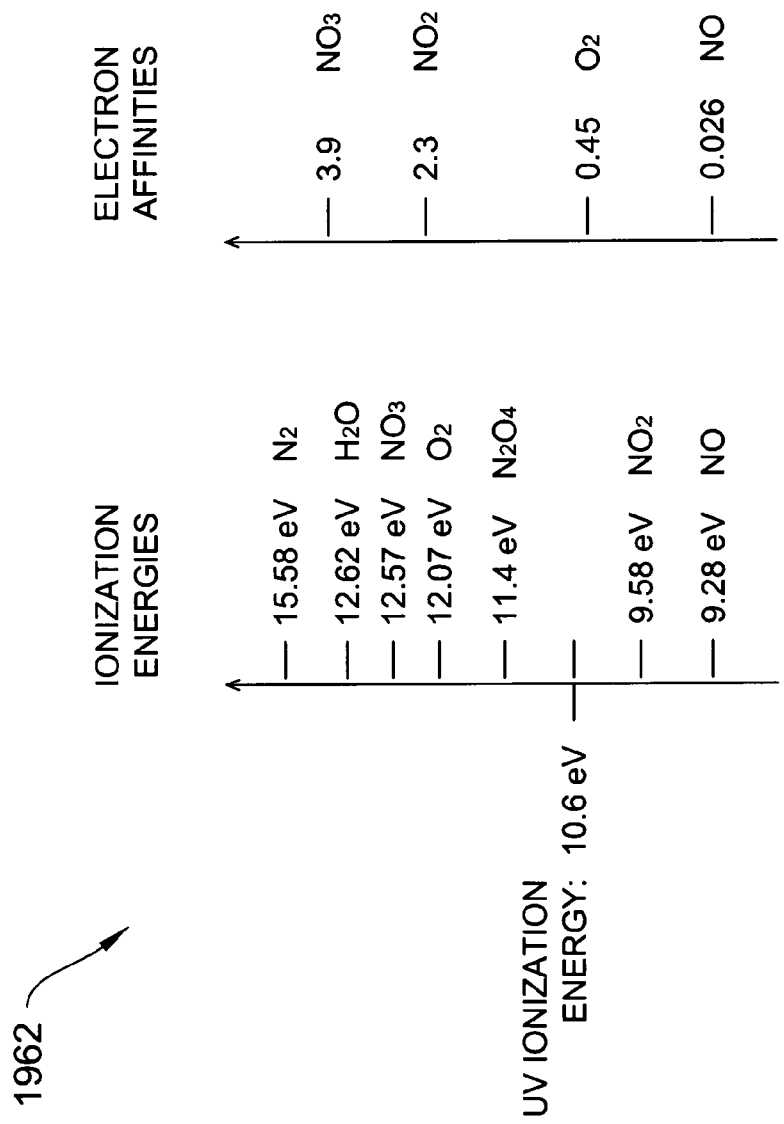
FIG. 60 is a graph of ionization energies required for various NOx ion species to form either positive or negative ions by direct photo ionization in air.

Assuming the sample matrix S includes NOx species, the negative polarity NOx compounds with the highest electron affinity such as $NO_2$ are $NO_3$ are removed as product ions. FIG. 60 shows the electron affinities for $NO_2$ are $NO_3$ respectively.

After ionization occurs with respect to the first $Ni^{63}$ ionization source 1922, the non-ionized or neutral molecules remaining in the gas flow channel 1912 proceed to the second $Ni^{63}$ ionization source 1924. Due to the competitive ionization process, the remaining molecules of the sample matrix S with the highest affinities are ionized to form product ions. These product ions are then deflected from the gas flow channel 1912 and/or attracted into the gas flow channel 1914 through the third opening 1930 by the electrode 1923. These product ions may then be delivered by the gas flow channel 1914 through the outlet 1934 to an analyzer or discarded. Any remaining neutral molecules may be delivered through the outlet 1932 to an analyzer for analysis.

Because the ionization process is dynamic and time dependent, the residence time for a sample matrix S within the proximity of an ionization source may be adjusted to form particular types of product ions. Thus, the interaction time between an ionization source and a sample matrix S may also be controlled to selectively remove certain product ion species. For example, with regard to the NOx ion species, the $NO_3^-$ ion species may be formed by direct photo-ionization using a UV ionization source according to the equations listed in Table 3.

FIG. 59B is a conceptual diagram of a sample pre-separation system 1936 having two flow channels wherein multiple ion separations are enabled by multiple ionization sources including a plasma ionization source 1950 according to an illustrative embodiment of the invention. The sample pre-separation system 1936 includes an inlet 1942, gas flow channel 1938, inlet 1944, gas flow channel 1940, UV ionization source 1946, $Ni^{63}$ ionization source 1948, plasma ionization source 1950, first opening 1952, second opening 1954, third opening 1956, outlet 1958, and outlet 1960.

In operation, a sample matrix S is introduced into gas flow channel 1938 through inlet 1942. The UV ionization source 1946 then ionizes the sample S matrix at a relatively low energy. Due to competitive ionization, the compound molecules of sample S having the lowest ionization energies and highest affinities, e.g., ionization energies at about or below the UV ionization energy level, are ionized to form product ions. These product ions are then deflected from gas flow channel 1938 and/or attracted into gas flow channel 1940 through the first opening 1952 by the electrode 1951. These low energy product ions may then be delivered by the gas flow channel 1940 through the outlet 1960 to an analyzer or discarded. The inlet 1944 accepts gas flow into gas flow channel 1940 to enable the flow of product ions delivered from the gas flow channel 1938.

After ionization occurs with respect to the UV ionization source 1946, the non-ionized or neutral molecules remaining in the gas flow channel 1938 proceed to the $Ni^{63}$ ionization source 1948. Due to the competitive ionization process, the remaining molecules of the sample matrix S with the highest affinities are ionized to form product ions. These product ions are then deflected from the gas flow channel 1938 and/or attracted into gas flow channel 1940 through the second opening 1954 by the electrode 1953. These product ions may then be delivered by the gas flow channel 1940 through the outlet 1960 to an analyzer or discarded.

After ionization occurs with respect to the $Ni^{63}$ ionization source 1948, the non-ionized or neutral molecules remaining in the gas flow channel 1938 proceed to the plasma ionization source 1950. Due to the competitive ionization process, the remaining molecules of the sample matrix S with the highest affinities are ionized to form product ions. These product ions are then deflected from gas flow channel 1938 and/or attracted into gas flow channel 1940 through the third opening 1956 by the electrode 1955. These product ions may then be delivered by gas flow channel 1940 through outlet 1960 to an analyzer or discarded. Any remaining neutral molecules may be delivered through the outlet 1958 to an analyzer for analysis.

Figure 61A:
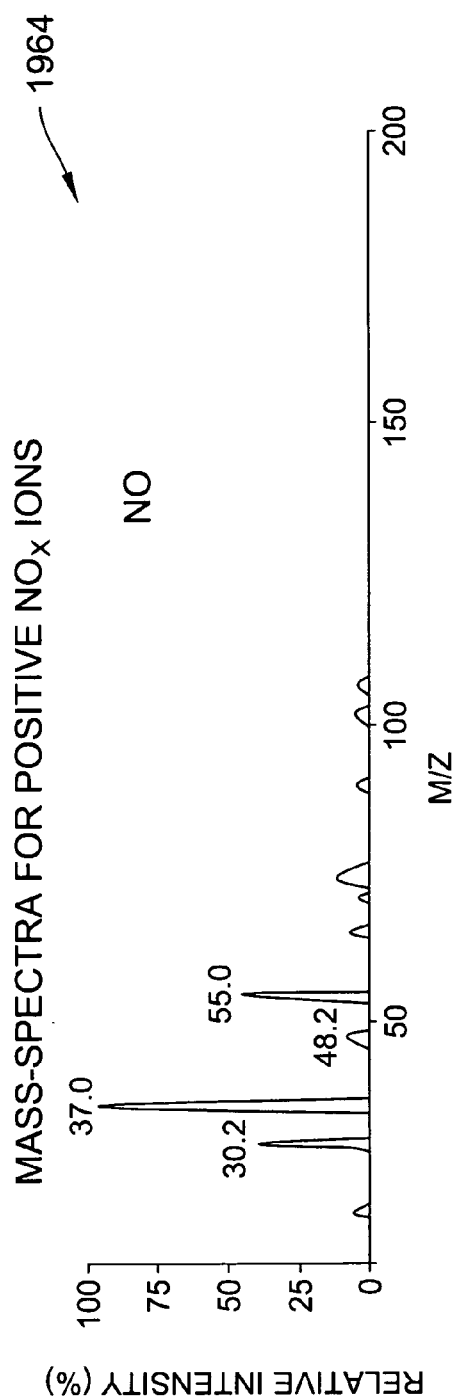
FIG. 61A is a graph of relative intensity versus mass units showing the mass-spectra to positive NOx ion NO.
Figure 61B:
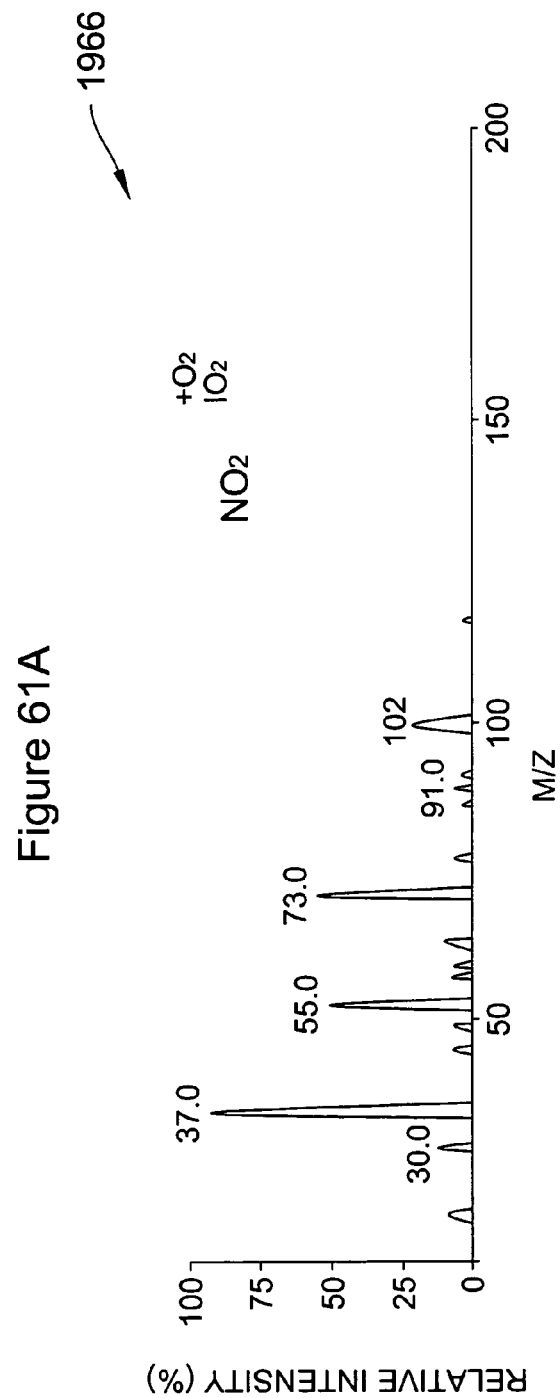
FIG. 61B is a graph of relative ion intensity versus mass units showing the mass-spectra for positive NOx ion $NO_2$.
Figure 61C:
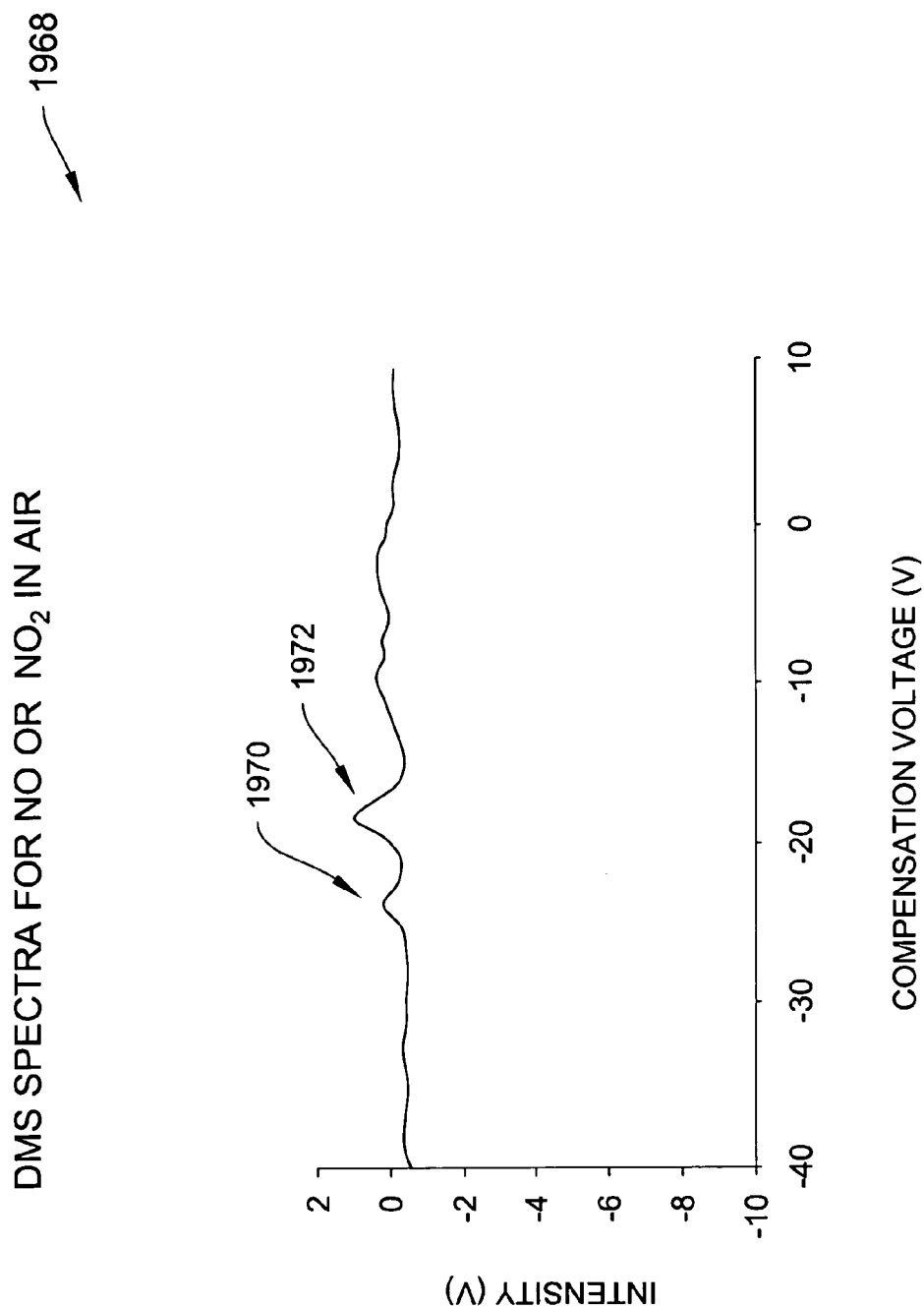
FIG. 61C is a graph of ion intensity versus field compensation voltage showing the ion intensity peaks for NO and $NO_2$.

FIG. 60 is a graph 1962 of ionization energies required for various NOx ion species to form either positive or negative ions by direct photo-ionization in air. The NOx species NO and $NO_2$ have relatively high affinities as reflected by their DMS and mass spectra which are shown in FIGS. 61A, 61B, and 61C. FIG. 61A is a graph 1964 of relative intensity versus mass units showing the mass-spectra to positive NOx ion NO. FIG. 61B is a graph 1966 of relative ion intensity versus mass units showing the mass-spectra for positive NOx ion $NO_2$. FIG. 61C is a graph 1968 of ion intensity versus field compensation voltage showing the ion intensity peaks 1970 and 1972 for NO and $NO_2$ respectively.

Figure 62:
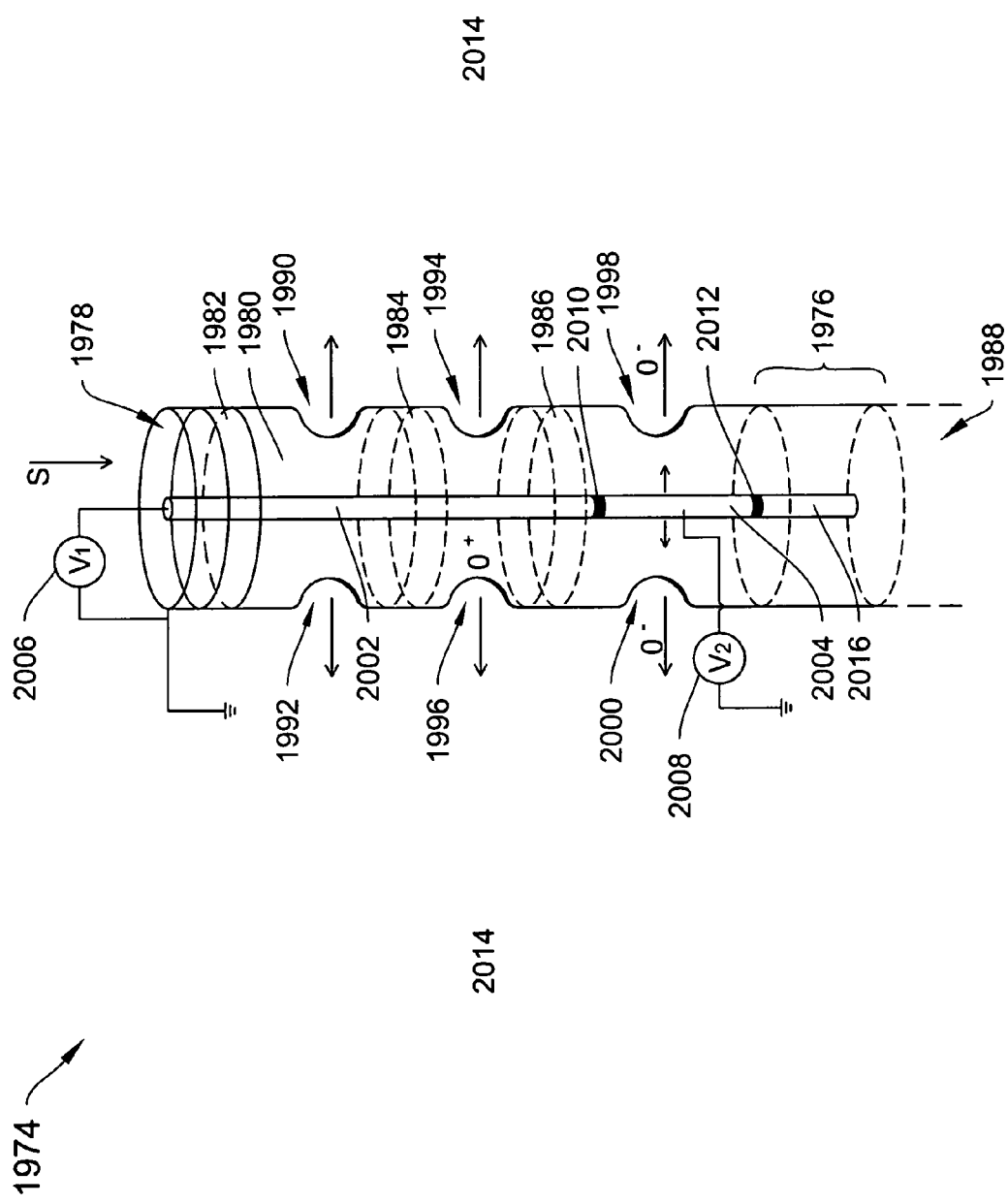
FIG. 62 is a conceptual diagram of a cylindrical sample pre-separation system including an integrated cylindrical DMS or other analyzer according to an illustrative embodiment of the invention.

FIG. 62 is a conceptual diagram of a cylindrical sample pre-separation system 1974 including an integrated cylindrical DMS 1976 or other analyzer according to an illustrative embodiment of the invention. The sample pre-separation system 1974 includes an inlet 1978, gas flow channel 1980, $Ni^{63}$ ionization source 1982, ionization region 1984, ionization region 1986, outlet 1988, and deflector outlets 1990, 1992, 1994, 1996, 1998, and 2000. The system 1974 also includes a deflector 2002, deflector 2004, voltage source 2006, voltage source 2008, insulator 2010, insulator 2012, and surrounding space 2014.

In operation, a sample matrix S is drawn into the gas flow channel and/or path 1980 and ionized by the $Ni^{63}$ ionization source. Due to competitive ionization, certain compounds within the sample matrix S within the highest affinities are ionized into product ions. These product ions are then deflected from the gas flow channel 1980 into the surrounding space 2014 through deflector outlets 1990 and 1992. The deflector 2002 resides within the center of the coaxial gas flow channel 1980 and holds an electric potential or voltage generated by the voltage source 2006. The deflector 2002 potential is high enough to create an electric field of sufficient strength to propel the product ions from the gas flow channel 1980 into the surrounding space 2014. The surrounding space 2014 may be an enclosed, substantially enclosed, or unenclosed path and/or channel. The surrounding space 2014 may be a second gas flow channel surrounding the system 1974 that directs product ions propelled from the gas flow channel 1980 to an analyzer or other system for further analysis.

The remaining neutral molecules of the sample matrix S then travel to the ionization region 1984. Due to competitive ionization, certain compound molecules within the remaining sample matrix S with the highest affinities are ionized into a new group of product ions. These product ions are then deflected from the gas flow channel 1980 into the surrounding space 2014 through deflector outlets 1994 and 1996. The deflector 2002 potential is high enough to create an electric field of sufficient strength to propel the product ions from the gas flow channel 1980 into the surrounding space 2014.

The remaining neutral molecules of the sample matrix S then travel to the ionization region 1986. Due to competitive ionization, certain compound molecules within the remaining sample matrix S with the highest affinities are ionized into a third group of product ions. These product ions are then deflected from the gas flow channel 1980 into the surrounding space 2014 through deflector outlets 1998 and 2000. The deflector 2004 resides within the center of the coaxial gas flow channel 1980 and holds an electric potential or voltage generated by the voltage source 2008. The deflector 2004 potential is high enough to create an electric field of sufficient strength to propel the product ions from the gas flow channel 1980 into the surrounding space 2014. An insulator 2010 provides electrical separation and enables an electrical potential difference between deflector 2002 and deflector 2004.

The remaining molecules of the sample matrix S, which preferably include the compound of interest for detection, are then delivered to the coaxial DMS system 1976 for analysis. The insulator 2012 provides electrical separation between the deflector 2004 and the DMS ion filter electrode 2016. The ionization regions 1984 and 1986 may use any one of the previously described ionization sources to ionize the sample matrix S.

In certain illustrative embodiments, a variable and/or adjustable ionization energy source may be employed by the forgoing pre-separation systems. For example, a tunable laser may be used as an adjustable ionization source. A sample may then be repeatedly exposed to the laser ionization source while the energy level of the laser is changed for each ionization. By adjusting the laser energy level and the resulting ionization energy, different molecules of a sample are ionized and separated from the sample matrix. The wavelength or frequency of a laser may be adjusted to enable the selective removal of molecules from a sample.

In certain illustrative embodiments, the sample matrix environmental conditions may be altered at various stages during the ionization and separation process. For example, the level of moisture may be set at one level during the ionization process and then adjusted to another level during the extraction or removal process. By altering the environmental conditions such as the moisture level at different stages of the ionization and separation process the extraction of particular ions from a sample may be improved.

In other illustrative embodiments, dopants may be intermixed with a sample in the mixing region of a pre-separation system to improve and/or control the charge transfer to sample molecules from reactant ions. Different dopants may be added to a sample at different times and/or at various stages of the ionization and separation process. The dopants may be added before, during, or after selected analytes or product ions are removed from a sample matrix. For example, an inkjet like printer head may be loaded with various types of dopants. The head may deploy one or more dopants using injection pulses at various times and/or stages of an ionization and separation process.

Figure 63:
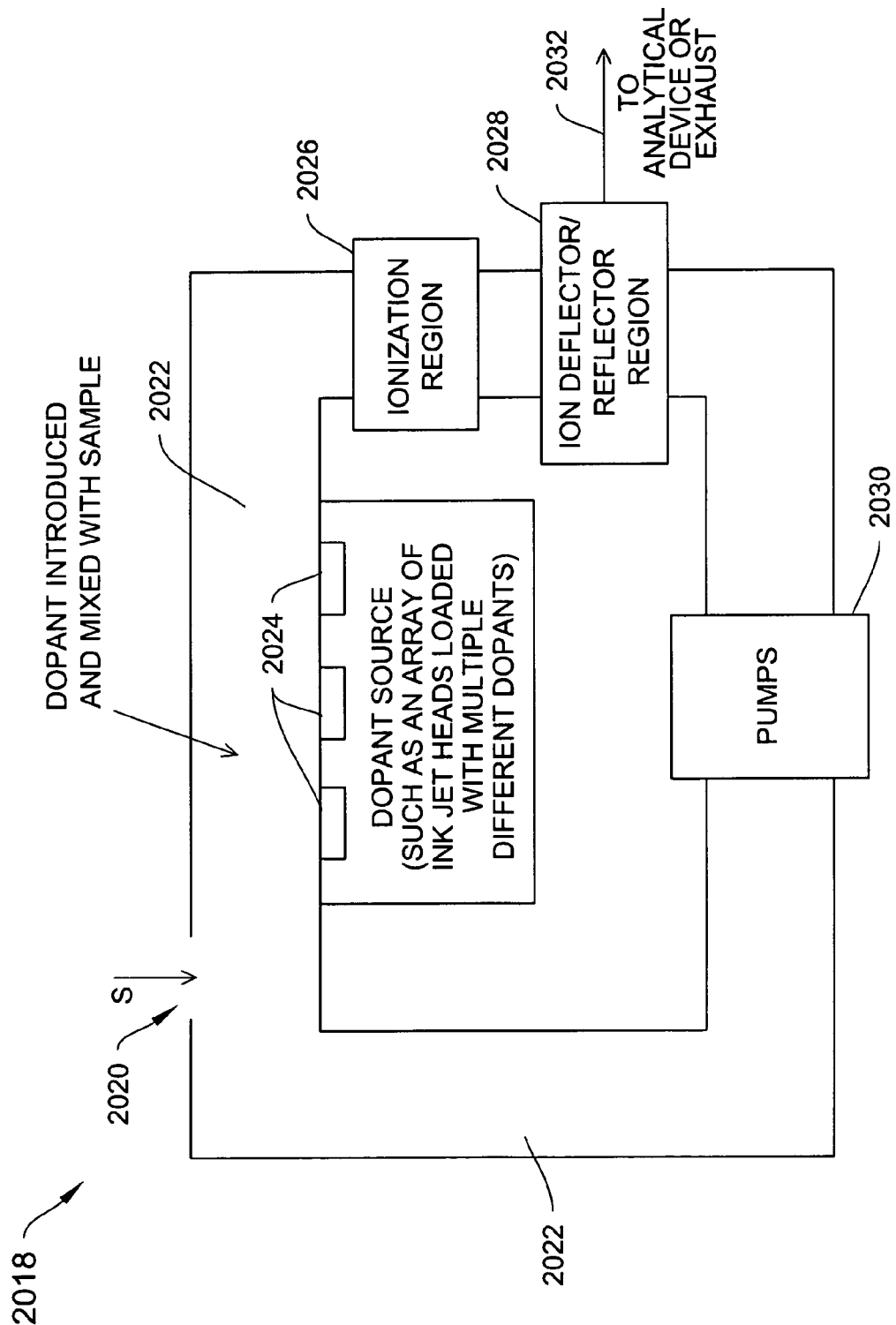
FIG. 63 is a conceptual block diagram of a sample pre-separation system capable of mixing dopants with a sample matrix in a controlled manner before or after the reactant ions are added according to an illustrative embodiment of the invention.

FIG. 63 is a conceptual block diagram of a sample pre-separation system 2018 capable of mixing dopants with a sample matrix S in a controlled manner before or after reactant ions are added according to an illustrative embodiment of the invention. The sample pre-separation system 2018 includes the inlet 2020, gas flow channel 2022, dopant sources 2024, ionization region 2026, ion deflector/reflector 2028, and pumps 2030.

In operation, a sample matrix S is drawn through inlet 2020 into the gas flow channel 2022. The dopant sources 2024 may include various types of dopants. Any one of the dopants or a combination of dopants may be added to the sample matrix S in the gas flow channel 2002. Each dopant source 2024 may include an injection mechanism to inject or pulse controlled amounts of dopant into the gas flow channel 2002. When the sample matrix S and dopant mixture enter the ionization region, certain types of compound molecules of the sample matrix S are ionized due to competitive ionization.

Upon leaving the ionization region 2026, the ionized molecules or product ion are deflected by the deflector/reflector 2028 through outlet 2032 to either an analyzer or an exhaust. The pumps 2030 re-circulate the remaining neutral molecules through the gas flow channel 2022. The dopant sources 2024 may again inject dopants into the gas flow channel 2022 to enable mixing of selected dopants with the remaining neutral molecules of the sample matrix S. This process may be repeated while the sample matrix S is re-circulated through the pre-separation system 2018 until a selected compound or group of compounds are extracted from the sample matrix S.

In one illustrative embodiment of the invention, a device and/or system may be employed that uses multiple flow paths to combine various combinations of ions to control the formation and delivery of a particular type of reactant ion species to a pre-separation system. By controlling the type of reactant ion species introduced into an ionization and mixing region, the type of compound of a sample that is ionized may be controlled. For example, logic circuits may arranged from an array of DMS, IMS, MS, and the like filters to control the flow and combination of various ion species into a pre-separation system.

Figure 64:
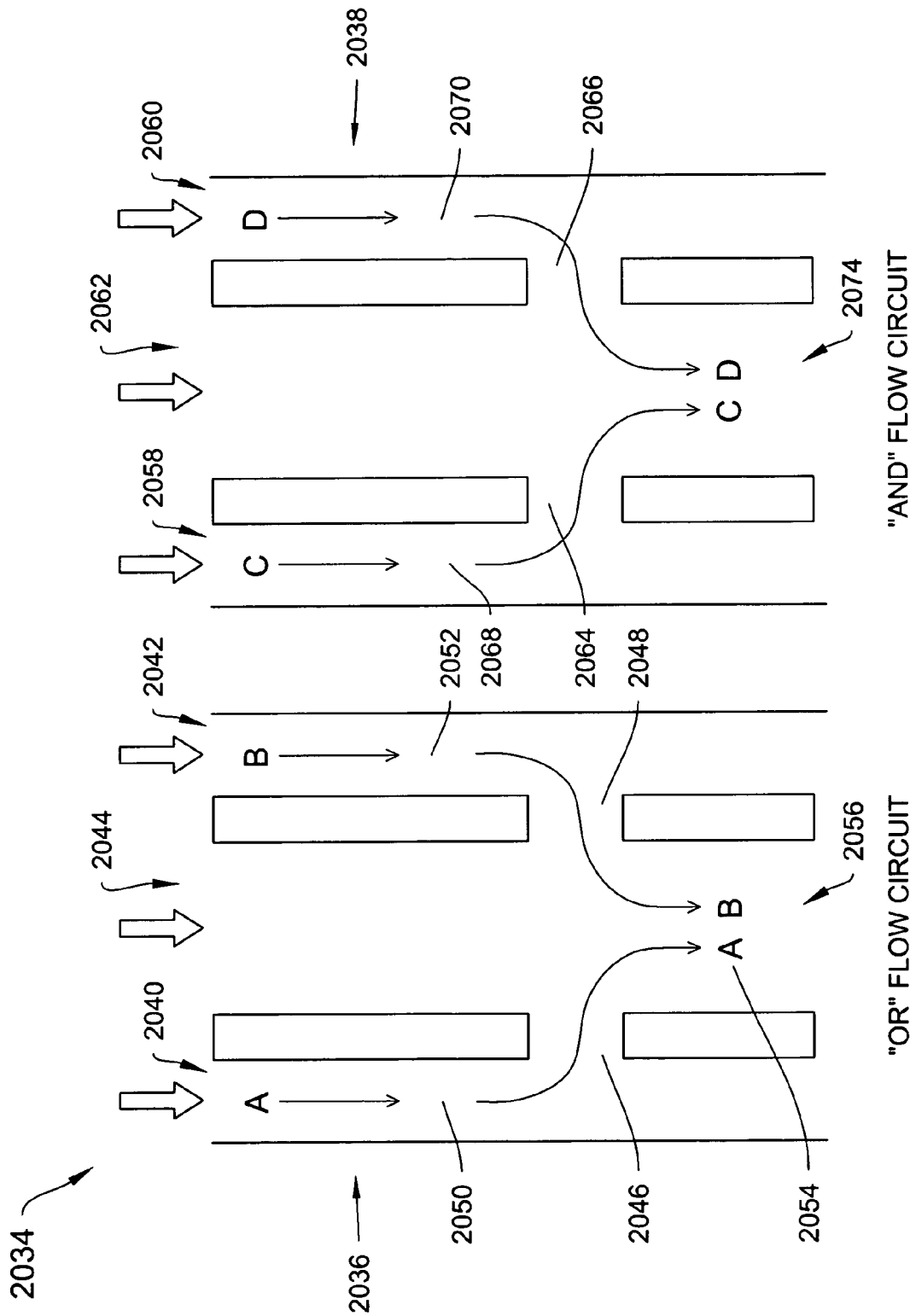
FIG. 64 is a conceptual diagram of an array of logic circuits including an "or" flow circuit and an "and" flow circuit used to cause multiple and different ions to interact and form a desired reactant ion species according to an illustrative embodiment of the invention.

FIG. 64 is a conceptual diagram of an array of logic circuits 2034 including an "or" flow circuit 2036 and an "and" flow circuit 2038 used to form a desired reactant ion species according to an illustrative embodiment of the invention. The "or" flow circuit includes the sample inlet 2040, sample inlet 2042, carrier gas inlet 2044, flow channel 2050, flow channel 2052, flow channel 2054, opening 2046, opening 2048, and outlet 2056. The "and" flow circuit includes the sample inlet 2058, sample inlet 2060, carrier gas inlet 2062, flow channel 2068, flow channel 2070, flow channel 2072, opening 2064, opening 2066, and outlet 2074.

In operation with regard to the "or" circuit 2036, a sample A is drawn into the flow channel 2050 through inlet 2040 while a sample B is drawn into the flow channel 2052 through inlet 2042. Either the sample A or the sample B, but not both sample A and B is deflected from the flow channels 2050 or 2052 into the center channel 2054. Other means such as a microvalve or electromechanical switch may be employed to control the flow of ions from either channel 2050 or 2052 into the center flow channel 2054. The deflected sample A or B is then delivered through the outlet 2056 to a target such as the ionization or mixing region of a pre-separation system.

In operation with regard to the "and" circuit 2038, a sample C is drawn into the flow channel 2068 through inlet 2058 while a sample D is drawn into the flow channel 2070 through inlet 2060. In this case both the sample C and D are deflected from the flow channels 2068 or 2070 into the center channel 2072. The deflected samples C and D are then delivered through the outlet 2074 to a target such as the ionization or mixing region of a pre-separation system.

The logic circuit 2034 may deliver multiple combinations of sample reactant ions such as the sample combinations A only, B only, ACD, and BCD. Other combinations of reactant ions may be enabled dependent on the configuration of the logic circuit 2034 array. For instance, logic circuit may be arranged in parallel, in series, or in a combination of series and parallel in order to achieve a desired mixture. Although only two circuits are shown in FIG. 64, the number and types of circuits may be increased to facilitate the delivery of numerous combinations of reactant ions to a target.

In certain illustrative embodiments, arrays of analyzers may be employed for detecting and characterizing various compounds within a sample matrix.

FIG. 65 is a conceptual diagram of a sample pre-separation and analysis system 2076 using multiple ionization zones and multiple analyzers to analyze various ions of a sample matrix according to an illustrative embodiment of the invention. The pre-separation and analysis system 2076 includes sample inlet 2078, gas flow channel 2080, ionization region 2082, ionization region 2084, ionization region 2086, analyzer 2088, analyzer 2090, analyzer 2092, and outlet 2094.

In operation, a sample matrix S is drawn into the gas flow channel 2080 through inlet 2078 and then ionized in ionization region 2082. Due to competitive ionization, certain compound molecules are ionized into product ions that are then extracted from gas flow channel 2080 using any of the various techniques described previously. The extracted ions are then analyzed by an analyzer 2088 such as a DMS, IMS, MS and like system.

The remaining neutral molecules of sample matrix S are then ionized in ionization region 2084. Again, the product ions are extracted and analyzed by an analyzer 2090. The remaining neutral molecules of sample matrix S are then ionized in ionization region 2086. The product ions are extracted and analyzed by an analyzer 2092. Any remaining neutral molecules exit the gas flow channel 2080 through outlet 2094. An additional analyzer may be employed at the outlet 2094 for further analysis of the sample matrix S. The number of analyzers and ionization regions may be varied depending on the number of product ions to be analyzed.

FIG. 66 is a conceptual diagram of a sample pre-separation and analysis system 2096 using multiple ionization zones and DMS analyzers, including a DMS analyzer 2116 with an arbitrarily curved drift tube and ion filter region 2122, according to an illustrative embodiment of the invention. The pre-separation and analysis system 2096 includes sample inlet 2098, gas flow channel 2100, ionization region 2102, ionization region 2104, ionization region 2106, DMS analyzer 2116 with a curved drift tube and ion filter region 2122, analyzer 2118, analyzer 2120, deflector 2110, deflector 2112, deflector 2114, and outlet 2124.

In operation, a sample matrix S is drawn into the gas flow channel 2100 through inlet 2098 and then ionized in ionization region 2102. Due to competitive ionization, certain compound molecules are ionized into product ions that are then deflected from gas flow channel 2100 by deflector 2110 into DMS analyzer 2116. The extracted ions are then analyzed by the DMS analyzer 2116. The DMS analyzer 2116 may include a arbitrarily curved drift tube and ion filter 2122 so that the electric field in the DMS is non-uniform.

A portion of the remaining neutral molecules of sample matrix S are then ionized in ionization region 2104. The product ions are deflected by deflector 2112 from the gas flow channel 2100 into the analyzer 2118 and analyzed. The remaining neutral molecules of sample matrix S are then ionized in ionization region 2108. The product ions are deflected by deflector 2114 into the analyzer 2120 and analyzed. Any remaining neutral molecules exit the gas flow channel 2100 through the outlet 2124. An additional analyzer may be employed at the outlet 2124 for further analysis of the sample matrix S. The number of analyzers and ionization regions may be varied depending on the number of product ions to be analyzed. Also, the spacing between the ionization regions and analyzers may not be uniform. Furthermore, while not shown in FIGS. 65 and 66, multiple flow channels, each with one or more analyzers, may be arranged in parallel. In yet a further configuration, multiple analyzers may be employed in series or parallel after each ionization region to enhance sample analysis.

Figure 67:
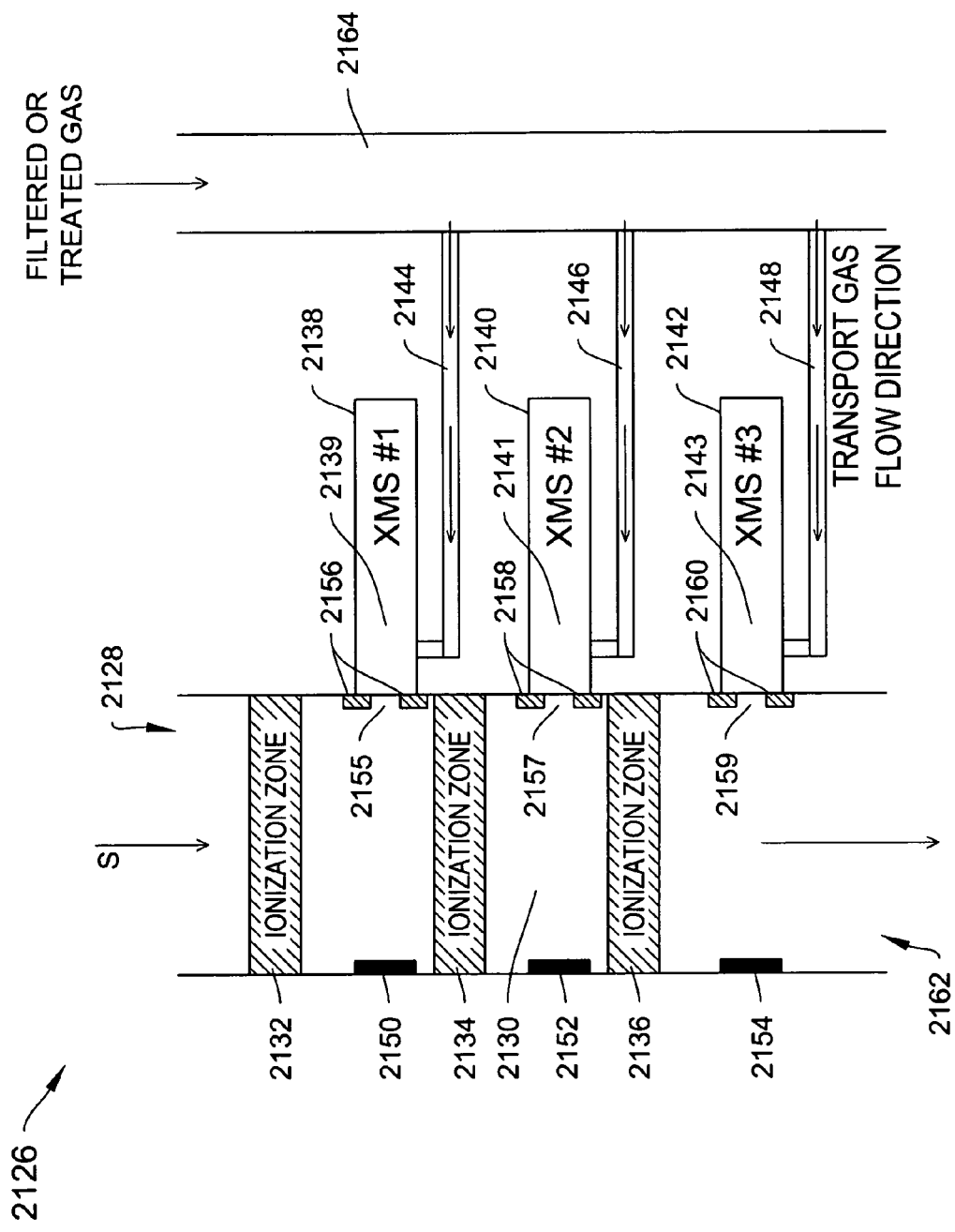
FIG. 67 is a conceptual diagram of a sample pre-separation and analysis system employing multiple ionization zones and analyzers along with a filtered gas source to control pressure within the analyzers according to an illustrative embodiment of the invention.

FIG. 67 is a conceptual diagram of a sample pre-separation and analysis system 2126 employing multiple ionization zones and analyzers along with a filtered gas source to control pressure within the analyzers according to an illustrative embodiment of the invention. The pre-separation and analysis system 2126 includes a sample inlet 2128, gas flow channel 2130, ionization region 2132, ionization region 2134, ionization region 2136, analyzer 2138, analyzer 2140, analyzer 2142, analyzer flow channel 2139, analyzer flow channel 2141, analyzer flow channel 2143, pressure channel 2144, pressure channel 2146, pressure channel 2148, deflector 2150, deflector 2152, deflector 2154, ion attractors 2156, exit port 2155, exit port 2157, exit port 2159, ion attractors 2158, ion attractor 2160, outlet 2162, and gas flow channel 2164.

In operation, a sample matrix S is drawn into the gas flow channel 2130 through inlet 2128 and then ionized in ionization region 2132. Due to competitive ionization, certain compound molecules are ionized into a group of product ions that are then deflected from gas flow channel 2130 by deflector 2150 and attracted by ion attractors 2156 through exit port and/or opening 2155 into the analyzer 2138. The gas flow channel 2164 provides filtered and/or treated gas to the analyzer 2138 through pressure channel 2144 to establish a relatively higher pressure within the analyzer 2138. The relatively higher and/or positive pressure within the analyzer 2138 and analyzer flow channel 2139 limits the entry of neutral molecules into the analyzer 2138. The extracted product ions are then analyzed by the analyzer 2138.

The remaining neutral molecules of sample matrix S are then ionized in ionization region 2134. The product ions are deflected by deflector 2152 and attracted by ion attractors 2158 from the gas flow channel 2130 through exit port 2157 into the analyzer 2140 and analyzed. The gas flow channel 2164 provides filtered and/or treated gas to the analyzer 2140 through pressure channel 2146 to establish a relatively higher pressure within the analyzer 2140. The relatively higher and/or positive pressure within the analyzer 2140 and analyzer flow channel 2141 inhibits and/or limits the entry of neutral molecules from gas flow channel 2130 into the analyzer 2140.

The remaining neutral molecules of sample matrix S are then ionized in ionization region 2136. The product ions are deflected by deflector 2154 and attracted by ion attractors 2160 through exit port 2159 into the analyzer 2142 and analyzed. The gas flow channel 2164 provides filtered and/or treated gas to the analyzer 2142 through pressure channel 2148 to establish a relatively higher pressure within the analyzer 2142. The relatively higher and/or relatively positive pressure within the analyzer 2142 and analyzer flow channel 2143 inhibits and/or limits the entry of neutral molecules from the gas flow channel 2130 into the analyzer 2142.

Any remaining group of neutral molecules exit the gas flow channel 2130 through the outlet 2162. An additional analyzer may be employed at the outlet 2164 for further analysis of the sample matrix S. The number of analyzers and ionization regions may be varied depending on the number of product ions to be analyzed. Furthermore, the spacing between the ionization regions and analyzers may be non-uniform.

Figure 68:
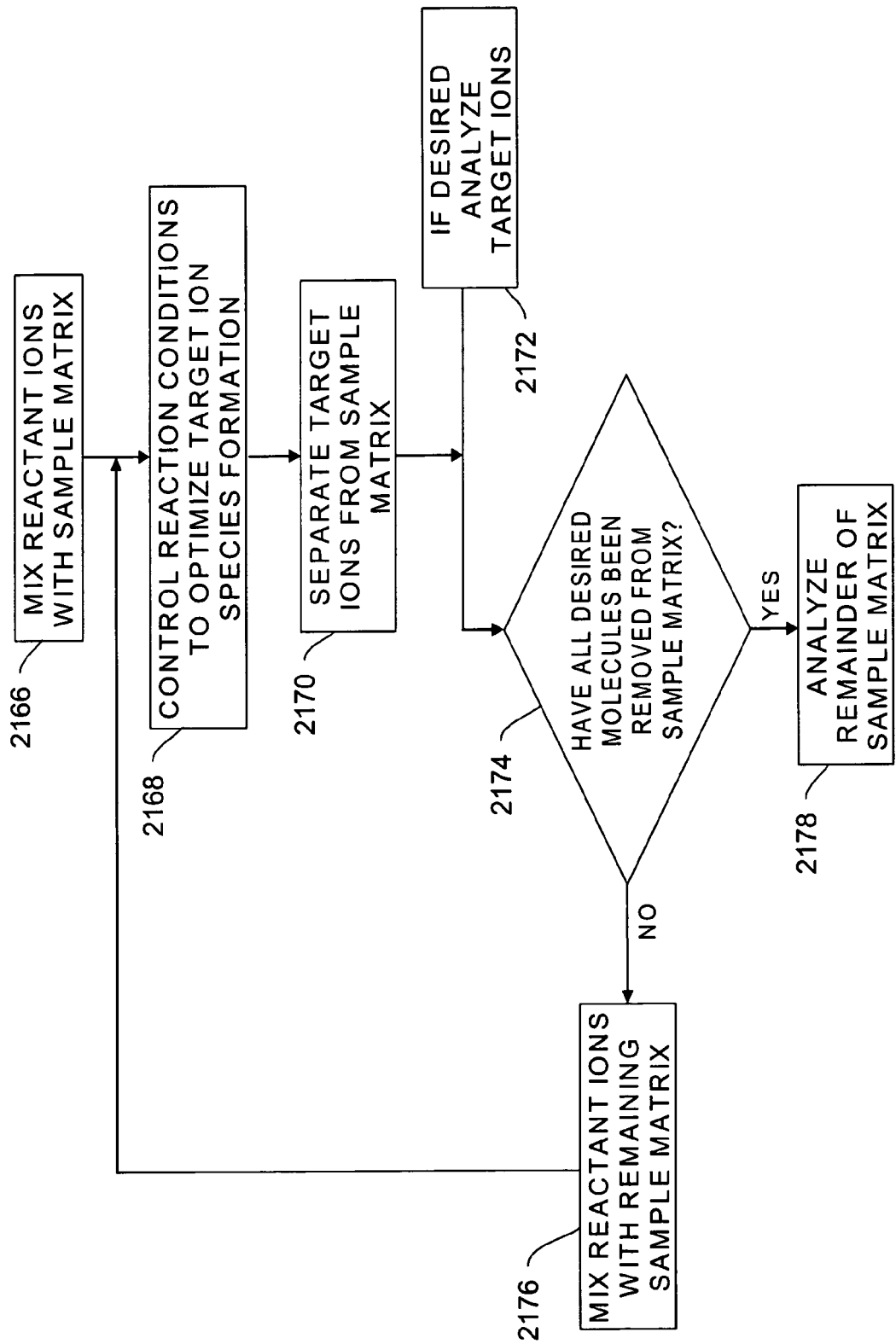
FIG. 68 is a flow diagram of a sample analysis process including sample re-circulation and pre-separation according to an illustrative embodiment of the invention.

FIG. 68 is a flow diagram of a process showing the analysis of a sample matrix including re-circulation of the sample according to an illustrative embodiment of the invention. First, a sample matrix is mixed with reactant ions (Step 2166). Then, the reaction conditions are controlled to optimize the transfer of charge and ion species formation (Step 2168). Once the sample matrix is ionized to form product ions, the product ions are separated from the sample matrix (Step 2170). If desired, the separated product ions may be analyzed (Step 2172). Next, it is determined whether all desired ion species of the sample matrix have been removed (Step 2174). If all of the desired or selected ion species have been removed, the remaining neutral molecules of the sample matrix may be analyzed (Step 2178). If all of the desired ion species have not been removed, the remaining neutral molecules of the sample matrix are mixed with the reactant ions and the process is repeated (Step 2176).

Figure 69:
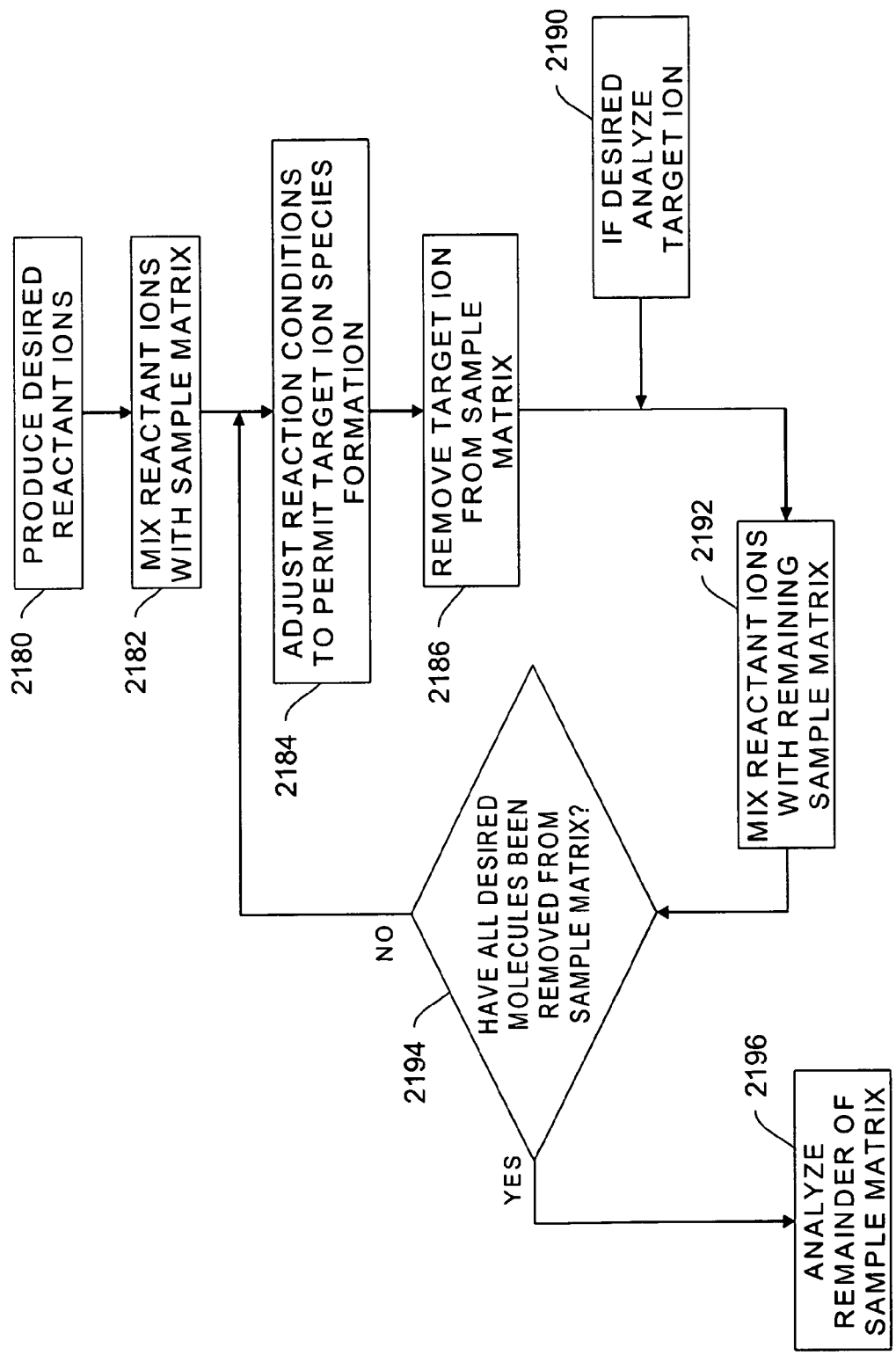
FIG. 69 is a flow diagram of a process showing the analysis of a sample matrix composed of multiple molecule species according to an illustrative embodiment of the invention.

FIG. 69 is a flow diagram of a process showing the analysis of a sample matrix composed of multiple molecule species according to an illustrative embodiment of the invention. First, the reactant ions are produced (Step 2180). Then, a sample matrix is mixed with the reactant ions (Step 2182). The reaction conditions are controlled to optimize the transfer of charge and permit target ion species formation (Step 2184).

Once ionized, the product or target ions are separated from the sample matrix (Step 2186). If desired, the separated product ions may be analyzed (Step 2190). Then, the remaining neutral molecules of the sample matrix are mixed with the reactant ions (2192). Next, it is determined whether all desired ion species of the sample matrix have been removed (Step 2194). If all of the desired or selected ion species have been removed, the remaining neutral molecules of the sample matrix may be analyzed (Step 2196). If not all of the desired ion species have been removed, the process is repeated.

Figure 70:
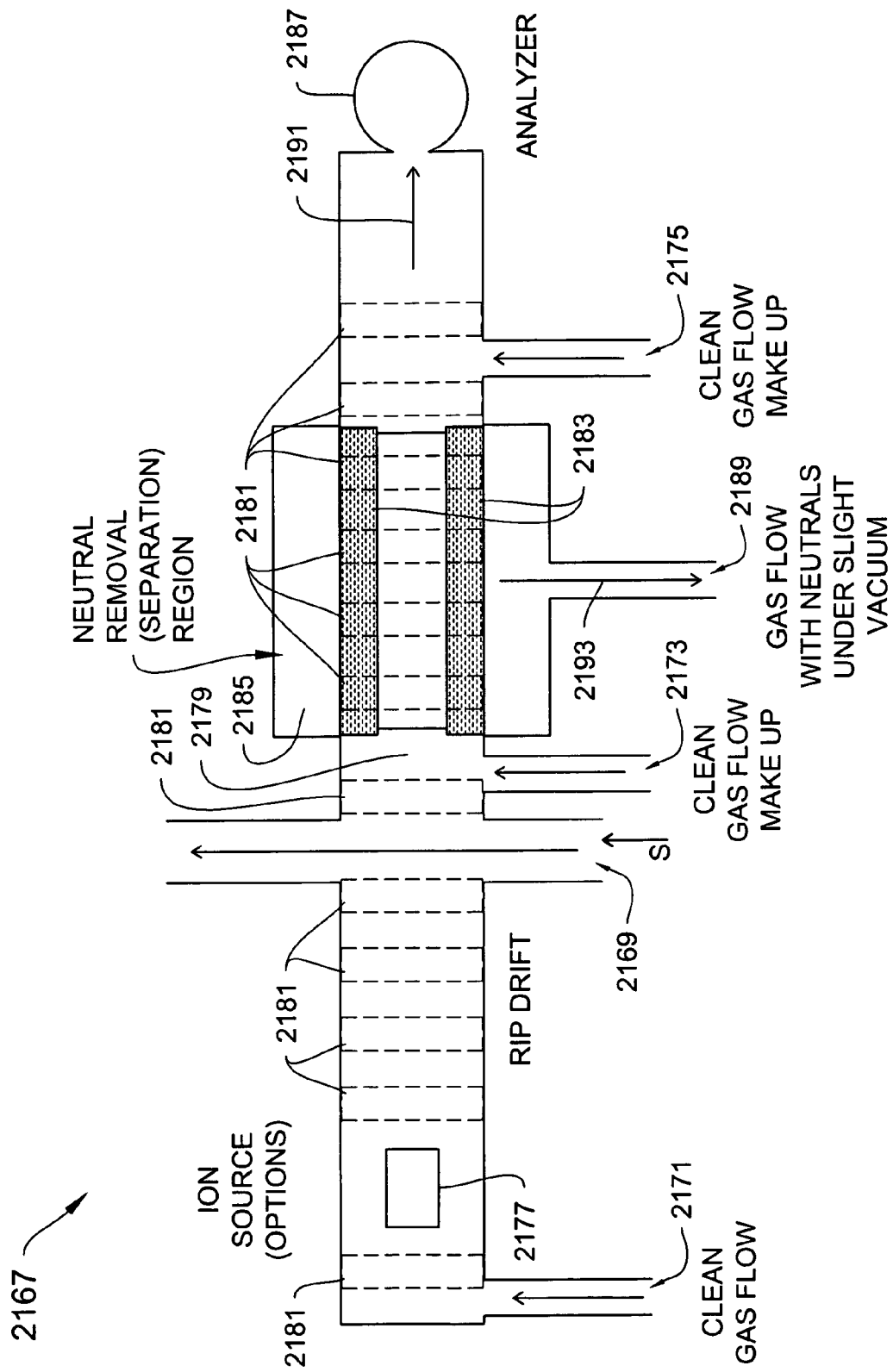
FIG. 70 is a conceptual diagram of a sample pre-separation (neutrals removal) system where the neutral molecules are removed from the ionized molecules rather than removing the ions from the neutral gas stream.

FIG. 70 is a conceptual diagram of a sample pre-separation (neutrals removal) system 2167 where the neutral molecules are removed from the ionized molecules rather than removing the ions from the neutral gas stream as described previously. The sample pre-separation system 2167 includes sample inlet 2169, clean gas inlet 2171, clean makeup gas inlet 2173, clean makeup gas inlet 2175, optional ionization source 2177, gas flow channel 2179, electrodes 2181, flow permitting medium 2183, neutral removal region 2185, analyzer 2187, and neutrals flow outlet 2189.

In operation, a sample matrix S is drawn into the pre-separation device through sample inlet 2169 and ionized by reactant ions. The ions are transported by an electric field, generated by electrodes 2181, towards an analyzer 2187 while sample S neutrals are drawn away from the sample ions through a "flow permitting" medium 2183. The flow permitting medium 2183 may include a porous material or a region with small openings and/or holes to allow the neutrals to pass from the gas flow channel 2179 through the neutrals flow outlet 2189. The sample S neutrals may then be removed from the sample S ions in the neutral removal region 2185 using a vacuum pump that creates a vacuum in the neutral removal region 2185. The vacuum draws the neutrals out of the gas flow channel 2179, e.g., a transport tube, while the ions are moved towards the analyzer 2187 by the electric fields of the electrodes 2181.

The ions may move in direction 2191 counter to a clean gas flow-makeup stream which is free of sample neutrals. A gas flow-makeup stream may originate from a clean makeup gas inlet 2173 and/or clean makeup gas inlet 2175. The sample pre-separation system 2167 may use discrete electrodes 2181, or resistive ink or semi-conducting coatings with suitable voltages and currents applied to induce the desired electric fields. The gas flow channel 2179 may be enclosed substantially by a substantially circular and/or rectangular housing. With a substantially circular housing, the electrodes 2181 may be circular rings along the gas flow channel 2179. With a substantially rectangular housing, the electrodes 2181 may reside on opposing facing planar surfaces with the gas flow channel 2179 in between. The sample pre-separation system 2167 may be planar in form.

The sample pre-separation (neutrals removal) system 2167 may interface with a DMS or IMS or MS or the like. In the illustrative embodiment of FIG. 70, the sample S may be mixed with reactant ions that are optionally introduced at inlet 2171 and ionized by ionization source 2177. The mixture is transported into the separation region 2185 where product ions and some reactant ions are separated from the sample neutrals and transported to an analyzer 2187. Alternatively, pre-ionized sample S molecules may be introduced into the gas flow channel 2179 at inlet 2169. The separation, or neutral removal, region 2185 may then use a clean gas flow in the direction 2193, which is transverse to the ion flow, to draw the neutral sample S molecules away from the ions in the gas flow channel 2179. The remaining sample S molecules are then delivered to the analyzer 2187 for analysis.

Figure 71:
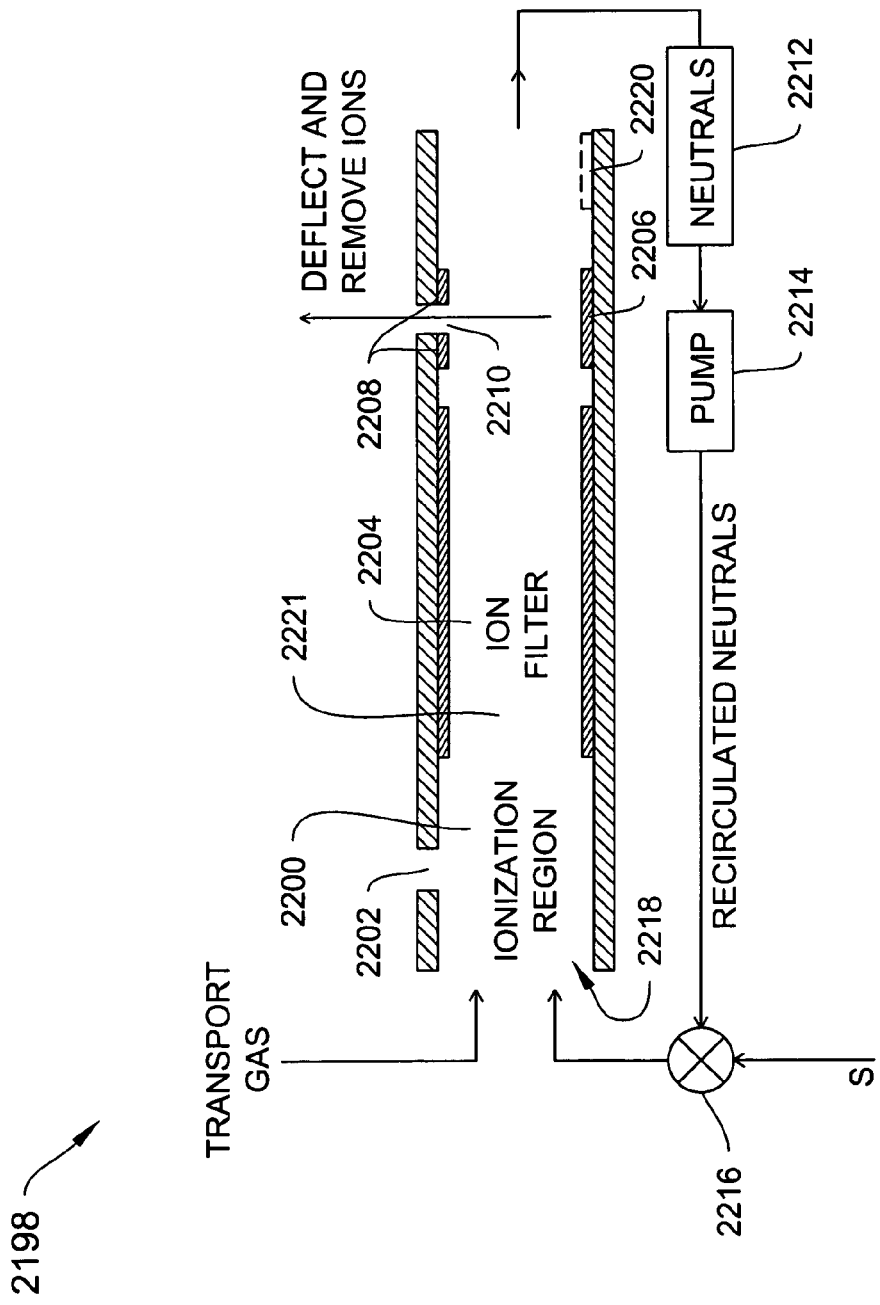
FIG. 71 is a conceptual diagram of a sample pre-separation system employing an ionization region, DMS filter, deflector, pump, and valve to selectively filter an ion species for analysis according to an illustrative embodiment of the invention.

FIG. 71 is a conceptual diagram of a sample pre-separation system 2198 employing an ionization region 2200, ionization source inlet 2202, analyzer flow channel 2221, DMS ion filter 2204, deflector 2206, ion attractors 2208, exhaust opening 2210, neutral molecules 2212, pump 2214, and valve 2216 to selectively filter ion species for analysis according to an illustrative embodiment of the invention. In operation, a sample matrix S is drawn through valve 2216 when the valve 2216 is positioned to accept the sample matrix S. The valve 2216 may alternatively be positioned to only allow neutral molecules 2212 to re-circulate to the DMS inlet 2218 and ionization region 2200. An ionization inlet 2202 may be employed to enable the introduction of reactant ions. The reactant ions may then mix with the sample matrix S and ionize selected compound molecules.

The DMS ion filter 2204 and an optional detector electrode 2220 may remain inactive until a sufficient amount of pre-separation iterations are performed to remove unwanted ion species from the sample matrix S. Once the sample matrix S is ionized, the deflector 2206 and ion attractors 2208 propel the product ions from the analyzer flow channel 2221 through the opening 2210. These product ions may be further analyzed or discarded.

The remaining neutral molecules 2212 of the sample matrix are then propelled by the pump 2214 through the valve 2216 back to the DMS inlet 2218. The remaining neutral molecules 2212 may be re-circulated until a desired type of compound remains. Then, the DMS filter 2204 and detector 2220 may be activated to analyze the remaining compound of the sample matrix S. Alternatively, the deflector 2206 and/or ion attractors 2208 may function as detector during the DMS analysis.

Figure 72:
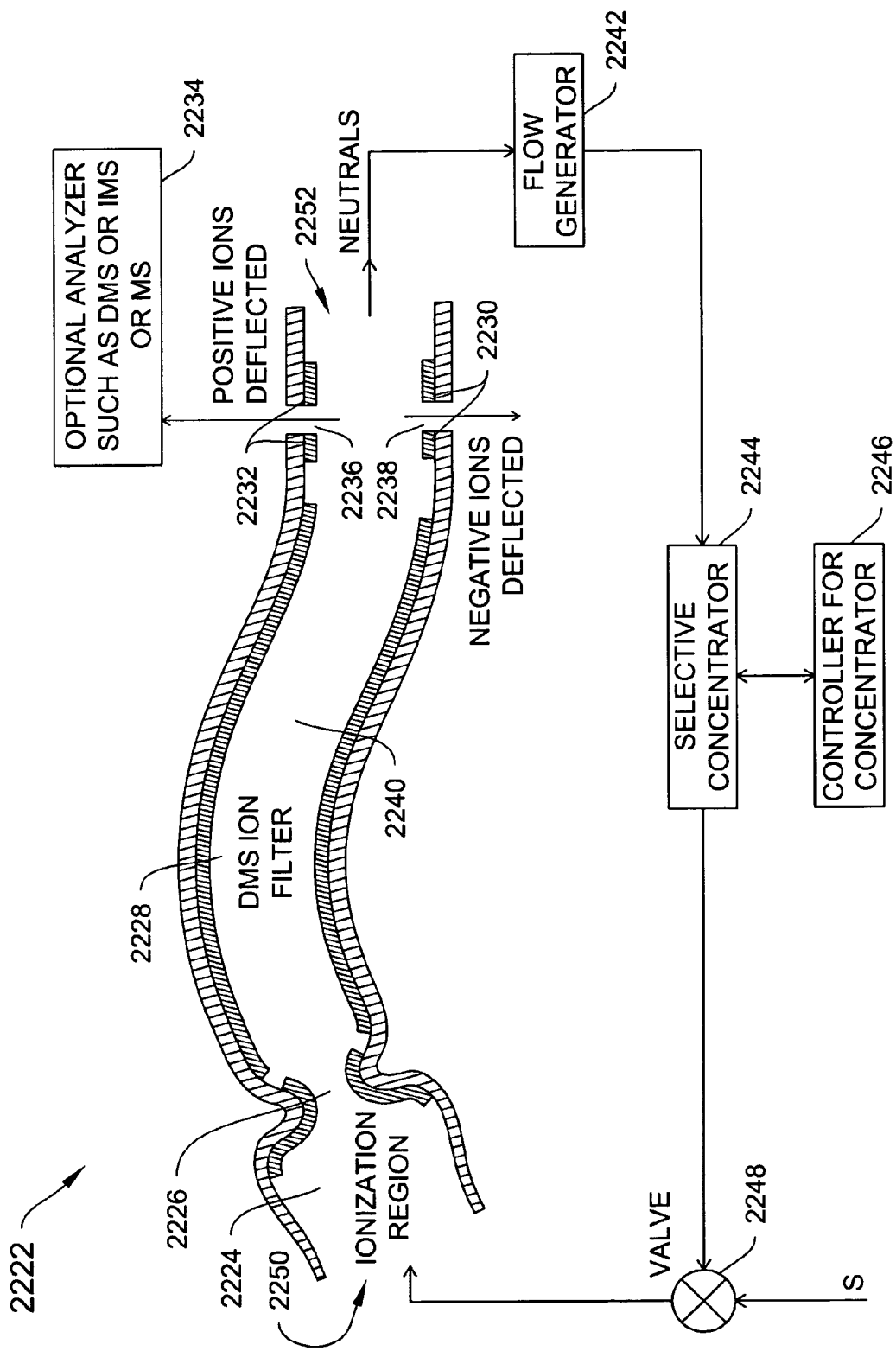
FIG. 72 is a conceptual diagram of a sample pre-separation system employing an ionization region, ion guiding region, DMS ion filter, positive and negative ion deflectors, optional analyzers, flow generator, selective concentrator and valve for ion species analysis according to an illustrative embodiment of the invention.

FIG. 72 is a conceptual diagram of a sample pre-separation system 2222 employing an ionization region 2224, ion guiding region 2226, DMS ion filter 2228, positive electrodes 2230, negative electrodes 2232, optional analyzers 2234, flow generator 2242, selective concentrator 2244 and valve 2248 for ion species analysis according to an illustrative embodiment of the invention. The pre-separation system 2222 also includes DMS inlet 2250, DMS flow channel 2240, DMS outlet 2252, flow generator 2242, opening 2236, and opening 2238.

In operation, a sample matrix S is drawn through the valve 2248 and the DMS inlet 2250 into the ionization region 2224. The sample matrix S is then ionized using one of the various ionization techniques previously described. Due to competitive ionization, certain compound molecules are ionized into product ions. The ion guiding region 2226 then concentrates the ions to the center of the DMS flow channel 2240. The DMS ion filter 2228 may be activated at certain times to perform ion filtering. Then, the product ions are deflected from the DMS flow channel 2240 by either positive electrodes 2230 or negative electrodes 2232. The positive electrodes 2230 act simultaneous as an attractor for negative product ions and as a deflector for positive product ions. Also, the negative electrodes 2232 act simultaneous as an attractor for positive product ions and as a deflector for negative product ions. Thus, both positive and negative product ions may be removed from the DMS flow channel 2240 simultaneously or at about the same time.

The remaining neutral molecules of the sample matrix S pass through the DMS outlet 2252 to the flow generator 2242. The flow generator 2242 establishes gas flow in the DMS flow channel 2240 from the DMS inlet 2250 toward the DMS outlet 2252. The flow generator 2242 may be a solid-state or electromechanical pump or the like. The flow generator 2242 then propels the neutral molecules through the selective concentrator 2244 which further concentrate the sample matrix S by removing unwanted compounds. The concentrator controller 2246 may regulate the conditions within the concentrator to enable sample matrix S concentration.

The remaining concentrated and neutral molecules of the sample matrix S then pass through the valve 2248 and return to the DMS inlet 2250 for further pre-separation if necessary. The valve 2248 may be positioned to allow an external sample matrix S to be collected, positioned to re-circulate only the neutral molecules, or positioned to allow both the external sample matrix S intake and re-circulation of the neutral molecules.

The previous pre-separation systems may be improved by use of molecular sieves, membranes, and the like, such as those described supra. For example, a membrane may be employed at various openings to maintain the pressure and re-circulated gas flow in a pre-separation system while allowing product ions to be removed. Also spectral changes may be monitored during the pre-separation process to provide an indication when adequate cleaning of a gas sample reached or when a particular compound may be sampled.

While current mobility based analyzers are sensitive, there is a need to detect concentrations in ranges lower than parts-per-trillion (ppt). For instance, a very small number of anthrax spores may cause significant health effects. However, existing analyzers may not be sensitive enough to detect the charge generated by such a small number of spores. One technique for overcoming this limitation is concentrating and/or amplifying the number of molecules of a sample, in time, to enable an analyzer to produce a larger signal for detection.

In certain embodiments of the invention, chemical amplification is employed to enable the detection of extremely low levels (e.g., concentrations of less than a few ppt) of analytes in a sample. The sample may be a fluid such as a vapor or liquid. By allowing selected molecules to circulate multiple times in an analyzer system, the concentration of an analyte may be increased to a detectable level.

Figure 73A:
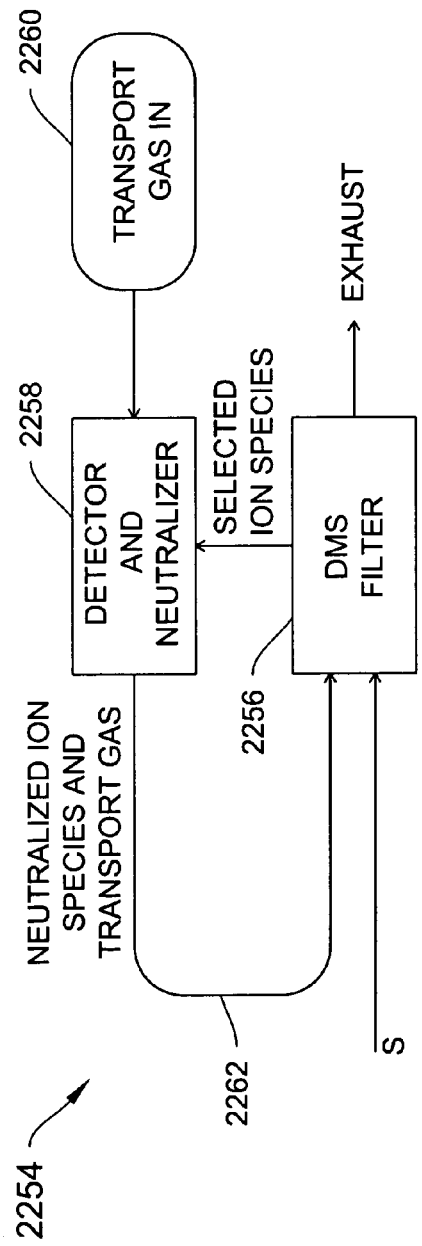
FIG. 73A is a conceptual diagram of a sample amplification system employing a DMS filter, detector and neutralizer, and recirculation loop for selected ion species analysis according to an illustrative embodiment of the invention.

FIG. 73A is a conceptual diagram of a sample amplification system 2254 employing a DMS filter 2256, detector and neutralizer 2258, transport gas input 2260 and re-circulation loop 2262 for selected ion species analysis according to an illustrative embodiment of the invention. In operation, a sample S is drawn into the DMS filter 2256 which filters out and exhausts unwanted ion species. The selected ion species are delivered to the detector and neutralizer 2258, which detects and neutralizes the selected ion species during the detection process. A transport effluent (e.g., a gas, liquid or vapor) input 2260 provides transport effluent (in the example a transport gas) to flow the neutralized ion species through the re-circulation loop 2262. Upon return to the DMS filter 2256, the neutralized ion species are mixed with more sample S molecules and then filtered by the DMS filter 2256. The sample amplification process is repeated for a period of time until enough of the selected ion species are filtered by the DMS filter 2256 for the detector and neutralizer 2258 to detect the ion species of interest.

Figure 73B:
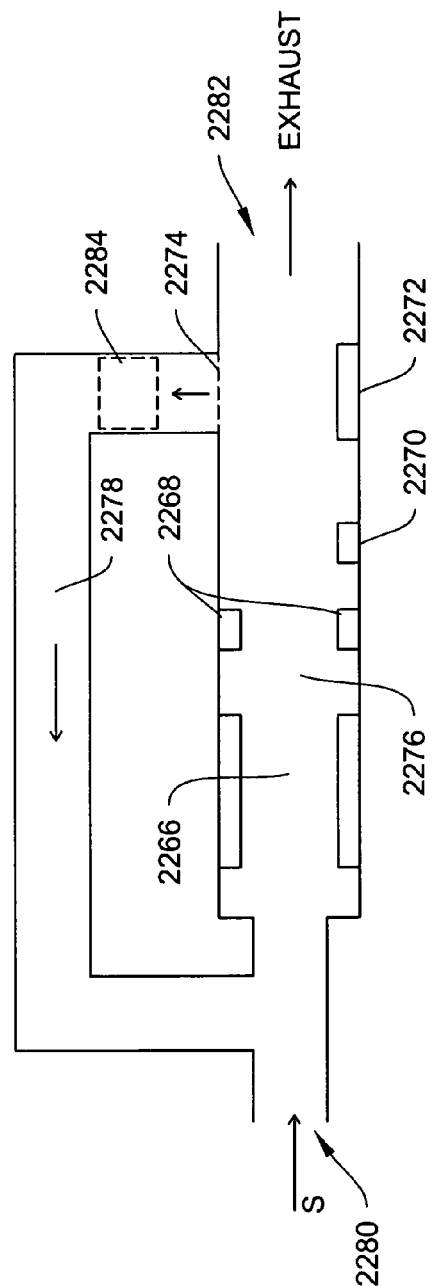
FIG. 73B is a conceptual diagram of a sample amplification system employing a DMS filter, detector, ionization source, deflector, and an optional DMS with a re-circulation channel for selected ion species analysis according to an illustrative embodiment of the invention.

FIG. 73B is a conceptual diagram of a sample amplification system 2264 employing a DMS filter 2266, detector 2268, ionization source 2270, deflector 2272, an attractor grid 2274, DMS flow channel 2276, re-circulation channel 2278, inlet 2280, exhaust 2282, and an optional DMS 2284 for analysis of selected ion species according to an illustrative embodiment of the invention.

In operation, a sample S is drawn into the DMS flow channel 2276 through the inlet 2280. The DMS filter 2266 filters out unwanted ion species while the detector electrodes 2268 detect the ion species of interest. Because the detected ions may be neutralized during detection, the ionization source 2270 then ionizes the sample S, including the neutralized ions. After ionization, the deflector 2272 propels the product ions through the attractor grid 2274 into the re-circulation channel 2278. The unwanted and filtered compounds are exhausted from the DMS flow channel 2276 through exhaust 2282.

The product ions may optionally be analyzed by analyzer 2284 before being circulated through re-circulation channel 2278 to inlet 2280 for mixing with more sample S molecules. Then, the mixture is circulated through the sample amplification system 2264 for another stage of filtering and detection. At the completion of each iteration of filtering and detection, the concentration of the target or desired ion species increases until the detector electrodes 2268 are able to detect the target species of interest.

Figure 74:
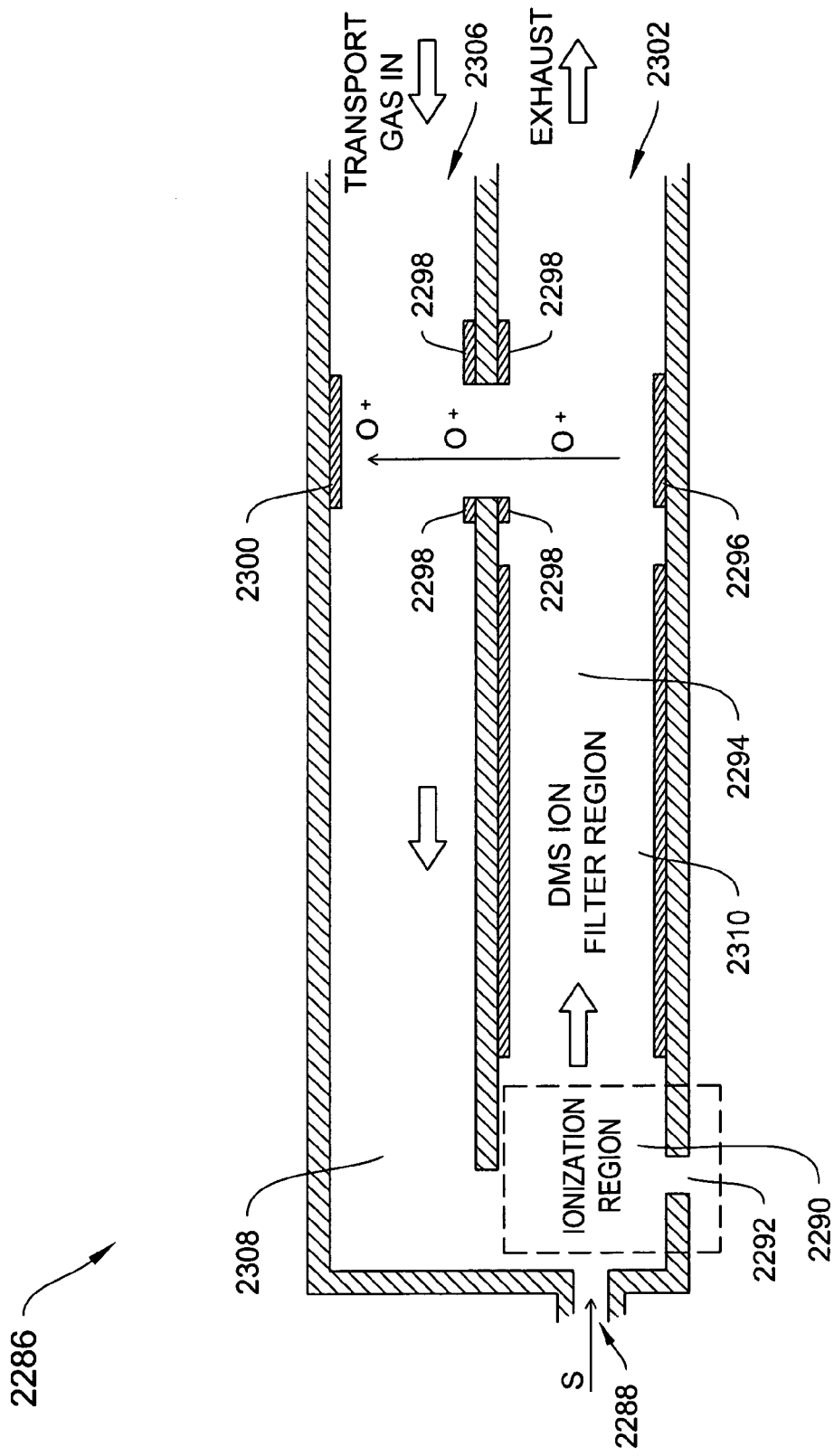
FIG. 74 is a conceptual diagram of a sample amplification and analysis system employing a re-circulation channel according to an illustrative embodiment of the invention.

FIG. 74 is a conceptual diagram of a sample amplification and analysis system 2286 employing a re-circulation channel according to an illustrative embodiment of the invention. The sample amplification and analysis system 2286 includes a inlet 2288, ionization region 2290, ionization source inlet 2292, DMS filter region 2294, deflection plate 2296, guiding electrodes 2298, detector and neutralizer electrode 2300, exhaust 2302, opening 2304, transport gas inlet 2306, re-circulation channel 2308, and DMS flow channel 2310.

In operation, a sample S is drawn into the DMS flow channel 2294 through the inlet 2288. The sample S is ionized in the ionization region 2290. The ionization source inlet 2292 enables the injection of reactant ions into the ionization region 2290. Alternatively, an ionization source may reside within the ionization regions such as a plasma generator, UV source, or radioactive source. Once ionized, the sample is filtered in the DMS filter region 2294 to allow only a desired or selected ion species to reach the deflector 2296. The unwanted, filtered, and neutralized ion species travel through the DMS flow channel 2310 and are discarded through the exhaust 2302.

The selected ion species, however, are deflected by the deflector 2296 through the opening 2304 into the re-circulation channel 2308. The guiding electrodes 2298 guide the selected ion species through the opening 2304 and toward the detector and neutralizer electrode 2300. Once the selected ion species are detected and neutralized by electrode 2300, transport gas from transport gas inlet 2306 propels the neutralized ions through the re-circulation channel 2308 toward the ionization region 2292. In the ionization region 2292, the neutralized ions are mixed with new sample molecules and ionized. The new mixture is then circulated through the amplification and analysis system 2286 and so on over a period of time until the concentration of the selected ion species reaches level that can be detected.

Figure 75:
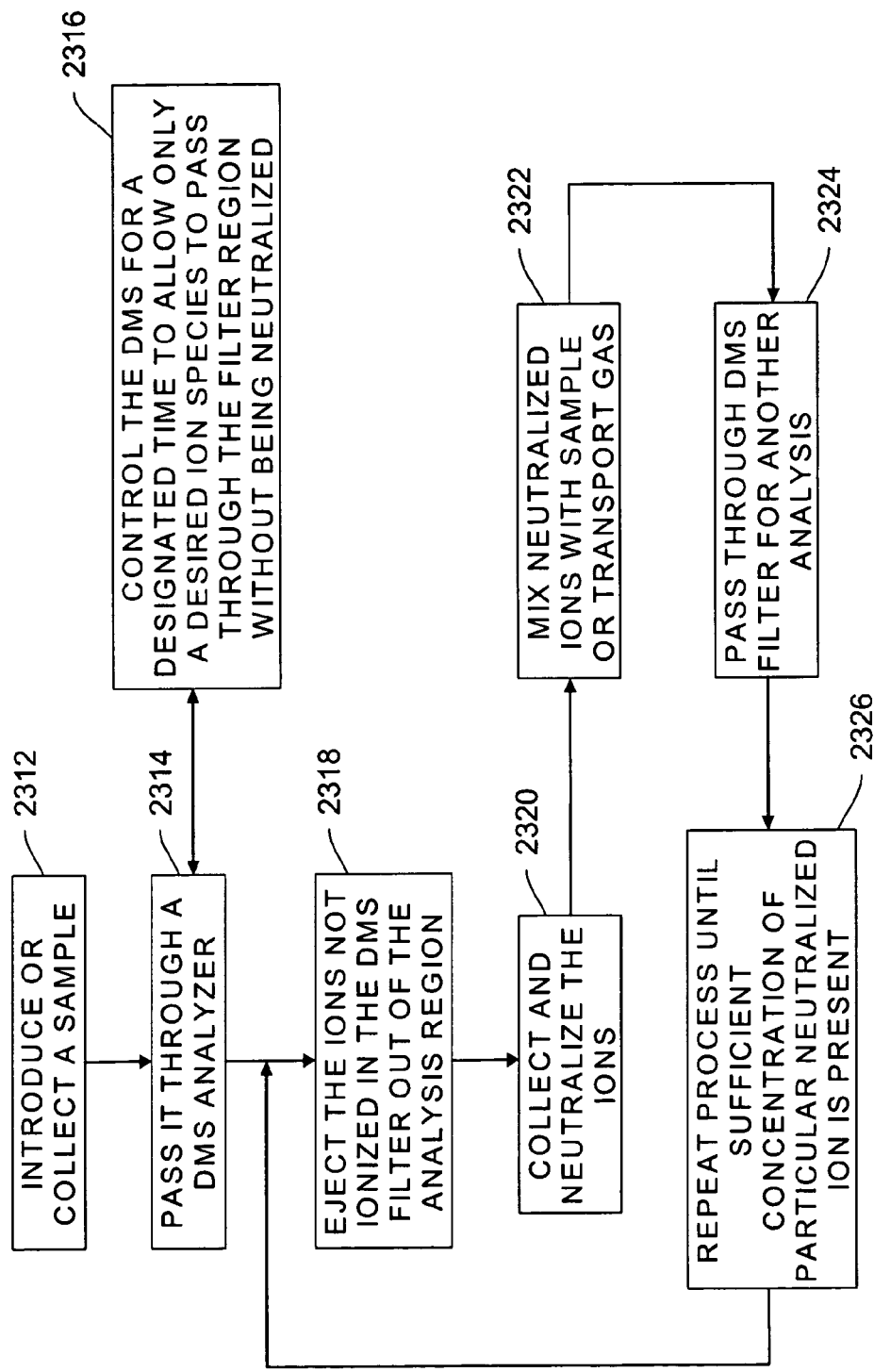
FIG. 75 is a flow diagram of a process for amplifying a selected ion species using an analyzer, such as a DMS analyzer, according to an illustrative embodiment of the invention.

FIG. 75 is a flow diagram of a process of amplification of a selected ion species using an analyzer such as a DMS. First, a sample is collected and introduced (Step 2312). The sample is then passed through a DMS filter (Step 2314). The DMS filter may be controlled for designated time period to allow only a desired ion species to pass through the filter region without being neutralized (Step 2316). The compounds that are neutralized and/or not ionized are ejected from the DMS filter and analyzer (Step 2318).

Next, the remaining filtered ions are collected and neutralized (Step 2320). The neutralized ions are then mixed with additional sample molecules and/or a transport gas (Step 2322). The mixture is passed through the DMS filter for second stage of analysis (Step 2324). The process is repeated until a sufficient concentration of the desired ion species or compound is present for detection and analysis (Step 2326).

Although the invention has been described with regard to particular illustrative embodiments, it should be appreciated that the invention is broader in scope and can be applied to any system for identification of unknown species of ions traveling through a varying controlled excitation field, the identification being based on the known characteristic travel behavior of the species under the varying field conditions. The ion or ions to be identified may be traveling alone or in a group of ions of same or differing characteristic travel behavior. Additionally, the ion or ions to be identified may be transported through the systems and devices of the invention by any suitable effluent, including transport gasses, liquids and/or vapors. The filter field may be compensated in any of various manners as long as a species of interest is returned to the center of the flow and permitted to pass through the filter while all other species are retarded or neutralized. Identification is made based on known field-dependent differential mobility behavior of at least one species of ions traveling in the field at known field conditions.

It should also be appreciated that in various practices, the invention provides improved systems, methods and devices for ion species identification. According to some features, the invention varies one or more filter field/flow channel conditions to improve species discrimination. For example, according to some illustrative embodiments, the invention determines changes in ion mobility, based, for example, on changes in: Vrf; Vcomp; field strength; Vrf duty cycle; Vrf wavelength; Vrf frequency; and/or flow channel temperature, pressure, humidity, flow rate, doping and/or carrier gas CG composition. According to other features, the invention takes multiple scans of the sample S, for example, by recirculating the sample S and/or processing the sample S in parallel and/or in series with one or more additional DMS, IMS, TOFIMS, GC, FTIR, MS, or LCMS, at differing flow channel/filter field conditions.

According to further features, the invention employs approaches, such as, fragmenting, lowering pressure, three-dimensional dispersion plotting, ion pre-separation, and/or ion amplification to enhance detection resolution. According to other features, the invention stores a library of signatures for known compounds and pattern matches data from unknown compounds with the stored library to identify the unknown compounds. It should be understood that the invention is applicable not only to planar DMS systems, but may be applied in general to ion mobility spectrometry devices of various types, including various geometries, ionization arrangements, detector arrangements, and the like, and brings new uses and improved results even as to structures that are all well known in the art.

Thus, the invention is not limited to configurations of the illustrative embodiments and may be practiced in any other suitable configurations, including radial and cylindrical DMS devices. Additionally, various modifications and variations may be made to the invention without departing from the spirit and scope herein.

What is claimed is:

1. A method of pre-separating a sample to compensate for competitive ionization comprising,
    prior to filtering:
        a) ionizing sample molecules to cause a subset of the sample molecules to form first product ions, the first product ions being formed from molecules having a higher affinity to take up charge,
        b) separating the first product ions from a first un-ionized group of sample molecules,
        c) subsequent to separating the first product ions, ionizing a subset of the first un-ionized group of sample molecules to form second product ions, the second product ions being formed from molecules having a lower affinity to take up charge than the molecules of the first product ions,
        d) separating the second product ions from a second un-ionized group of sample molecules, and
    filtering, based on ion mobility, particular ions of at least one of the first and second product ions.

2. The method of claim 1 comprising,
    flowing the first un-ionized group of sample molecules and the first product ions through a first field to separate the first product ions from the first un-ionized group of sample molecules.

3. The method of claim 2 comprising,
    flowing the second un-ionized group of sample molecules and the second product ions through a second field to separate the second product ions from the second un-ionized group of sample molecules.

4. The method of claim 3, wherein the first and second fields are the same field.

5. The method of claim 3, wherein the first and second fields are different fields.

6. The method of claim 1 comprising,
    employing a mechanical separation for separating the first product ions from the first un-ionized group of sample molecules.

7. The method of claim 1 comprising,
    employing a chemical process for separating the first product ions from the first un-ionized group of sample molecules.

8. The method of claim 1 comprising,
    subsequent to extracting the second product ions, ionizing a subset of the second un-ionized group of sample molecules to form third product ions, and
    separating the third product ions from a third un-ionized group of sample molecules.

9. The method of claim 1 comprising,
    mixing first reactant ions with the sample molecules to form the first product ions.

10. The method of claim 9 comprising,
    mixing second reactant ions with the first un-ionized group of sample molecules to form the second product ions.

11. The method of claim 9 comprising,
    controlling an effluent flow to control contact time between the first reactant ions and the sample molecules.

12. The method of claim 9 comprising,
    injecting the first reactant ions into a flow of the sample molecules to mix the sample molecules to with first reactant ions.

13. The method of claim 1 comprising,
    exposing the sample molecules to a first ionization source to form the first product ions, and
    re-circulating the first un-ionized group of sample molecules to expose them to the first ion source to form the second product ions.

14. The method of claim 1 comprising,
    exposing the sample molecules to a first ion source to form the first product ions, and
    flowing the first un-ionized group of sample molecules to expose them to a second ion source to form the second product ions.

15. The method of claim 1 comprising,
    flowing the sample molecules along a first flow path past a first ionization source to form the first product ions, and directing the first product ions along a second flow path to separate the first product ions from the first un-ionized group of sample molecules.

16. The method of claim 15 comprising,
flowing the first un-ionized group of sample molecules past a second ionization source in the first flow path to form the second product ions, and
directing the second product ions into the second flow channel to separate the second product ions from a second un-ionized group of sample molecules.

17. The method of claim 16 comprising,
flowing the second un-ionized group of sample molecules past a third ionization source in the first flow channel to form the third product ions, and
directing the third product ions into the second flow channel to separate the third product ions from a third un-ionized group of sample molecules.

18. The method of claim 15, wherein the directing includes attracting the first product ions into the second flow channel.

19. The method of claim 15, wherein the directing includes deflecting the first product ions into the second flow channel.

20. The method of claim 15, wherein the directing includes directing the first product ions into the second flow channel via an opening in a barrier between the first and second flow channels.

21. The method of claim 15, wherein the first flow path includes a substantially cylindrical portion.

22. The method of claim 15, wherein the second flow channel is substantially enclosed.

23. The method of claim 15, wherein the second flow path is substantially unenclosed.

24. The method of claim 1 comprising,
mixing the sample molecules with one or more dopants to improve separation of the first product ions from the first un-ionized group of sample molecules.

25. The method of claim 24, wherein the one or more dopants included at least one of methylene bromide ($CH_2Br_2$), methylene chloride ($CH_2Cl_2$), chloroform ($CHCl_3$), water ($H_2O$), methanol ($CH_3OH$), and isopropanol.

26. A method of pre-separating ions of a sample to compensate for competitive ionization comprising,
prior to analyzing:
a) ionizing sample molecules to cause a subset of the sample molecules to combine to form first product ions, the first product ions being formed from molecules having a higher affinity to take up charge,
b) separating the first product ions from a first un-ionized group of sample molecules,
c) subsequent to separating the first product ions, ionizing a subset of the first un-ionized group of sample molecules to form second product ions, the second product ions being formed from molecules having a lower affinity to take up charge than the molecules of the first product ions,
d) separating the second product ions from a second un-ionized group of sample molecules, and
analyzing the sample using an ion filter based at least in part on the first and second product ions.

27. The method of claim 26 comprising,
flowing the first product ions to a first analyzer,
flowing the second product ions to the first analyzer, and
processing information from the first analyzer about the first and second product ions to perform the analysis of the sample.

28. The method of claim 26 comprising,
flowing the first product ions to a first analyzer,
flowing the second product ions to a second analyzer, and
processing information from the first and second analyzers about the first and second product ions to perform the analysis of the sample.

29. The method of claim 28, wherein the first and second analyzers are in parallel with each other.

30. The method of claim 28, wherein the first and second analyzers are in series with each other.

31. The method of claim 26 comprising,
analyzing the sample based at least in part on at least one of the first and second groups of un-ionized sample molecules.

32. The method of claim 26 comprising,
directing the first product ions from a first flow channel into an analyzer flow channel,
causing a flow from the analyzer flow channel toward the first flow channel containing the first product ions and the first group of un-ionized sample molecules to inhibit the first un-ionized groups of sample molecules from entering the analyzer flow channel.

33. A system for pre-separating a sample to compensate for competitive ionization comprising,
an ion mobility based filter for filtering particular ions of at least one of a first and second product ions,
a first ionizer for ionizing sample molecules to cause a subset of the sample molecules to combine to form first product ions prior to entering the ion filter, wherein the first product ions are formed from molecules having a higher affinity to take up charge,
a first separator for separating the first product ions from a first un-ionized group of sample molecules prior to entering the ion filter,
a second ionizer for ionizing a subset of the first un-ionized group of sample molecules to form second product ions prior to entering the ion filter, wherein the second product ions are formed from molecules having a lower affinity to take up charge than the molecules of the first product ions, and
a second separator for separating the second product ions from a second un-ionized group of sample molecules prior to entering the ion filter.

34. The system of claim 33, wherein the first and second ionizers are the same ionizer.

35. The system of claim 33, wherein the first and second ionizers are different ionizers.

36. The system of claim 33, wherein the first and second separators are the same separator.

37. The system of claim 33, wherein the first and second separators are different separators.

* * * * *